(12) United States Patent
Harats et al.

(10) Patent No.: US 8,039,261 B2
(45) Date of Patent: Oct. 18, 2011

(54) PROMOTERS EXHIBITING ENDOTHELIAL CELL SPECIFICITY AND METHODS OF USING SAME FOR REGULATION OF ANGIOGENESIS

(75) Inventors: Dror Harats, Ramat-Gan (IL); Shoshana Greenberger, Modiln (IL); Eyal Breitbart, Hashmonaim (IL); Livnat Bangio, Petach-Tikva (IL); Michael Peled, Ramat-Gan (IL)

(73) Assignee: Vascular Biogenics Ltd., Or Yehuda (IL)

( * ) Notice: Subject to any disclaimer, the term of this patent is extended or adjusted under 35 U.S.C. 154(b) by 728 days.

(21) Appl. No.: 11/359,513

(22) Filed: Feb. 23, 2006

(65) Prior Publication Data

US 2006/0204478 A1 Sep. 14, 2006

Related U.S. Application Data

(63) Continuation-in-part of application No. 10/988,487, filed on Nov. 14, 2004, which is a continuation-in-part of application No. 10/135,447, filed on May 1, 2002, now Pat. No. 7,067,649, which is a continuation-in-part of application No. PCT/IL01/01059, filed on Nov. 15, 2001, application No. 11/359,513, which is a continuation-in-part of application No. 10/490,746, filed as application No. PCT/IL02/00339 on May 1, 2002, now Pat. No. 7,585,666.

(60) Provisional application No. 60/248,582, filed on Nov. 17, 2000, provisional application No. 60/330,118, filed on Oct. 19, 2001.

(51) Int. Cl.
*C12N 15/63* (2006.01)
*C12N 15/00* (2006.01)
*A01N 61/00* (2006.01)
*A01N 43/04* (2006.01)
*C07H 21/04* (2006.01)

(52) U.S. Cl. ........... 435/455; 435/320.1; 514/1; 514/44; 536/23.5; 536/24.1

(58) Field of Classification Search ............ 435/455, 435/320.1; 514/1, 44; 536/23.5, 24.1
See application file for complete search history.

(56) References Cited

U.S. PATENT DOCUMENTS

| | | | |
|---|---|---|---|
| 4,866,042 A | 9/1989 | Neuwelt | |
| 5,464,764 A | 11/1995 | Capecchi et al. | |
| 5,635,385 A | 6/1997 | Leopold et al. | |
| 5,686,281 A | 11/1997 | Roberts | |
| 5,734,039 A | 3/1998 | Calabretta et al. | |
| 5,747,340 A | 5/1998 | Harats et al. | |
| 5,792,453 A | 8/1998 | Hammond et al. | |
| 5,830,880 A | 11/1998 | Sedlacek et al. | |
| 5,882,893 A | 3/1999 | Goodearl | |
| 5,906,827 A | 5/1999 | Khouri et al. | |
| 5,916,763 A | 6/1999 | Williams et al. | |
| 6,027,743 A | 2/2000 | Khouri et al. | |
| 6,110,480 A | 8/2000 | Chu et al. | |
| 6,180,355 B1 | 1/2001 | Alexander et al. | |
| 6,183,737 B1 | 2/2001 | Zaleske et al. | |
| 6,200,751 B1 | 3/2001 | Gu et al. | |
| 6,206,917 B1 | 3/2001 | Williams et al. | |
| 6,239,151 B1 | 5/2001 | Broadhurst et al. | |
| 6,265,216 B1 | 7/2001 | Bennett et al. | |
| 6,300,127 B1 | 10/2001 | Hair et al. | |
| 6,300,490 B1 | 10/2001 | Huber et al. | |
| 6,348,209 B2 * | 2/2002 | Placke et al. | 424/435 |
| 6,376,244 B1 | 4/2002 | Atala | |
| 6,403,944 B1 | 6/2002 | MacKenzie et al. | |
| 6,438,802 B1 | 8/2002 | Beeman et al. | |
| 6,444,803 B1 | 9/2002 | Hair et al. | |
| 6,479,064 B1 | 11/2002 | Atala | |
| 6,497,725 B2 | 12/2002 | Williams et al. | |
| 6,503,886 B1 | 1/2003 | Baird et al. | |
| 6,521,750 B2 | 2/2003 | Hair et al. | |
| 6,545,048 B1 | 4/2003 | Patterson et al. | |
| 6,576,265 B1 | 6/2003 | Spievack | |
| 6,579,697 B1 | 6/2003 | Wallach et al. | |
| 6,627,189 B1 | 9/2003 | Roth et al. | |
| 6,652,583 B2 | 11/2003 | Hopkins et al. | |
| 6,783,776 B2 | 8/2004 | Spievack | |
| 6,866,864 B2 | 3/2005 | Mousa | |
| 7,067,649 B2 | 6/2006 | Harats | |
| 7,585,666 B2 | 9/2009 | Harats et al. | |
| 7,625,558 B2 * | 12/2009 | Greene et al. | 424/130.1 |
| 2003/0124100 A1 | 7/2003 | Harats | |
| 2003/0167002 A1 | 9/2003 | Nagar et al. | |
| 2004/0048280 A1 | 3/2004 | Harats | |
| 2004/0197860 A1 | 10/2004 | Harats et al. | |
| 2004/0224389 A1 | 11/2004 | Bellgrau et al. | |
| 2005/0112110 A1 | 5/2005 | Harats | |
| 2005/0186179 A1 | 8/2005 | Harats et al. | |
| 2006/0204478 A1 | 9/2006 | Harats et al. | |

FOREIGN PATENT DOCUMENTS

EP 1313396 5/2003

(Continued)

OTHER PUBLICATIONS

Deonarain, 1998, Expert Opin. Ther. Pat., vol. 8, pp. 53-69.*

(Continued)

*Primary Examiner* — Shin-Lin Chen

(57) ABSTRACT

Isolated polynucleotide sequences exhibiting endothelial cell specific promoter activity, novel cis regulatory elements and methods of use thereof enabling treatment of diseases characterized by aberrant neovascularization or cell growth are disclosed.

39 Claims, 95 Drawing Sheets
(63 of 95 Drawing Sheet(s) Filed in Color)

FOREIGN PATENT DOCUMENTS

| WO | WO 98/00013 | 1/1998 |
|---|---|---|
| WO | WO 98/37901 | 9/1998 |
| WO | WO 00/06759 | 2/2000 |
| WO | WO 02/15776 | 2/2002 |
| WO | WO 02/40629 | 5/2002 |
| WO | WO 03/033514 | 4/2003 |
| WO | WO 03/093409 | 11/2003 |
| WO | WO 2004/113497 | 12/2004 |
| WO | WO 2006/051545 | 5/2006 |
| WO | WO 2007/096882 | 8/2007 |
| WO | WO 2008/132729 | 11/2008 |

OTHER PUBLICATIONS

Verma et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Thomas et al., 2003, Nature Reviews/ Genetics, vol. 4, p. 346-358.*
Kaye et al., 1990, Proc. Natl. Acad. Sci. USA, vol. 87, pp. 6922-6926.*
Davis, C. G., 1990, The New Biologist, vol. 2, No. 5, p. 410-419.*
Skolnick et al., 2000, Trends in Biotech, vol. 18, p. 34-39.*
Varda-Bloom et al., 2001, Gene Therapy, vol. 8, p. 819-827.*
Boldin et al., 1995, The Journal of Biological Chemistry, vol. 270, No. 14, pp. 7795-7798.*
Kaplan et al., 1999, Nature Medicine, vol. 5, No. 3, p. 292-297.*
Percy et al., 1997, Biochemical and Molecular Medicine, vol. 62, p. 132-134.*
Communication Pursuant to Article 94(3) EPC Dated May 29, 2008 From the European Patent Office Re.: Application No. 05806361.1 Mailed by Associate on Jun. 16, 2008.
Communication Pursuant to Article 96(2) EPC Dated Apr. 17, 2007 From the European Patent Office Re.: Application No. EP 02801473.6.
Examination Report Dated Sep. 5, 2005 from the Intellectual Property Office of New Zealand Re.: Application 536578 Mailed by Associate Oct. 12, 2005.
Examiner's Report Dated Dec. 10, 2008 From the Australian Government, IP Australia Re.: Application No. 2003222427.
International Preliminary Examination Report Dated May 26, 2005 From the International Preliminary Examining Authority Re.: Application No. PCT/IL03/00347.
Official Action Dated Nov. 14, 2008 From the US Patent and Trademark Office Re.: U.S. Appl. No. 10/490,746.
Official Action Dated May 28, 2008 From the Japanese Patent Office Re.: Application No. 202-543626 Mailed by Associate Jun. 9, 2008.
Requisition by the Examiner Dated Dec. 16, 2008 From the Canadian Intellectual Property Re.: 2,429,342.
Communication Pursuant to Article 94(3) EPC Dated Feb. 10, 2009 From the European Patent Office Re.: Application No. 02801473.6.
Communication Pursuant to Article 94(3) EPC Dated Feb. 16, 2009 From the European Patent Office Re.: Application No. 05806361.1.
Translation of Notice of the Reason for Rejection Dated Jan. 7, 2009 From the Korean Intellectual Property Office Re.: Application No. 2008-7018598.
Communication Pursuant to Article 94(3) EPC Dated Apr. 27, 2007 From the European Patent Office Re.: Application No. 01996590.4.
Communication Pursuant to Article 96(2) EPC Dated Dec. 21, 2006 From the European Patent Office Re.: Application No. 01996590.4.
Examination Report Dated Apr. 3, 2009 From the Intellectual Property Office of New Zealand Re.: Application No. 555612.
International Preliminary Examination Report Dated Jan. 5, 2005 From the International Preliminary Examining Authority Re.: Application No. PCT/IL02/00339.
International Preliminary Report on Patentability Dated Jan. 22, 2009 From the International Bureau of WIPO Re.: Application No. PCT/IL2007/000242.
International Preliminary Report on Patentability Dated May 24, 2007 From the International Bureau of WIPO Re.: Application No. PCT/IL2005/001195.
International Search Report Dated Apr. 29, 2009 From the International Searching Authority Re.: Application No. PCT/IL08/00543.
Invitation to Pay Additional Fees Dated Jun. 1, 2006 From the International Searching Authority Re.: Application No. PCT/IL05/01195.
Notice of Allowance Dated Aug. 14, 2008 From the US Patent and Trademark Office Re.: U.S. Appl. No. 10/075,619.
Office Action Dated Jan. 10, 2008 From the Israeli Patent Office Re.: Application No. 155940.
Office Action Dated Sep. 20, 2007, From the Israeli Patent Office Re.: Application No. 155940.
Official Action Dated Jan. 4, 2008 From the US Patent and Trademark Office Re.: U.S. Appl. No. 10/988,487.
Official Action Dated Jun. 4, 2007 From the US Patent and Trademark Office Re.: U.S. Appl. No. 10/975,619.
Official Action Dated Apr. 9, 2008 From the US Patent and Trademark Office Re.: U.S. Appl. No. 10/940,746.
Official Action Dated Jul. 10, 2007 From the US Patent and Trademark Office Re.: U.S. Appl. No. 10/490,746.
Official Action Dated Dec. 29, 2006 From the US Patent and Trademark Office Re.: U.S. Appl. No. 10/490,746.
Supplementary European Search Report Dated Mar. 21, 2006 From the European Patent Office Re.: Application No. 02801473.6.
Written Opinion Dated Apr. 29, 2009 From the International Searching Authority Re.: Application No. PCT/IL08/00543.
Bu et al., "Identification of An Endothelial Cell-Specific Regulatory Region in the Murine Endothelin-1 Gene", The Journal of Biological Chemistry, 272(51): 32613-32622, 1997.
Notice of Allowance Dated Jun. 11, 2009 From the US Patent and Trademark Office Re.: U.S. Appl. No. 10/490,746.
Search Report and Written Opinion Dated Apr. 21, 2009 From the Intellectual Property Office of Singapore Issued by the Austrian Patent Office Re.: Application No. 200703466-3.
Aird et al. "Human von Willebrand Factor Gene Sequences Target Expression to A Subpopulation of Endothelial Cells in Transgenic Mice", Proc. Natl. Acad. Sci. USA, 92: 4567-4571, 1995.
Aoki et al. "In Vivo Transfer Efficiency of Antisense Oligonucleotides Into the Myocardium Using HVJ-Liposome Method", Biochemical and Biophysical Research Communications, 231: 540-545, 1997.
Araki et al. "Ninjurin2, A Novel Homophilic Adhesion Molecule, Is Expressed in Mature Sensory and Enteric Neurons and Promotes Neurite Outgrowth", The Journal of Neuroscience, 20(1): 187-195, 2000.
Arap et al. "Cancer Treatment by Targeted Drug Delivery to Tumor Vasculature in A Mouse Model", Science, New Series, 279(5349): 377-380, 1998.
Ausprunk et al. "Migration and Proliferation of Endothelial Cells in Preformed and Newly Formed Blood Vessels During Tumor Angiogenesis", Microvascular Research, 14: 53-65, 1977.
Barcelos et al. "Impaired Inflammatory Angiogenesis, But Not Leukocyte Influx, in Mice Lacking TNFR1", Journal of Leukocyte Biology, 78: 352-358, Aug. 2005.
Bobek et al. "Gene Therapy of the Ischemic Lower Limb—Therapeutic Angiogenesis", Vascular Pharmacology, 44: 395-405, 2006.
Brown et al. "Neovascularisation and Its Role in the Osteoarthritic Process", Annals of the Rheumatic Diseases, 47: 881-885, 1988.
Chen et al. "Upstream Stimulatory Factors Regulate Aortic Preferentially Expressed Gene-I Expression in Vascular Smooth Muscle Cells", The Journal of Biological Chemistry, 276(50): 47658-47663, 2001.
Collins et al. "Molecular Cloning of the Human Gene for Von Willebrand Factor and Identification of the Transcription Initiation Site", Proc. Natl. Acad. Sci. USA, 84: 4393-4397, 1987.
Collins et al. "Strucutre and Chromosomal Location of the Gene for Endothelial-Leukocyte Adhesion Molecule 1", The Journal of Biological Chemistry, 266(4): 2466-2473, 1991.
Dor et al. "Induction of Vascular Networks in Adult Organs: Implications to Proangiogenic Therapy", Annals of the NY Academy of Sciences, 995: 208-216, 2003.
Edelberg et al. "Platelet-Derived Growth Factor-AB Limits the Extent of Myocardial Infarction in A Rat Model: Feasibility of Restoring Impaired Angiogenic Capacity in the Aging Heart", Circulation, 105: 608-613, 2002.

Epstein et al. "Therapeutic Interventions for Enhancing Collateral Development by Administration of Growth Factors: Basic Principles, Early Results and Potential Hazards", Cardiovascular Research, 49: 532-542, 2001.

Faries et al. "Assessing the Role of Gene Therapy in the Treatment of Vascular Disease", Annals of Vascular Surgery, 14(2): 181-188, 2000.

Feldman et al. "Progress in Antiangiogenic Gene Therapy of Cancer", Cancer, 89: 1181-1194, 2000.

Folkman "How Is Blood Vessel Growth Regulated in Normal and Neoplastic Tissue?—G.H.A. Clowes Memorial Award Lecture", Cancer Research, 46: 467-473, 1986.

French Anderson "Human Gene Therapy", Nature, 392: 25-30, 1998.

Garlanda et al. "Heterogeneity of Endothelial Cells . Specific Markers", Arteriosclerosis, Thrombosis, and Vascular Biology, 17(7): 1193-1202, 1997.

Goldman et al. "Influence of Pressure on Permeability of Normal and Diseased Muscular Arteries to Horseradish Peroxidase. A New Catheter Approach", Atherosclerosis, 65: 215-225, 1987.

Gorski et al. "Potentiation of the Antitumor Effect of Ionizing Radiation by Brief Concomitant Exposures to Angiostatin", Cancer Research, 58: 5686-5689, 1998.

Gu et al. "HTERT Promoter Induces Tumor-Specific Bax Gene Expression and Cell Killing in Syngenic Mouse Tumor Model and Prevents Systemic Toxicity", Gene Therapy, 9: 30-37, 2002.

Harada et al. "Basic Fibroblast Growth Factor Improves Myocardial Function in Chronically Ischemic Porcine Hearts", Journal of Clinical Investigation, 94: 623-630, 1994.

Hoefer et al. "Direct Evidence for Tumor Necrosis Factor-α Signaling in Arteriogenesis", Circulation, 105: 1639-1641, Apr. 9, 2002.

Iris et al. "Dense Alu Clustering and A Potential New Member of the NFκB Family Within A 90 Kilobase HLA Class III Segment", Nature Genetics, 3: 137-145, 1993.

Jäger et al. "Endothelial Cell-Specific Transcriptional Targeting From A Hybrid Long Terminal Repeat Retrovirus Vector Containing Human Prepro-Endothelin-1 Promoter Sequences", Journal of Virology, 73(12): 9702-9709, 1999.

Jones et al. "A Portable Regulatory Element Directs Specific Expression of the Caenorhabditis Elegans Ubiquitin Gene UBQ-2 in the Somatic Gonad", Developmental Biology, 171: 60-72, 1995.

Joshi et al. "Endothelial Cells Adhere to the RGD Domain and the Fibrinogen-Like Terminal Knob of Tenascin", Journal of Cell Science, 106: 389-400, 1993.

Kaiser et al. "Platelet-Derived Growth Factor, Intimal Hyperplasia, and Ischemic Complications in Giant Cell Arteritis", Arthritis & Rheumatism, 41(4): 623-633, 1998.

Kaito et al. "Potentiation of the Activity of Bone Morphogenetic Protein-2 in Bone Regeneration by A PLA-PEG/Hydroxyapatite Composite", Biomaterials, 26: 73-79, 2005.

Khan et al. "Gene Therapy Progeress and Prospects: Therapeutic Angiogenesis for Limb and Myocardial Ischemia", Gene Therapy, 10: 285-291, 2003.

Kolesnick et al. "Radiation and Ceramide-Induced Apoptosis", Oncogene, 22: 5897-5906, 2003.

Kong et al. "Gene Therapy Strategies for Tumor Antiangiogenesis", Journal of the National Cancer Institute, 90(4): 273-286, 1998.

Korhonen et al. "Endothelial-Specific Gene Expression Directed by the TIE Gene Promoter In Vivo", Blood, 86(5): 1828-1835, 1995.

Koshikawa et al. "Therapeutic Efficacy of the Suicide Gene Driven by the Promoter of Vascular Endothelial Growth Factor Gene Against Hypoxic Tumor Cells", Cancer Research, 60(11): 2936-2941, 2000.

Koyama et al. "Migratory and Proliferative Effect of Platelet-Derived Growth Factor in Rabbit Retinal Endothelial Cells: Evidence of An Autocrine Pathway of Platelet-Derived Growth Factor", Journal of Cellular Physiology, 158: 1-6, 1994.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Lavigne et al. "Enhanced Antisense Inhibition of Human Immunodeficiency Virus Type 1 in Cell Cultures by DLS Delivery System", Biochemical and Biophysical Research Communications, 237: 566-571, 1997.

Layne et al. "Characterization of the Mouse Aortic Carboxypeptidase-Like Protein Promoter Reveals Activity in Differentiated and Dedifferentiatid Vascular Smooth Muscle Cells", Circulation Research, 90: 728-736, 2002.

Liu et al. "Restenosis After Coronary Angioplasty. Potential Biologic Determinants and Role of Intimal Hyperplasia", Circulation, 79: 1374-1387, 1989.

Lowe et al. "Osteopetrosis in Src-Deficient Mice Is Due to An Autonomous Defect of Osteoclasts", Proc. Natl. Acad. Sci. USA, 90: 4485-4489, 1993.

Luft "Making Sense Out of Antisense Oligodeoxynucleotide Delivery: Getting There Is Half the Fun", Journal of Molecular Medicine, 76: 75-76, 1998.

Lyden "Impaired Recruitment of Bone-Marrow-Derived Endothelial and Hematopoietic Precursor Cells Blocks Tumor Angiogenesis and Growth", Nature Medicine, 7(11): 1194-1201, 2001.

Micheau et al. "STAT-1-Independent Upregulation of FADD and Procaspase-3 and -8 in Cancer Cells Treated With Cytotoxic Drugs", Biochemical and Biophysical Research Communications, 256: 603-607, 1999.

Morishita et al. "A Novel Promoter for Vascular Endothelial Growth Factor Receptor (Flt-1) That Confers Endothelial-Specific Gene Expression", The Journal of Biological Chemistry, 270(46): 27948-27953, 1995.

Newman et al. "PECAM-1 (CD31) Cloning and Relation to Adhesion Molecules of the Immunoglobulin Gene Superfamily", Science, New Series, 247(4947): 1219-1222, 1990.

Nicklin et al. "Selective Targeting of Gene Transfer to Vascular Endothelial Cells by Use of Peptides Isolated by Phage Display", Circulation, 102: 231-237, 2000.

O'Reilly et al. "Endostatin: An Endogenous Inhibitor of Angiogenesis and Tumor Growth", Cell, 88: 277-285, 1997.

Ozawa et al. "Histologic Changes of Nonbiodegradable and Biodegradable Biomaterials Used to Repair Right Ventricular Heart Defects in Rats", The Journal of Thoracic and Cardiovascular Surgery, 124(6): 1157-1164, 2002.

Palù et al. "In Pursuit of New Developments for Gene Therapy of Human Diseases", Journal of Biotechnology, 68: 1-13, 1999.

Patan et al. "Intussusceptive Microvascular Growth in A Human Colon Adenocarcinoma Xenograft: A Novel Mechanism of Tumor Angiogenesis", Microvascular Research, 51: 260-272, 1996.

Peng et al. "The Use of the L-Plastin Promoter for Adnoviral-Mediated, Tumor-Specific Gene Expression in Ovarian and Bladder Cancer Cell Lines", Cancer Research, 61: 4405-4413, 2001.

Plump et al. "Severe Hypercholesterolemia and Atherosclerosis in Apolipoprotein E-Deficient Mice Created by Homologous Recombination in ES Cells", Cell, 71: 343-353, 1992.

Rajur et al. "Covalent Protein-Oligonucleotide Conjugates for Efficient Delivery of Antisense Molecules", Bioconjugate Chemistry, 8: 935-940, 1997.

Risau "Mechanisms of Angiogenesis", Nature, 386: 671-674, 1997.

Ríus et al. "Cloning of the Promoter Region of Human Endoglin, the Target Gene for Hereditary Hemorrhagic Telangiectasia Type 1", Blood, 92(12): 4677-4690, 1998.

Sano et al. "Functional Blockade of Platelet-Derived Growth Factor Receptor-β But Not of Receptor-α Prevents Vascular Smooth Muscle Cell Accumulation in Fibrous Cap Lesions in Apolipoprotein E-Deficient Mice", Circulation, 103: 2955-2960, 2001.

Sato et al. "Tie-1 and Tie-2 Define Another Class of Putative Receptor Tyrosine Kinase Genes Expressed in Early Embryonic Vascular System", Proc. Natl. Acad. Sci. USA, 90: 9355-9358, 1993.

Schlaeger et al. "Vascular Endothelial Cell Lineage-Specific Promoter in Transgenic Mice", Development, 121: 1089-1098, 1995.

Shimo et al. "Connective Tissue Growth Factor as A Major Angiogenic Agent That Is Induced by Hypoxia in A Human Breast Cancer Cell Line", Cancer Letters, 174: 57-64, 2001.

Soriano et al. "Targeted Disruption of the C-SRC Proto-Oncogene Leads to Osteopetrosis in Mice", Cell, 64: 693-702, 1991.

Stefanidakis et al. "Identification of A Negatively Charged Peptide Motif Within the Catalytic Domain of Progelatinases That Mediates Binding to Leukocyte β2 Integrins", The Journal of Biological Chemistry, 278(36): 34674-34684, 2003.

Van de Stolpe et al. "Intercellular Adhesion Molecule-1", Journal of Molecular Medicine, 74(1): 13-33, 1996. Abstract.
Verma et al. "Gene Therapy—Promises, Problems and Prospects", Nature, 389: 239-242, 1997.
Wang et al. "Molecular Cloning of the Complementary DNA for Human Tumor Necrosis Factor", Science, New Series, 228(4696): 149-154, 1985.
Watkins et al. "The 'Adenobody' Approach to Viral Targeting: Specific and Enhanced Adenoviral Gene Delivery", Gene Therapy, 4: 1004-1012, 1997.
West et al. "Endothelial Cell Proliferation and Diabetic Retinopathy", The Lancet, 1: 715-716, 1988.
Whitaker et al. "Induction of Functional Neovascularization by Wisker Stimulation After Focal Ischemia", Abstract Viewer and Itinery Planner, Society for Neuroscience, 2003: Abstract No. 789.12, Nov. 2003. 33rd Annual Meeting of the Society of Neuroscience, New Orleans, LA, USA, Nov. 8-12, 2003.
Williams et al. "Hypoxia and Oxidative Stress in Breast Cancer Tumour Hypoxia—Therapeutic Considerations", Breast Cancer Research, 3: 328-331, 2001.
Wong et al. "Human GM-CSF: Molecular Cloning of the Complementary DNA and Purification of the Natural and Recombinant Proteins", Science, New Series, 228(4701): 810-815, 1985.
Wu et al. "Chimeric PSA Enhancers Exhibit Augmented Activity in Prostate Cancer Therapy Vectors", Gene Therapy, 8: 1416-1426, 2001.
Yanagisawa-Miwa et al. "Salvage of Infarcted Myocardium by Angiogenic Action of Basic Fibroblast Growth Factor", Science, New Series, 257(5075): 1401-1403, 1992.
Examination Report Dated Aug. 6, 2009 From the Intellectual Property Office of New Zealand Re.: Application No. 555612.
Official Action Dated Jun. 24, 2009 From the US Patent and Trademark Office Re.: U.S. Appl. No. 12/222,439.
Summons to Attend Oral Proceedings Pursuant to Rule 115(1) EPC Dated Jul. 13, 2009 From the European Patent Office Re.: Application No. 05806361.1.
Folkman "Angiogenesis and Apoptosis", Seminars in Cancer Biology, 13: 159-167, 2003.
Juengst "What Next for Human Gene Therapy? Fene Transfer Often Has Multiple and Unpredictable Effects on Cells", BMJ, 326: 1410-1411, Jun. 28, 2003.
Kay et al. "Viral Vectors for Gene Therapy: The Art of Turning Infectious Agents Into Vehicles of Therapeutics", Nature Medicine, 7(1): 33-40, Jan. 2001.
Lebedeva et al. "Restoring Apoptosis as A Strategy for Cancer Gene Therapy: Focus on P53 and MDA-7", Seminars in Cancer Biology, 13: 169-178, 2003.
Patil et al. "DNA-Based Therapeutics and DNA Delivery Systems: A Comprehensive Review", The AAPS Journal, 7(1): E61-E77, 2005.
Savontaus et al. "Transcriptional Targeting of Conditionally Replicating Adenovirus to Dividing Endothelial Cells", Gene Therapy, 9: 972-979, 2002.
Official Action Dated May 13, 2010 From the US Patent and Trademark Office Re.: U.S. Appl. No. 12/222,439.
Official Action Dated Jul. 6, 2010 From the US Patent and Trademark Office Re.: U.S. Appl. No. 11/790,992.
Official Action Dated Jul. 8, 2010 From the US Patent and Trademark Office Re.: U.S. Appl. No. 10/988,487.
Examination Report Dated Oct. 16, 2009 From the Intellectual Property Office of New Zealand Re.: Application No. 580289.
International Preliminary Report on Patentability Dated Nov. 12, 2009 From the International Bureau of WIPO Re.: Application No. PCT/IL2008/000543.
Official Action Dated Nov. 12, 2009 From the US Patent and Trademark Office Re.: U.S. Appl. No. 10/988,487.
Official Action Dated Jul. 29, 2009 From the US Patent and Trademark Office Re.: U.S. Appl. No. 10/490,746.
Official Action Dated Aug. 31, 2009 From the US Patent and Trademark Office Re.: U.S. Appl. No. 11/790,992.
Summons to Attend Oral Proceedings Pursuant to Rule 115(1) EPC Dated Sep. 14, 2009 From the European Patent Office Re.: Application No. 02801473.6.
Invitation to Remedy Deficiencies Pursuant to Rule 30(3) EPC / Rule 163(3) EPC Dated Mar. 16, 2010 From the European Patent Office Re.: Application No. 09176343.3.
Response Dated May 12, 2010 to Invitation to Remedy Deficiencies Pursuant to Rule 30(3) EPC / Rule 163(3) EPC of Mar. 16, 2010 From the European Patent Office Re.: Application No. 09176343.3.
Response Dated Apr. 22, 2010 to Official Action of Dec. 23, 2009 From the US Patent and Trademark Office Re.: U.S. Appl. No. 12/222,439.
Response Dated Apr. 29, 2010 to Office Action of Dec. 29, 2009 From the Israel Patent Office Re.: Application No. 183187.
Triozzi et al. "A Phase I Study to Assess the Safety and Distribution of GT-111 in Patients With Advanced Metastatic Cancer", Vascular Biogenics, Ltd., Clinical Trials Identifier: NCT00559117, Jun. 9, 2009.
Communication Relating to the Results of the Extended International Search Dated Apr. 8, 2010 From the European Patent Office Re.: Application No. 09174998.6.
European Search Report and the European Search Opinion Dated May 17, 2010 From the European Patent Office Re. Application No. 09168899.4.
Response Dated May 20, 2010 to Communication Relating to the Results of the Extended International Search of Apr. 8, 2010 From the European Patent Office Re.: Application No. 09174998.6.
Official Action Dated Jun. 4, 2010 From the US Patent and Trademark Office Re.: U.S. Appl. No. 12/457,200.
Requisition by the Examiner Dated May 14, 2010 From the Canadian Intellectual Property Office Re. Application No. 2,483,996.
Office Action Dated Dec. 29, 2009 From the Israel Patent Office Re.: Application No. 183187 and Its Translation Into English.
Official Action Dated Jan. 14, 2010 From the US Patent and Trademark Office Re.: U.S. Appl. No. 11/359,513.
Official Action Dated Dec. 15, 2009 From the US Patent and Trademark Office Re.: U.S. Appl. No. 11/790,992.
Official Action Dated Jan. 22, 2010 From the US Patent and Trademark Office Re.: U.S. Appl. No. 12/457,200.
Official Action Dated Dec. 23, 2009 From the US Patent and Trademark Office Re.: U.S. Appl. No. 12/222,439.
Partial European Search Report Dated Feb. 23, 2010 From the European Patent Office Re.: Application No. 09168899.4.
Requisition by the Examiner Dated Jan. 18, 2010 From the Canadian Intellectual Property Office Re.: Application No. 2,463,816.
Response Dated Nov. 4, 2009 to Official Action of Aug. 4, 2009 From the US Patent and Trademark Office Re.: U.S. Appl. No. 11/359,513.
Response Dated Jan. 10, 2010 to Examiner's Report of Dec. 10, 2008 From the Australian Government, IP Australia Re.: Application No. 2003222427.
Response Dated Apr. 12, 2010 to Official Action of Nov. 12, 2009 From the US Patent and Trademark Office Re.: U.S. Appl. No. 10/988,487.
Response Dated Feb. 22, 2010 to Official Action of Jan. 22, 2010 From the US Patent and Trademark Office Re.: U.S. Appl. No. 12/457,200.
Peled et al. "Systemic Administration of A Conditionally Replicating Adenovirus, Targeted to Angiogenesis, Reduced Lung Metastasis Burden in Cotton Rats", Clinical Cancer Research, 15(5): 1664-1673, Mar. 1, 2009.
Wadhwa et al. "Cancer Gene Therapy: Scientific Basis", Annual Review of Medicine, XP002568022, 53: 437-453, 2002. p. 438.
Response Dated Apr. 14, 2010 to Official Action of Dec. 15, 2009 From the US Patent and Trademark Office Re.: U.S. Appl. No. 11/790,992.
Response Dated Jul. 14, 2010 to Requisition by the Examiner of Jan. 18, 2010 From the Canadian Intellectual Property Office Re.: Application No. 2,463,816.
Communication Pursuant to Article 96(2) EPC Dated May 3, 2006 From the European Patent Office Re.: Application No. EP 01996590.4.
Communication Pursuant to Article 96(2) EPC Dated Jul. 31, 2006 From the European Patent Office Re.: Application No. EP 03717516.3. Mailed by Associate on Aug. 17, 2006.

Examination Report Dated Aug. 3, 2006 From the Intellectual Property Office of New Zealand Re.: Application No. 536578. Mailed by Associate Aug. 6, 2006.
Examination Report Dated Jun. 20, 2007 From the Government of India, Patent Office Re.: Application No. 2679/CHENP/2004.
Examination Report Dated Jul. 12, 2007 From the Government of India, Patent Office Re.: Application No. 801/CHENP/2004 . Mailed by the Associate on Aug. 31, 2007.
Examination Report Dated Apr. 13, 2006 From the Government of India, Patent Office Re.: Application No. 743/CHENP/2003—in English only. Mailed by the Associate on Jun. 2, 2006.
International Preliminary Examination Report Dated Jan. 28, 2005 From the International Preliminary Examining Authority Re.: Application No. PCT/IL01/01059.
International Search Report Dated Dec. 2, 2002 From the International Searching Authority Re.: Application No. PCT/IL02/00339.
International Search Report Dated Aug. 4, 2006 From the International Searching Authority Re.: Application No. PCT/IL05/01195.
International Search Report Dated May 4, 2004 From the International Searching Authority Re.: Application No. PCT/IL01/01059.
International Search Report Dated Sep. 18, 2008 From the International Searching Authority Re.: Application No. PCT/IL07/00242.
International Search Report or the Declaration Dated Jan. 28, 2005 From the International Searching Authority Re: Application No. PCT/IL03/00347.
Office Action Dated Oct. 13, 2006 From the Patent Office of the People's Republic of China Re.: Application No. CN 03815262.2— English Translation only. (mailed by Associate only on Nov. 13, 2006.
Office Action Dated Apr. 27, 2008 From the Korean Intellectual Property Office Re.: Application No. 2004-7005720 and its translation in English. Mailed by Associate May 23, 2008.
Office Action Dated Jul. 31, 2007 From the Japanese Patent Office Re.: Application No. 2004-501545. Mailed by the Associate on Aug. 8, 2007.
Office Action Dated Jul. 31, 2007 From the Japanese Patent Office Re.: Application No. 2002-543626 Mailed by Associate Aug. 23, 2007.
Official Action Dated Oct. 2, 2008 From the US Patent and Trademark Office Re.: U.S. Appl. No. 11/359,513.
Official Action Dated Apr. 6, 2007 From the US Patent and Trademark Office Re.: U.S. Appl. No. 10/975,619.
Official Action Dated May 6, 2009 From the US Patent and Trademark Office Re.: U.S. Appl. No. 11/359,513.
Official Action Dated Oct. 7, 2010 From the US Patent and Trademark Office Re.: U.S. Appl. No. 12/224,178.
Official Action Dated Apr. 10, 2008 From the US Patent and Trademark Office Re.: U.S. Appl. No. 10/975,619.
Official Action Dated Oct. 11, 2006 From the US Patent and Trademark Office Re.: U.S. Appl. No. 10/490,746.
Official Action Dated Jul. 14, 2004 From the US Patent and Trademark Office Re.: U.S. Appl. No. 10/135,447.
Official Communication Dated Feb. 1, 2008 From the Instituto Mexicano de la Propiedad Industrial Re.: Application No. PA/a/2004/003514 and its summary in English by Associate.. Mailed by Associate May 7, 2008.
Official Communication Dated Jul. 14, 2010 From the Instituto Mexicano de la Propiedad Industrial Re.: Application No. PA/a/2004/003514 and Its Summary in English by Associate.
Official Communication Dated Jul. 18, 2007 From the Instituto Mexicano de la Propiedad Industrial Re.: Application No. PA/a/2004/010711 and its English summary by Associate. Mailed by Associate Sep. 20, 2007.
Official Communication Dated Feb. 28, 2008 From the Instituto Mexicano de la Propiedad Industrial Re.: Application No. PA/a/2003/004325, and its Summary in English by Associate. Mailed by Associate Apr. 16, 2008.
Response Dated Oct. 5, 2010 to Official Action of Jul. 6, 2010 From the US Patent and Trademark Office Re.: U.S. Appl. No. 11/790,992.
Supplementary European Search Report and the European Search Opinion Dated Oct. 17, 2007 From the European Patent Office Re.: Application EP 05806361. Mailed Oct. 18, 2007 by Associate.
Supplementary European Search Report Dated Mar. 21, 2006 From the European Patent Office Re.: Application No. EP 02801473.6.
Supplementary European Search Report Dated Oct. 28, 2005 From the European Patent Office Re.: Application No. EP 03717516.
Supplementary Partial European Search Report Dated Nov. 15, 2004 From the European Patent Office Re.: Application EP 01996590.
Supplementary Partial European Search Report Dated Nov. 15, 2004 From the European Patent Office Re. Application No. 01996590.4.
Translation of Notice of Reason for Rejection Dated Oct. 16, 2007 From the Japanese Patent Office Re.: Application No. 2003-536253 Mailed by Associate on Oct. 25, 2007.
Translation of Notice of Reason for Rejection Dated May 28, 2008 From the Japanese Patent Office Re.: Application No. 202-543626 Mailed by Associate Jun. 9, 2008.
Written Opinion Dated Nov. 2, 2004 From the International Preliminary Examining Authority Re.: Application PCT/IL01/01059.
Written Opinion Dated Sep. 18, 2008 From the International Searching Authority Re.: Application No. PCT/IL07/00242.
Written Opinion Dated Oct. 29, 2003 From the International Preliminary Examining Authority Re.: Application No. PCT/IL02/00339.
Written Opinion of the International Searching Authority Dated Aug. 4, 2006 From the International Searching Authority by the Patent Cooperation Treaty Re.: Application No. PCT/IL05/01195.
Carmeliet et al. "Growing Better Blood Vessels", Nature Biotechnology, 19: 1019-1020, 2001.
Cho et al. "Development of an Efficient Endothelial Cell Specific Vector Using Promoter and 5' Untranslated Sequences From the Human Proproendothelin-1 Gene", Experimental and Molecular Medicine, 35(4): 269-274, 2003.
Greenberger et al. "Transcription-Controlled Gene Therapy Against Tumor Angiogenesis", The Journal of Clinical Investigation, XP002349281, 113(7): 1017-1024, Apr. 1, 2004. Abstract, p. 1018, p. 1019, LLC Model, Fig.2A.
Harats et al. "Targeting Gene Expression to the Vascular Wall in Transgenic Mice Using the Murine Preproendothelin-1 Promoter", Journal of Clinical Investigation, 95(3): 1335-1344, 1995. p. 1336, Fig.1.
Koshikawa et al. "Therapeutic Efficacy of the Suicide Gene Driven by the Promoter of Vascular Endothelial Growth Factor Gene Against Hypoxic Tumor Cells", Cancer Research, XP001024127, 60(11): 2936-2941, 2000.
Lee et al. "Functional Analysis of the Endothelin-1 Gene Promoter", Journal of Biological Chemistry, 265(18): 10446-10450, 1990. Fig.1, wherein Nucleotides -124 to -118 Are Identical to SEQ ID NO: 5.
Minchenko et al. "Regulation of Endothelin-1 Gene Expression in Human Microvascular Endothelial Cells by Hypoxia and Cobalt: Role of Hypoxia Responsive Element", Molecular and Cellular Biochemistry, 208(1-2): 53-62, 2000. p. 57, 1-h Col., § 2, p. 57, r-h Col., Last §, Fig.2.
Peled et al. "Systemic Administration of A Conditionally Replicating Adenovirus, Targeted to Angiogenesis, Reduced Lung Metastasis Burden in Cotton Rats", Clinical Cancer Research, XP002579967, 15(5): 1664-1673, Mar. 1, 2009.
Richardson et al. "Polymeric System for Dual Growth Factor Delivery", Nature Biotechnology, 19: 1029-1034, 2001.
Savontaus et al. "Transcriptional Targeting of Conditionally Replicating Adenovirus to Dividing Endothelial Cells", Gene Therapy, XP002579436, 9(14): 972-979, Jul. 2002. Fig. 1.
Strasser et al. "Apoptosis Signaling", Annual Review of Biochemistry, XP002283497, 69: 217-245, 2000.
Sun et al. "Functional Analysis of the Preproendothelin-1 Gene Promoter in Pulmonary Epithelial Cells and Monocytes", Biochemical and Biophysical Research Communications, 221(3): 647-652, 1996. p. 649, last §-p. 651, § 1.
Communication Pursuant to Rules 70(2) and 70a(2) EPC and Reference to Rule 39(1) EPC Dated Jun. 21, 2010 From the European Patent Office Re. Application No. 09168899.4.
European Search Report and the European Search Opinion Dated Jul. 29, 2010 From the European Patent Office Re. Application No. 09176343.3.
Response Dated Aug. 12, 2010 to Official Action of May 13, 2010 From the US Patent and Trademark Office Re.: U.S. Appl. No. 12/222,439.

Response Dated Aug. 25, 2010 to Official Communication of Jul. 14, 2010 From the Instituto Mexicano de la Propiedad Industrial Re.: Application No. PA/a/2004/003514.
Response Dated Aug. 25, 2010 to Official Action of Jun. 4, 2010 From the US Patent and Trademark Office Re.: U.S. Appl. No. 12/457,200.
Translation of Office Action Dated Jul. 30, 2010 From the State Intellectual Property Office of the People's Republic of China Re. Application No. 200580046412.8.
Response Dated Oct. 7, 2010 to Official Action of Jul. 8, 2010 From the US Patent and Trademark Office Re.: U.S. Appl. No. 10/988,487.
Official Action Dated Oct. 13, 2010 From the US Patent and Trademark Office Re.: U.S. Appl. No. 12/222,439.
Invitation to Remedy Deficiencies Pursuant to Rule 30(3) EPC / Rule 163(3) EPC Dated Apr. 11, 2011 From the European Patent Office Re. Application No. 10185193.9.
European Search Report and the European Search Opinion Dated Feb. 24, 2011 From the European Patent Office Re. Application No. 10184033.8.
Dancer et al. "Expression of Thymidine Kinase Driven by An Endothelial-Specific Promoter Inhibits Tumor Growth of Lewis Lung Carcinoma Cells in Transgenic Mice", Gene Therapy, XP002522579, 10(14): 1170-1178, Jul. 2003.
Examination Report Dated Oct. 1, 2010 From the Intellectual Property Office of New Zealand Re. Application No. 581511.
Response Dated Mar. 15, 2011 to Examination Report of Oct. 1, 2010 From the Intellectual Property Office of New Zealand Re. Application No. 581511.
Response Dated Apr. 5, 2011 to Search Report and Written Opinion of Nov. 11, 2010 From the Intellectual Property Office of Singapore Issued by the Austrian Patent Office Re. Application No. 200907209-1.
Response Dated May 5, 2011 to Official Action of Dec. 6, 2010 From the US Patent and Trademark Office Re.: U.S. Appl. No. 12/224,178.
Response Dated Apr. 27, 2011 to Communication Pursuant to Article 94(3) EPC of Jan. 25, 2011 From the European Patent Office Re. Application No. 09168899.4.
Lahav et al. "Endothelin Receptor B Inhibition Triggers Apoptosis and Enhances Angiogenesis in Melanomas", Cancer Research, 64: 8945-8953, Dec. 16, 2004.
Office Action Dated Oct. 31, 2010 From the Israel Patent Office Re.: Application No. 183187 and Its Translation Into English.
Official Action Dated Dec. 6, 2010 From the US Patent and Trademark Office Re.: U.S. Appl. No. 12/224,178.
Official Action Dated Nov. 10, 2010 From the US Patent and Trademark Office Re.: U.S. Appl. No. 12/457,200.
Response Dated Dec. 2, 2010 to Office Action of Jul. 30, 2010 From the State Intellectual Property Office of the People's Republic of China Re. Application No. 200580046412.8.
Response Dated Nov. 7, 2010 to Examination Report of Oct. 16, 2009 From the Intellectual Property Office of New Zealand Re.: Application No. 580289.
Response Dated Nov. 8, 2010 to Official Action of Oct. 7, 2010 From the US Patent and Trademark Office Re.: U.S. Appl. No. 12/224,178.
Response Dated Dec. 15, 2010 to European Search Report and the European Search Opinion of May 17, 2010 From the European Patent Office Re. Application No. 09168899.4.
Search Report and Written Opinion Dated Oct. 7, 2010 From the Intellectual Property Office of Singapore Issued by the Austrian Patent Office Re. Application No. 200907209-1.
Hu et al. "Hypoxia Regulates Expression of the Endothelial-1 Gene Through A Proximal-Inducible Factor-1 Binding Site on the Antisence Strand", Biochemical and Biophysical Research Communication, 245: 894-899, 1998.
Jornot et al. "N-Acetylsyteine Augments Adenovirus-Mediated Gene Expression in Human Endothelial Cells by Enhancing Tansgene Transcription and Virus Entry", The Journal of Gene Medicine, 4: 54-65, 2002.
Kaplan et al. "Fas Ligand (CD95 Ligand) Controls Angiogenesis Beneath the Retina", Nature Medicine, 5(3): 292-297, Mar. 1999.

Kaye et al. "A Single Amino Acid Substitution Results in A Retinoblastoma Protein Defective in Phosphorylation and Oncoprotein Binding", Proc. Natl. Acad. Sci. USA, 87: 6922-6926, Sep. 1990.
Modlich et al. "Increasing Endothelial Cell Specific Expression by the Use of Heterologous Hypoxic and Cytokine-Iducible Enhancers", Gene Therapy, 7: 896-902, 2000.
Response Dated Jan. 3, 2011 to Official Action of Oct. 13, 2010 From the US Patent and Trademark Office Re.: U.S. Appl. No. 12/222,439.
Response Dated Dec. 31, 2010 to Office Action of Sep. 14, 2010 From the State Intellectual Property Office of the People's Republic of China Re. Application No. 200910137707.6.
Translation of Office Action Dated Sep. 14, 2010 From the State Intellectual Property Office of the People's Republic of China Re. Application No. 200910137707.6.
European Search Report and the European Search Opinion Dated Jan. 19, 2011 From the European Patent Office Re. Application No. 10177257.2.
Notice of Allowance Dated Jan. 12, 2011 From the US Patent and Trademark Office Re.: U.S. Appl. No. 10/988,487.
Communicaiton Pursuant to Article 94(3) EPC Dated Jan. 25, 2011 From the European Patent Office Re. Application No. 09168899.4.
Communication Pursuant to Rules 70(2) and 70a (2) EPC and Reference to Rule 39(1) EPC Dated Feb. 21, 2011 From the European Patent Office Re. Application No. 10177257.2.
European Search Report and the European Search Opinion Dated Feb. 22, 2011 From the European Patent Office Re. Application No. 10185195.4.
Communication Pursuant to Rules 70(2) and 70a(2) EPC and Reference to Rule 39(1) EPC Dated Apr. 4, 2011 From the European Patent Office Re. Application No. 10184033.8.
Communication Pursuant to Rules 70(2) and 70a(2) EPC and Reference to Rule 39(1) EPC Dated Apr. 4, 2011 From the European Patent Office Re. Application No. 10185195.4.
Response Dated Feb. 15, 2011 to European Search Report and the European Search Opinion of Jul. 29, 2010 From the European Patent Office Re. Application No. 09176343.3.
Response Dated Feb. 3, 2011 to Official Action of Nov. 10, 2010 From the US Patent and Trademark Office Re.: U.S. Appl. No. 12/457,200.
Response Dated Feb. 28, 2011 to Office Action of Oct. 31, 2010 From the Israel Patent Office Re.: Application No. 183187.
Office Action Dated Jul. 4, 2011 From the Israel Patent Office Re.: Application No. 183187 and Its Translation Into English.
Official Action Dated Jul. 12, 2011 From the US Patent and Trademark Office Re. U.S. Appl. No. 12/591,252.
Gridley et al. "Combining Gene Therapy and Radiation Against Cancer", Current Gene Therapy, 4(3): 281-284, Sep. 2004. Abstract.
Penland et al. "Combining Anti-VEGF Approaches With Oxaliplatin in Advanced Colorectal Cancer", Clinical Colorectal Cancer Supplement, 4(Suppl. 2): S74-S80, Oct. 2004.
Wachsberger et al. "Tumor Response to Ionizing Radiation Combines With Antiangiogenesis or Vascular Targeting Agents: Exploring Mechanisms of Interaction", Clinical Cancer Research, 9: 1957-1971, Jun. 1, 2003. Examiner.
Response Dated Aug. 1, 2011 to Notice of Non-Compliant Amendment of Jul. 12, 2011 From the US Patent and Trademark Office Re.: U.S. Appl. No. 12/224,178.
Response Dated Aug. 14, 2011 to Communication Pursuant to Rules 70(2) and 70a (2) EPC and Reference to Rule 39(1) EPC of Feb. 21, 2011 From the European Patent Office Re. Application No. 10177257.2.
Response Dated Jul. 18, 2011 to Examiner's Report of Dec. 7, 2010 From the Australian Government, IP Australia Re. Application No. 2005303385.
Freytag et al. "Gene Therapy Strategies to Enhance the Effectiveness of Cancer Radiotherapy", Current Opinion in Molecular Therapeutics, 6(5): 513-524, 2004.

* cited by examiner

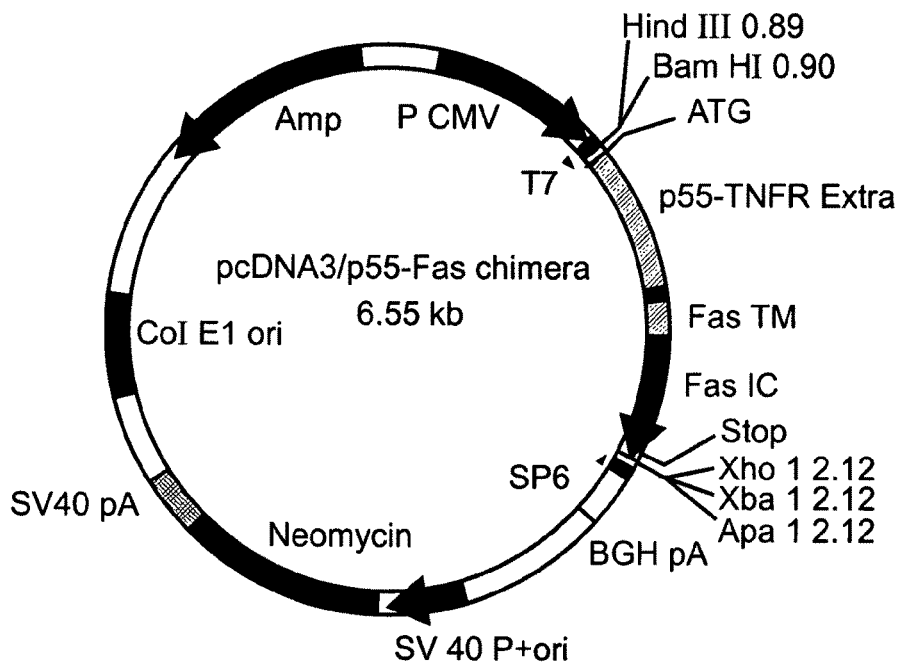
Fig. 1a
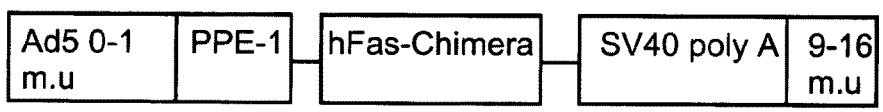
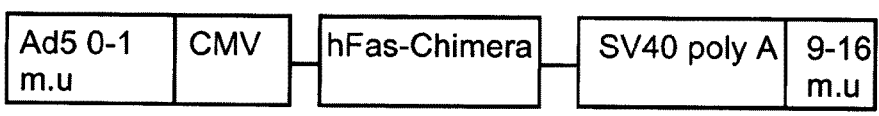
Fig. 1b

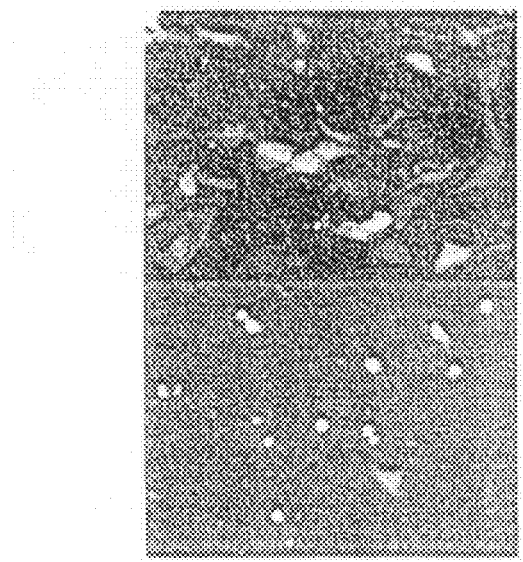
Fig. 2a  Fig. 2b
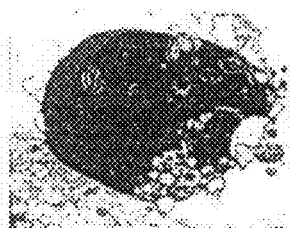
Fig. 3a
Fig. 3b
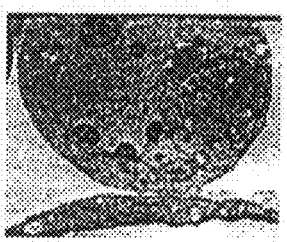
Fig. 3c
Fig. 3d
Fig. 3e
Fig. 3f

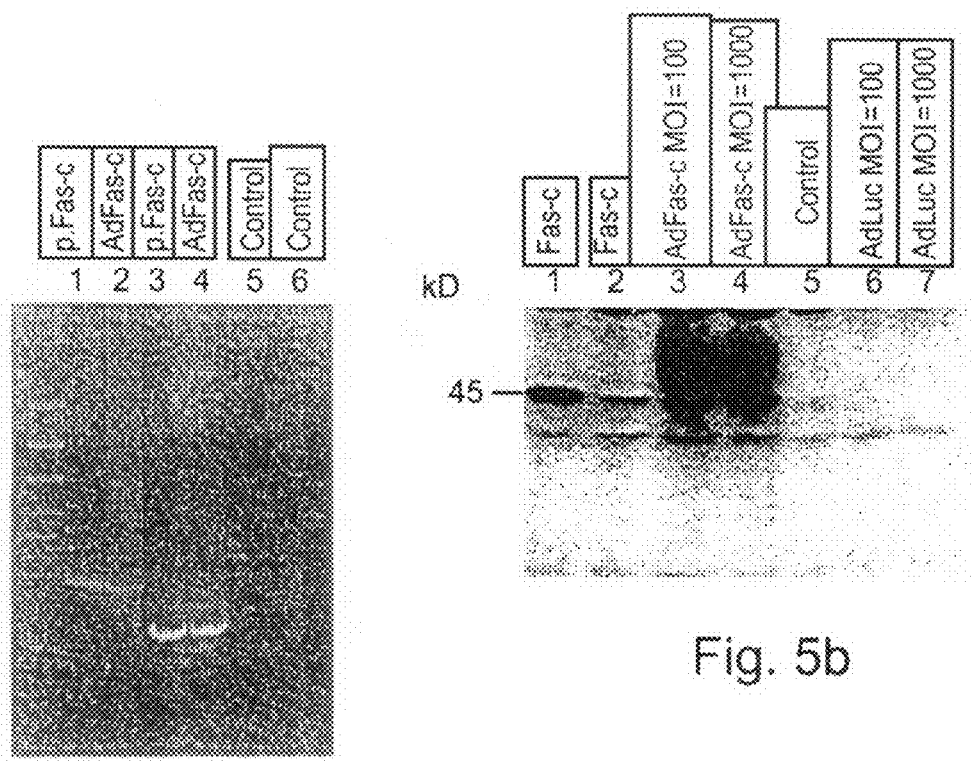
Fig. 5a
Fig. 5b
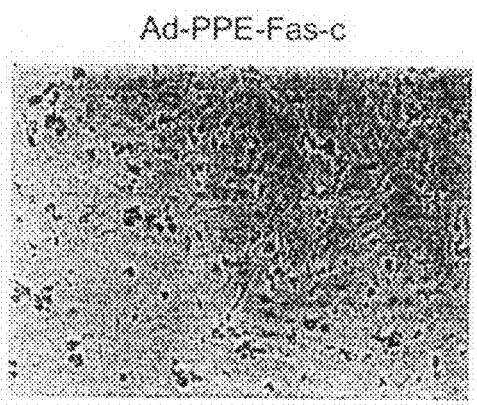
Fig. 6a
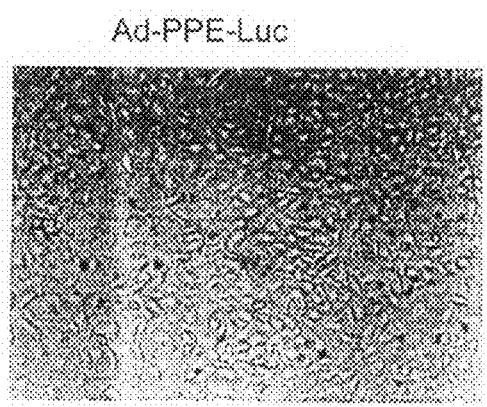
Fig. 6b

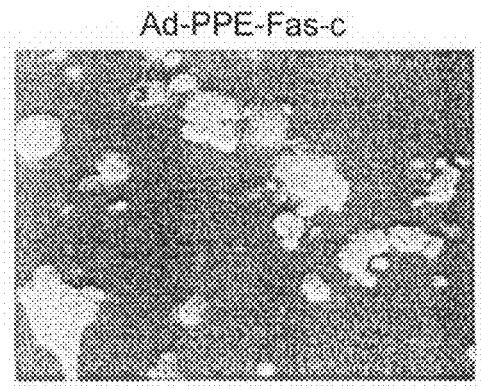
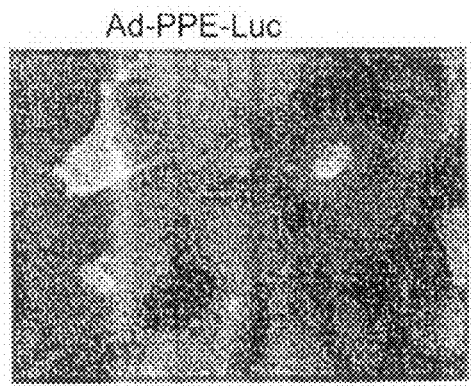
Fig. 6c  Fig. 6d
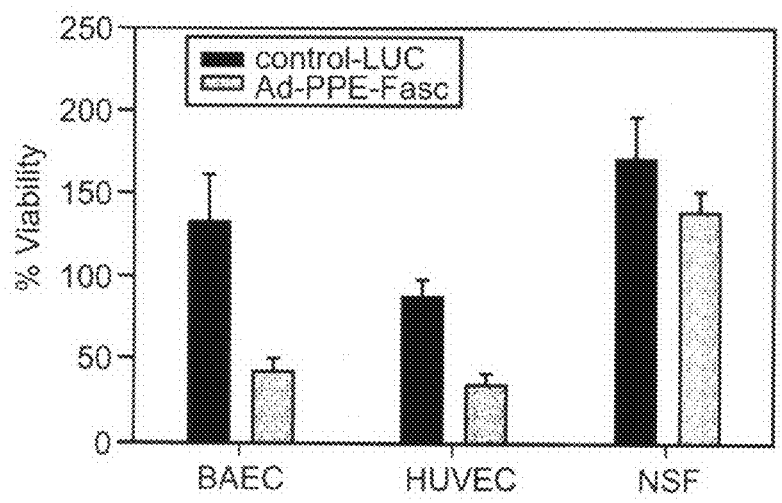
Fig. 7

Apoptotic tumor cells

Apoptotic tumor cells

AdPPE-1(3x)TK + GCV 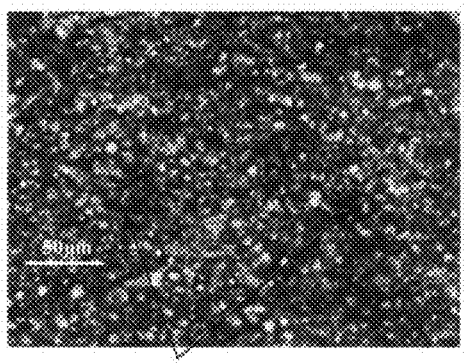 AdPPE-1(3x)TK no GCV 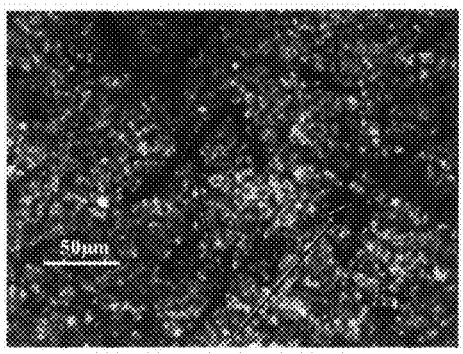
Short blood vessels, without branching or continuity.
Numerous blood vessels, with distinct borders and branching.
Fig. 75a Blood vessels Central necrosis Mitosis Fibroblast Capillary AdPPE-1(3x)TK+GCV+radiotherapy        AdPPE-1(3x)TK no GCV
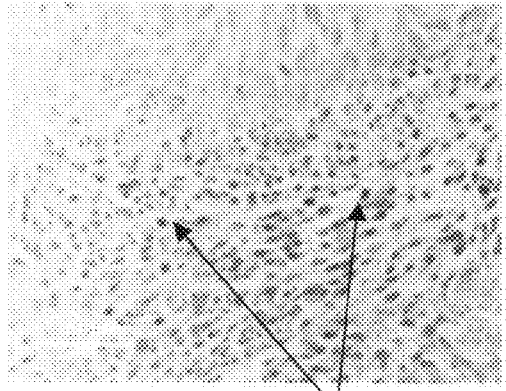 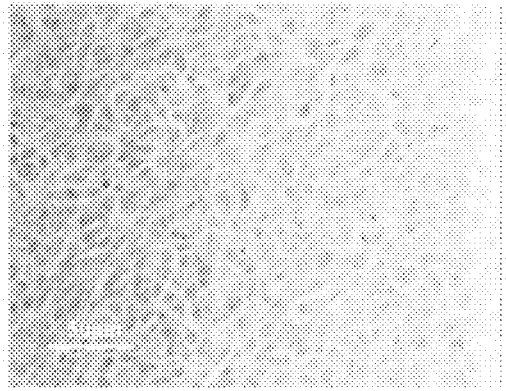
Fig. 81a    Apoptotic tumor cells
AdPPE-1(3x)TK+GCV+radiotherapy        AdPPE-1(3x)TK no GCV
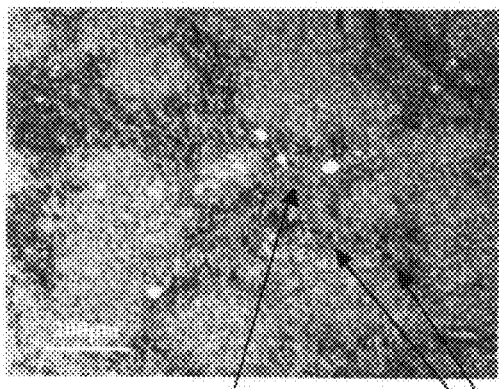 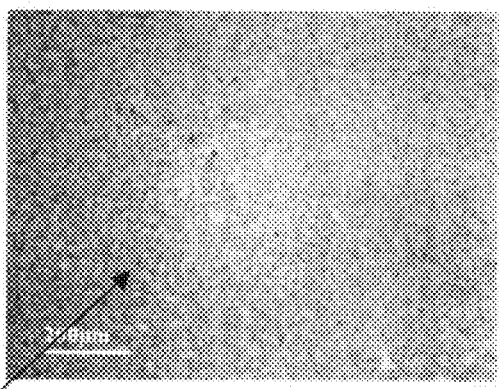
Fig. 81b   Serpentine-like central    Apoptotic tumor cells

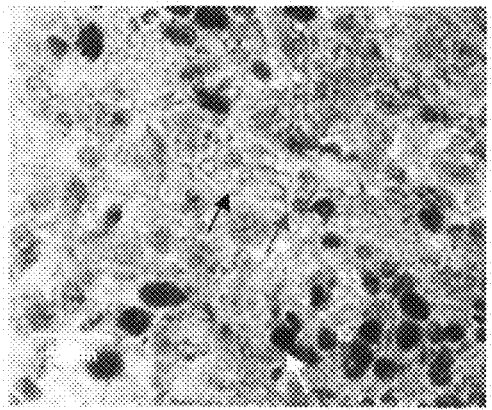 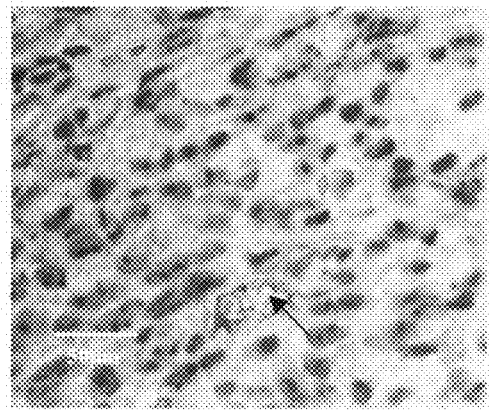
Fig. 82

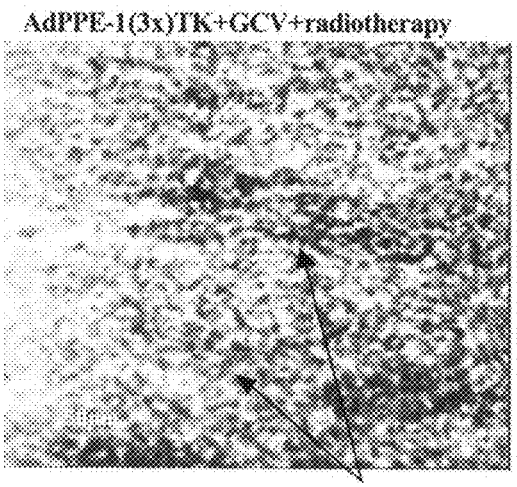 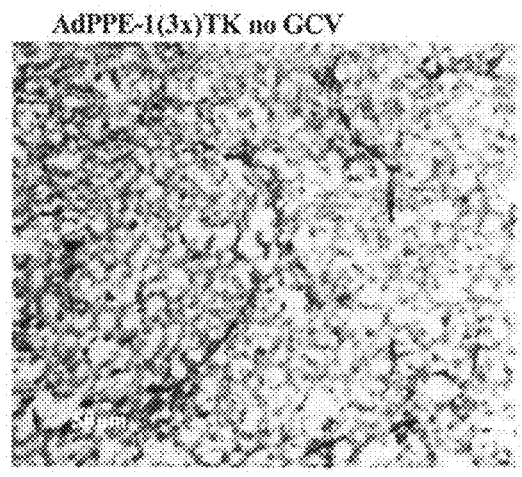
Fig. 83a — Short vessel without continuity
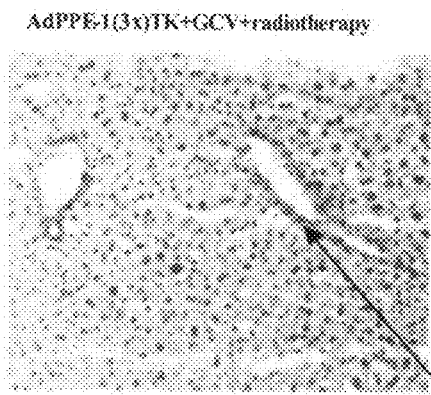 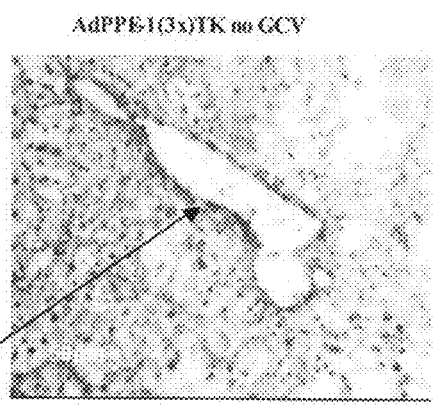
Fig. 83b — Blood vessels Kupfer cell hyperplasia    Enlarged hepatocyte nuclei    Endothelial cell

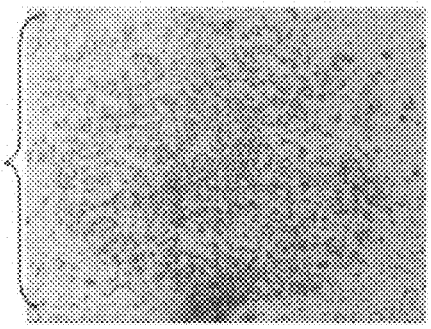
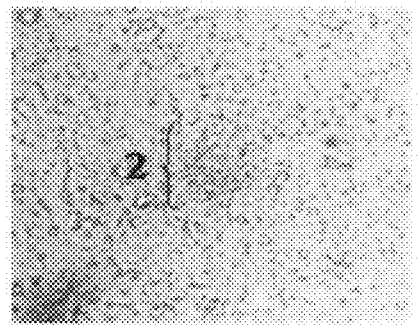
Fig. 89a          Fig. 89b
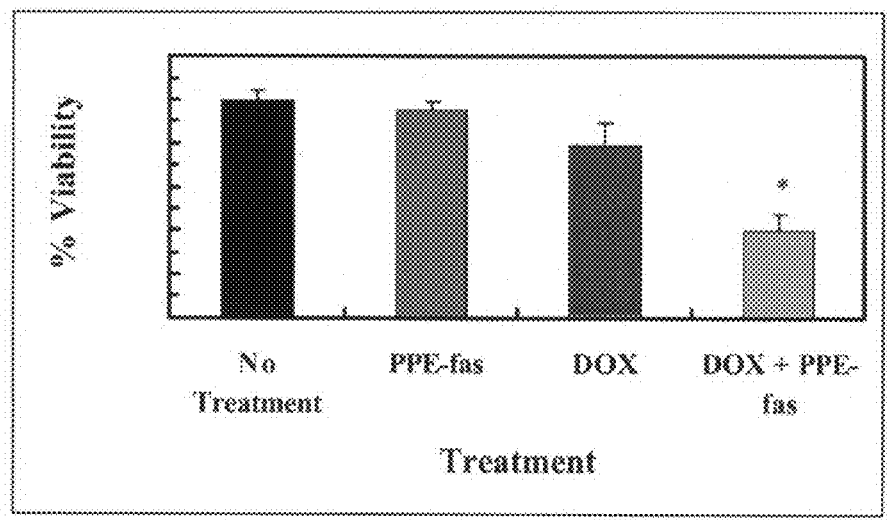
Fig. 90 gtgtgtgt gtgtgtgt gtgtgtgt gtgtgtgt gtgtgtgta ctctgatcg gcgatactg ggagatagg
atgacctga caaaaccaca ttgtgtgt tatcattatt atttagtttt cctcctgc taactctga cggaatctt
ctcaccctcaa atgcgaagta cttagtttta gaaaagtactt ggtggaaggg gtggtggtgg aaaagtaggg tgatcttcca
aactaatctg gttcccgcc cgccccagta gctgggatc aagagcgaag agtggggatc gtcccctgt ttgatcagaa
agxetaaaa ggaaatcaa gtgaacaatg atcagcccca cctccaccc acccctgc gcgcgcacaa
tacaatctat ttaatt *gtacttcatactttcattccaatggggtgacttgcttctggag* aaactcttg attcttgaac
tctgggctg gcagctagcc aaagggggaag cgggctgctg ctctctgcag gtctgcagc ggtctctgc
tagtgggtgt ttcttttc ttagccctgc ccctggattg tcagacgcg ggctctgcc tctgaagta gccgtgattt
cctcagagc cgggtctac ctcctggctgc acgatgcctg tgggtgacta atcacaaaat aacattgtt agggctggaa
taaagtcaga gctgttacc cccactctat aggggtcaa tataaaaggg cggcggagaa ctgccgagt cagcgcgt
cctgaccgg cgctgagagc ctgaccggt ctgctccgct gtcctgcgc gctgcctcc ggctgccgc gacgcttcg
ctccagtgga agggcctactt gctgaggacc gcgctgagat ctaaaaaaa aactaaaaac aaaaaatcaaa
aaaaaccaga ggcgatcaga gcgaccagac accgtcctct tcgttttgca ttgagttcca ttgcaaccg agtttcatt
attccttt tccccactct tctgaccct ttgcagaatg gattatttc ccgtgatctt ctctctgctg ttcgtgactt
tccaggagc tccagaatca ggtaggcgcc actgcgaat cttctactt cagcgcagca gtatcgctt ctgttctca
ctttctttc ttcttttctt ttcatttctt cctttttatt tattttttta attactgaag ctccagcagc aagtgcctta caattaatta
acttctgtgt gaagcgaagg aaataaaaacc cctgttgaa tacagctgac tacaaccgag tatcgcatag ctc-1334

Fig. 92

5'- gtacttcatactttcattccaatggggtgacttgcttctggag ggtgacttgcttctggag cca gtacttcatactttcatt gtacttcatactttcattccaatggggtgacttgcttctggag gctagctgccag

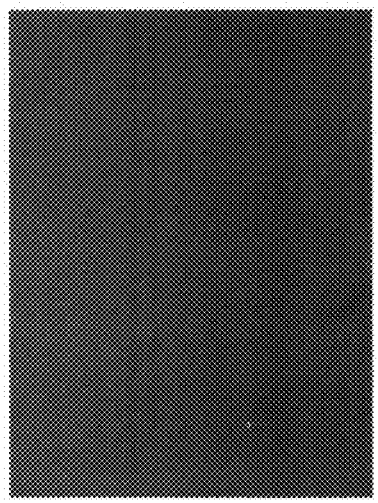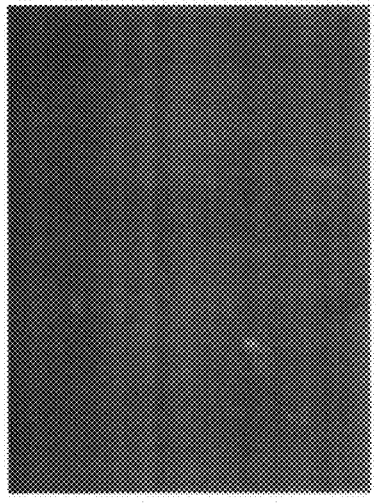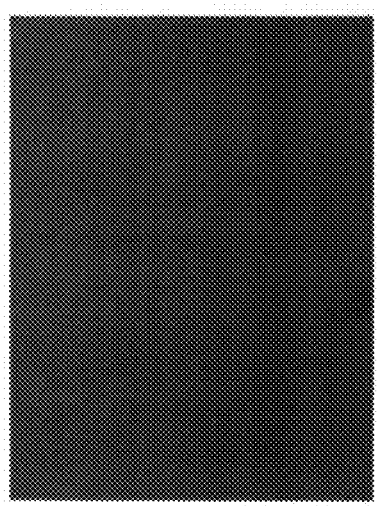
AdPPE-GFP (100 MOI)
No treatment
Dex 3µM
Fig. 99

PROMOTERS EXHIBITING ENDOTHELIAL CELL SPECIFICITY AND METHODS OF USING SAME FOR REGULATION OF ANGIOGENESIS

RELATED APPLICATIONS

This application is a Continuation-In-Part (CIP) of U.S. patent application Ser. No. 10/988,487, filed on Nov. 14, 2004, which is a Continuation-in-Part (CIP) of U.S. patent application Ser. No. 10/135,447, filed on May 1, 2002, which is a Continuation-In-Part (CIP) of PCT Application No. PCT/IL01/01059, filed on Nov. 15, 2001, which claims priority from U.S. Provisional Patent Application No. 60/248,582, filed on Nov. 17, 2000, the specifications of which are hereby incorporated by reference.

This application is also a Continuation-In-Part (CIP) of U.S. patent application Ser. No. 10/490,746, filed on Apr. 12, 2004, which is a U.S. National Phase Patent Application of PCT Application No. PCTIL02/00339, filed on May 1, 2002, which claims priority from U.S. Provisional Patent Application No. 60/330,118, filed on Oct. 19, 2001, the specifications of which are hereby fully incorporated by reference.

FIELD AND BACKGROUND OF THE INVENTION

The present invention relates to nucleic acid constructs, pharmaceutical compositions and methods which can be used to regulate angiogenesis in specific tissue regions of a subject. More particularly, the present invention relates to isolated polynucleotide sequences exhibiting endothelial cell specific promoter activity, and methods of use thereof and, yet more particularly, to a modified-preproendothelin-1 (PPE-1) promoter which exhibits increased activity and specificity in endothelial cells, and nucleic acid constructs, which can be used to either activate cytotoxicity in specific cell subsets, thus, enabling treatment of diseases characterized by aberrant neovascularization or cell growth or induce the growth of new blood vessels, thus, enabling treatment of ischemic diseases. The invention further relates to modifications of the PPE promoter, which enhance its expression in response to physiological conditions including hypoxia and angiogenesis, and novel angiogenic endothelial-specific combined therapies.

Angiogenesis:

Angiogenesis is the growth of new blood vessels, a process that depends mainly on locomotion, proliferation, and tube formation by capillary endothelial cells. During angiogenesis, endothelial cells emerge from their quiescent state and proliferate rapidly. Although the molecular mechanisms responsible for transition of a cell to angiogenic phenotype are not known, the sequence of events leading to the formation of new vessels has been well documented [Hanahan, D., Science 277, 48-50, (1997)]. The vascular growth entails either endothelial sprouting [Risau, W., Nature 386, 671-674, (1997)] or intussusceptions [Patan, S., et al; Microvasc. Res. 51, 260-272, (1996)]. In the first pathway, the following sequence of events may occur: (a) dissolution of the basement of the vessel, usually a post capillary venule, and the interstitial matrix; (b) migration of endothelial cells toward the stimulus; (c) proliferation of endothelial cells trailing behind the leading endothelial cell (s); (d) formation of lumen (canalization) in the endothelial array/sprout; (e) formation of branches and loops by confluencial anastomoses of sprouts to permit blood flow; (f) investment of the vessel with pericytes (i.e., periendothelial cells and smooth muscle cells); and (g) formation of basement membrane around the immature vessel. New vessels can also be formed via the second pathway: insertion of interstitial tissue columns into the lumen of pre-existing vessels. The subsequent growth of these columns and their stabilization result in partitioning of the vessel lumen and remodeling of the local vascular network.

Angiogenesis occurs under conditions of low oxygen concentration (ischemia and tumor metastases etc.) and thus may be an important environmental factor in neovascularization. The expression of several genes including erythropoietin, transferrin and its receptor, most of glucose transport and glycolytic pathway genes, LDH, PDGF-BB, endothelin-1 (ET-1), VEGF and VEGF receptors is induced under hypoxic conditions by the specific binding of the Hypoxia Inducible Factor (HIF-1) to the Hypoxic Response Element (HRE) regulating the transcription of these genes. Expression of these genes in response to hypoxic conditions enables the cell to function under low oxygen conditions.

The angiogenic process is regulated by angiogenic growth factors secreted by tumor or normal cells as well as the composition of the extracellular matrix and by the activity of endothelial enzymes (Nicosia and Ottinetti, 1990, Lab. Invest., 63, 115). During the initial stages of angiogenesis, endothelial cell sprouts appear through gaps in the basement membrane of pre-existing blood vessels (Nicosia and Ottinetti, 1990, supra; Schoefl, 1963, Virehous Arch, Pathol. Anat. 337, 97-141; Ausprunk and Folkman, 1977, Microvasc. Res. 14, 53-65; Paku and Paweletz, 1991, Lab. Invest. 63, 334-346). As new vessels form, their basement membrane undergoes complex structural and compositional changes that are believed to affect the angiogenic response (Nicosia, et. al., 1994, Exp Biology. 164, 197-206).

Angiogenesis and Pathology:

A variety of angiogenic factors govern the angiogenic process. It is understood that during pathology, the fine balance between pro-angiogenic factors and anti-angiogenic factors is disrupted, thereby eliciting nonself-limiting endothelial and periendothelial cell-proliferation. Although angiogenesis is a highly regulated process under normal conditions, many diseases (characterized as "angiogenic diseases") are driven by persistent unregulated angiogenesis. In such disease states, unregulated angiogenesis can either cause a particular disease directly or exacerbate an existing pathological condition. For example, ocular neovascularization has been implicated as the most common cause of blindness and underlies the pathology of approximately twenty diseases of the eye. In certain previously existing conditions such as arthritis, newly formed capillary blood vessels invade the joints and destroy cartilage. In diabetes, new capillaries formed in the retina invade the vitreous humor, causing bleeding and blindness. Until recently, the angiogenesis that occurs in diseases of ocular neovascularization, arthritis, skin diseases, and tumors, had been difficult to suppress therapeutically.

Unbalanced angiogenesis typifies various pathological conditions and often sustains progression of the pathological state. For example, in solid tumors, vascular endothelial cells divide about 35 times more rapidly than those in normal tissues (Denekamp and Hobson, 1982 Br. J. Cancer 46:711-20). Such abnormal proliferation is necessary for tumor growth and metastasis (Folkman, 1986 Cancer Res. 46:467-73).

Vascular endothelial cell proliferation is also important in chronic inflammatory diseases such as rheumatoid arthritis, psoriasis and synovitis, where these cells proliferate in response to growth factors released within the inflammatory site (Brown & Weiss, 1988, Ann. Rheum. Dis. 47:881-5).

In atherosclerosis, formation of an atherosclerotic plaque is triggered by a monoclonal expansion of endothelial cells in blood vessels (Alpem-Elran 1989, J. Neurosurg. 70:942-5). Furthermore, in diabetic retinopathy, blindness is thought to be caused by basement membrane changes in the eye, which stimulate uncontrolled angiogenesis and consumption of the retina (West and Kumar, 1988, Lancet 1:715-6).

Endothelial cells are also involved in graft rejection. In allograft rejection episodes, endothelial cells express proadhesive determinants that direct leukocyte traffic to the site of the graft. It is believed that the induction of leukocyte adhesion molecules on the endothelial cells in the graft may be induced by locally-released cytokines, as is known to occur in an inflammatory lesion.

Abrogated angiogenesis, on the other hand, is also a major factor in disease development, such as in atherosclerosis induced coronary artery blockage (e.g., angina pectoris), in necrotic damage following accidental injury or surgery, or in gastrointestinal lesions such as ulcers.

Hence, regulating or modifying the angiogenic process can have an important therapeutic role in limiting the contributions of this process to pathological progression of an underlying disease state as well as providing a valuable means of studying their etiology.

Recently significant progress in the development of endothelial regulating agents, whether designed to be inhibitory or stimulatory, has been made. For example, administration of βFGF protein, within a collagen-coated matrix, placed in the peritoneal cavity of adult rats, resulted in a well-vascularized and normally perfused structure (Thompson, et al., PNAS 86:7928-7932, 1989). Injection of βFGF protein into adult canine coronary arteries during coronary occlusion reportedly led to decreased myocardial dysfunction, smaller myocardial infarctions, and increased vascularity (Yanagisawa-Miwa, et al., Science 257:1401-1403, 1992). Similar results have been reported in animal models of myocardial ischemia using βFGF protein (Harada, et al., J Clin Invest 94:623-630, 1994, Unger, et al., Am J Physiol 266:H1588-H1595, 1994).

However, for mass formation of long lasting functional blood vessel there is a need for repeated or long term delivery of the above described protein factors, thus limiting their use in clinical settings. Furthermore, in addition to the high costs associated with the production of angiogenesis-regulating factors, efficient delivery of these factors requires the use of catheters to be placed in the coronary arteries, which further increases the expense and difficulty of treatment.

Therefore, the fundamental goal of all anti-angiogenic therapy is to return foci of proliferating microvessels to their normal resting state, and to prevent their regrowth [Cancer: Principles & Practice of Oncology, Fifth Edition, edited by Vincent T. DeVita, Jr., Samuel Hellman, Steven A. Rosenberg. Lippincott-Raven Publishers, Philadelphia. (1997)]. Likewise, proangiogenic therapy is directed not only to restoring required angiogenic factors, but to reestablishing the proper balance between them (Dor, et al, Ann NY Acad Sci 2003; 995:208-16)(for an extensive review of pro- and antiangiogenic therapies see Zhang et al Acta Bioch and Biophys Cinica, 2003: 35:873-880, and Mariani et al. Med Gen Med 2003, 5:22; and Folkman, Semin. One 2002, 29:15-18).

Antiangiogenic Therapy:

Anti-angiogenic therapy is a robust clinical approach, as it can delay the progression of tumor growth (e.g., retinopathies, benign and malignant angiogenic tumors).

In general, every disease caused by uncontrolled growth of capillary blood vessels such as diabetic retinopathy, psoriasis, arthritis, hemangiomas, tumor growth and metastasis is a target for anti-angiogenic therapy.

For example, the progressive growth of solid tumors beyond clinically occult sizes (e.g., a few $mm^3$) requires the continuous formation of new blood vessels, a process known as tumor angiogenesis. Tumor growth and metastasis are angiogenesis-dependent. A tumor must continuously stimulate the growth of new capillary blood vessels to deliver nutrients and oxygen for the tumor itself to grow. Therefore, either prevention of tumor angiogenesis or selective destruction of tumor's existing blood vessels (vascular targeting therapy) underlies anti-angiogenic tumor therapy.

Recently, a plethora of anti-angiogenic agents has been developed for the treatment of malignant diseases, some of which are already under clinical trials (for review see Herbst et al. (2002) Semin. Oncol. 29:66-77, and Mariani et al, Med Gen Med 2003; 5:22).

The most studied target for tumor anti-angiogenic treatment is the dominant process regulating angiogenesis in human i.e., the interaction of vascular endothelial growth factor (VEGF) with its receptor (VEGFR). Agents which regulate VEGFR pro-angiogenic action include (i) antibodies directed at the VEGF protein itself or to the receptor (e.g., rhuMAb VEGF, Avastin); (ii) small molecule compounds directed to the VEGFR tyrosine kinase (e.g., ZD6474 and SU5416); (iii) VEGFR targeted ribozymes.

Other novel angiogenesis inhibitors include 2-Methoxyestradiol (2-ME2) a natural metabolite of estradiol that possesses unique anti-tumor and anti-angiogenic properties and angiostatin and endostatin—proteolytic cleavage fragments of plasminogen and collagen XVIII, respectively.

Though promising in pre-clinical models, to date systemic administration of all anti-angiogenic agents tested in clinical trials, have shown limited rate of success and considerable toxicities including thrombocytopenia, leukopenia and hemoptysis. These results suggest that there may be limits to the use of current tumor anti-angiogenic agents as therapy for advanced malignancies. O'Reilly et al. have shown that the latency between the initiation of anti-angiogenic therapy and antitumor effect may result in initial tumor progression before response to therapy [O'Reilly S et al. (1998) Proc Am Soc Clin Oncol 17:217a]. Furthermore, recent studies suggest that the regulation of angiogenesis may differ among capillary beds, suggesting that anti-angiogenic therapy may need to be optimized on an organ/tissue-specific basis [Arap et al. (1998) Science 279:377-380].

Interestingly, poor results have also been obtained when anti-angiogenic therapy (e.g., heparin, heparin-peptide treatment) directed at smooth muscle cell proliferation has been practiced on myocardial ischemia in patients with coronary artery disease [Liu et al., Circulation, 79: 1374-1387 (1989); Goldman et al., Atherosclerosis, 65: 215-225 (1987); Wolinsky et al., JACC, 15 (2): 475-481 (1990)]. Various limitations associated with the use of such agents for the treatment of cardiovascular diseases included: (i) systemic toxicity creating intolerable level of risk for patients with cardiovascular diseases; (ii) interference with vascular wound healing following surgery; (iii) possible damage to surrounding endothelium and/or other medial smooth muscle cells.

Thus, these and other inherent obstacles associated with systemic administration of anti-angiogenic factors (i.e., manufacturing limitations based on in-vitro instability and high doses required; and peak kinetics of bolus administration attributing to sub-optimal effects) limit the effective use of angiogenic factors in treating neo-vascularization associated diseases.

Anti-angiogenic Gene Therapy for Cancer

Tumor cell proliferation in primary tumors as well as in metastases is offset by an increased rate of apoptosis due to a restricted supply of nutrients. Dormant primary or metastatic tumors begin to develop metastases whenever an "angiogenic switch" occurs and nutrient supply is adequate for the size of the tumor.

An angiogenic switch may occur via several mechanisms:

1. Up-regulation of pro-angiogenic genes such as VEGF and bFGF by oncogenes, or down-regulation of angio-suppressors such as thrombospondin.

2. Activation of hypoxic inducible factor-1 (HIF-1) by tumor-related hypoxic conditions.

3. Pro-angiogenic protein secretion by tumor bed fibroblasts, which are induced by tumor cells.

4. Bone marrow endothelial progenitors trafficking to the tumor.

TABLE 1

Endogenous regulators of tumor angiogenesis.

Endogenous Regulators of Tumor Angiogenesis

| Activators | Inhibitors |
| --- | --- |
| Vascular Endothelial Growth Factor (VEGF) | P53 |
| Fibroblast Growth Factor 1 (FGF1) | Thrombospondin-1* |
| Fibroblast Growth Factor 2 (FGF2) | Thrombospondin-2 |
| Platelet Derived Growth Factor (PDGF) | Tissue Inhibitors of Metalloproteinases (TIMPs) |
| Angiopoietin 2* | Angiostatin |
| Angiopoietin 1** | Endostatin |
| Transforming Growth Factor-β* (TGF-β) | Antiangiogenic Antithrombin III |
| | Angiostatic C-X-C Chemokines |
| Tumor Necrosis Factor-α*(TNF-α) | (PF4, IP-10, MIG) |
| Interleukin-8 (IL-8) | Pigment Endothelial Derived Factor (PEDF) |
| Platelet Derived Endothelial Cell Growth Factor (PD-ECGF) | Interleukin-12 (IL-12) |
| Hepatocyte Growth Factor (HGF) | Interferon (INF)-αβγ |

*Dose-dependent
**Weak Angiogenic Activator

The relative balance between activators and inhibitors of angiogenesis (see Table 1 hereinabove) is important for maintaining tumors in a quiescent state. Reducing inhibitors or increasing activator levels alters the balance and leads to tumor angiogenesis and tumor growth.

Oxygen diffusion to neoplastic tissue is inadequate when tumor tissue thickness exceeds 150-200 μm from the nearest vessel. So, by definition, all tumors that exceed these dimensions are already angiogenically switched-on. The tumor cell proliferation rate is independent of the vascular supply. However, as soon as the angiogenic switch occurs, the rate of apoptosis decreases by 3-4 fold (24). Furthermore, nutrient supply and catabolite release are not the only contribution of angiogenic vessels to the decline in tumor apoptosis. Microvasculature endothelial cells also secrete anti-apoptotic factors, mitogens and survival factors such as b-FGF, HB-EGF, IL-6, G-CSF, IGF-1 and PDGF that further suppress tumor cell apoptosis.

Tumor cells are genetically unstable due to high mutation rates, which provide them with an advantage over native cells. For example, mutations in the p53 gene suppress the rate of apoptosis. Moreover, oncogene alteration of pro-angiogenic or angiogenic suppressor control (such as the ras oncogene) may induce an angiogenic switch. However, a high mutation rate is not the only mechanism for cancer's genetic instability. There is evidence of "apoptotic bodies" phagocytosed by tumor cells, resulting in aneuploidy and a further increase in genetic instability. All in all, cancer relies on angiogenesis. Due to genetic instability, cancer may orchestrate a pro-angiogenic cytokine balance, which suppresses its apoptotic rate and enables metastatic seeding.

The human vasculature system contains more than one trillion endothelial cells. The lifetime of normal quiescent endothelial cells exceeds 1000 days. Although angiogenic endothelial cells involved in tumor progression proliferate rapidly, they differ from tumor cells by their genomic stability, and thus also in minimal drug resistance and low likelihood of the development of mutant clones. Moreover, since the rate-limiting factor for tumor progression is angiogenesis, treatment directed against angiogenic endothelial cells could yield highly effective treatment modalities. Indeed, several anti-angiogenic substances could serve as potential candidates for systemic therapy. However, since these agents are proteins and their administration therefore depends on frequent intravenous administration, their use poses serious manufacturing and maintenance difficulties. Delivery of anti-angiogenic genes offers a potential solution for continuous protein secretion.

With the identification of new genes that regulate the angiogenic process, somatic gene therapy has been attempted to overcome these limitations. Although, great efforts have been directed towards developing methods for gene therapy of cancer, cardiovascular and peripheral vascular diseases, there is still major obstacles to effective and specific gene delivery [for review see, Feldman A L. (2000) Cancer 89(6): 1181-94]. In general, the main limiting factor of gene therapy with a gene of interest, using a recombinant viral vector as a shuttle is the ability to specifically direct the gene of interest to the target tissue.

Attempts to overcome these limitations included the use of tissue-specific promoters conjugated to cytotoxic genes. For example, endothelial cell targeting of a cytotoxic gene, expressed under the control endothelial-specific promoters has been described by Jagger et al who used the KDR or E-selectin promoter to express TNFα specifically in endothelial cells [Jaggar R T. Et al. Hum Gene Ther (1997) 8(18): 2239-47]. Ozaki et al used the von-Willebrand factor (vWF) promoter to deliver herpes simplex virus thymidine kinase (HSV-tk) to HUVEC [Hum Gene Ther (1996) 7(13):1483-90]. However, these promoters showed only weak activity and did not allow for high levels of expression.

Several endothelial cell specific promoters have been described in the prior art. For example, Aird et al., [Proc. Natl. Acad. Sci. (1995) 92:7567-571] isolated 5' and 3' regulatory sequences of human von Willebrand factor gene that may confer tissue specific expression in-vivo. However, these sequences could mediate only a heterogeneous pattern of reporter transgene expression. Bacterial LacZ reporter gene placed under the regulation of von Willebrand regulatory elements in transgenic mice revealed transgene expression in a subpopulation of endothelial cells in the yolk sac and adult brain. However, no expression was detected in the vascular beds of the spleen, lung, liver, kidney, heart, testes and aorta as well as in the thrombomodulin locus.

Korhonen J et al [Blood (1995) 96:1828-35] isolated the human and mouse TIE gene promoter which contributed to a homogeneous expression of a transgene throughout the vascular system of mouse embryos. However, expression in adult was limited to the vessels of the lung and kidney and no expression was detected in the heart, brain, liver. Similar results were obtained by Schlaeger M et al. who isolated a 1.2 kb 5' flanking region of the TIE-2 promoter, and showed transgene expression limited to endothelial cells of embryonic mice [Schlaeger T M et al. (1995) Development 121: 1089-1098].

Thus, none of these sequences work uniformly in all endothelial cells of all developmental stages or in the adult animal. Furthermore, some of these sequences were not restricted to the endothelium.

An alternate approach presented by Kong and Crystal included a tumor specific expression of anti-angiogenic factors. To date, however, the toxicity of recombinant forms of endogenous anti-angiogenic agents has not been demonstrated although some synthetic anti-angiogenic agents have been associated with toxicity in preclinical models [Kong and Crystal (1998) J. Natl. Cancer Inst. 90:273-76].

Angiostatin has also been used as a possible anti-angiogenic agent (Folkman et al, Cell 1997 Jan. 24; 88(2):277-85), however due to the redundancy of factors involved in regulation of angiogenesis in tumors, it is highly unlikely that angiostatin therapy alone would be effective.

To date, promising clinical trials have shown that anti angiogenic treatments like Avastin® or Bay-43906®, can slow the metastatic progression by limiting new growth of blood vessels surrounding the tumors. However, inhibiting the formation of new blood vessels and/or partially destroying them may be insufficient in cancer pathologies where a dramatic anti angiogenic effect that destroys most or all existing angiogenic blood vessels and induce tumor necrosis is required.

The Pre-proendothelin-1 (PPE-1) Promoter

The endothelins (ET), which were discovered by Masaki et al. in 1988, consist of three genes: ET-1, ET-2 and ET-3. Endothelin-1 (ET-1), a 21 amino acid peptide, was first described as a potent vasoconstrictor and smooth muscle cell mitogen, synthesized by endothelial cells. ET-1 is expressed in the vascular endothelium, although there is some expression in other cells such as smooth muscle cells, the airways and gastrointestinal epithelium, neurons and glomerular mesangial cells. Its expression is induced under various pathophysiological conditions such as hypoxia, cardiovascular diseases, inflammation, asthma, diabetes and cancer. Endothelin-1 triggers production and interacts with angiogenic factors such as VEGF and PDGF and thus plays a role in the angiogenic process.

Hu et al. identified a hypoxia responsive element (HRE) that is located on the antisense strand of the endothelin-1 promoter. This element is a hypoxia-inducible factor-1 binding site that is required for positive regulation of the endothelin-1 promoter (of the human, rat and murine gene) by hypoxia. Hypoxia is a potent signal, inducing the expression of several genes including erythropoietin (Epo), VEGF, and various glycolytic enzymes. The core sequence (8 base pairs) is conserved in all genes that respond to hypoxic conditions and the flanking regions are different from other genes. The ET-1 hypoxia responsive element is located between the GATA-2 and the AP-1 binding sites.

Bu et al. identified a complex regulatory region in the murine PPE-1 promoter (mET-1) that appears to confer endothelial cell specific transcriptional activity and to bind proteins or protein complexes that are restricted to the endothelial cell. This region, designated endothelial specific positive transcription element, is composed of at least three functional elements, positioned between the −364 bp and −320 bp of the murine PPE-1 promoter. All three elements are required for full activity. When one or three copies are constructed into a minimal mET-1 promoter, reporter gene expression in endothelial cells in vitro increased 2-10 times, compared to a minimal promoter with no element.

U.S. Pat. No. 5,747,340 teaches use of the murine PPE-1 promoter and portions thereof. However, this patent neither implies nor demonstrates that an endothelial-specific enhancer can be employed to increase the level of expression achieved with the PPE promoter while preserving endothelial specificity. Further, this patent does not teach that the PPE-1 promoter is induced to higher levels of transcription under hypoxic conditions.

Gene-directed Enzyme Prodrug Therapy (GDEPT):

This strategy is also called "suicide gene therapy". It involves the conversion of an inert prodrug into an active cytotoxic agent within the cancer cells. The two most widely used genes in GDEPT are herpes simplex virus thymidine kinase (HSV-TK) coupled with ganciclovir (GCV) administration and the *E. coli* cytosine deaminase (CD) coupled with 5-fluorocytosine (5FC) administration. The HSV-TK/GCV system has undergone extensive preclinical evaluation, as well as clinical trials. To date, the HSV-TK/GCV system has demonstrated non-significant side effects such as fever, systemic toxicity of GCV, myelosuppression and mild-moderate hepatotoxicity.

The HSV-TK/GCV system was first described by Kraiselburd et al. in 1976. Cells transfected with an HSV-TK containing plasmid or transduced with an HSV-TK containing vector, are becoming sensitive for a super family of drugs including aciclovir, ganciclovir (GCV), valciclovir and famciclovir. The guanosine analog GCV is the most active drug in the setup of gene therapy. HSV-TK positive cells produce a viral TK, which is three orders of magnitude more efficient in phosphorylating GCV into GCV monophosphate (GCV-MP) than the human TK. GCV-MP is subsequently phosphorylated by the native thymidine kinase into GCV diphosphate and finally to GCV triphosphate (GCV-TP).

GCV-TP is a potent DNA polymerase inhibitor leading to termination of DNA synthesis by incorporation into the nascent strand, terminating DNA elongation and eventually causing cell death. Since GCV affects predominantly HSV-TK positive cells, its adverse effects are minimal and rare, and include mainly thrombocytopenia, neutropenia and nephrotoxicity. Moreover, since GCV toxicity is based on DNA synthesis, it affects mainly proliferating cells. The HSV-TK/GCV system has recently been utilized extensively in clinical trials of cancer gene therapy. Nevertheless, results are disappointing, mostly limited in vivo by a low transduction percentage.

Recent studies have characterized the HSV-TK/GC-V cell cytotoxicity mechanism. They revealed cell cycle arrest in the late S or G2 phase due to activation of the G2-M DNA damage checkpoint. These events were found to lead to irreversible cell death as well as a bystander effect related to cell death. Profound cell enlargement is a well-known morphological change in cells administered with the HSV-TK/GCV system. These morphological changes are due to specific cytoskeleton rearrangement. Stress actin fibers and a net of thick intermediate filaments appear following cell cycle arrest.

The HSV-TK/GCV system utilizes an amplification potential designated as the "bystander effect". The bystander effect stands for the phenomenon by which HSV-TK positive cells induce the killing of HSV-TK negative cells.

Bystander effect: The bystander effect was first described by Moolten et al., who found that a 1:9 mixture of HSV-TK positive and HSV-TK negative cells, respectively, results in complete cell killing following the addition of GCV. Several characteristics of the bystander effect have been described:

1. The bystander effect was found to be highly dependent on cell-cell contact.
2. Its extent was different in different cell types.

3. It is not limited to homogenous cell types, but also to mixtures of different cell types.

4. Higher levels of HSV-TK expression were found to correlate with a higher bystander effect.

Culver et al. were the first to demonstrate a bystander effect in an in vivo model. They demonstrated tumor regression when implanted with HSV-TK positive tumor cells in different ratios. Unlike in vitro models, cell-cell contact was not found to be essential for the bystander effect in vivo. Kianmanesh et al. demonstrated a distant bystander effect by implanting tumor cells in different liver lobes, where only some were HSV-TK positive. Both HSV-TK positive and negative foci regressed. A bystander effect was also demonstrated in vivo between cells from different origins. All in all, HSV-TK and its bystander effect facilitate an effective means for tumor suppression when implemented in gene delivery systems. However, to date, clinical studies have demonstrated only limited results.

There is thus a widely recognized need for, and it would be highly advantageous to have highly specific, reliable angiogenic-specific promoters and nucleic acid constructs providing a novel approach for efficiently regulating angiogenesis in specific tissue regions of a subject while being devoid of the toxic side effects and limited success characterizing prior art anti-angiogenesis approaches.

SUMMARY OF THE INVENTION

According to one aspect of the present invention there is provided an isolated polynucleotide comprising a cis regulatory element including at least a portion of the sequence set forth in SEQ ID NO:15 covalently linked to at least a portion of the sequence set forth in SEQ ID NO:16, the isolated polynucleotide being capable of directing transcription of a polynucleotide sequence transcriptionally linked thereto in eukaryotic cells. Also provided are nucleic acid constructs comprising the isolated polynucleotide, cells comprising the nucleic acid constructs of the invention, and scaffolds seeded with the cells.

According to still further features in the described preferred embodiments the nucleic acid constructs further comprising a nucleic acid sequence positioned under the regulatory control of the cis regulatory element. The nucleic sequence can further encode an angiogenesis regulator.

According to still further features in the described preferred embodiments the nucleic acid sequence is selected from the group consisting of VEGF, p55, angiopoietin-1, bFGF and PDGF-BB.

According to yet further features in the described preferred embodiments the scaffold is composed of a synthetic polymer, a cell adhesion molecule, or an extracellular matrix protein.

According to still further features in the described preferred embodiments the synthetic polymer is selected from the group consisting of polyethylene glycol (PEG), Hydroxyapatite (HA), polyglycolic acid (PGA), epsilon-caprolactone and 1-lactic acid reinforced with a poly-1-lactide knitted [KN-PCLA], woven fabric (WV-PCLA), interconnected-porous calcium hydroxyapatite ceramics (IP-CHA), poly D,L,-lactic acid-polyethyleneglycol (PLA-PEG), unsaturated polyester poly(propylene glycol-co-fumaric acid) (PPF), polylactide-co-glycolide (PLAGA), polyhydroxylkanoate (PHA), poly-4-hydroxybutyrate (P4HB), and polyphosphazene.

According to yet further features in the described preferred embodiments the cell adhesion molecule is selected from the group consisting of integrin, intercellular adhesion molecule (ICAM) 1, N-CAM, cadherin, tenascin, gicerin, and nerve injury induced protein 2 (ninjurin2).

According to still further features in the described preferred embodiments the extracellular matrix protein is selected from the group consisting of fibrinogen, Collagen, fibronectin, vimentin, microtubule-associated protein ID, Neurite outgrowth factor (NOF), bacterial cellulose (BC), laminin and gelatin.

According to yet another aspect of the present invention there is provided a method of expressing a nucleic acid sequence of interest in eukaryotic cells, the method effected by administering to a subject a nucleic acid construct including the nucleic acid sequence of interest positioned under transcriptional control of a cis regulatory element including at least a portion of the sequence set forth in SEQ ID NO:15 covalently linked to at least a portion of the sequence set forth in SEQ ID NO:16.

According to still another aspect of the present invention there is provided a method of regulating angiogenesis in a tissue, the method effected by expressing in the tissue a nucleic acid construct including: (a) an endothelial cell specific promoter; (b) at least one copy of a hypoxia response element set forth in SEQ ID NO:5; and (c) a nucleic acid sequence encoding an angiogenesis regulator, the nucleic acid sequence being under regulatory control of the promoter and the hypoxia response element.

According to another aspect of the present invention there is provided a method of regulating angiogenesis in a tissue, the method effected by expressing in the tissue a nucleic acid construct including a nucleic acid sequence encoding an angiogenesis regulator, the nucleic acid sequence being under regulatory control of a cis regulatory element including at least a portion of the sequence set forth in SEQ ID NO:15 covalently linked to at least a portion of the sequence set forth in SEQ ID NO:16, thereby regulating angiogenesis in the tissue.

According to still further features in the described preferred embodiments, administering is effected by a method selected from the group consisting of, systemic in-vivo administration, ex-vivo administration to cells removed from a body of a subject and subsequent reintroduction of the cells into the body of the subject; and local in-vivo administration.

According to yet further features in the described preferred embodiments, the tissue is a natural or an engineered tissue.

According to still further features in the described preferred embodiments the nucleic acid sequence encodes a proangiogenic factor and regulating angiogenesis is upregulating angiogenesis.

According to yet further features in the described preferred embodiments the nucleic acid sequence encodes an inhibitor of angiogenesis and regulating angiogenesis is downregulating angiogenesis.

According to yet another aspect of the present invention there is provided a nucleic acid construct comprising: (a) a first polynucleotide region encoding a chimeric polypeptide including a ligand binding domain fused to an effector domain of a cytotoxic molecule; and (b) a second polynucleotide region encoding a cis regulatory element being capable of directing expression of said chimeric polypeptide in a specific tissue or cell. The ligand binding domain is selected such that it is capable of binding a ligand present in the specific tissue or cell, and binding of said ligand to the ligand binding domain activates the effector domain of the cytotoxic molecule. Also provided are eukaryotic cells transformed with the nucleic acid construct of the invention.

According to yet further features in the described preferred embodiments the cis regulatory element is an endothelial cell-specific or periendothelial cell-specific promoter selected from the group consisting of the PPE-1 promoter, the PPE-1-3x promoter, the TIE-1 promoter, the TIE-2 promoter, the Endoglin promoter, the von Willerband promoter, the KDR/flk-1 promoter, The FLT-1 promoter, the Egr-1 promoter, the ICAM-1 promoter, the VCAM-1 promoter, the PECAM-1 promoter and the aortic carboxypeptidase-like protein (ACLP) promoter.

According to further features in the described preferred embodiments the ligand binding domain is a ligand-binding domain of a cell-surface receptor. The cell-surface receptor can be selected from the group consisting of a receptor tyrosine kinase, a receptor serine kinase, a receptor threonine kinase, a cell adhesion molecule and a phosphatase receptor.

According to yet further features in the described preferred embodiments the cytotoxic molecule is selected from the group consisting of Fas, TNFR, and TRAIL.

According to yet another aspect of the present invention there is provided method of downregulating angiogenesis in a tissue of a subject, the method effected by administering to the subject a nucleic acid construct designed and configured for generating cytotoxicity in a sub-population of angiogenic cells. The nucleic acid construct includes: (a) a first polynucleotide region encoding a chimeric polypeptide including a ligand binding domain fused to an effector domain of a cytotoxic molecule; and (b) a second polynucleotide region encoding a cis regulatory element being for directing expression of the chimeric polypeptide in the sub-population of angiogenic cells. The ligand binding domain is selected such that it is capable of binding a ligand present in, or provided to, the sub-population of angiogenic cells, and binding of the ligand to the ligand binding domain activates the effector domain of said cytotoxic molecule, thereby down-regulating angiogenesis in the tissue.

According to still another aspect of the present invention there is provided a method of down-regulating angiogenesis in a tissue of a subject, the method effected by: (a) expressing in the tissue of the subject a nucleic acid construct designed and configured for generating cytotoxicity in a sub-population of angiogenic cells, the nucleic acid construct including: (i) a first polynucleotide region encoding a chimeric polypeptide including a ligand binding domain fused to an effector domain of a cytotoxic molecule, wherein the effector domain is selected such that it is activated following binding of a ligand to the ligand binding domain; and (ii) a second polynucleotide region encoding a cis acting regulatory element for directing expression of the chimeric polypeptide in the subpopulation of angiogenic cells; and (b) administering to the subject the ligand, thereby down-regulating angiogenesis in the tissue.

According to a further aspect of the present invention there is provided a pharmaceutical composition for down regulating angiogenesis in a tissue of a subject including, as an active ingredient, a nucleic acid construct designed and configured for generating cytotoxicity in a subpopulation of angiogenic cells and a pharmaceutical acceptable carrier. The nucleic acid construct includes: (a) a first polynucleotide region encoding a chimeric polypeptide including a ligand binding domain fused to an effector domain of a cytotoxic molecule; and (b) a second polynucleotide region encoding a cis regulatory element for directing expression of the chimeric polypeptide in the subpopulation of angiogenic cells, wherein the ligand binding domain is selected capable of binding a ligand present in the specific tissue or cell, so that the binding of the ligand to the ligand binding domain activates the effector domain of the cytotoxic molecule.

According to yet a further aspect of the present invention there is provided a method of treating a disease or condition associated with excessive neo-vascularization. The method is effected by administering a therapeutically effective amount of a nucleic acid construct designed and configured for generating cytotoxicity in a sub-population of angiogenic cells, the nucleic acid construct including: (i) a first polynucleotide region encoding a chimeric polypeptide including a ligand binding domain fused to an effector domain of a cytotoxic molecule; and (ii) a second polynucleotide region encoding a cis acting regulatory element for directing expression of the chimeric polypeptide in the sub-population of angiogenic cells; and where the ligand binding domain is selected capable of binding a ligand present in, or provided to, the sub-population of angiogenic cells, and binding of the ligand to the ligand binding domain activates the effector domain of the cytotoxic molecule, thereby down-regulating angiogenesis in the tissue and treating the disease or condition associated with excessive neo-vascularization. Also provided is a method of treating a tumor in a subject, the method effected by administering a therapeutically effective amount of the nucleic acid construct designed and configured for generating cytotoxicity in cells of the tumor.

According to still a further aspect of the present invention there is provided a method of treating a disease or condition associated with ischemia, the method effected by administering a therapeutically effective amount of a nucleic acid construct designed and configured for generating angiogenesis in a sub-population of angiogenic cells, thereby up-regulating angiogenesis in the tissue and treating the disease or condition associated with ischemia. The nucleic acid construct includes: (i) a first polynucleotide region encoding a proangiogenic factor; and (ii) a second polynucleotide region encoding a cis regulatory element being for directing expression of the proangiogenic factor in a sub-population of angiogenic cells.

According to further features in the described preferred embodiments, the disease or condition associated with ischemia is selected from the group consisiting of wound healing, ischemic stroke, ischemic heart disease and gastrointestinal lesions.

According to yet a further aspect of the present invention there is provided a method of down-regulating angiogenesis in a tissue of a subject, the method effected by: (a) expressing in the tissue a nucleic acid construct designed and configured for cytotoxicity in angiogenic cells, the nucleic acid construct including: (i) a first polynucleotide region encoding a suicide gene and (ii) a second polynucleotide region encoding a cis acting regulatory element capable of directing expression of the suicide gene in the angiogenic cells; and (b) administering to the subject a therapeutic amount of a prodrug sufficient to cause apoptosis of the tissue when the prodrug is converted to a toxic compound by the suicide gene, thereby down-regulating angiogenesis in the tissue.

According to still a further aspect of the present invention there is provided a pharmaceutical composition for down regulating angiogenesis in a tissue of a subject, the pharmaceutical composition including as an active ingredient a nucleic acid construct designed and configured for generating cytotoxicity in angiogenic cells and a pharmaceutical acceptable carrier. The nucleic acid construct includes: (a) a first polynucleotide region encoding a suicide gene, the suicide gene being capable of converting a prodrug to a toxic compound and (b) a second polynucleotide region encoding a cis acting regulatory element capable of directing expression of the suicide gene in the angiogenic cells.

According to yet another aspect of the present invention there is provided a nucleic acid construct including: (a) a first polynucleotide region encoding a suicide gene, the suicide gene being capable of converting a prodrug to a toxic compound, and (b) a second polynucleotide region encoding a cis regulatory element capable of directing expression of the suicide gene in angiogenic cells. Also provided are eukaryotic cells transformed with the nucleic acid construct of the invention.

According to yet a further aspect of the present invention there is provided a method of down-regulating angiogenesis in a tissue of a subject, the method effected by administering to the subject a nucleic acid construct designed and configured for generating cytotoxicity in angiogenic cells. The nucleic acid construct includes: (a) a first polynucleotide region encoding a suicide gene; and (b) a second polynucleotide region encoding a cis regulatory element capable of directing expression of the suicide gene in the angiogenic cells, where the suicide gene is selected capable of converting a prodrug to a toxic compound capable of causing cytotoxicity, thereby down-regulating angiogenesis in the tissue.

According to still a further aspect of the present invention there is provided a method of treating a disease or condition associated with excessive neo-vascularization, the method effected by administering a therapeutically effective amount of the nucleic acid construct of the invention designed and configured for cytotoxicity in angiogenic cells, thereby down-regulating angiogenesis in the tissue and treating the disease or condition associated with excessive neo-vascularization.

According to still a further aspect of the present invention there is provide a method of treating a tumor in a subject, the method effected by administering a therapeutically effective amount of a nucleic acid construct designed and configured for generating cytotoxicity in cells of the tumor, the nucleic acid construct including: (i) a first polynucleotide region encoding a suicide gene; and (ii) a second polynucleotide region encoding a cis acting regulatory element capable of directing expression of the suicide gene in the cells of the tumor, where the suicide gene is selected capable of converting a prodrug to a toxic compound capable of causing cytotoxicity in the cells of the tumor.

According to yet further features in the described preferred embodiments the suicide gene is selected from the group consisting of thymidine kinase of herpes simplex virus, thymidine kinase of varicella zoster virus and bacterial cytosine deaminase.

According to still further features in the described preferred embodiments the prodrug is selected from the group consisting of ganciclovir, acyclovir, 1-5-iodouracil FIAU, 5-fluorocytosine, 6-methoxypurine arabinoside and their derivatives.

According to yet further features in the described preferred embodiments the suicide gene is thymidine kinase of herpes simplex virus and the prodrug is ganciclovir, acyclovir, FIAU or their derivatives.

According to still further features in the described preferred embodiments the suicide gene is bacteria cytosine deaminase and said prodrug is 5-fluorocytosine or its derivatives.

According to yet further features in the described preferred embodiments the suicide gene is varicella zoster virus thymidine kinase and said prodrug is 6-methoxypurine arabinoside or its derivatives.

According to yet further features in the described preferred embodiments the method further comprises administering to the subject, in combination, at least one additional therapeutic modality, additional therapeutic modality selected capable of further potentiating said cytotoxicity in a synergic manner. The at least one additional therapeutic modality can be selected from the group comprising chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

According to further features in preferred embodiments of the invention described below, the nucleic acid sequence includes an isolated polynucleotide comprising a cis regulatory element including at least a portion of the sequence set forth in SEQ ID NO:15 covalently linked to at least a portion of the sequence set forth in SEQ ID NO:16, the isolated polynucleotide being capable of directing transcription of a polynucleotide sequence transcriptionally linked thereto in eukaryotic cells. The at least a portion of the sequence set forth in SEQ ID NO:15 can be positioned upstream of the at least a portion of the sequence set forth in SEQ ID NO:16 in said cis regulatory element, or the least a portion of the sequence set forth in SEQ ID NO:16 can be positioned upstream of said at least a portion of the sequence set forth in SEQ ID NO:15.

According to still further features in the described preferred embodiments the cis regulatory element further includes at least one copy of the sequence set forth in SEQ ID NO: 6, or at least two copies of SEQ ID NO:6. The at least two copies of SEQ ID NO:6 can be contiguous.

According to yet further features in the described preferred embodiments the at least a portion of the sequence set forth in SEQ ID NO:15 is covalently linked to the at least a portion of the sequence set forth in SEQ ID NO:16 via a linker polynucleotide sequence. The linker polynulceotide sequence can be a promoter and/or an enhancer element.

According to still further features in the described preferred embodiments the isolated polynucleotide includes at least one copy of the sequence set forth in SEQ ID NO:1.

According to yet further features in the described preferred embodiments the isolated polynucleotide further includes a hypoxia response element, the hypoxia response element preferably including at least one copy of the sequence set forth in SEQ ID NO: 5.

According to still further features in the described preferred embodiments the cis regulatory element is as set forth in SEQ ID NO: 7.

According to still further features in the described preferred embodiments the nucleic acid construct further includes a conditionally replicating adenovirus.

According to yet further features in the described preferred embodiments the cis regulatory element is an endothelial cell-specific or periendothelial cell-specific promoter selected from the group consisting of the PPE-1 promoter, the PPE-1-3x promoter, the TIE-1 promoter, the TIE-2 promoter, the Endoglin promoter, the von Willerband promoter, the KDR/flk-1 promoter, The FLT-1 promoter, the Egr-1 promoter, the ICAM-1 promoter, the VCAM-1 promoter, the PECAM-1 promoter and the aortic carboxypeptidase-like protein (ACLP) promoter.

According to yet further features in the described preferred embodiments the method further comprising administering to the tissue, or to the subject, at least one compound selected capable of enhancing copy number of the adenovirus and/or enhancing expression of the angiogenesis regulator.

According to further features in the described preferred embodiments the additional compound is a corticosteroid and/or N-acetyl cysteine.

According to still further features in the described preferred embodiments the method further comprising administering to the tissue or to the subject, at least one modulator of angiogenesis selected capable of further potentiating activity of the cis regulatory element or endothelial specific promoter in a synergic manner.

According to further features in the described preferred embodiments the at least one modulator of angiogenesis is an endothelin receptor antagonist. The endothelial receptor antagonist can be a dual A-form and B-form endothelin receptor antagonist, or a B-form specific antagonist.

According to yet further features in the described preferred embodiments the B-form specific endothelin receptor antagonist is selected from the group consisting of A192,621; BQ788; Res 701-1 and Ro 46-8443.

According to yet further features in the described preferred embodiments the endothelin receptor antagonist is an endothelin receptor antagonist excluding Bosentan.

The present invention successfully addresses the shortcomings of the presently known configurations by providing isolated polynucleotide sequences comprising cis regulating elements with novel enhancer elements, and methods of use thereof. The novel enhancer elements can be used to make nucleic acid constructs and pharmaceutical compositions for tissue-specific regulation of transgene expression, and for treating a variety of disorders, diseases and conditions by gene therapy. Specifically, the cis regulatory elements, isolated polynucleotides and pharmaceutical compositions of the present invention can be used, along with selected transgenes, to specifically upregulate and/or downregulate angiogenesis in endothelial cells, thus treating tumors, metastatic disease, and ischemic disease.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 4:
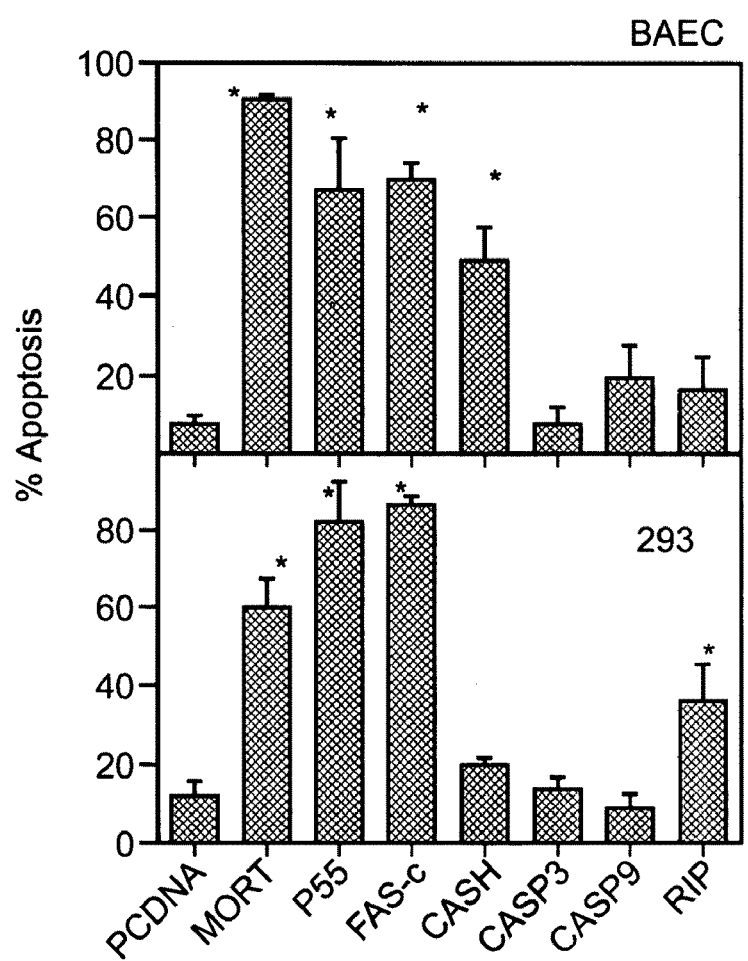
Figure 8:
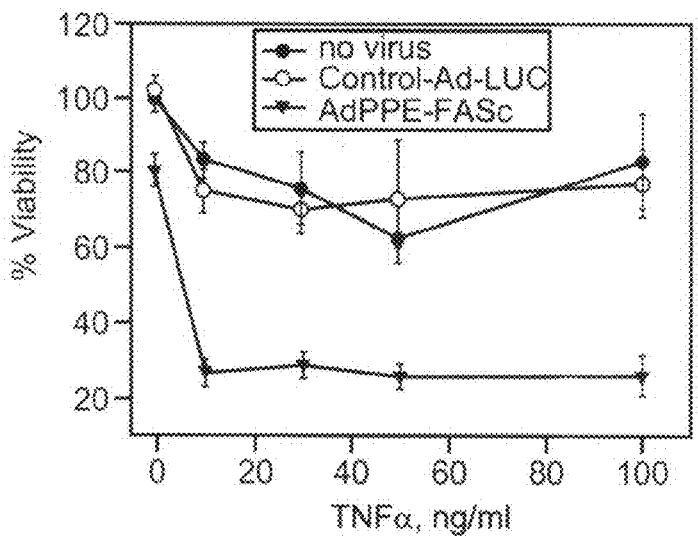
Figure 9A:
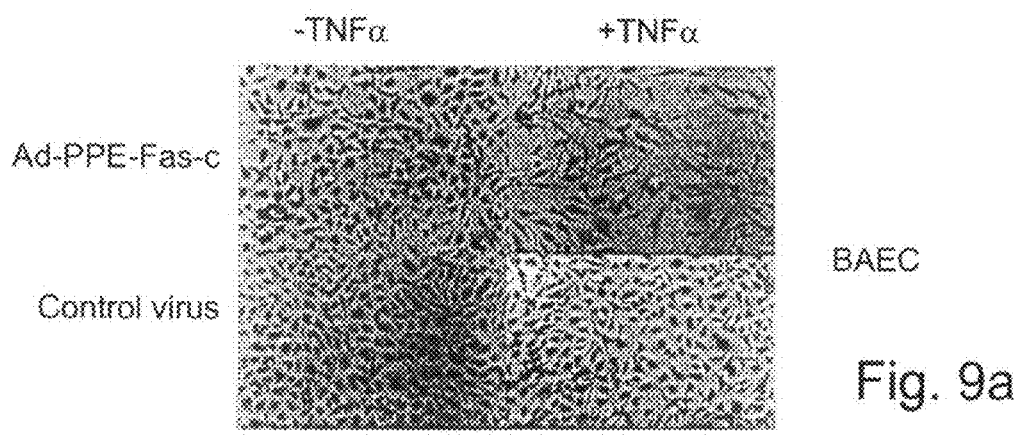
Figure 9B:
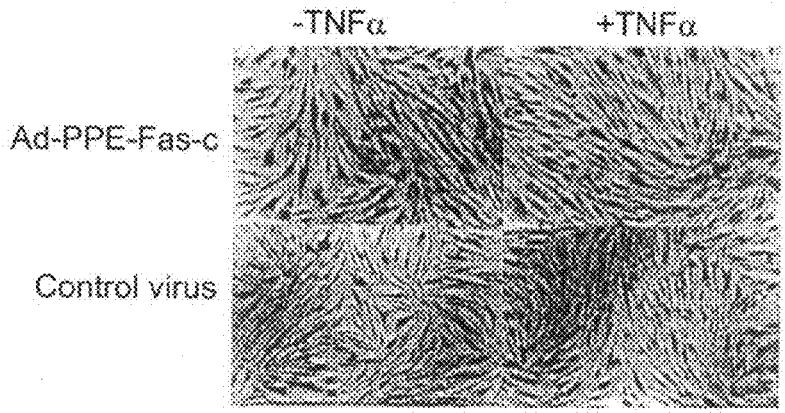
Figure 9C:
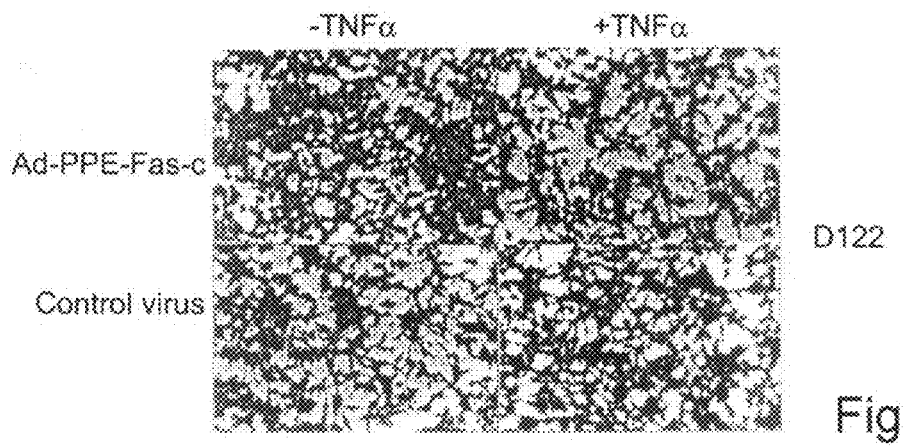
Figure 9D:
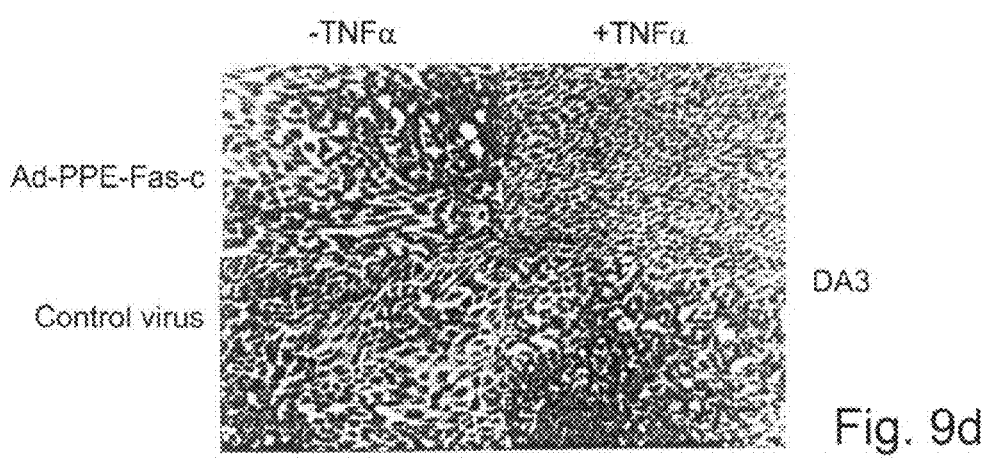
Figure 9E:
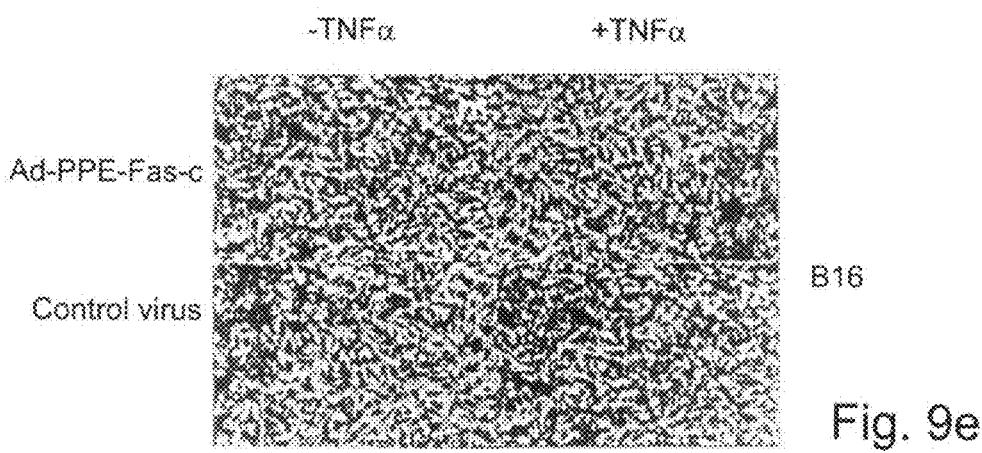
Figure 10A:
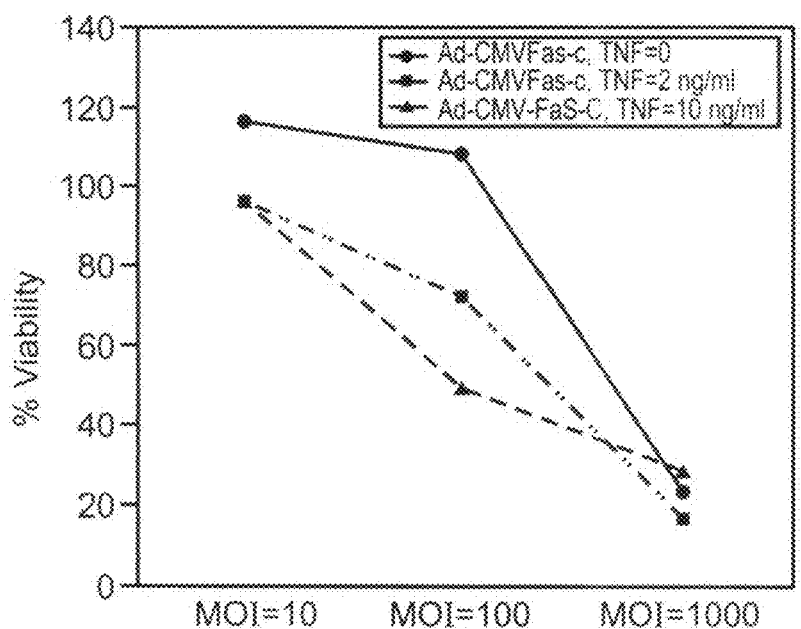
Figures 10B, 10C, 10D:
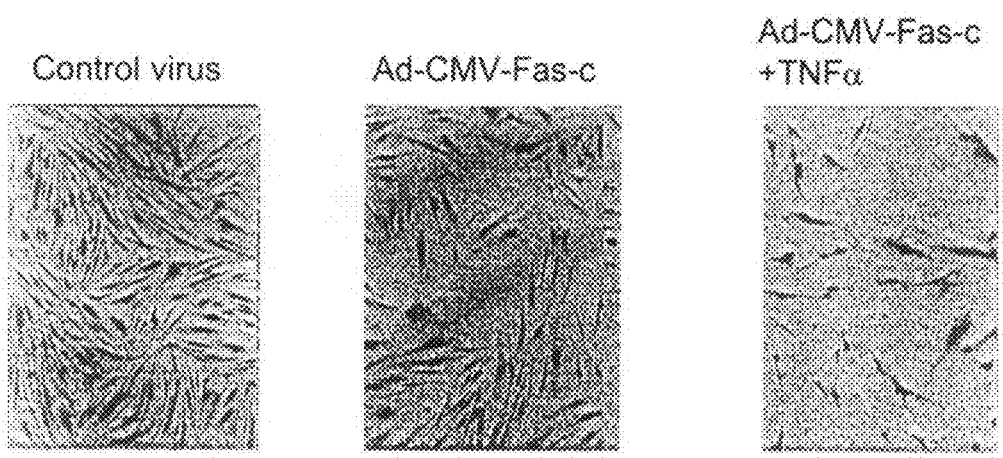
Figure 11A:
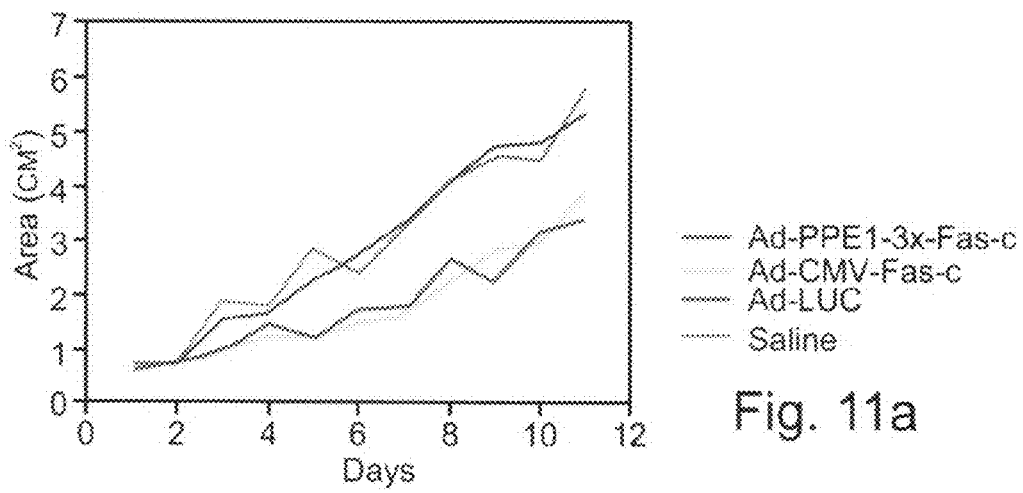
Figure 11B:
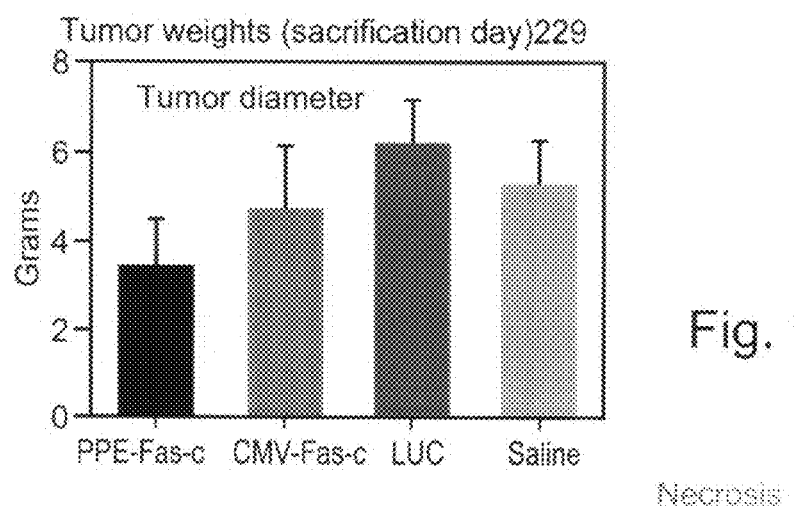
Figure 11C:
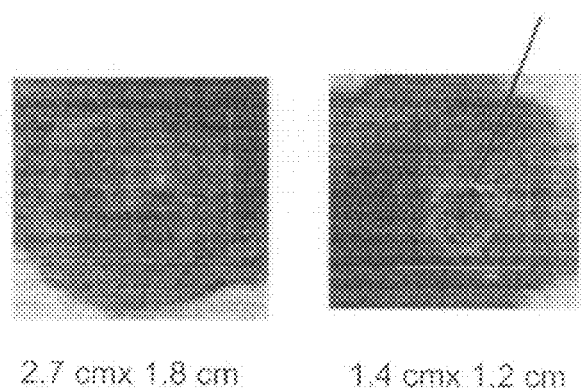
Figure 12:
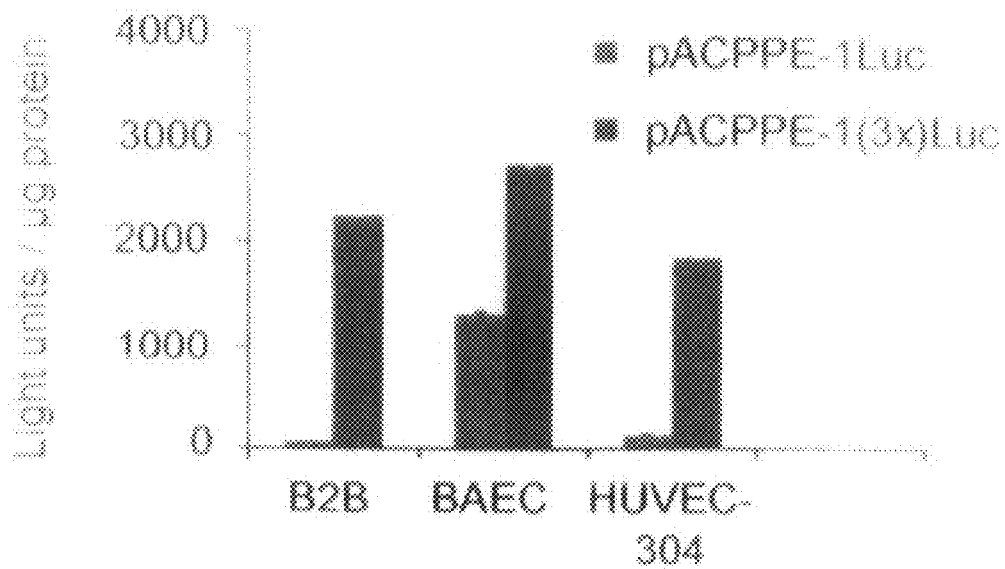
Figure 13:
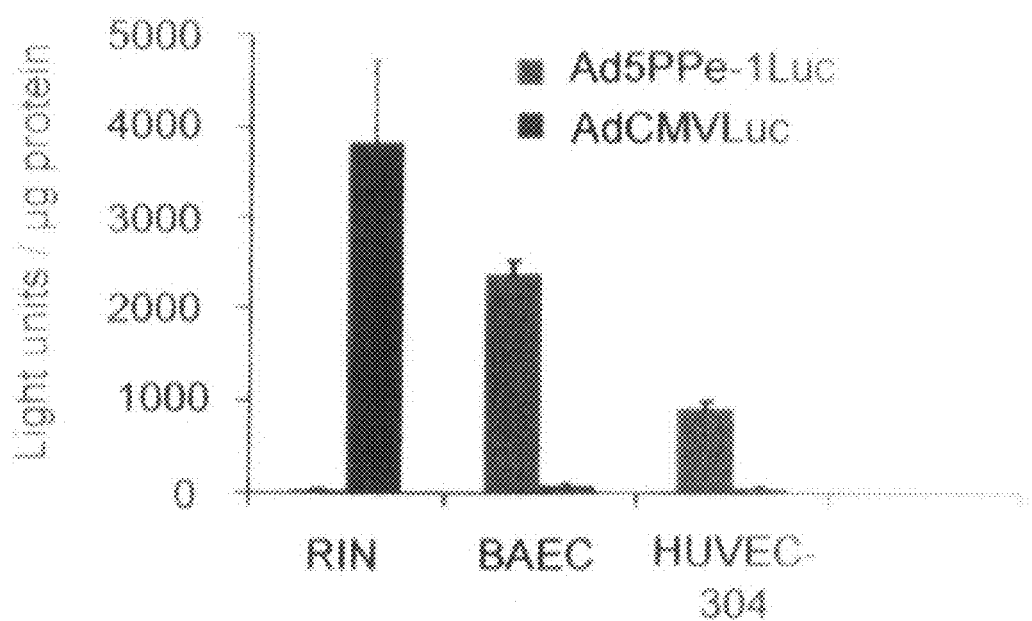
Figure 14A:
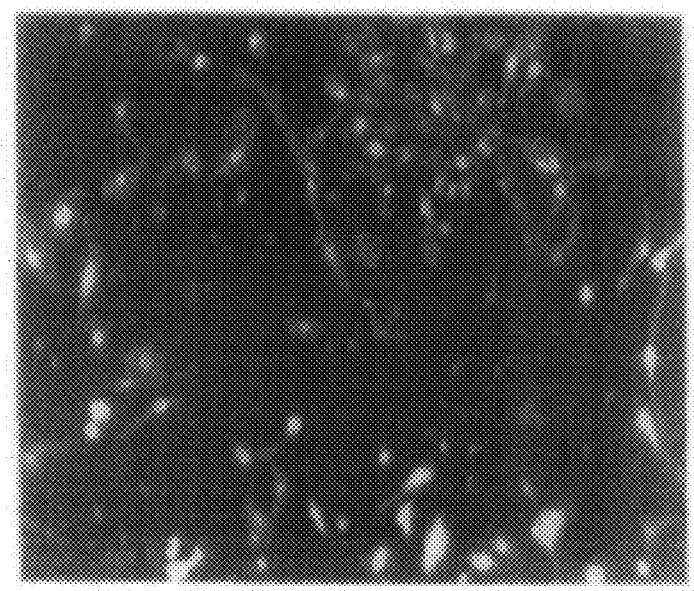
Figure 14B:
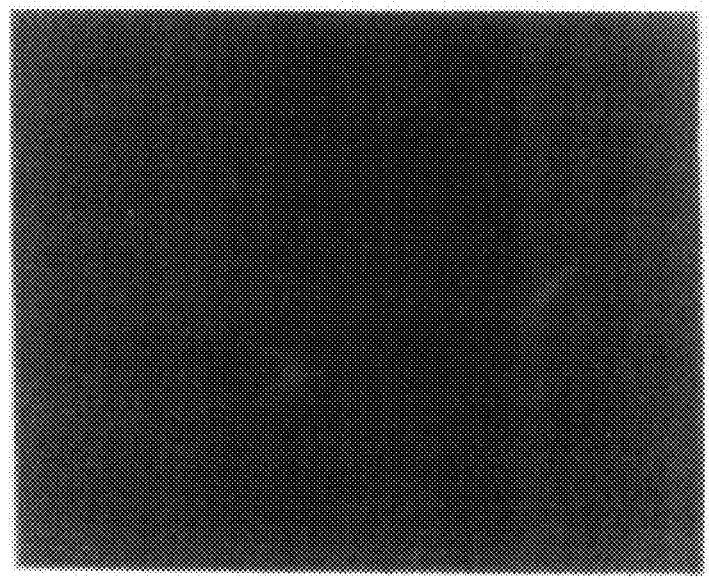
Figure 15:
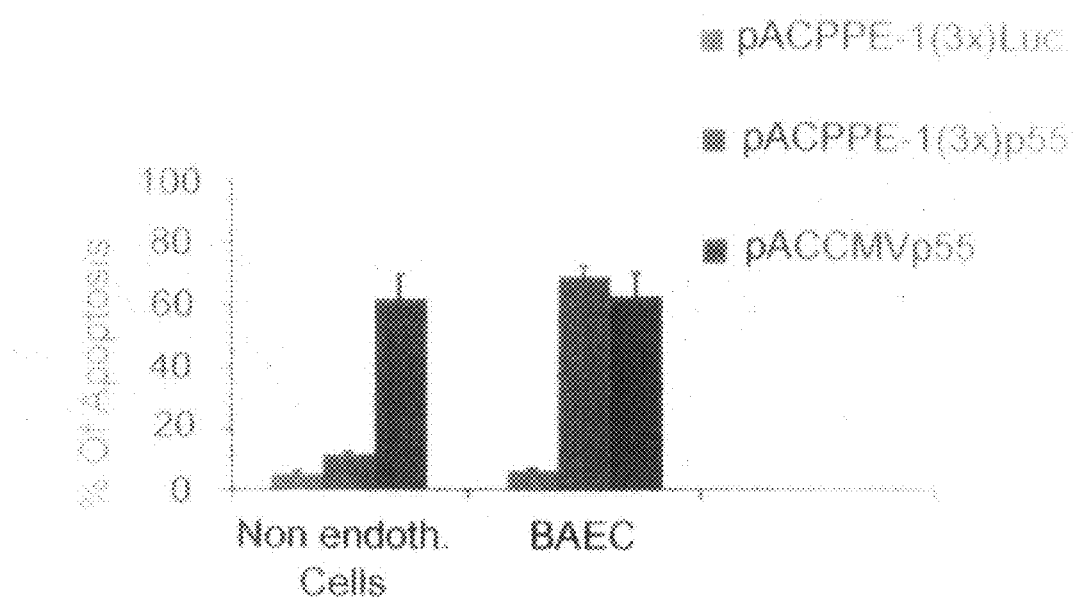
Figure 16:
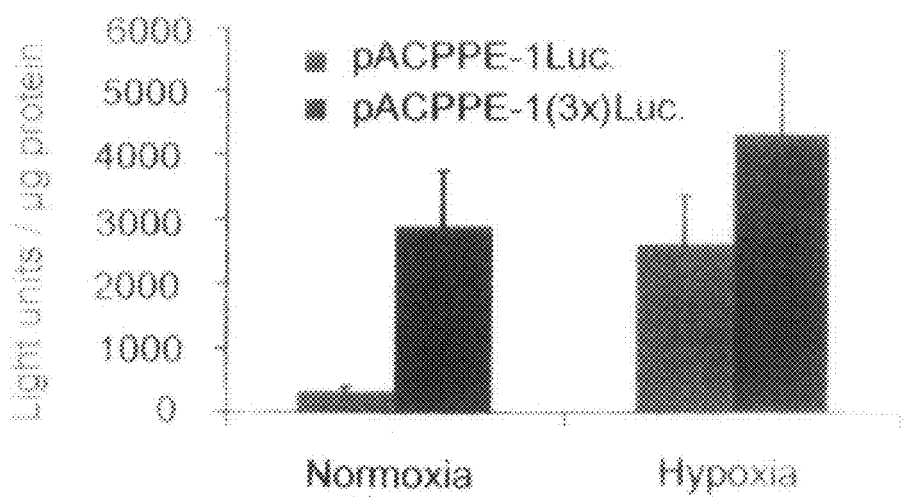
Figure 17:
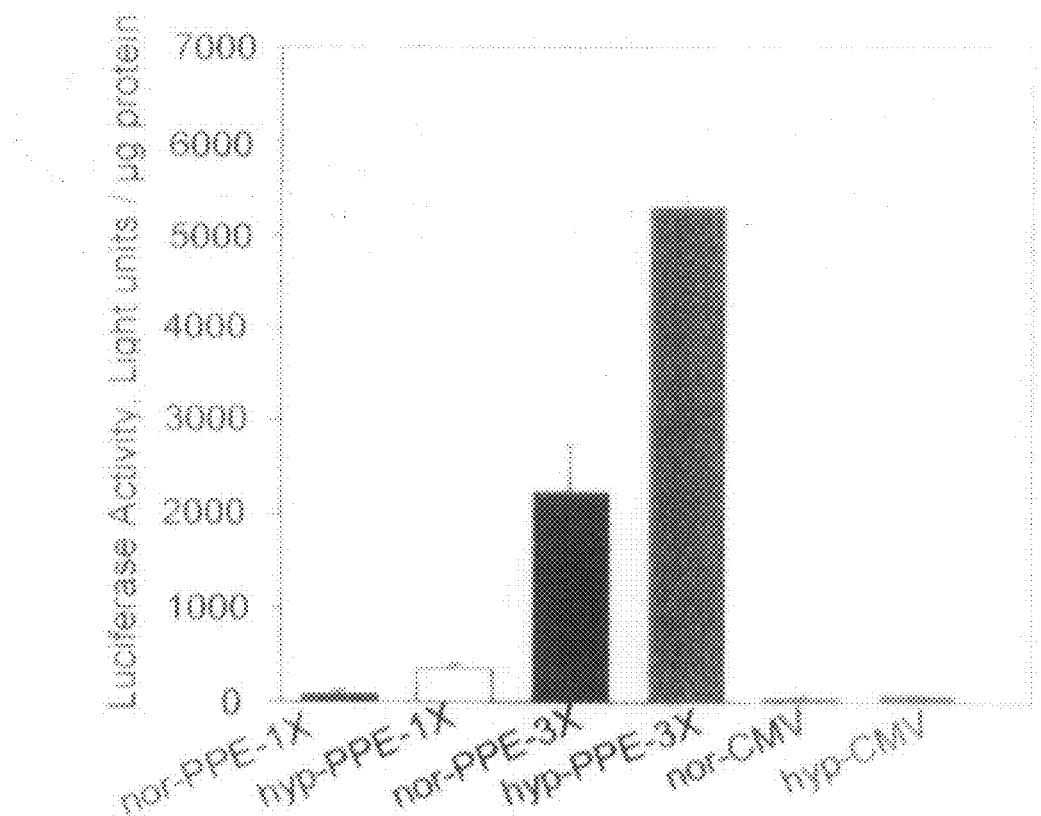
Figure 18:
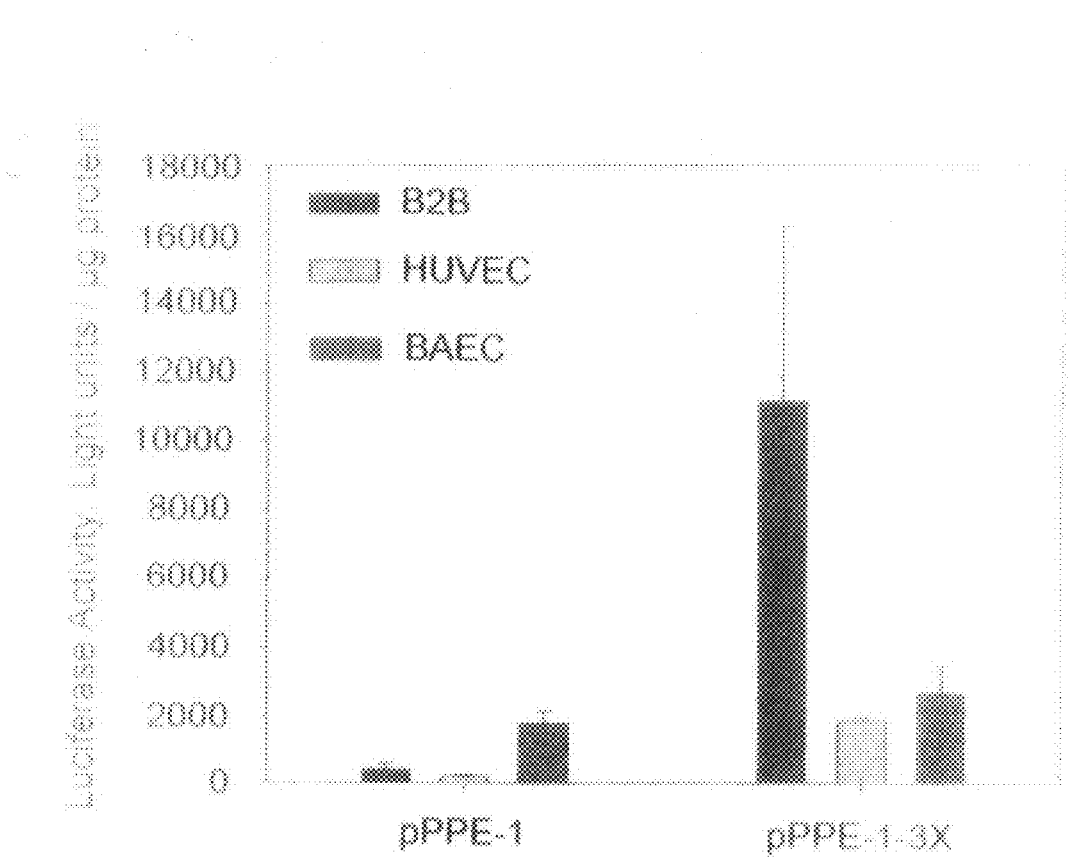
Figure 19:
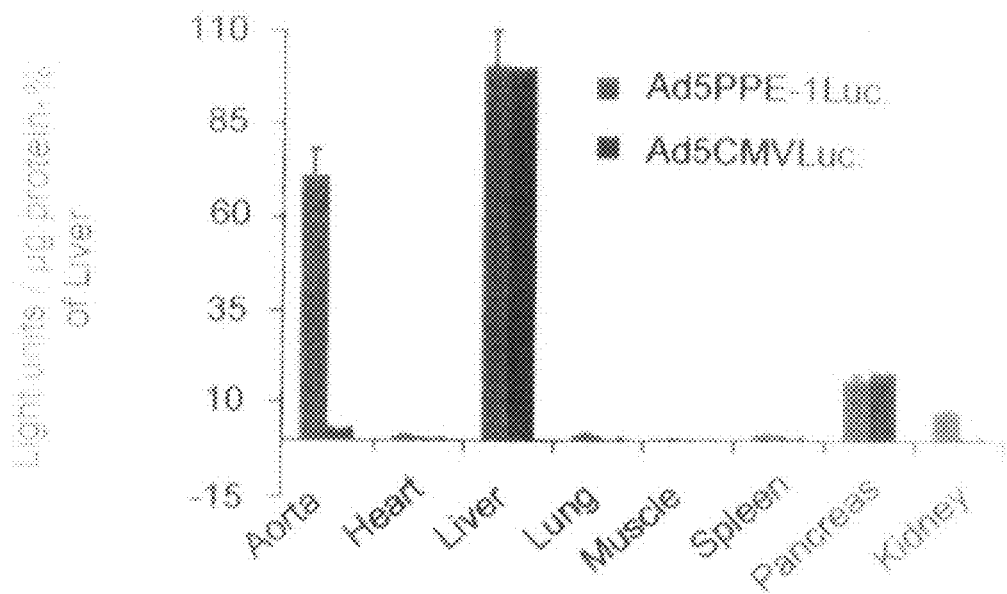
Figure 20A:
Figure 20B:
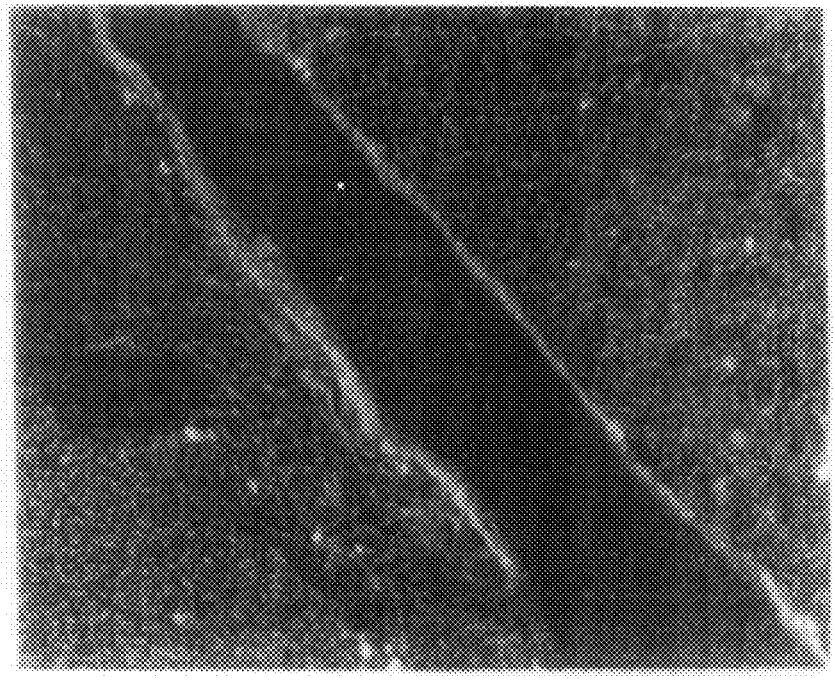
Figure 21:
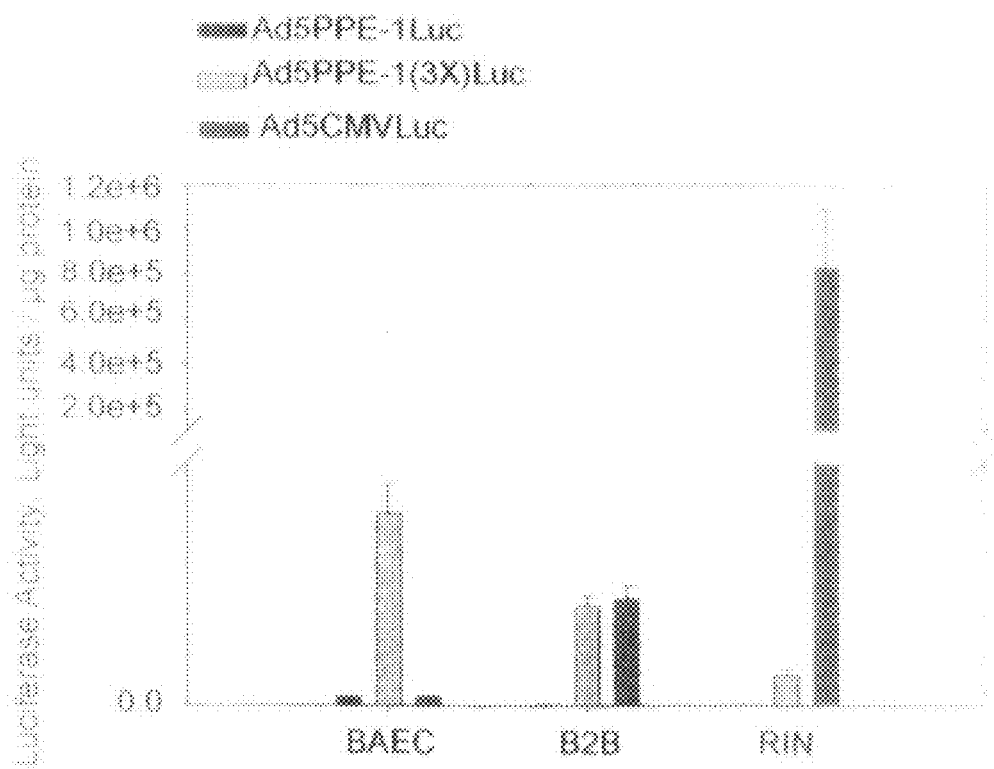
Figure 22:
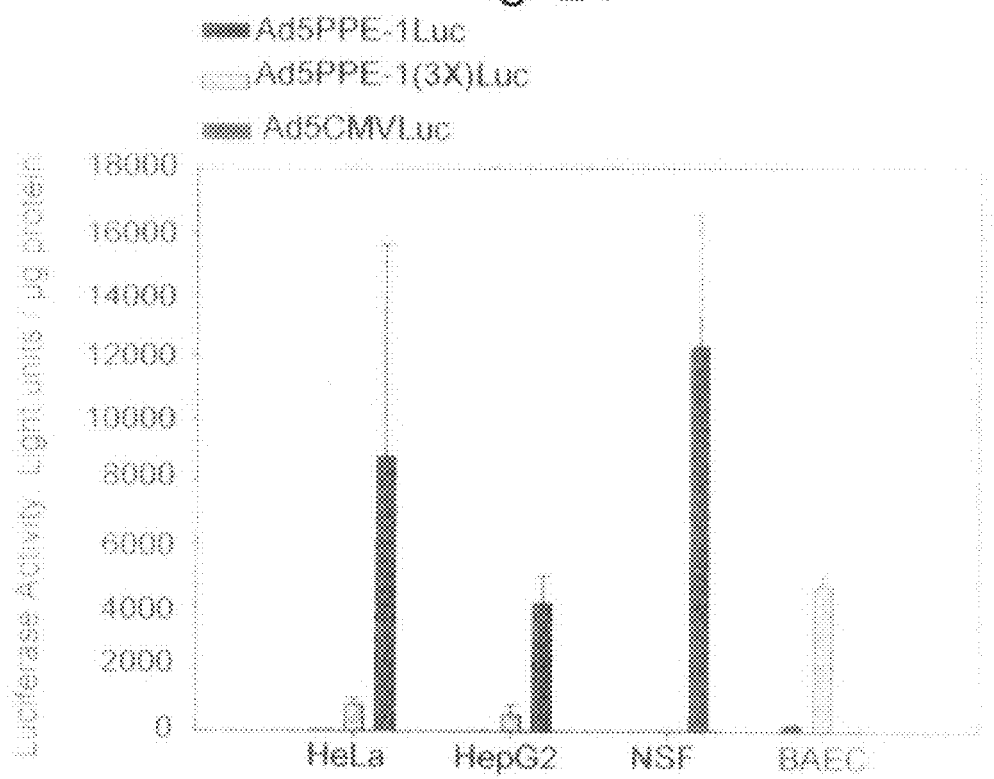
Figure 23A:
Figure 24A:
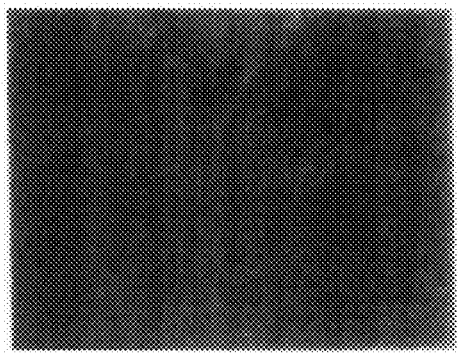
Figure 23B:
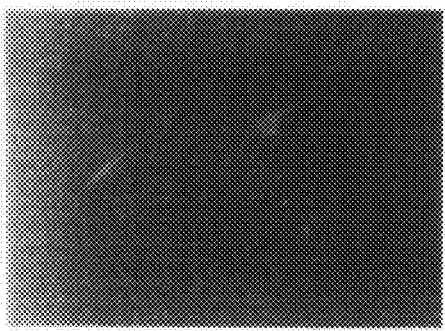
Figure 24B:
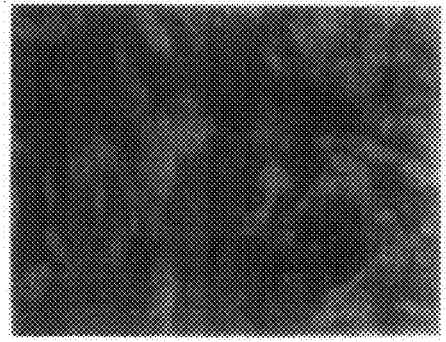
Figure 23C:
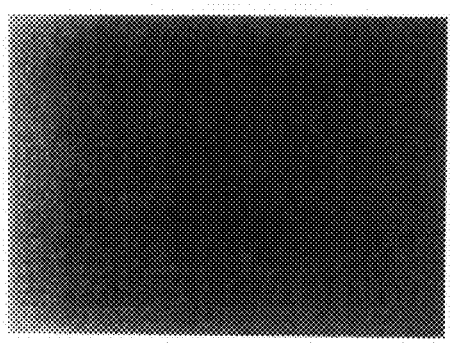
Figure 25A:
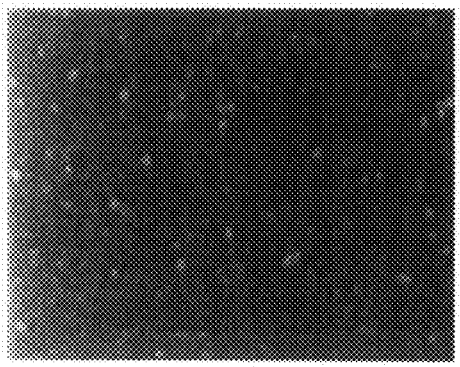
Figure 26A:
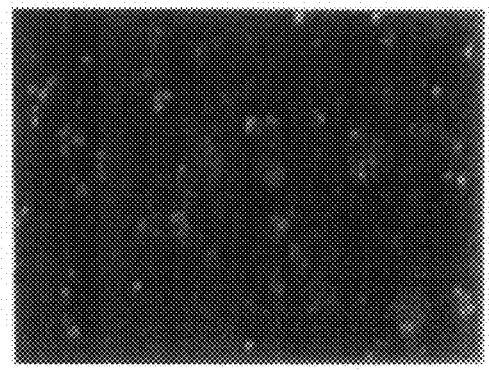
Figure 25B:
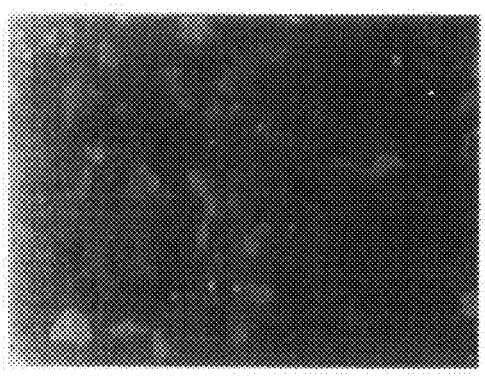
Figure 26B:
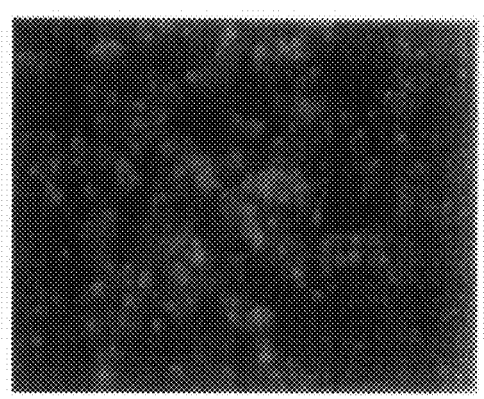
Figure 27A:
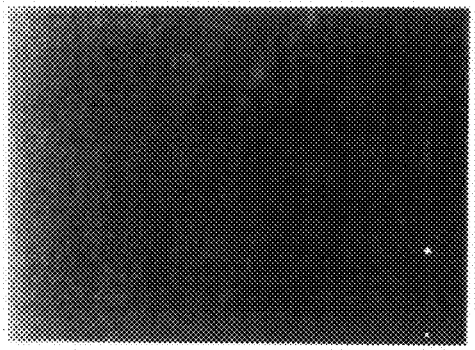
Figure 27B:
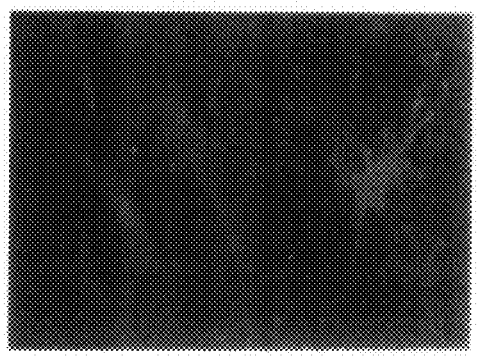
Figure 28A:
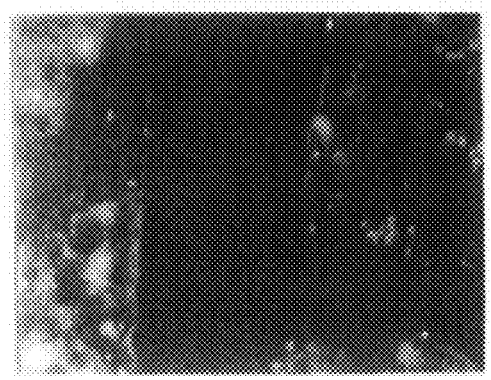
Figure 28B:
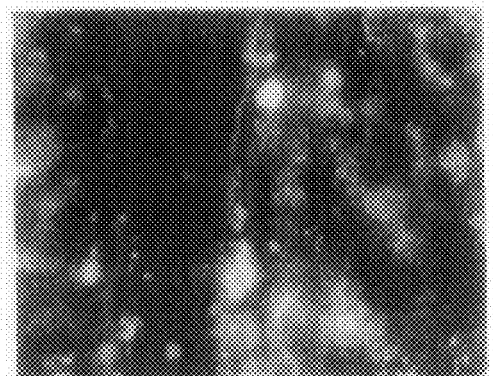
Figure 29A:
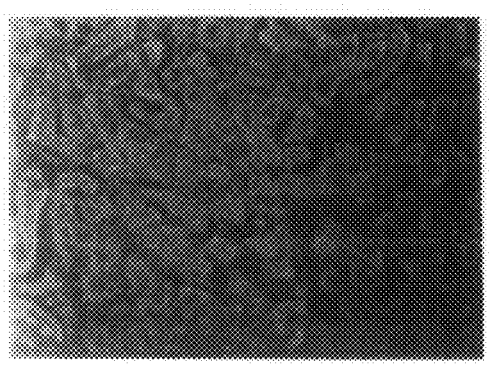
Figure 29B:
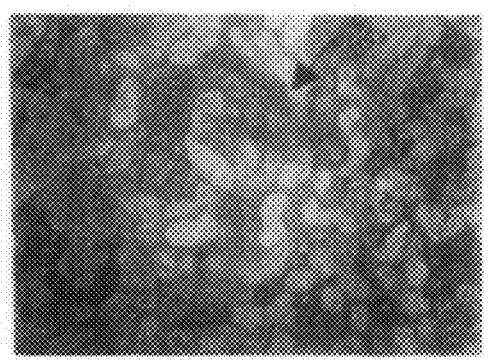
Figure 29C:
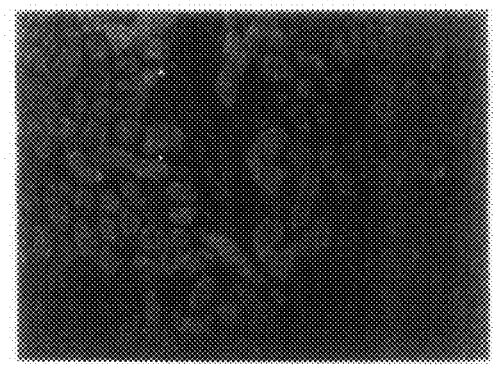
Figure 30A:
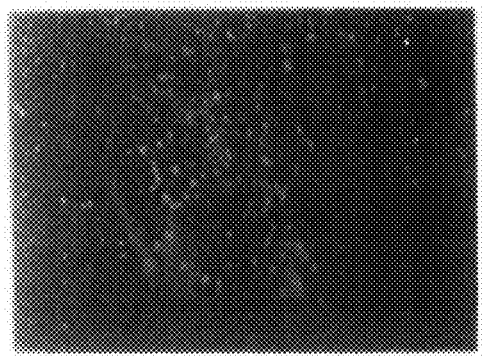
Figure 30B:
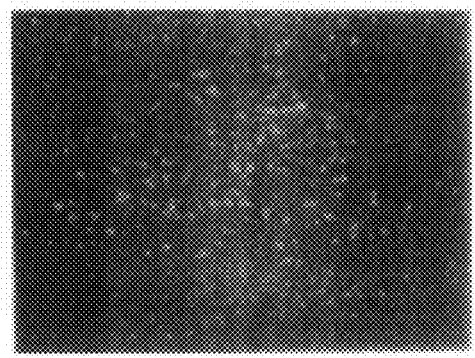
Figure 30C:
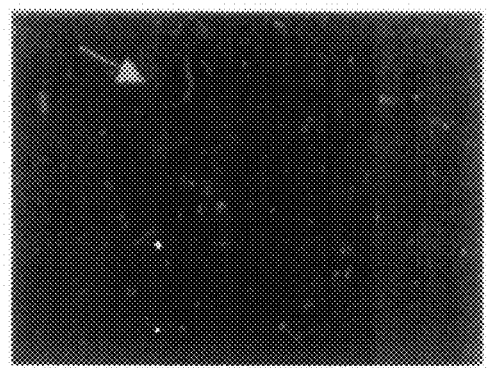
Figure 31A:
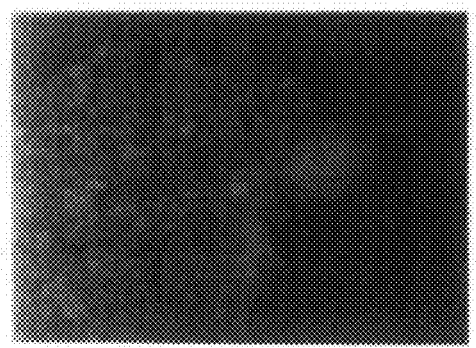
Figure 31B:
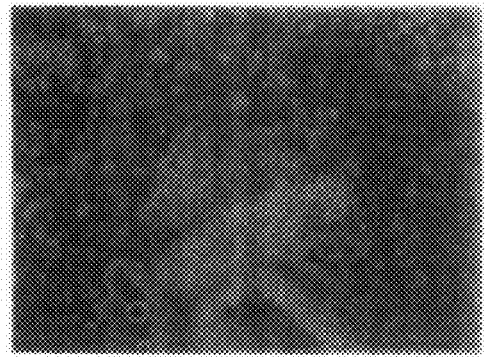
Figure 31C:
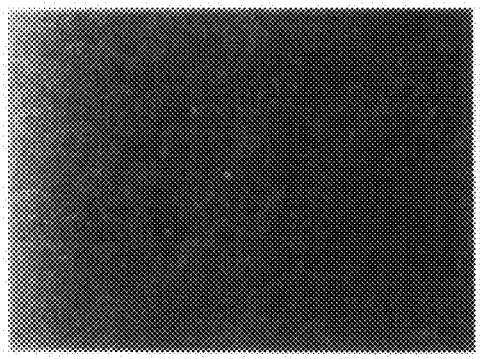
Figure 31C:
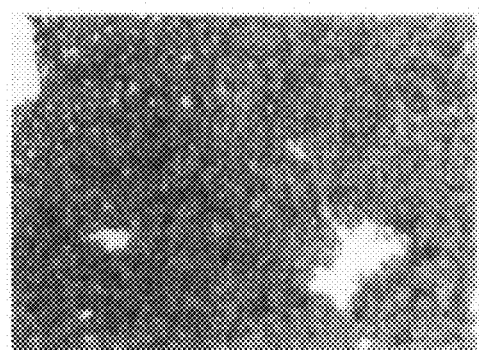
Figure 31D:
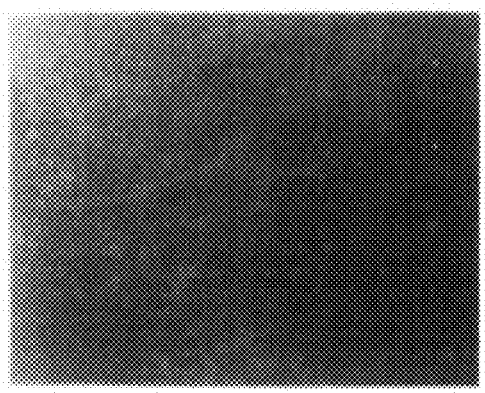
Figure 31D:
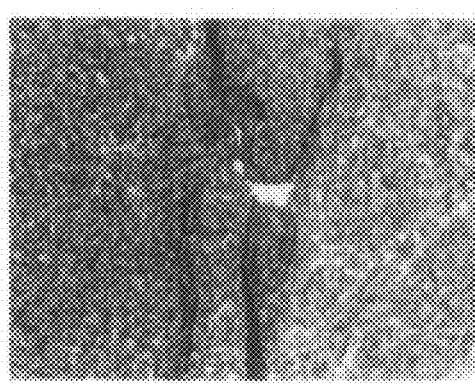
Figure 32:
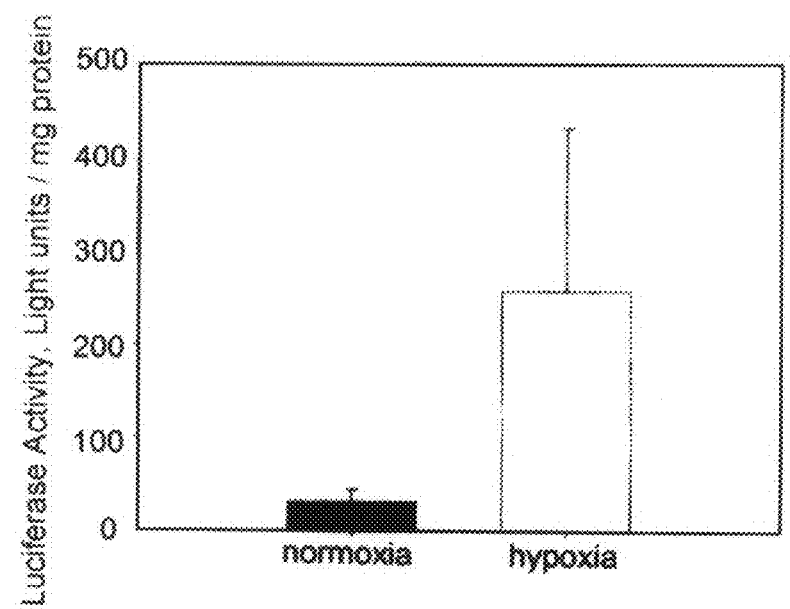
Figure 33:
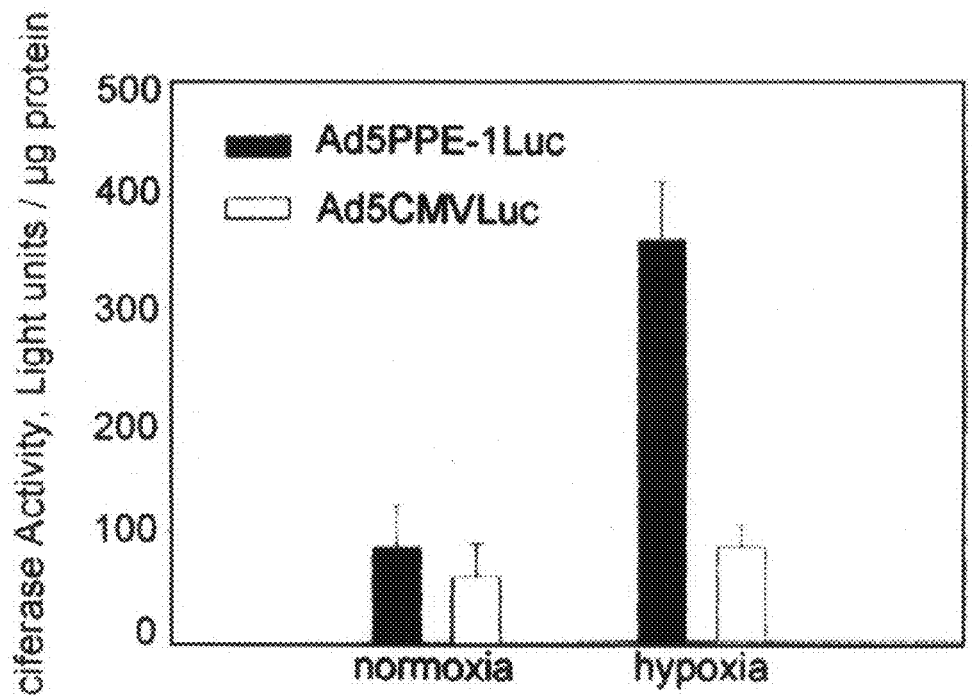
Figure 34:
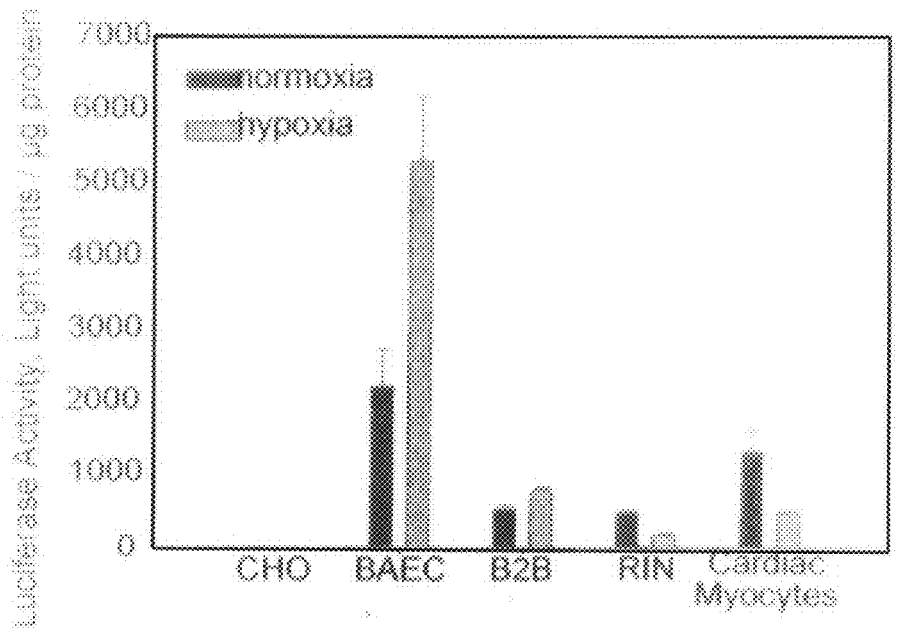
Figure 35:
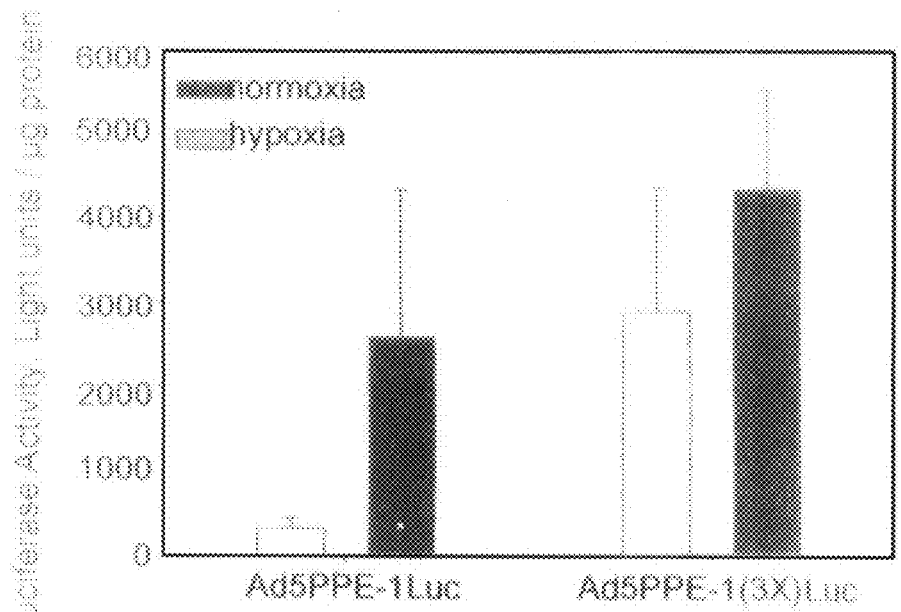
Figure 36:
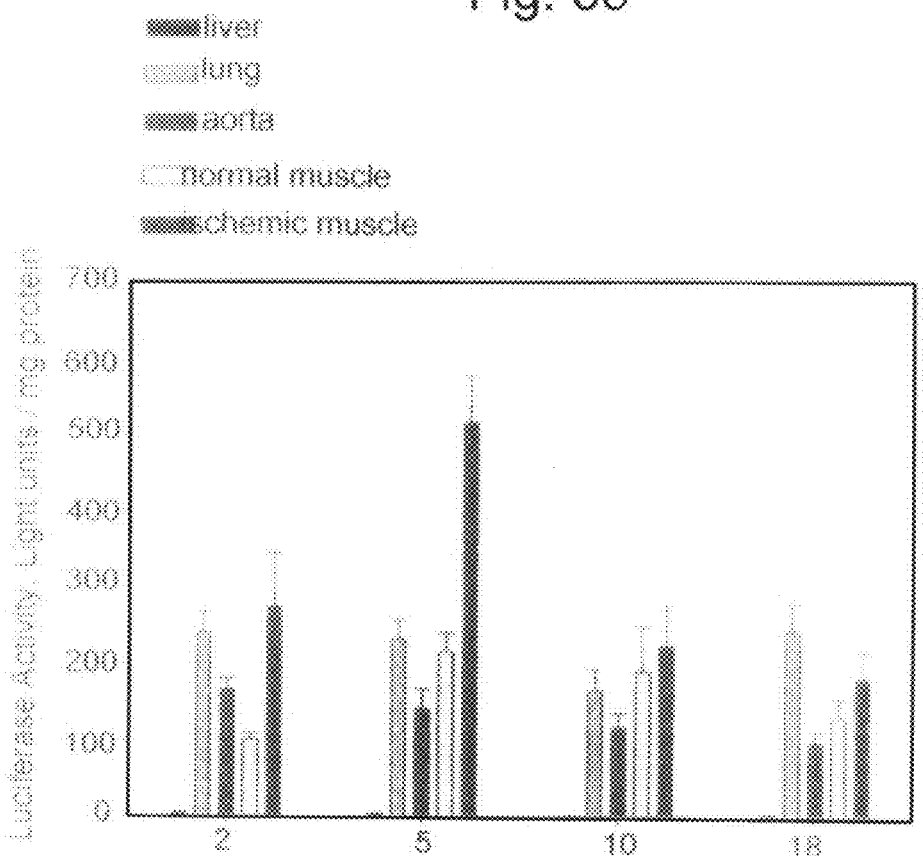
Figure 37A:
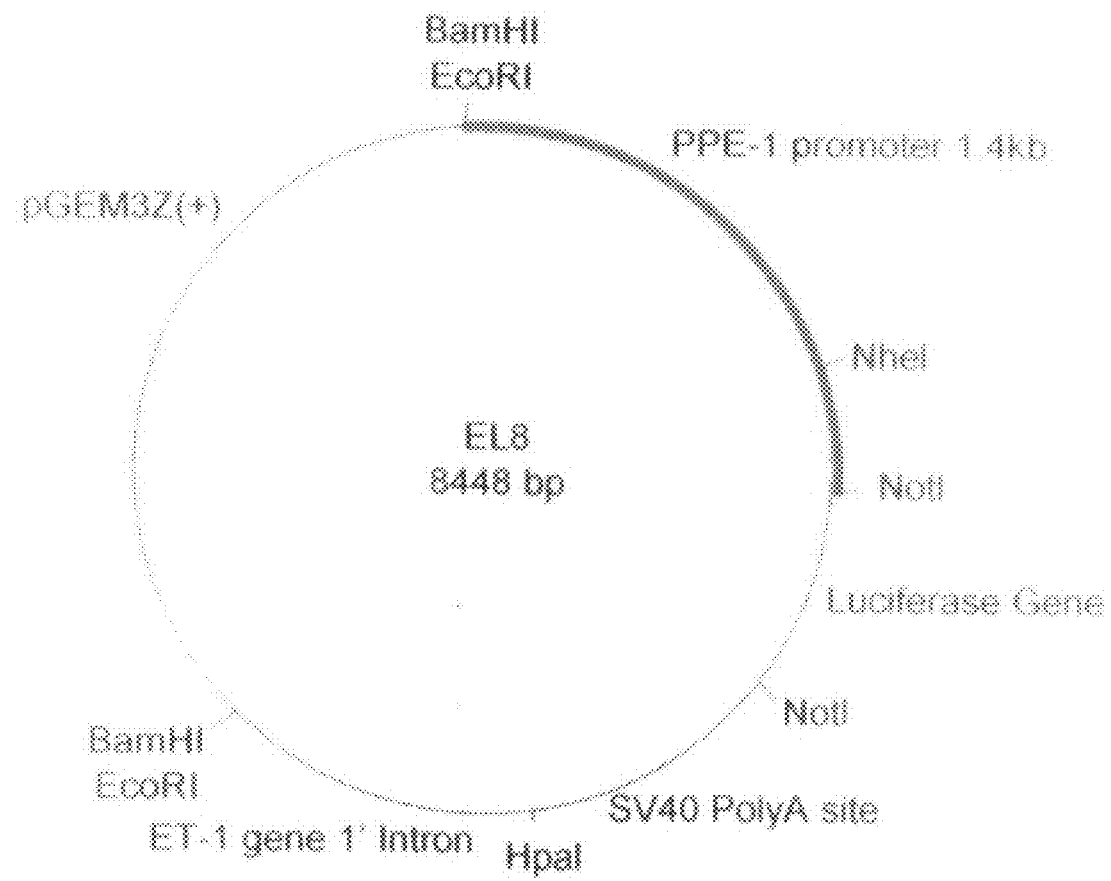
Figure 37B:
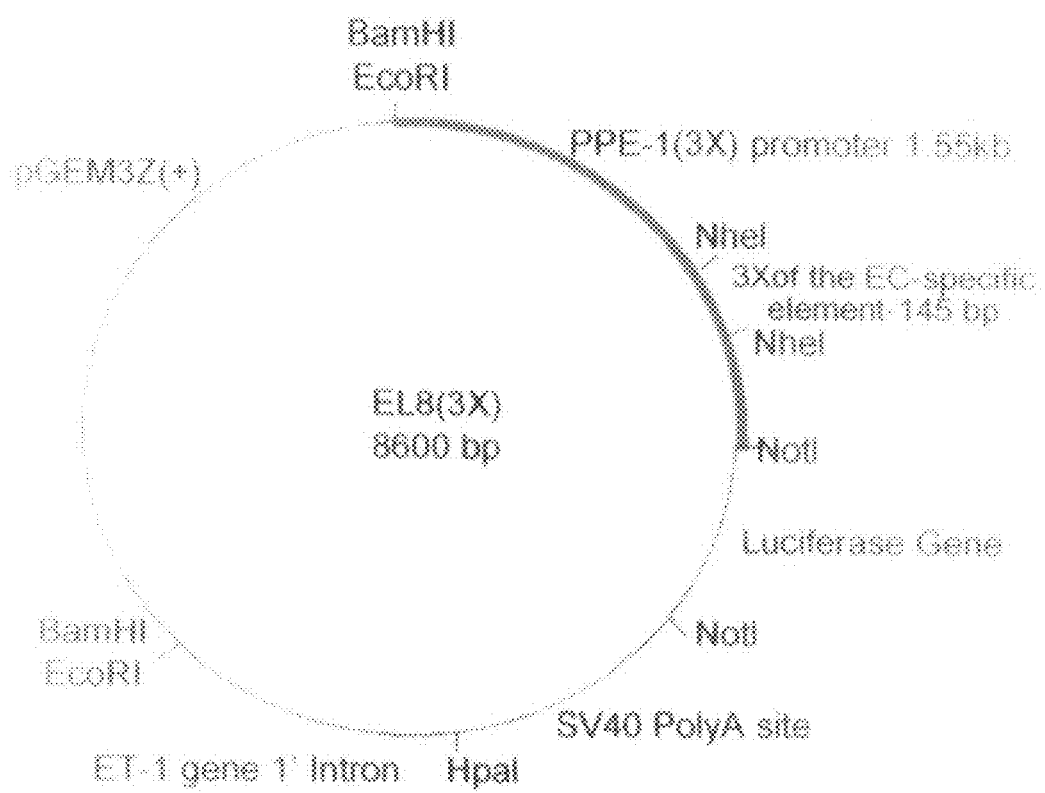
Figure 38A:
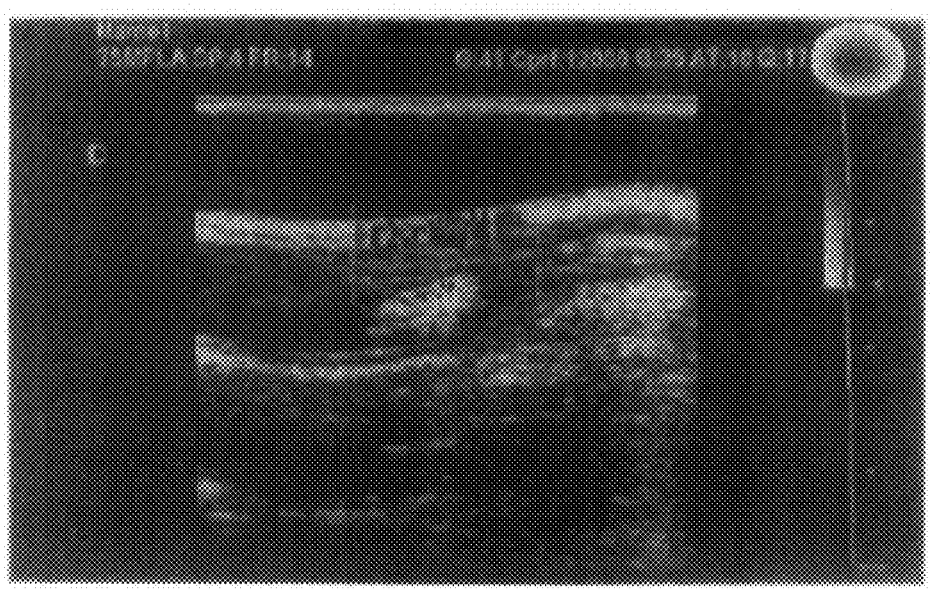
Figure 38B:
Figure 38C:
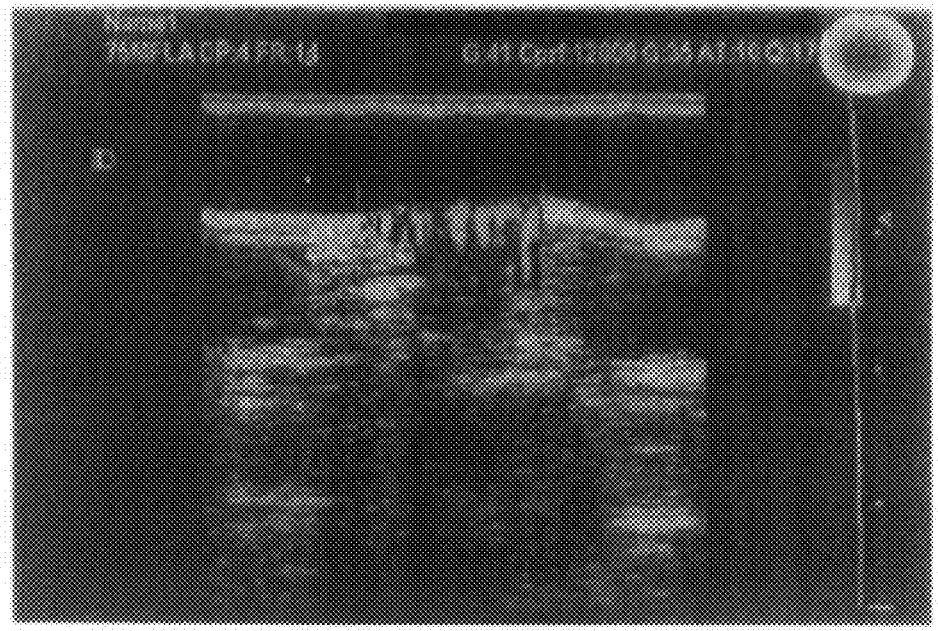
Figure 38D:
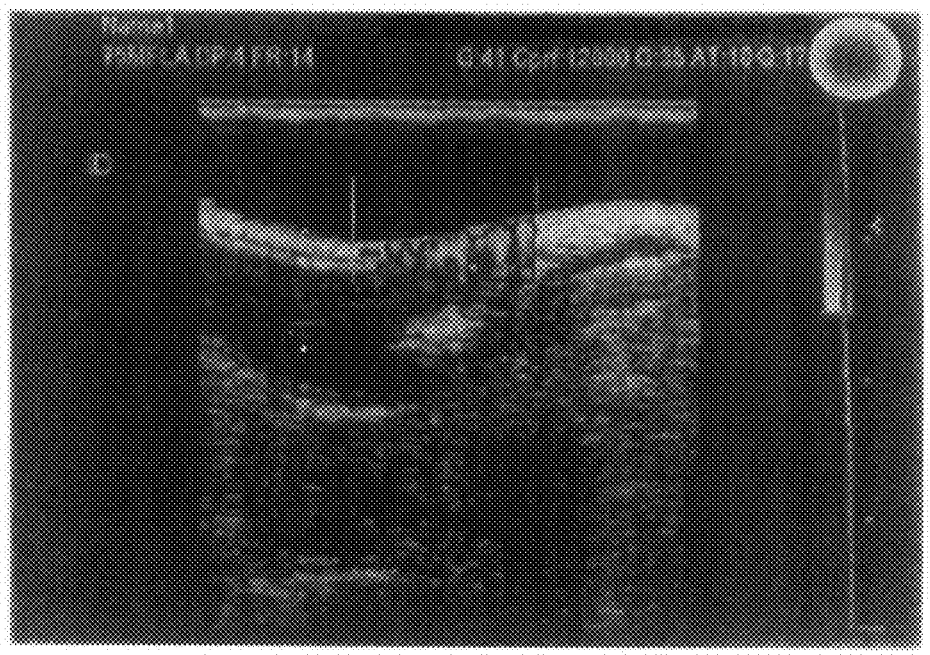
Figure 38E:
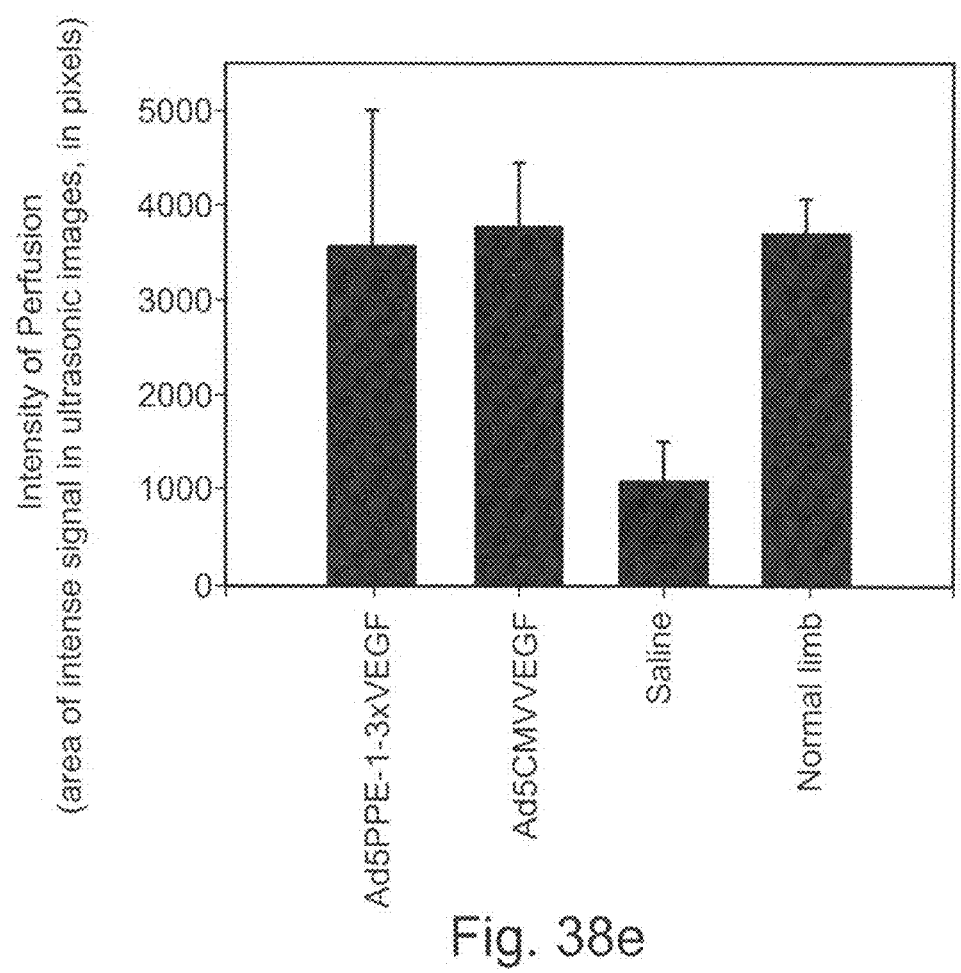
Figure 38F:
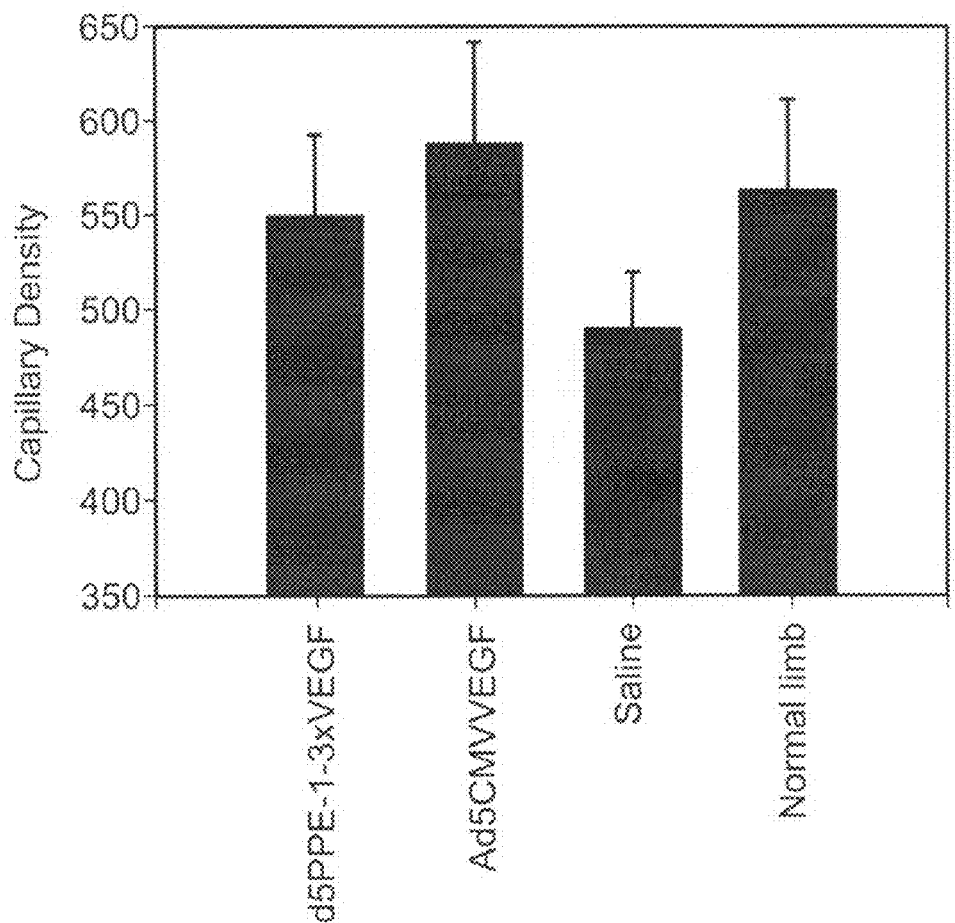
Figure 39:
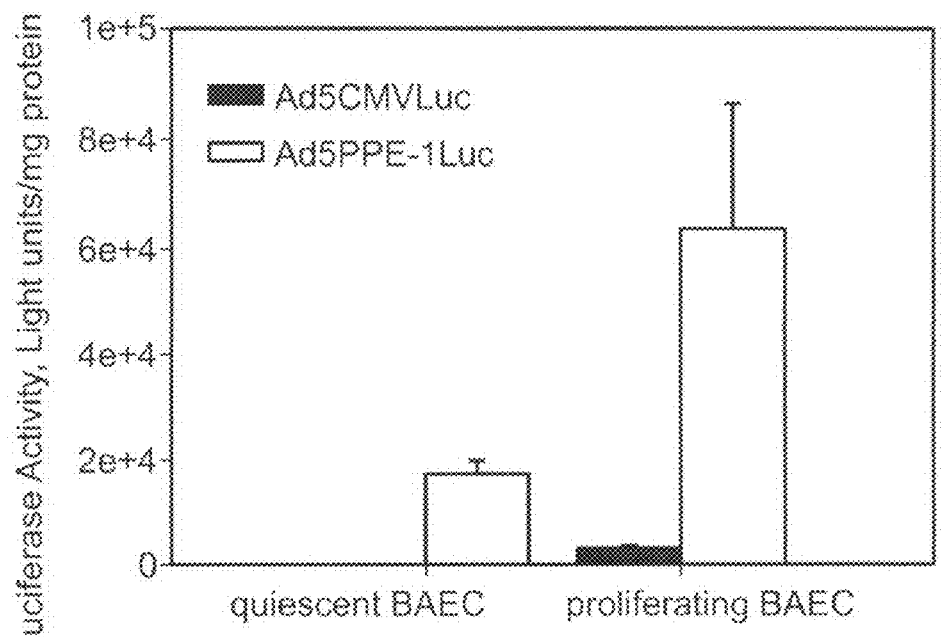
Figure 40:
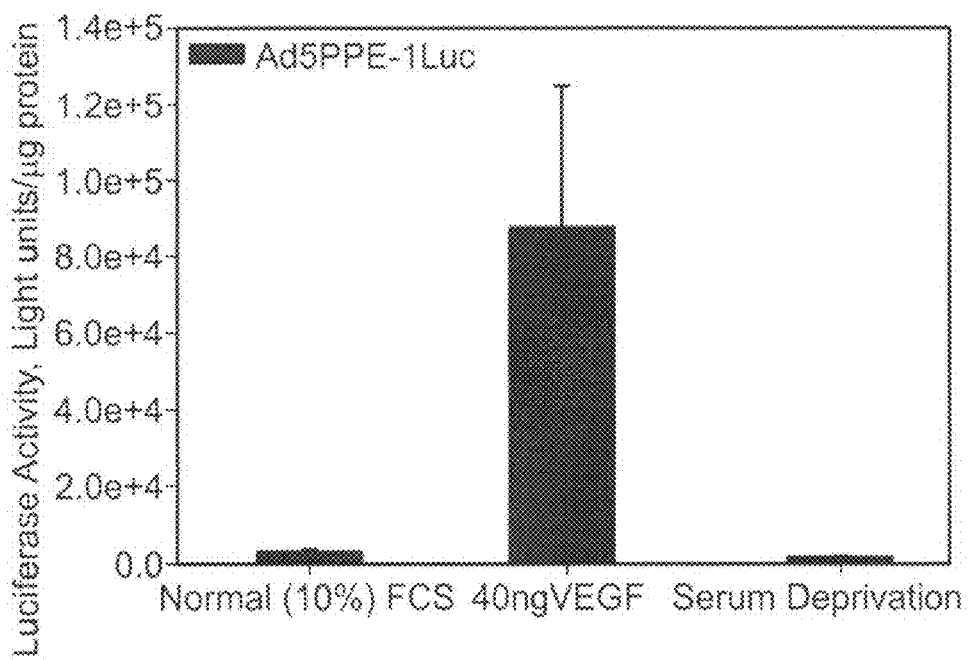
Figure 41A:
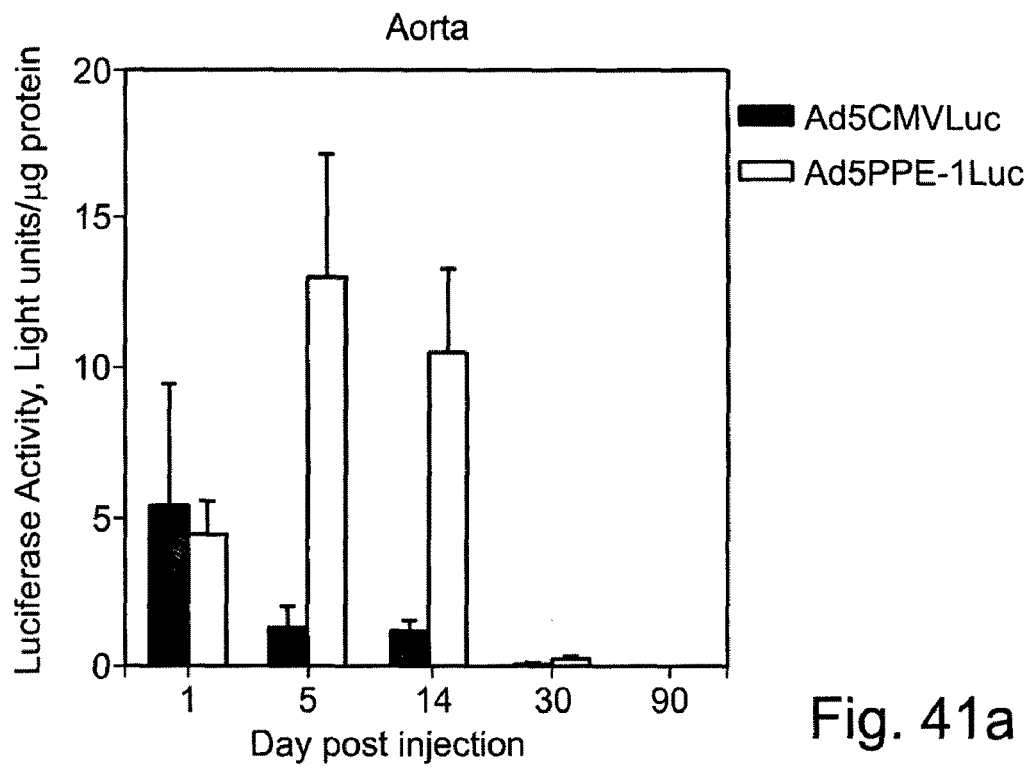
Figure 41B:
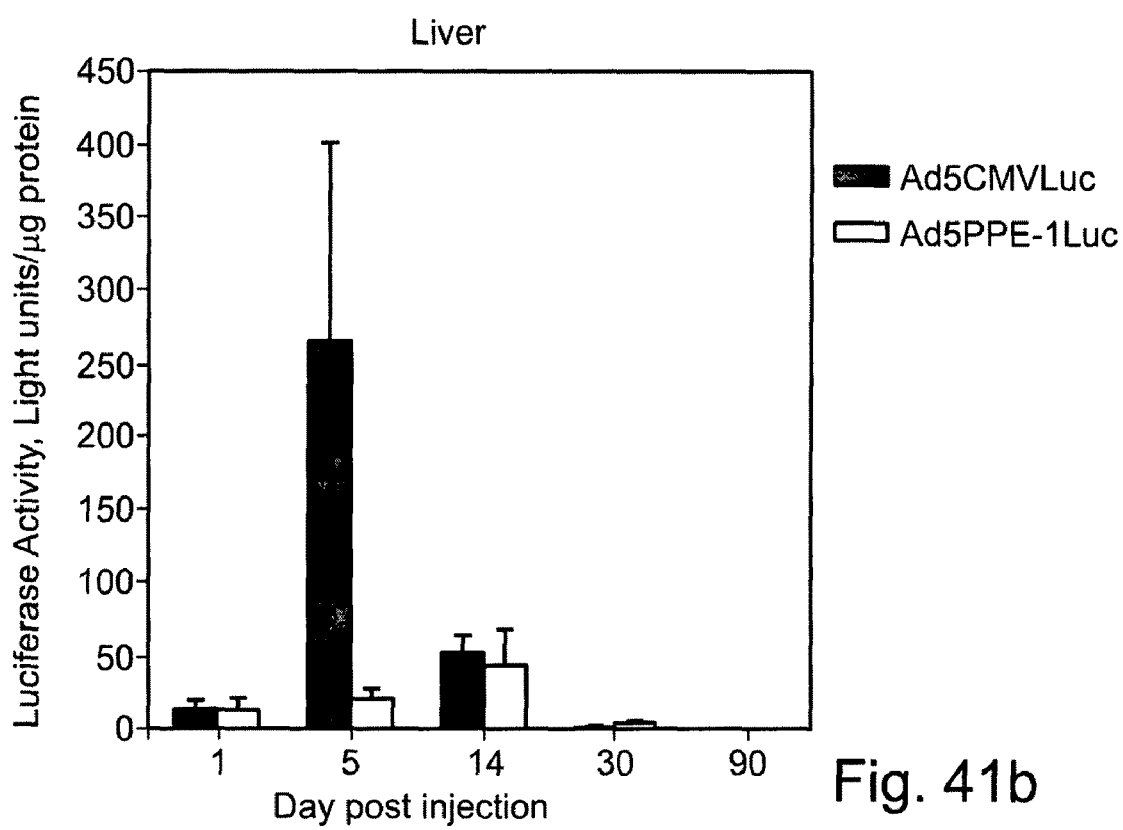
Figure 42A:
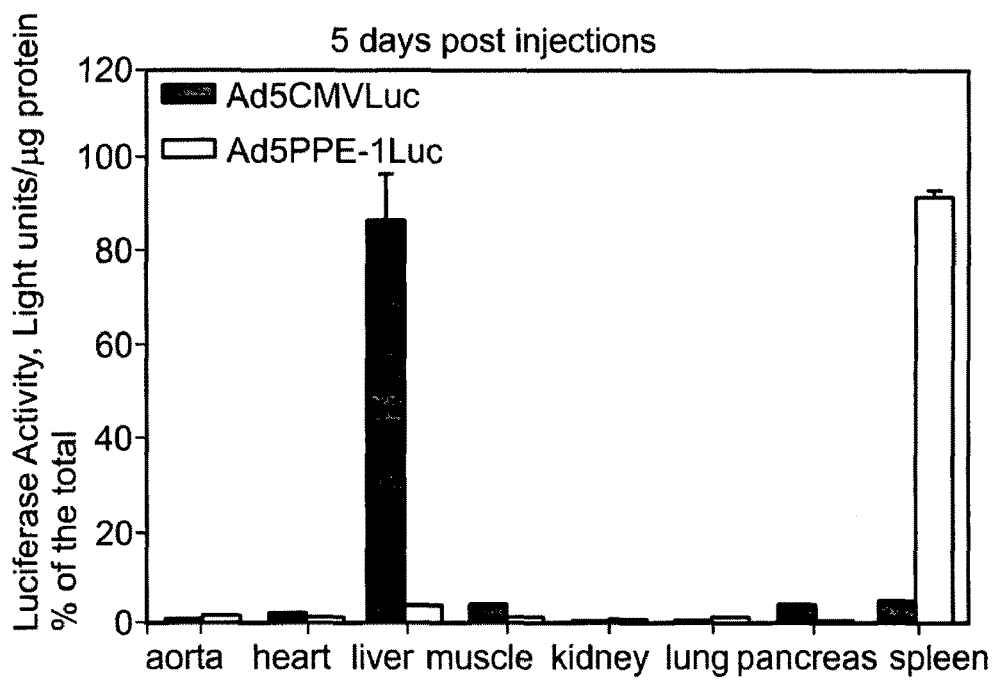
Figure 42B:
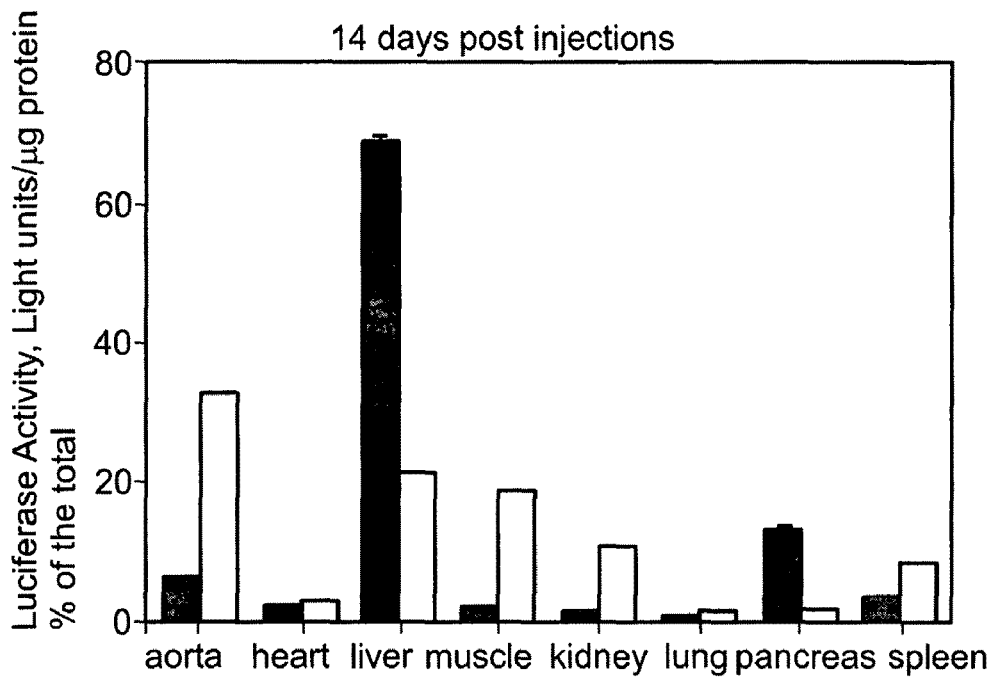
Figure 43:
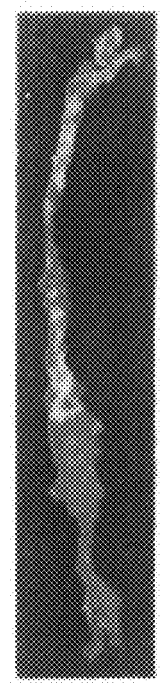
Figure 44:
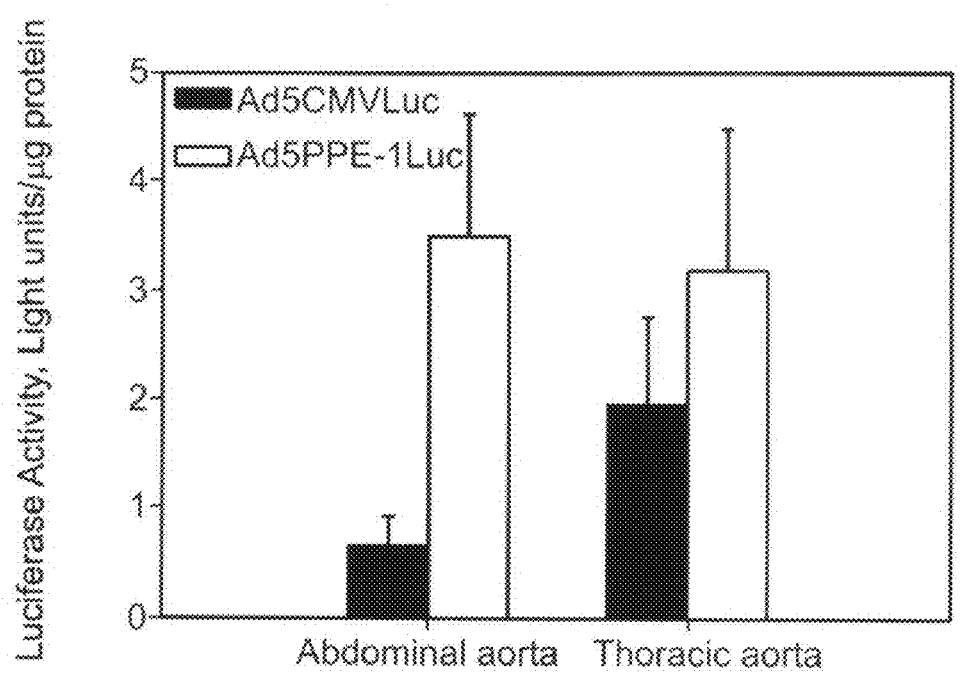
Figure 45:
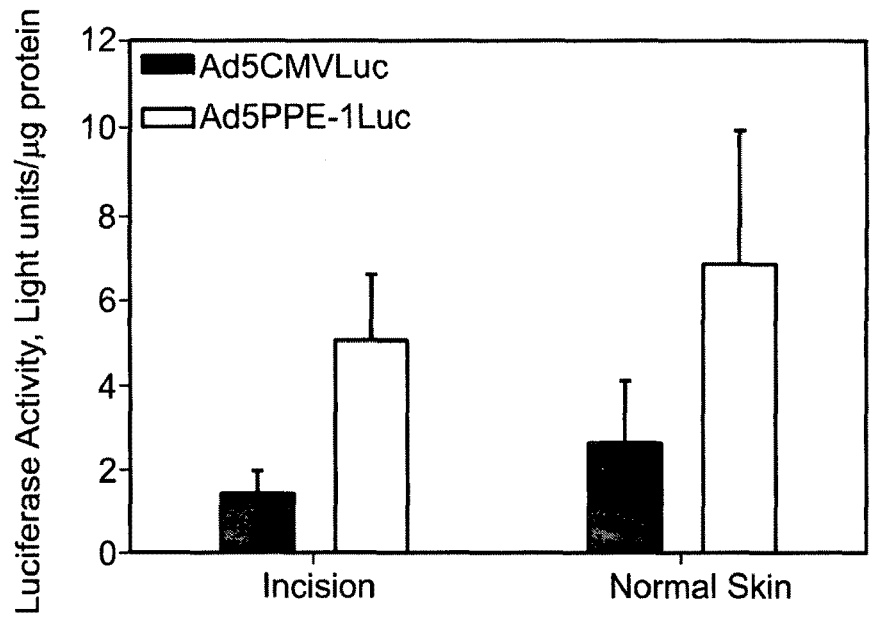
Figure 46:
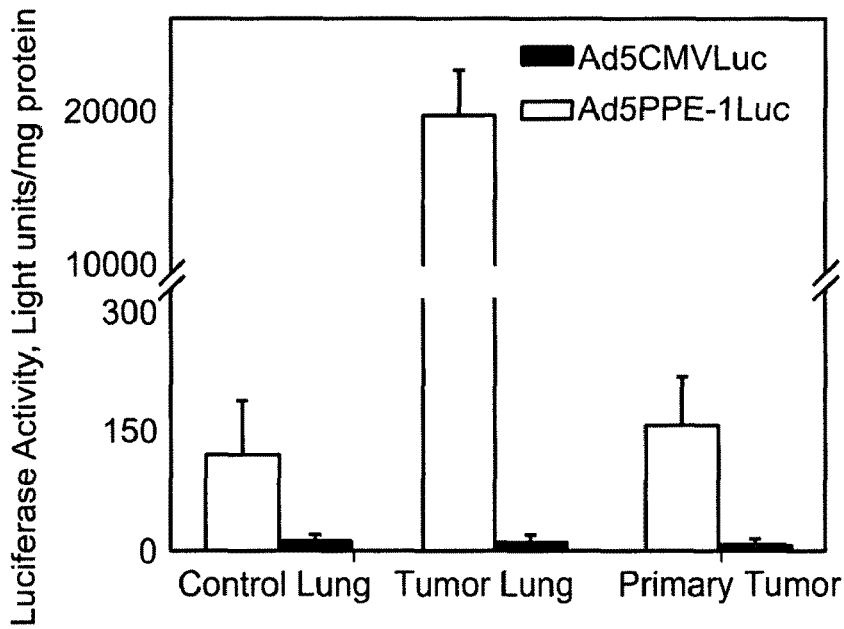
Figure 47A:
Figure 47B:
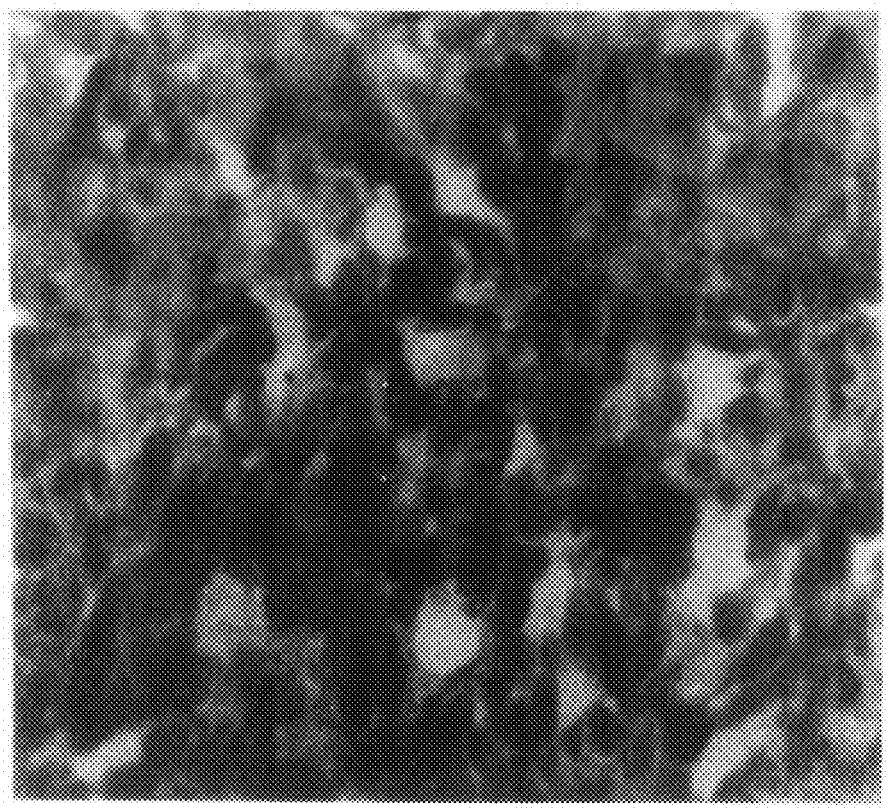
Figure 47C:
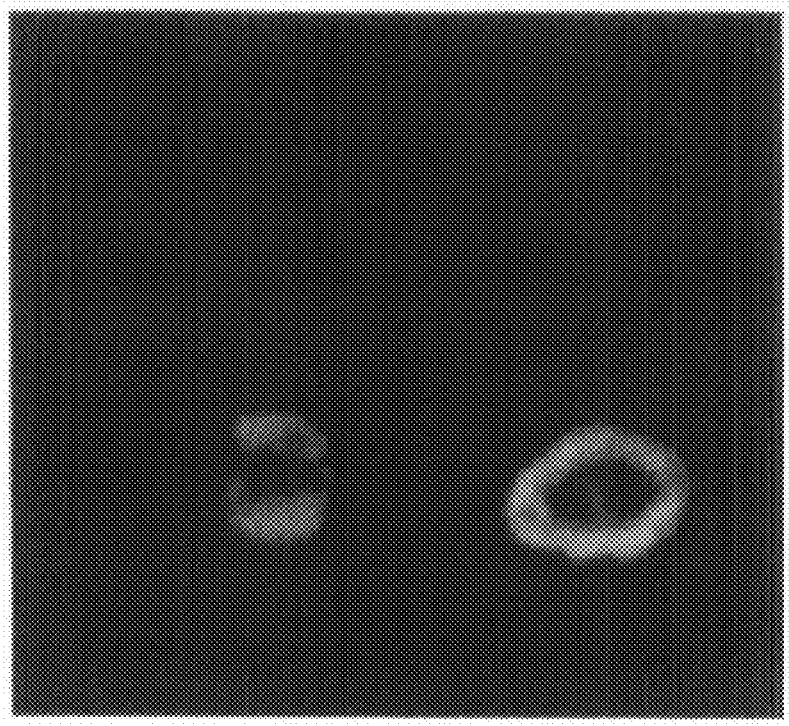
Figure 47D:
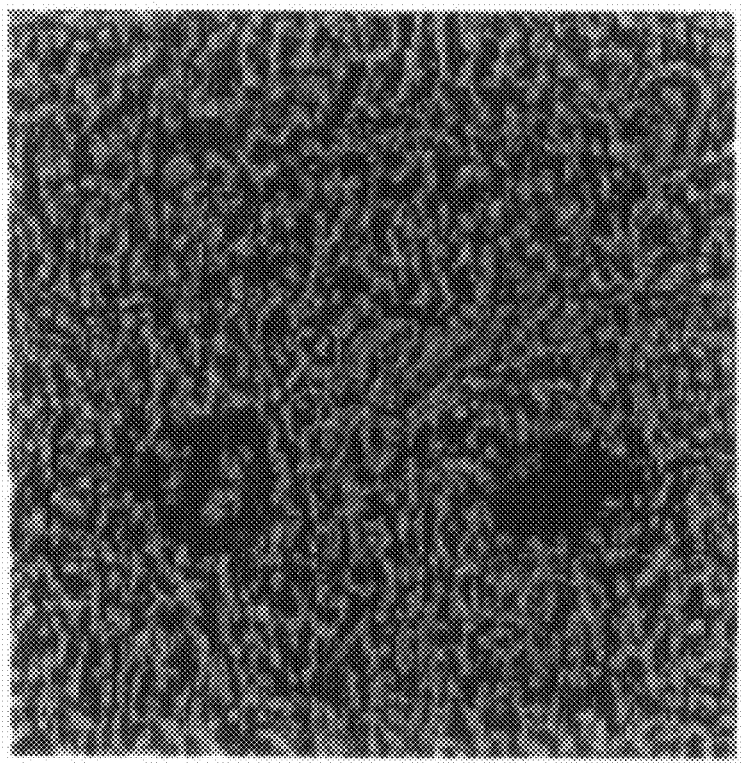
Figure 48:
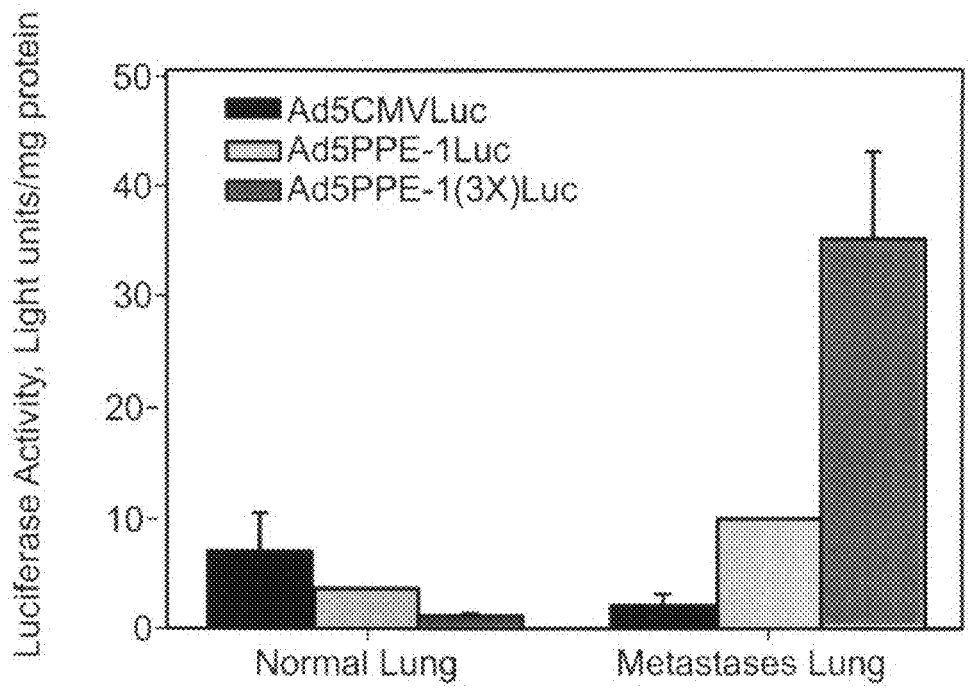
Figure 49:
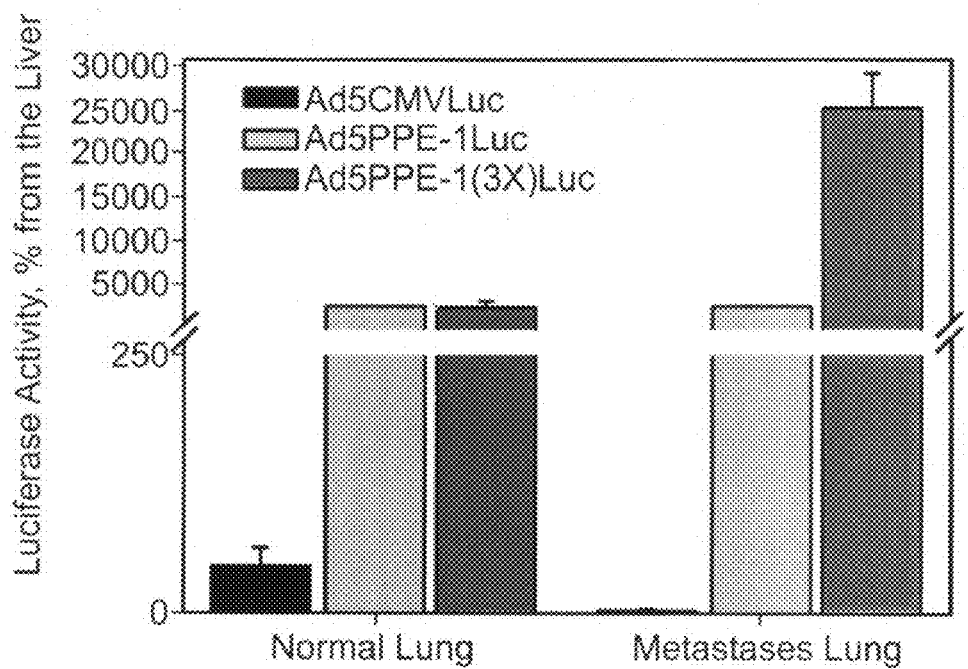
Figure 50A:
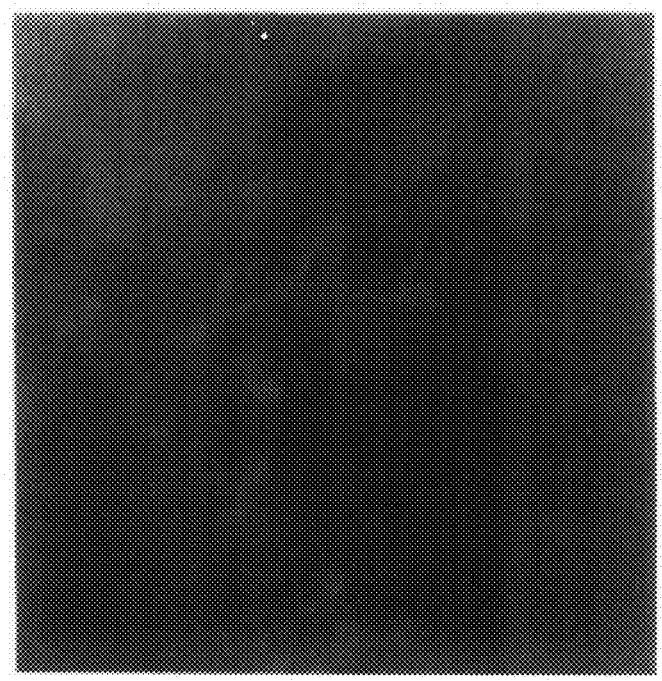
Figure 50B:
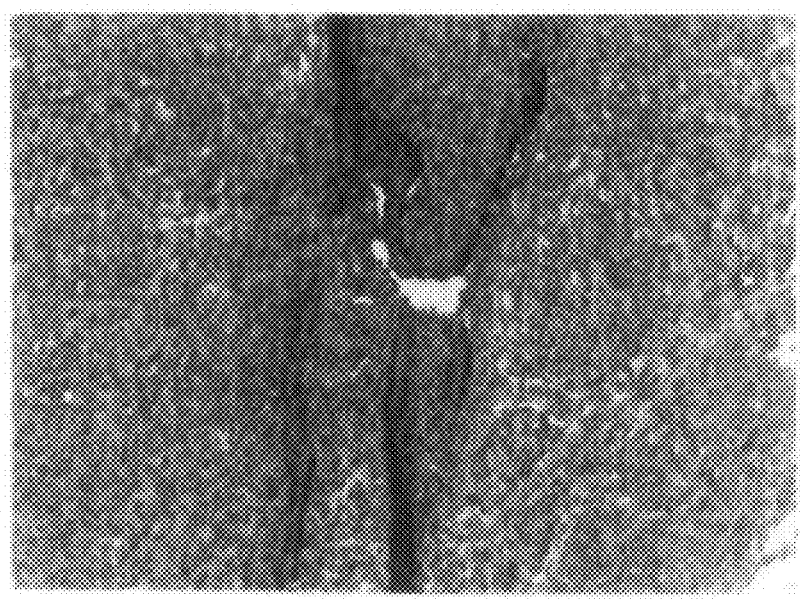
Figure 51:
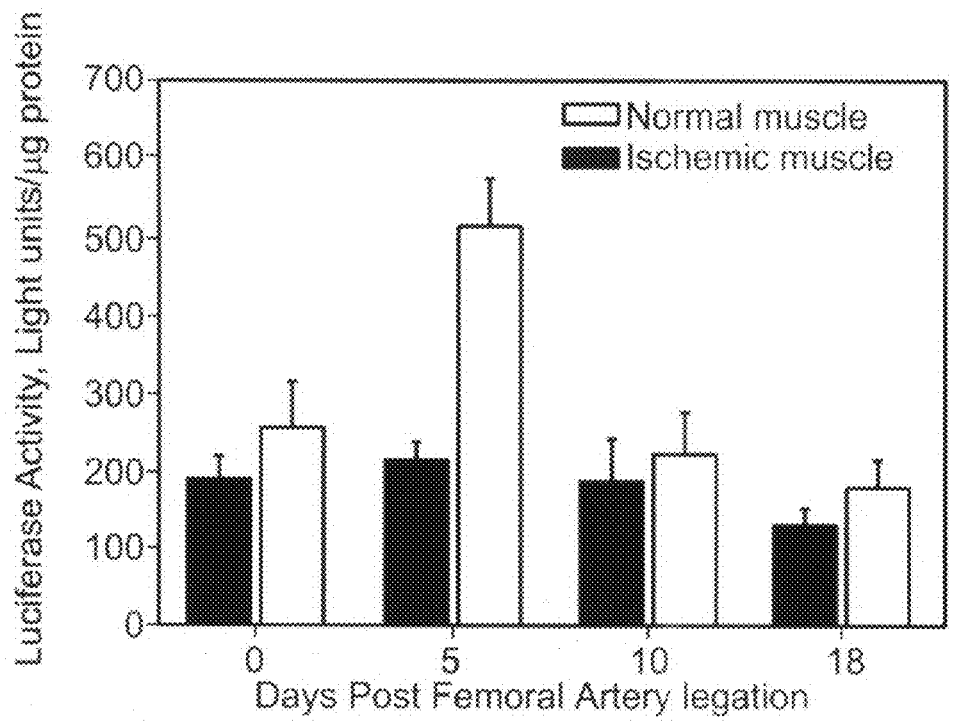
Figure 52:
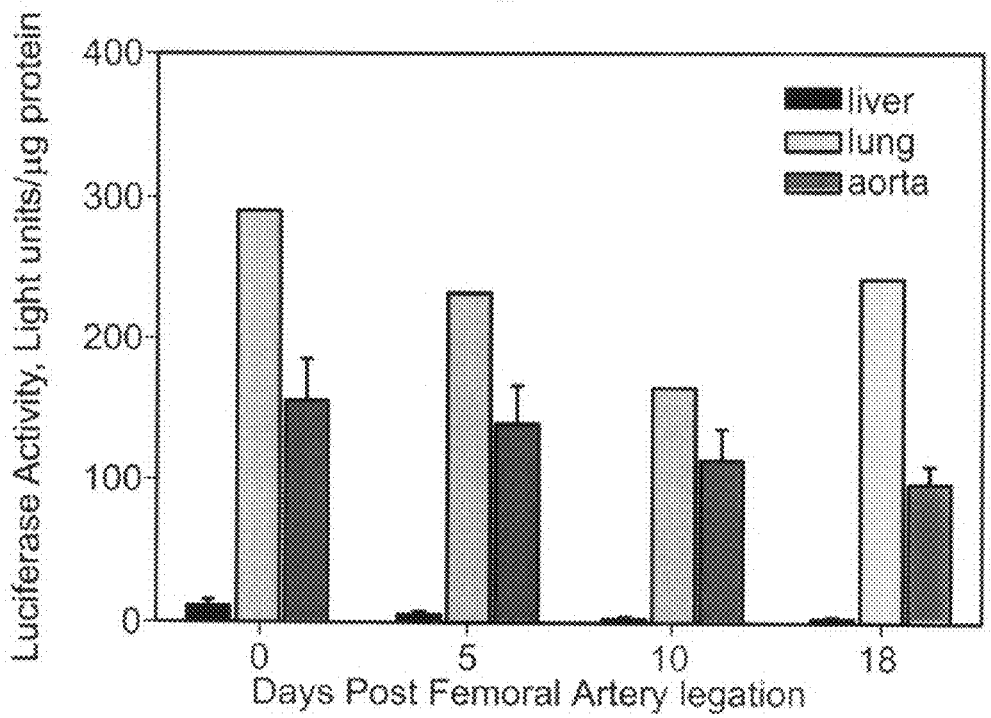
Figure 53:
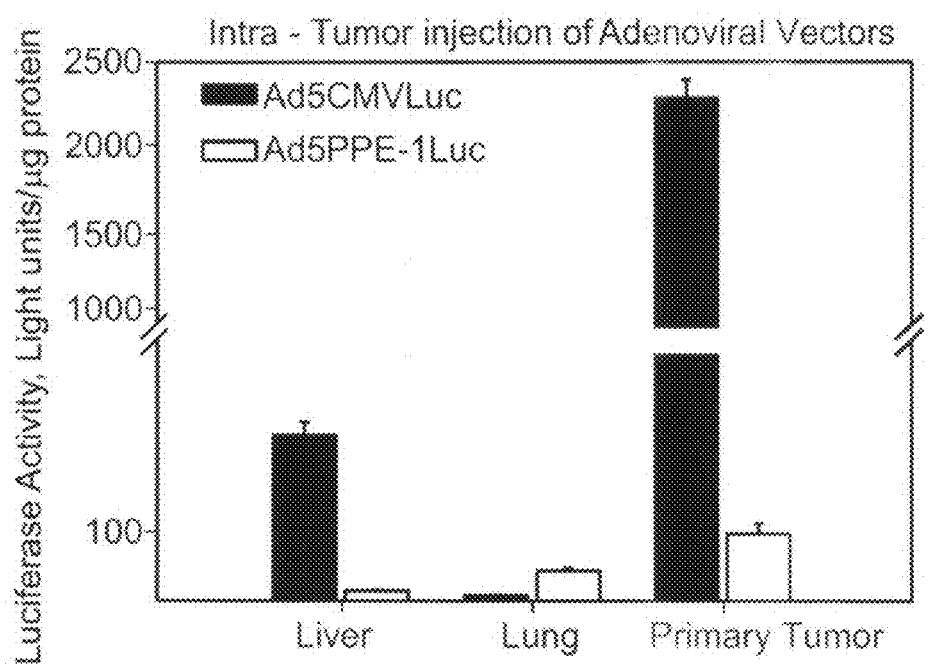
Figure 54A:
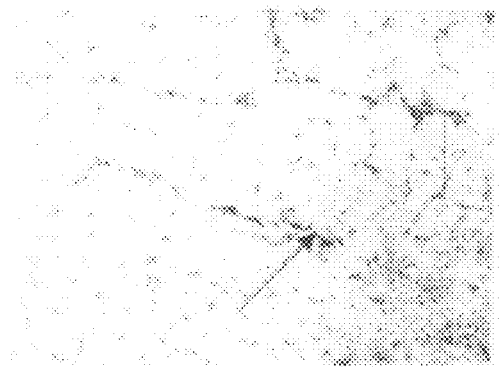
Figure 54C:
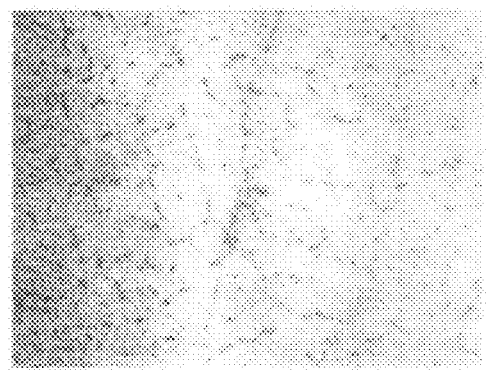
Figure 54B:
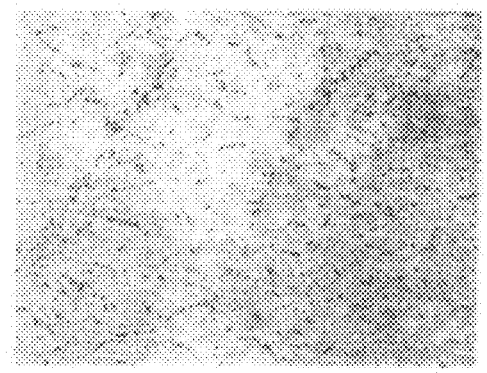
Figure 54D:
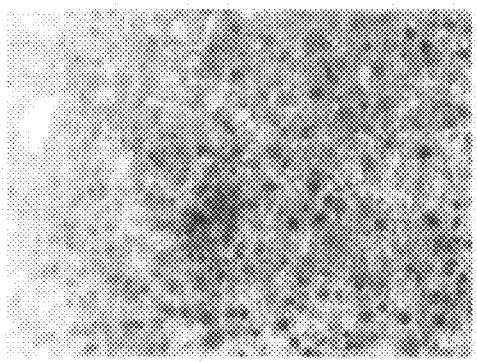
Figure 54E:
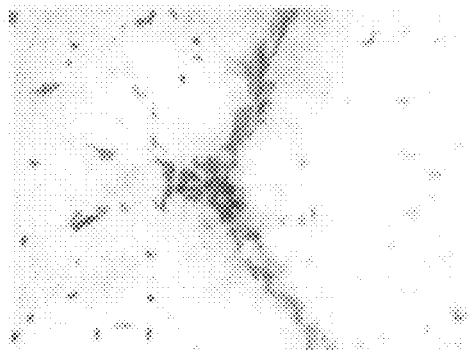
Figure 54F:
Figure 54G:
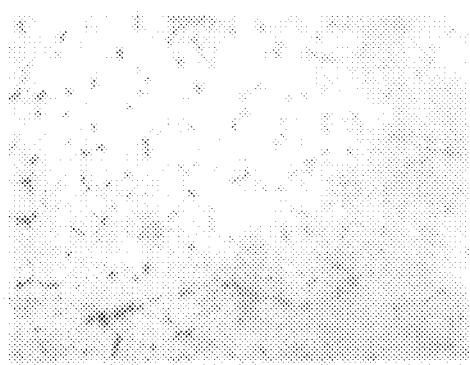
Figure 54H:
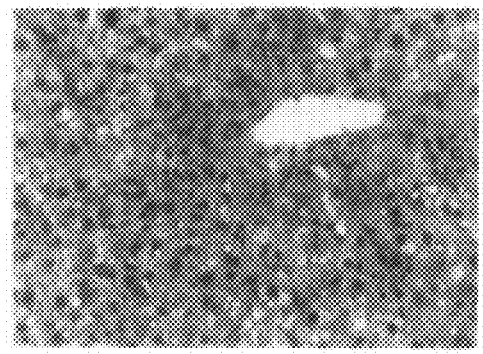
Figure 55A:
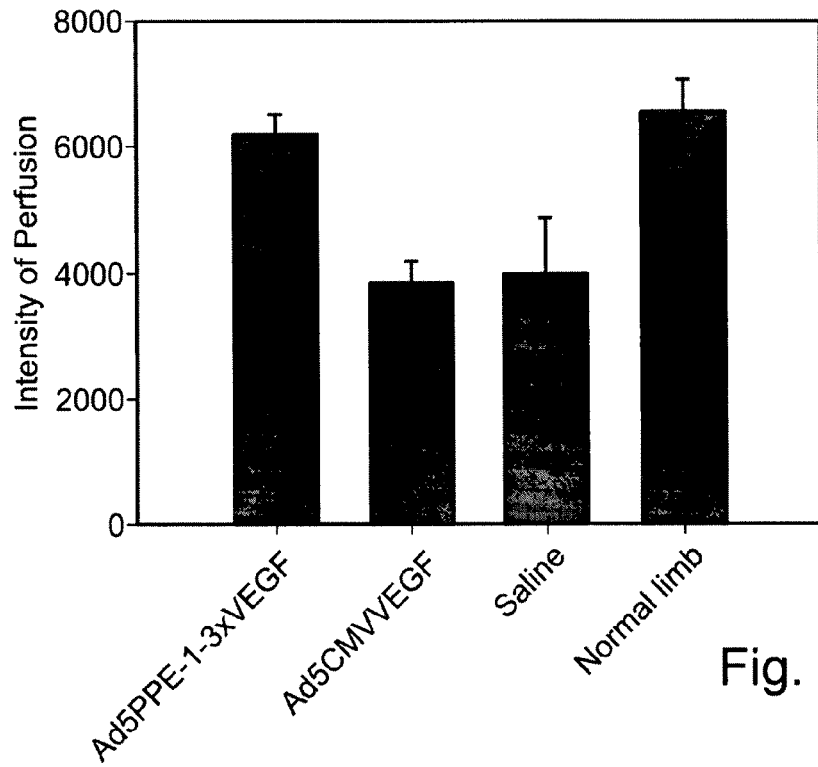
Figure 55B:
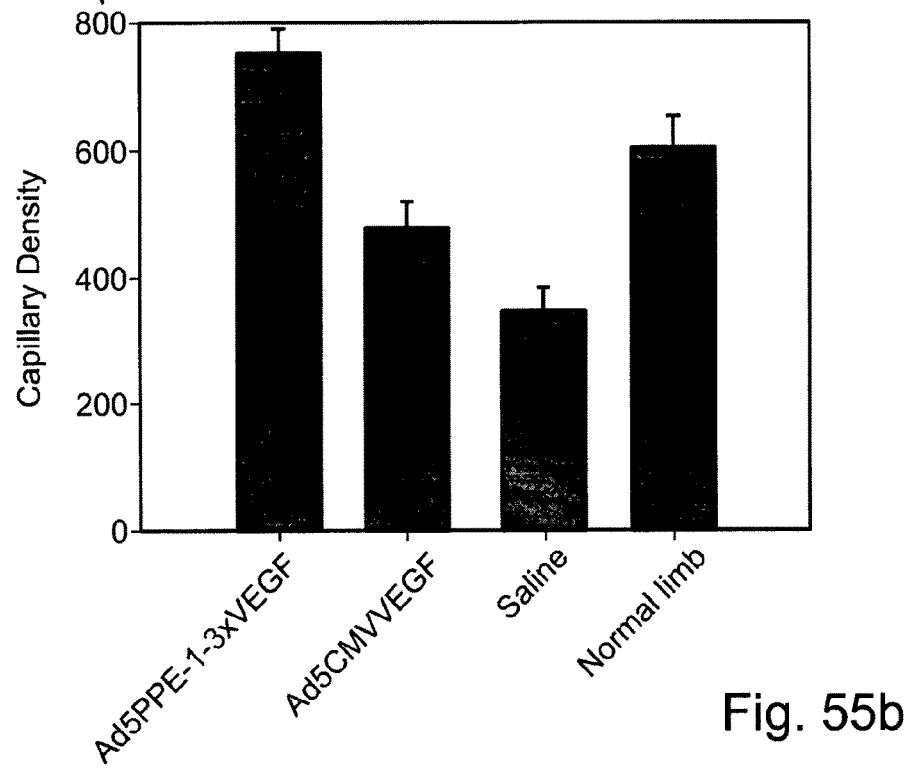
Figure 56A:
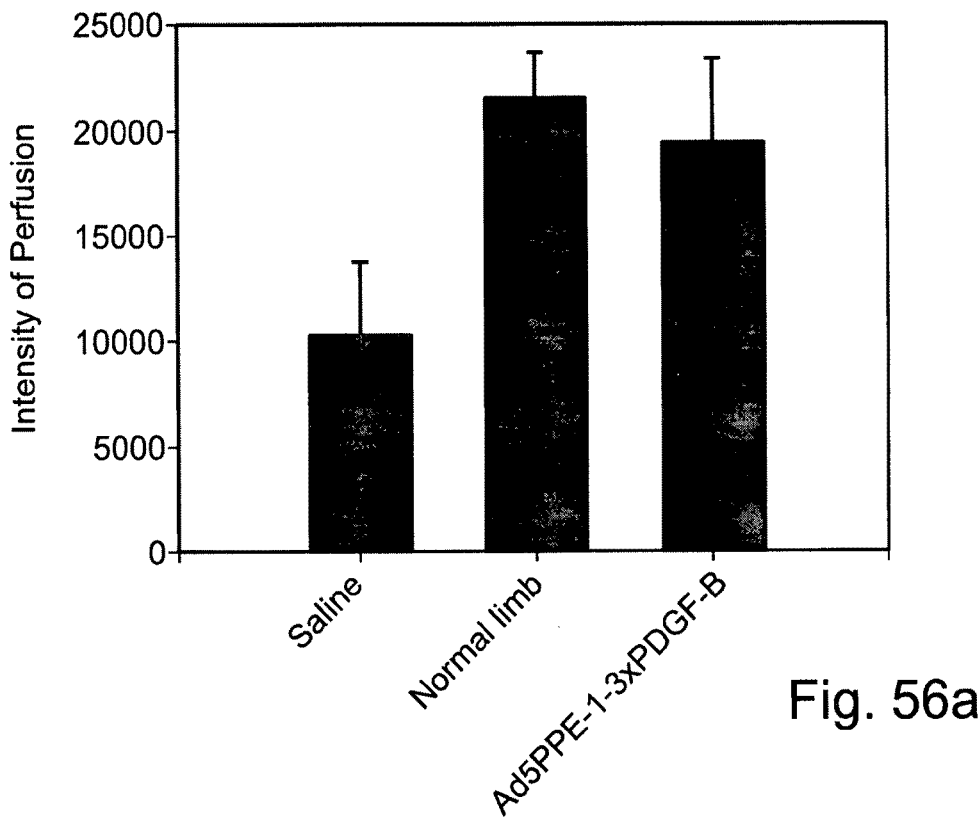
Figure 56B:
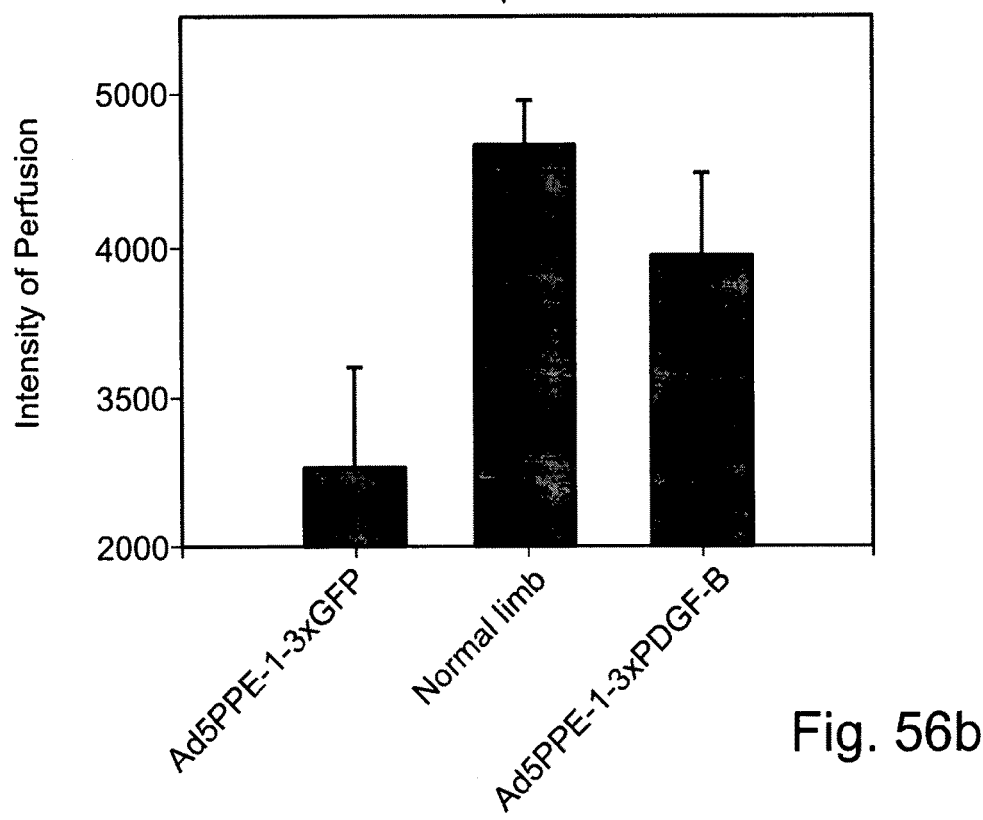
Figure 56C:
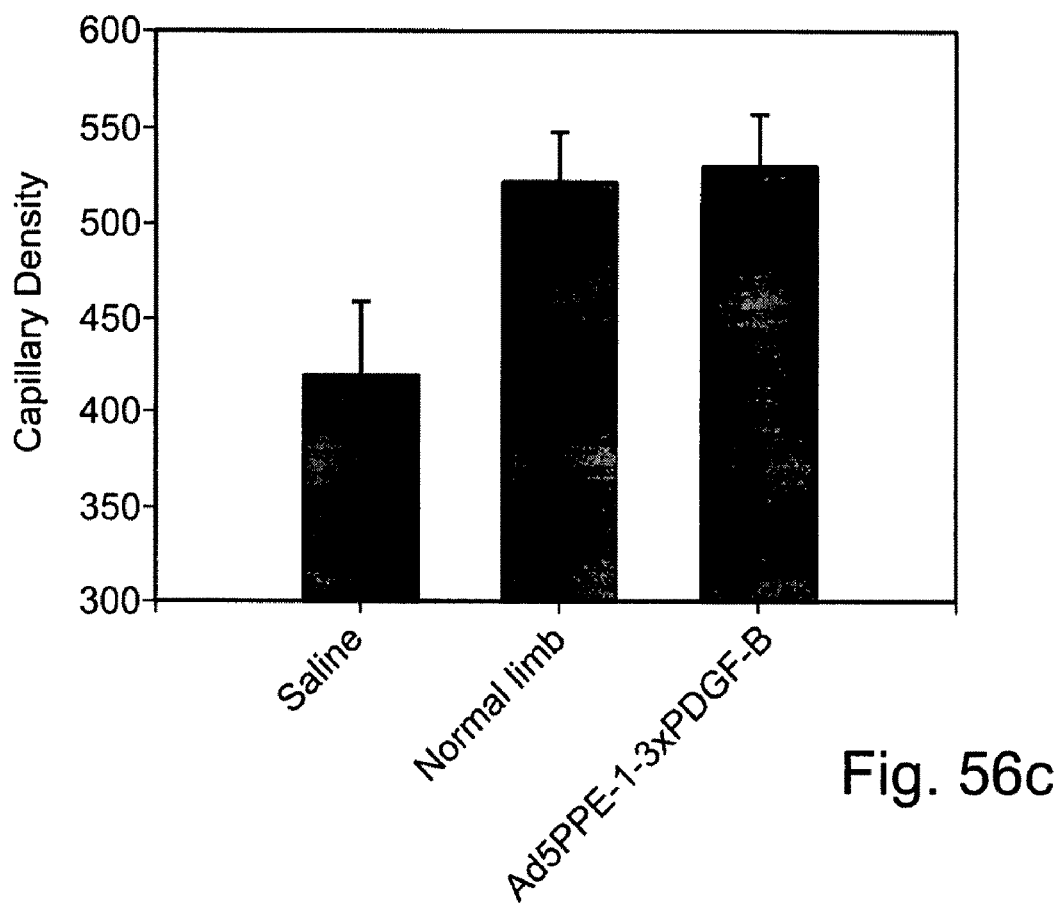
Figure 56D:
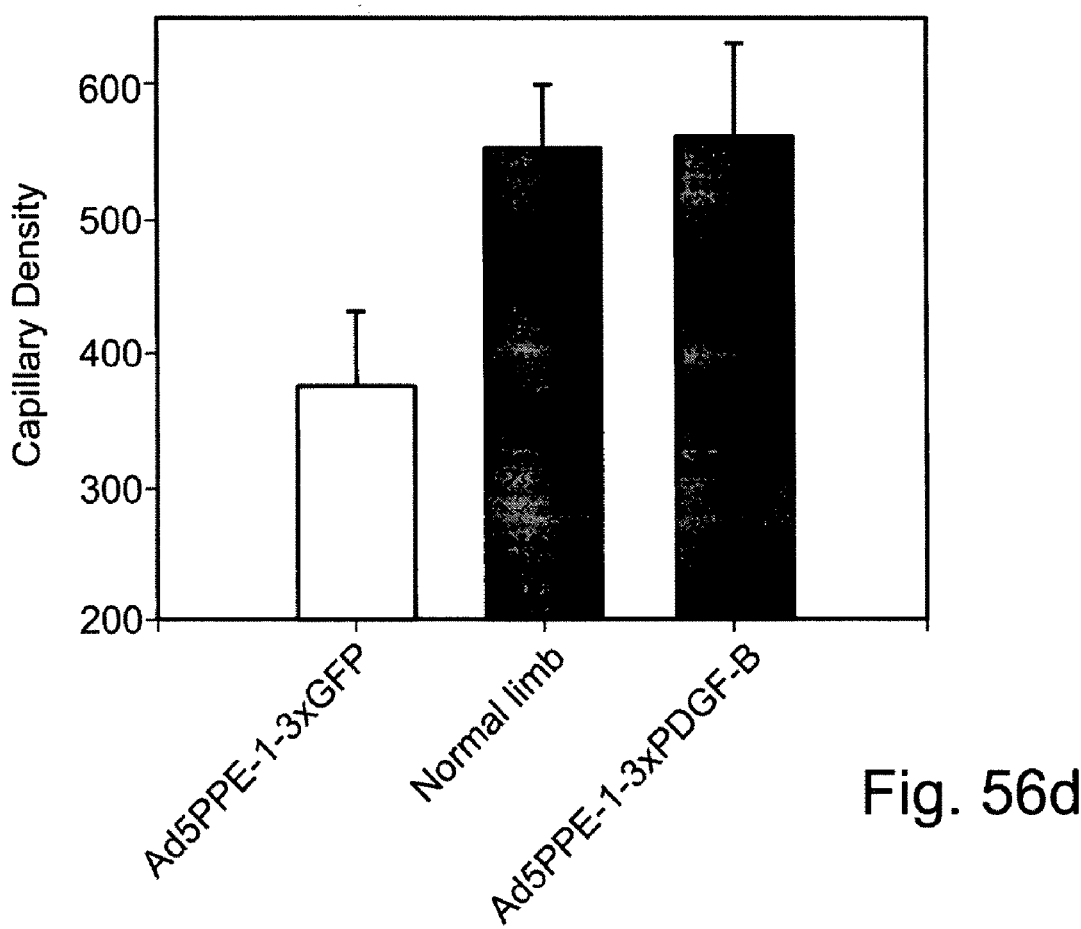
Figure 58:
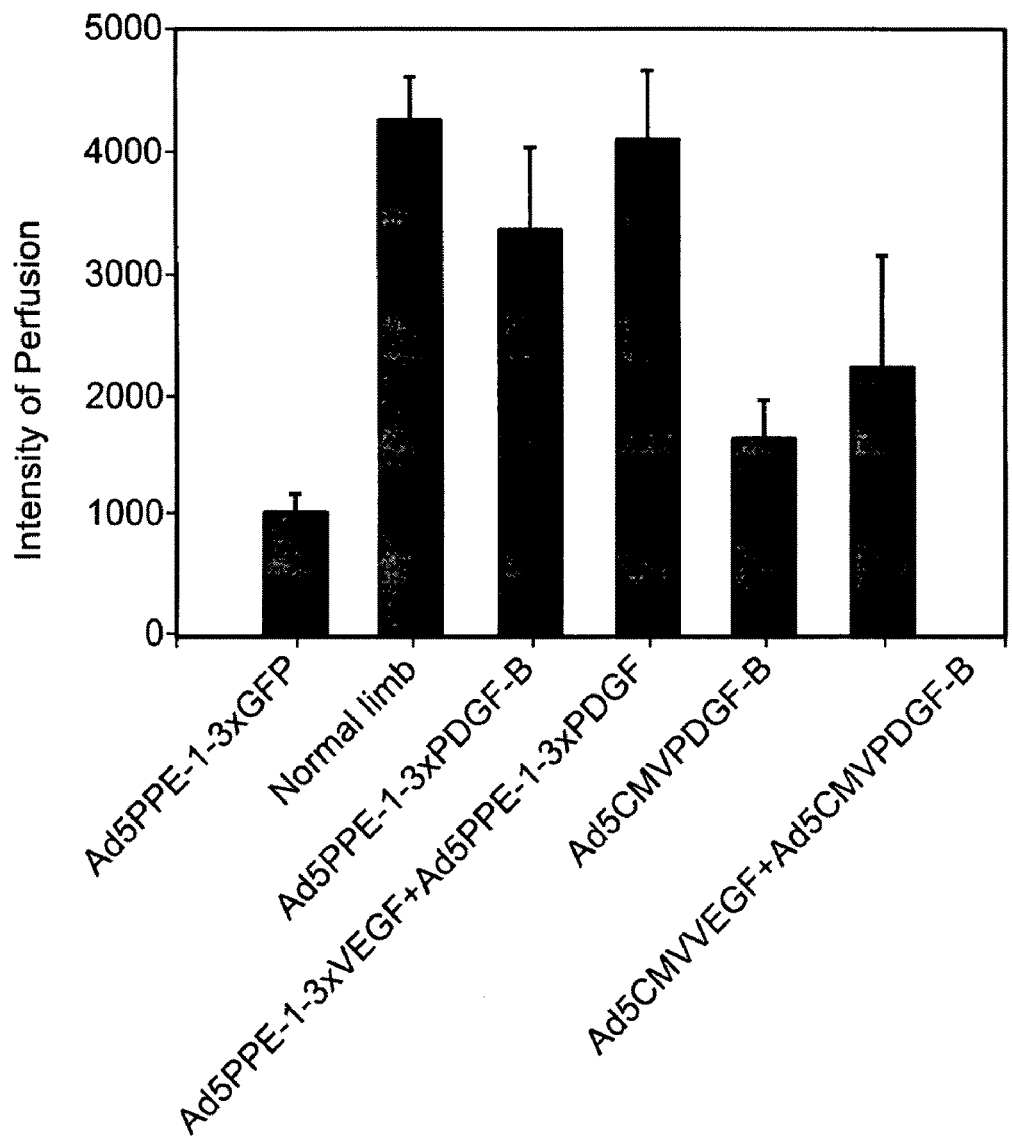
Figure 59:
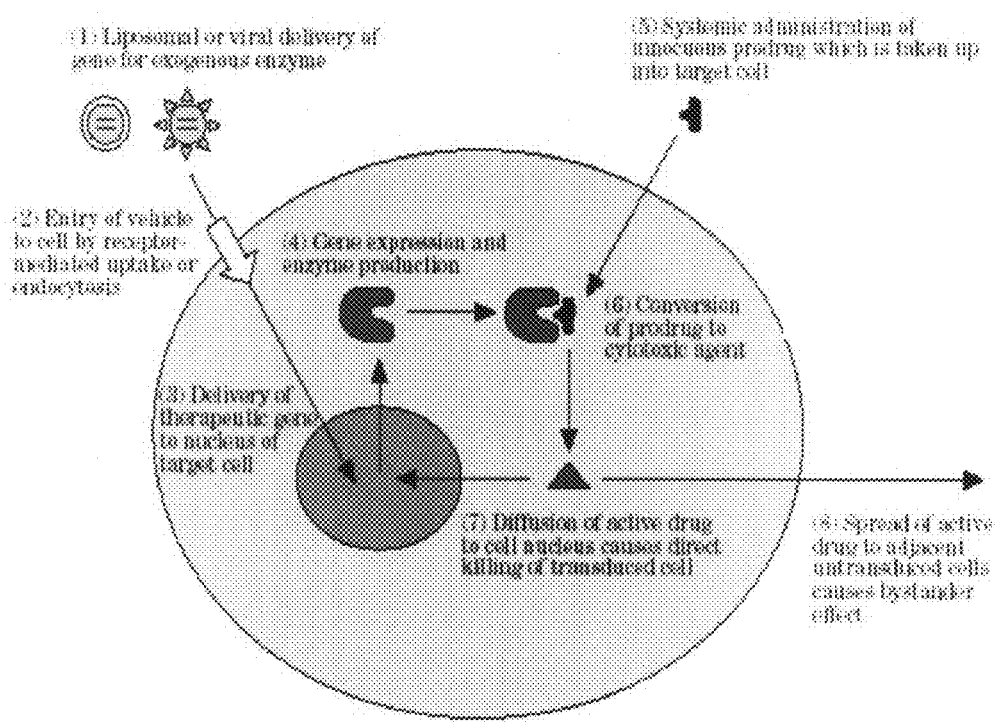
Figure 60A:
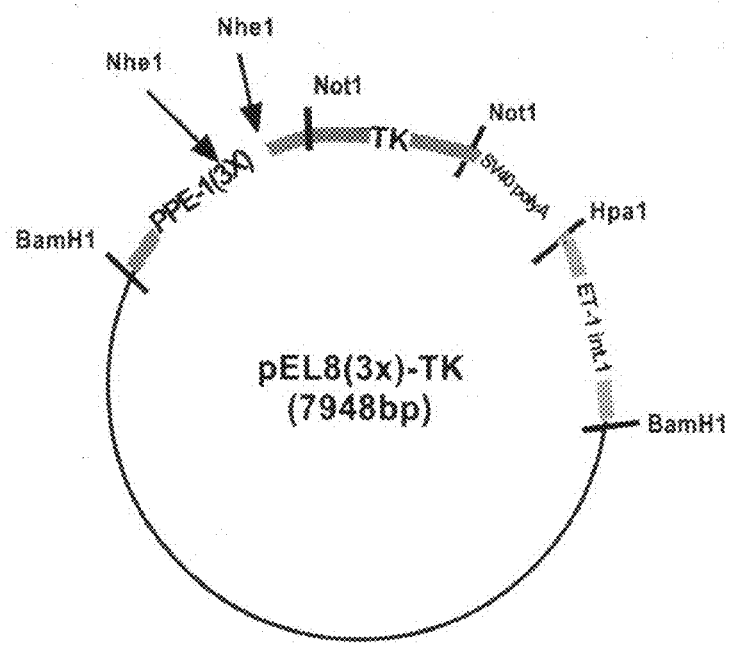
Figure 60B:
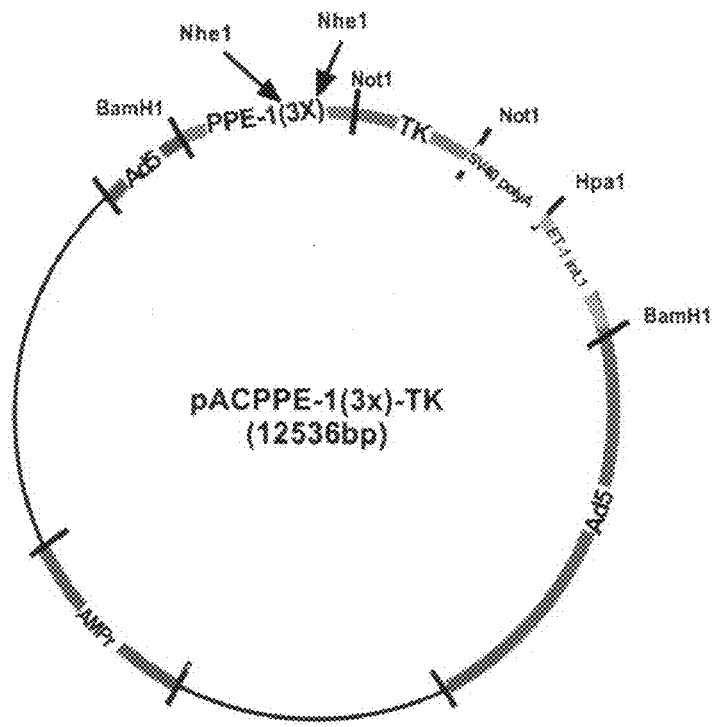
Figure 61:
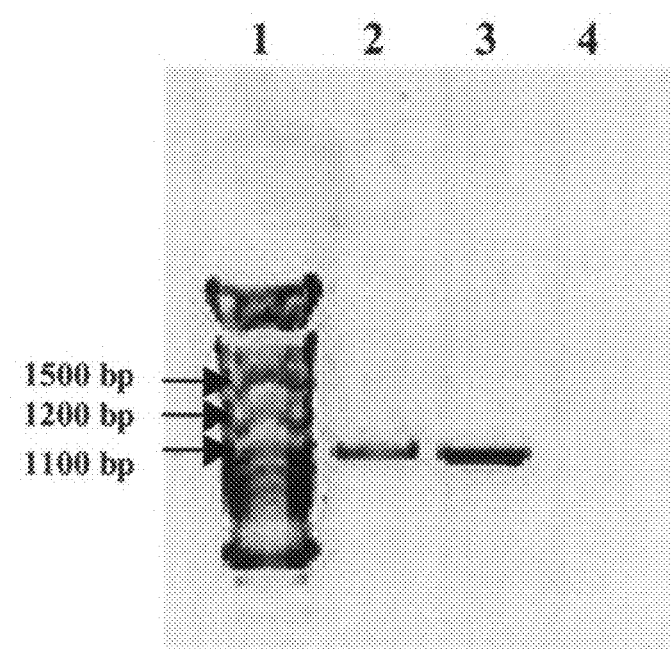
Figure 62A:
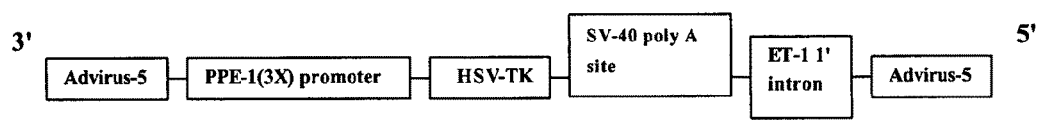
Figure 62B:
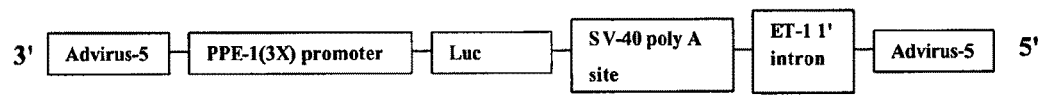
Figure 62C:
Figure 63:
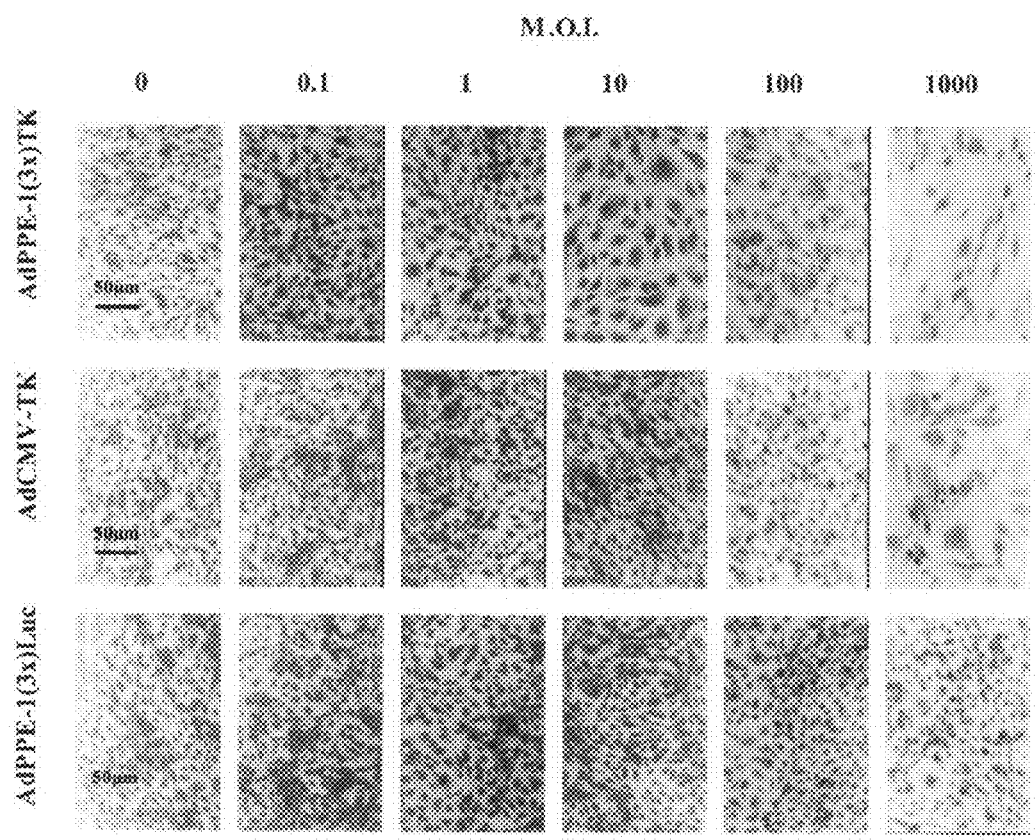
Figure 64:
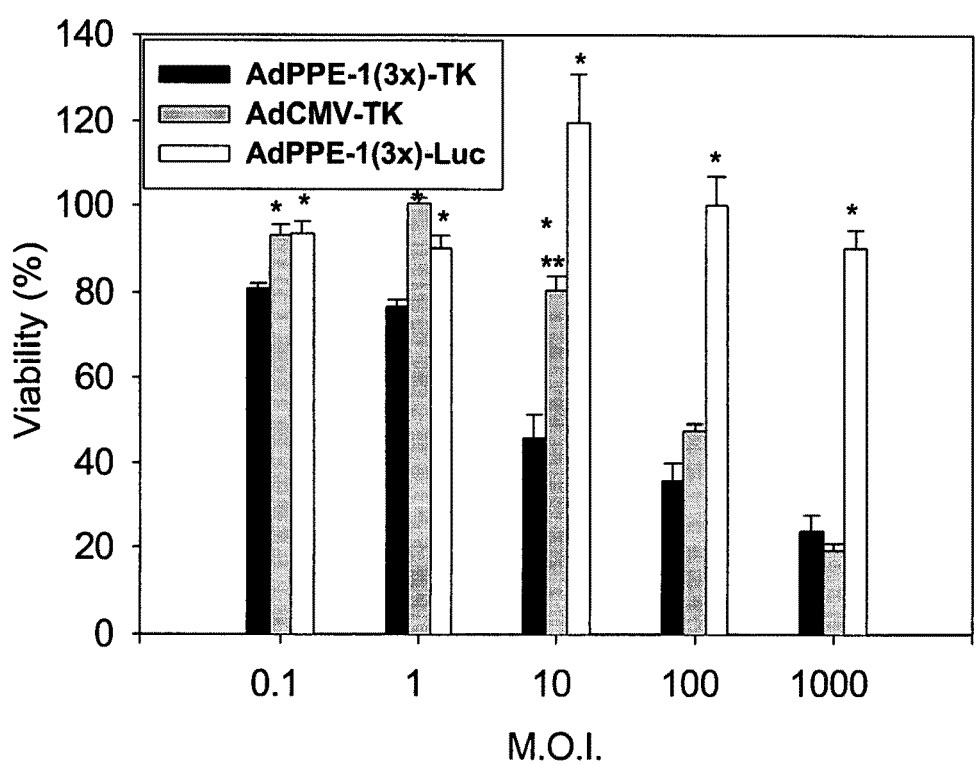
Figure 65:
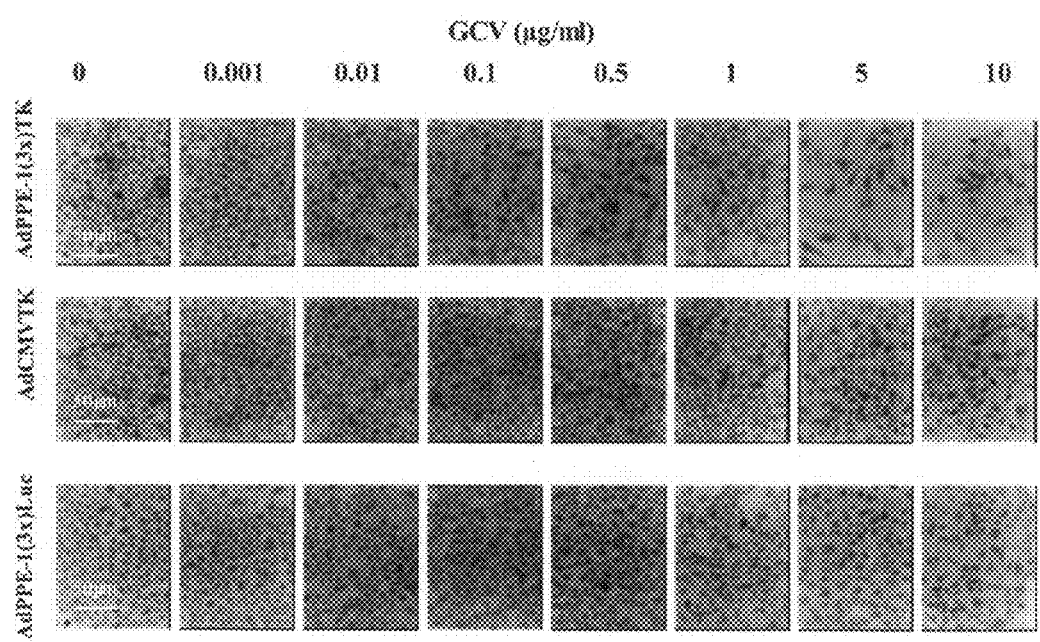
Figure 66:
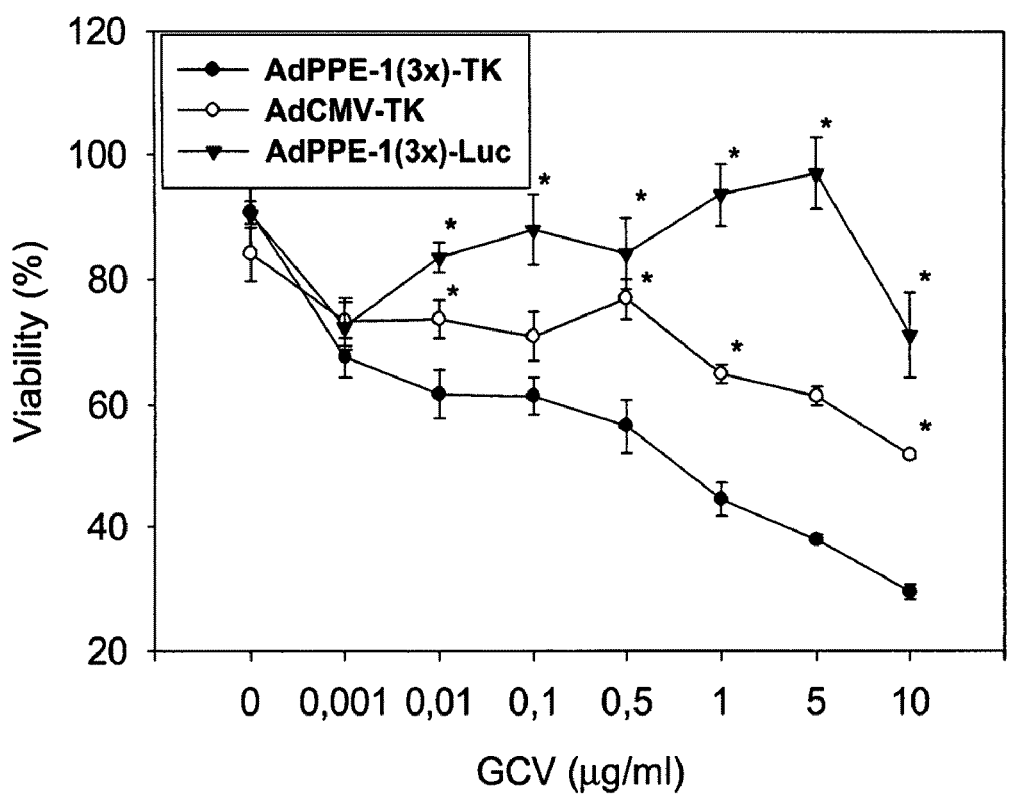
Figure 67:
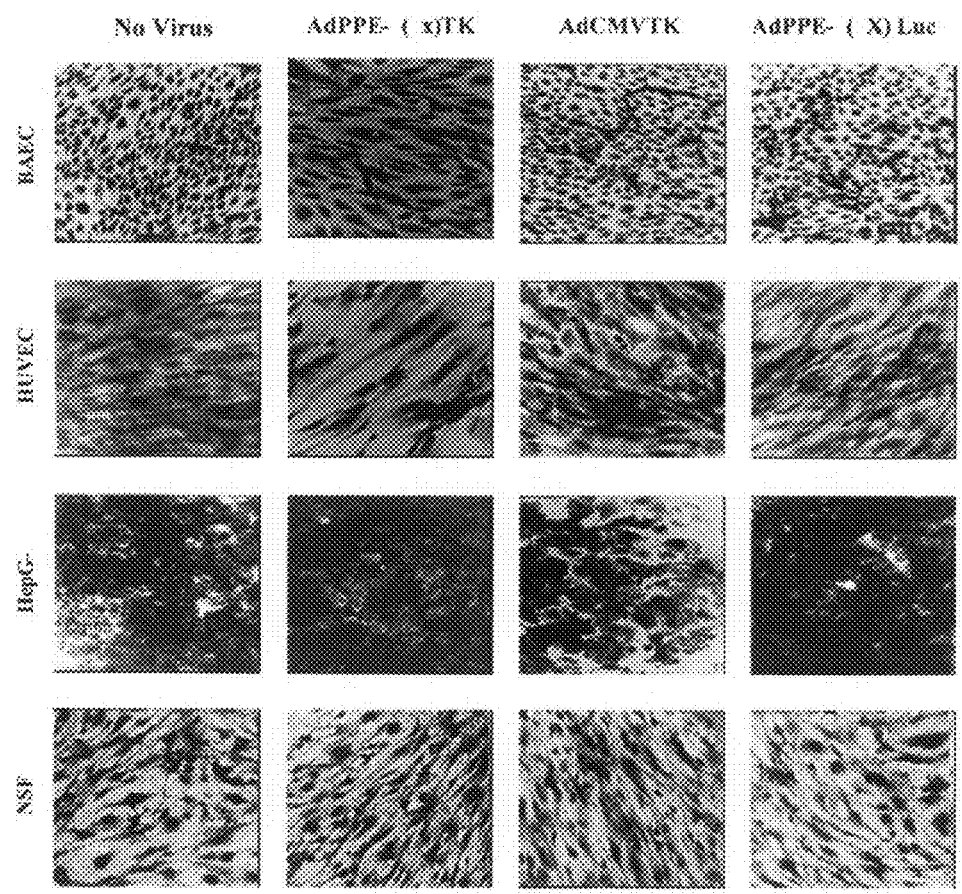
Figure 68:
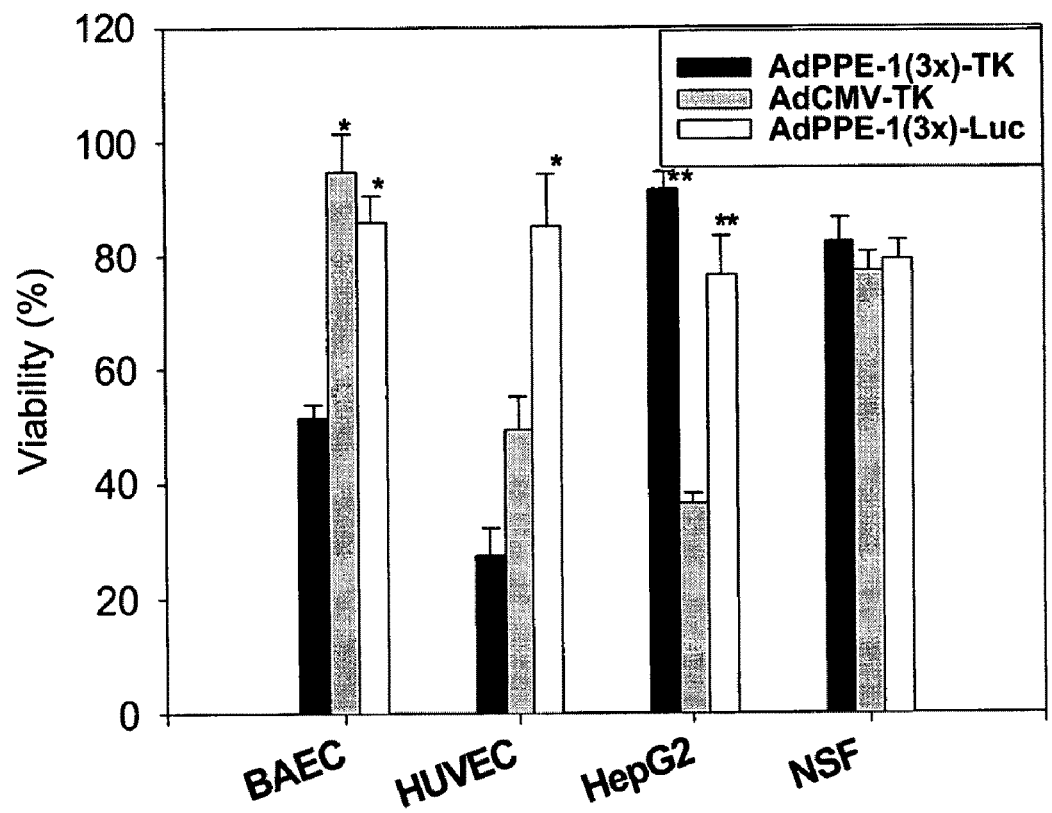
Figure 69:
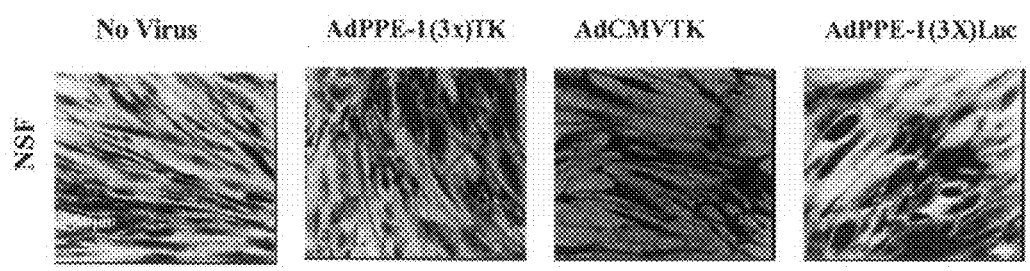
Figure 70:
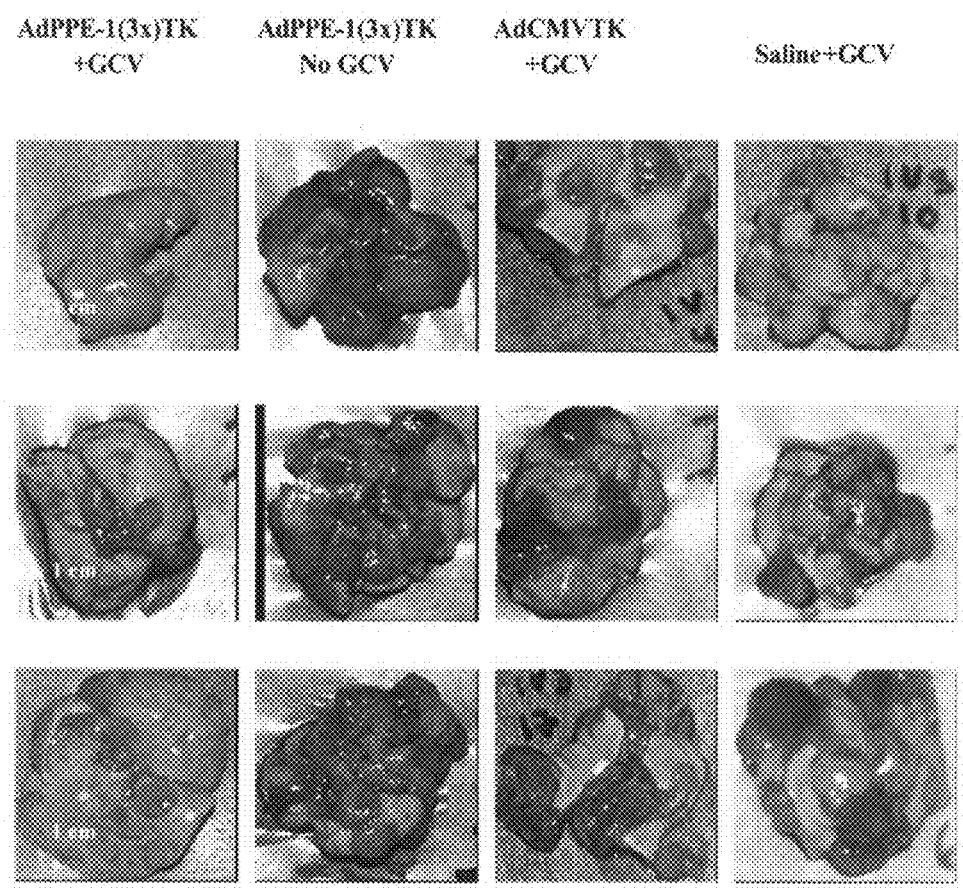
Figure 71:
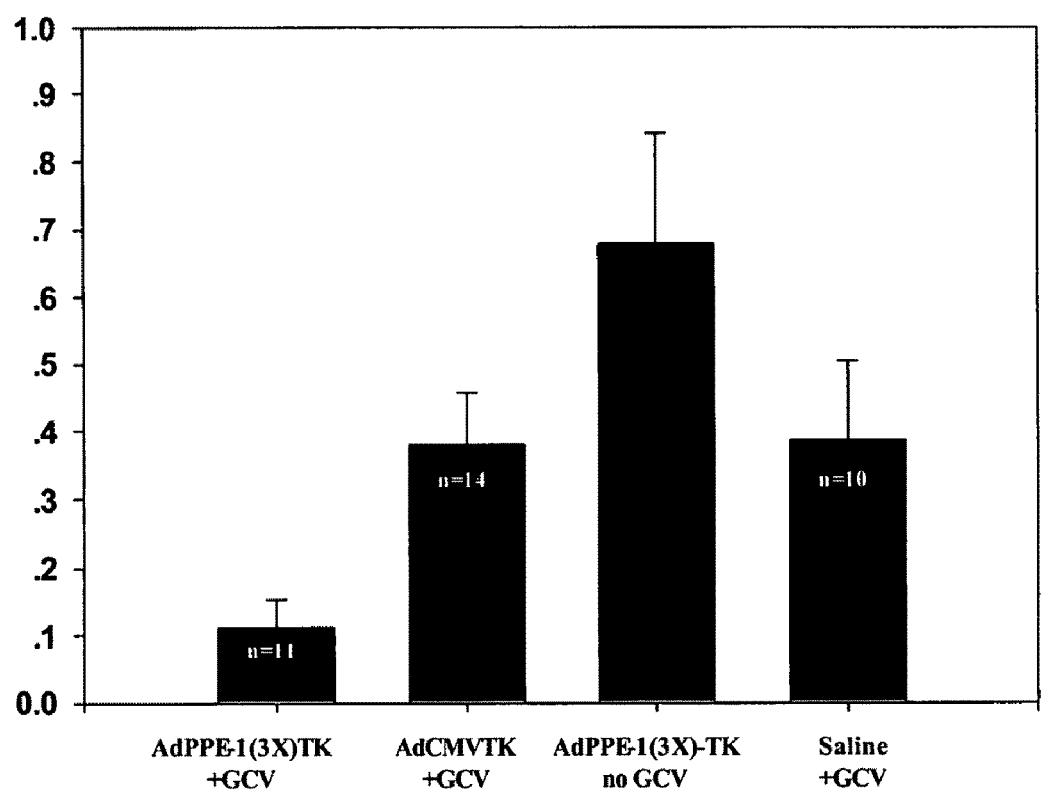
Figure 72A:
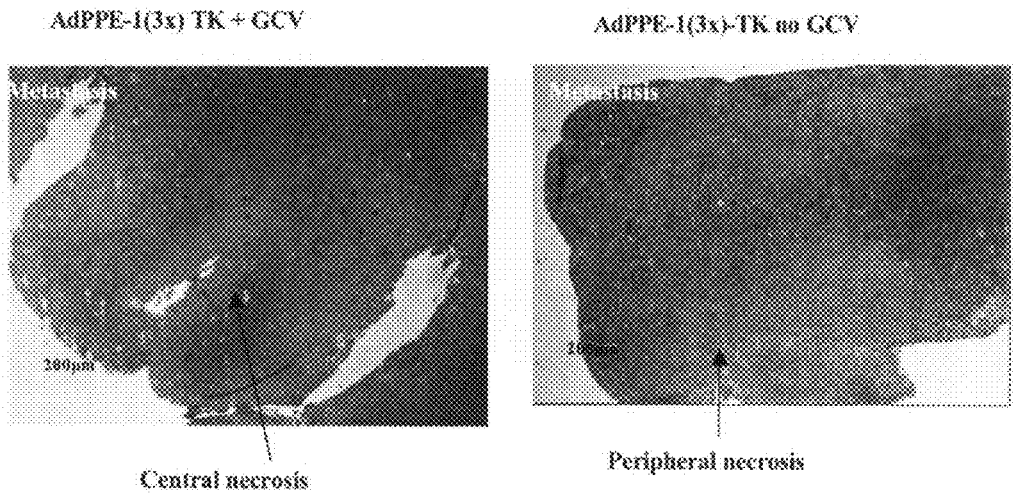
Figure 72B:
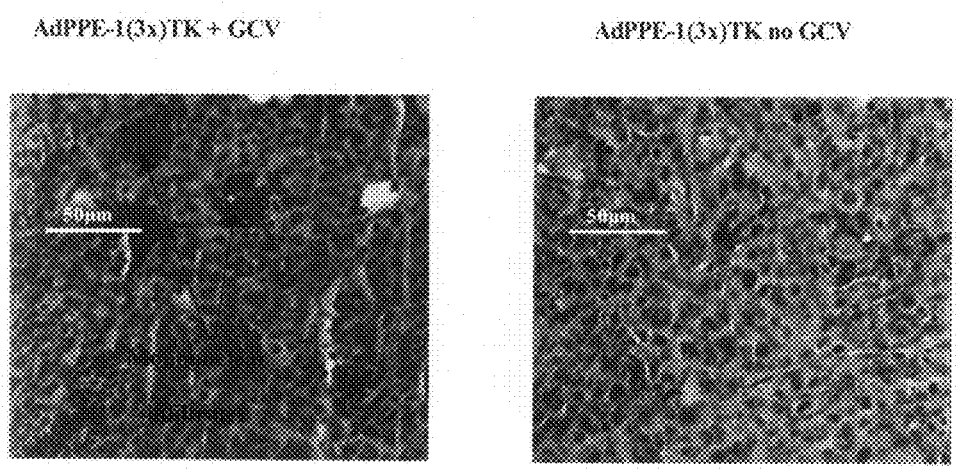
Figure 72C:
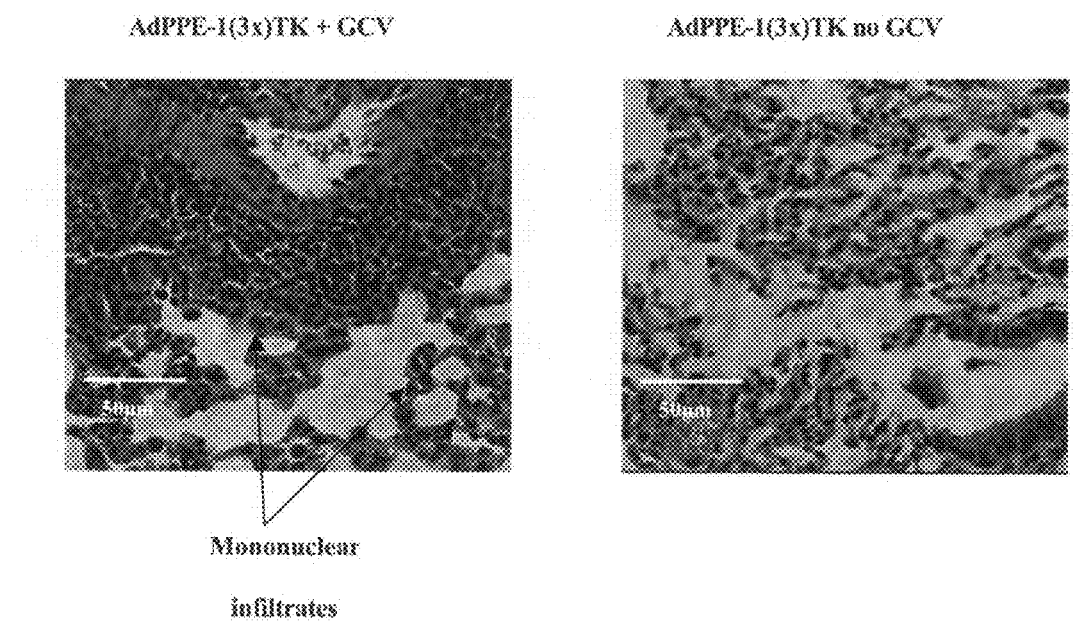
Figure 73A:
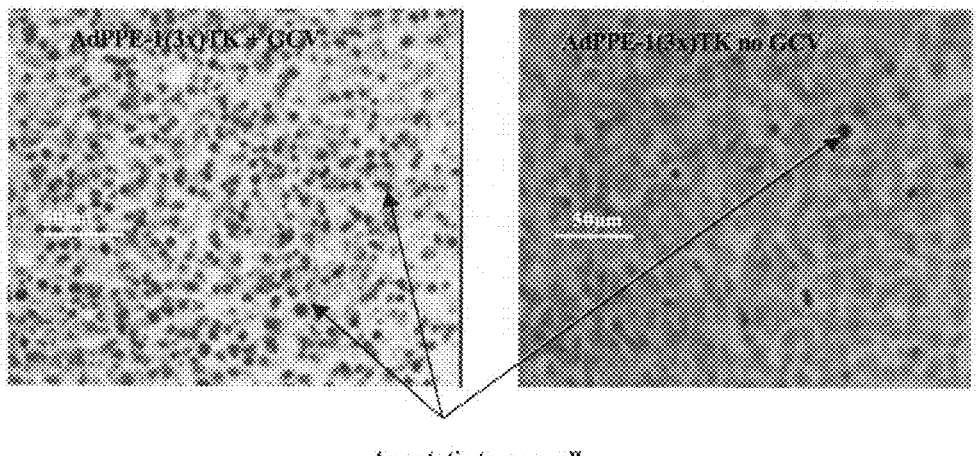
Figure 73B:
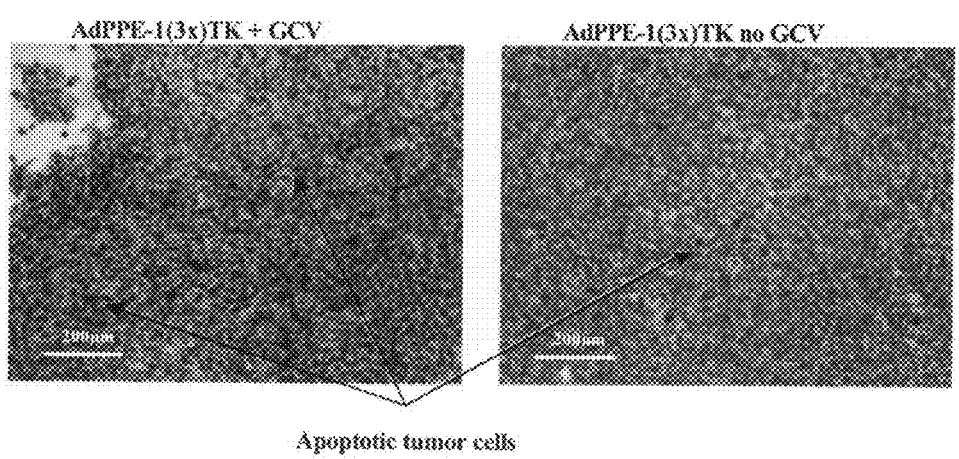
Figure 74A:
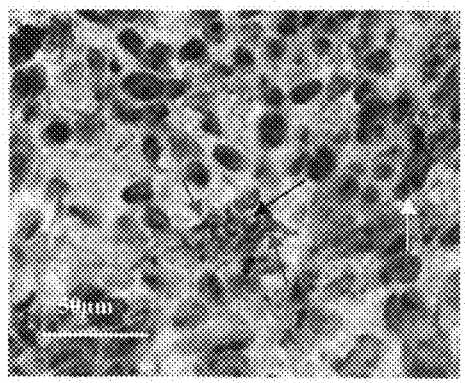
Figure 74B:
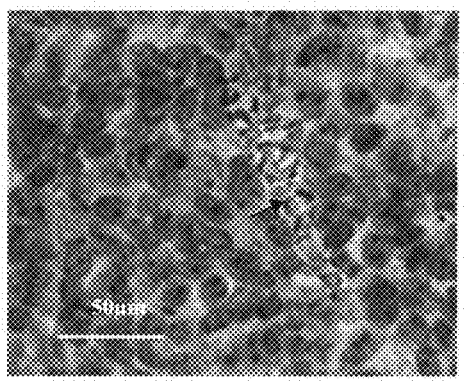
Figure 75B:
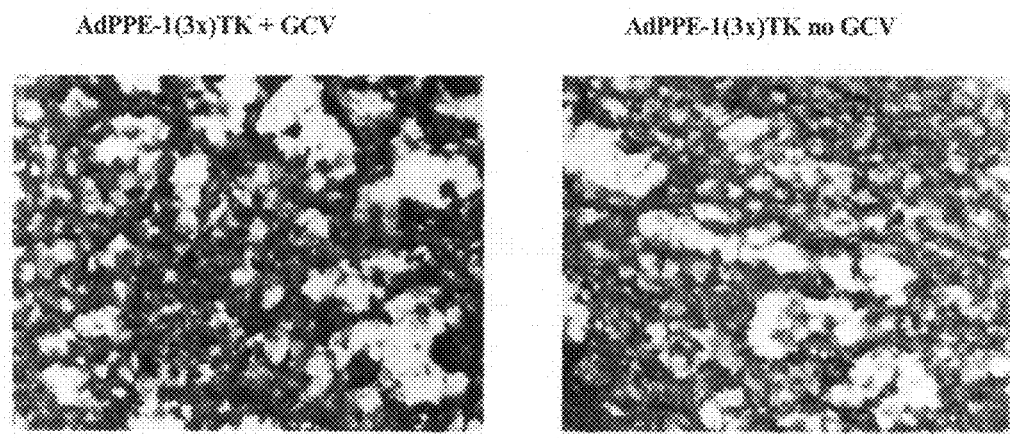
Figure 75C:
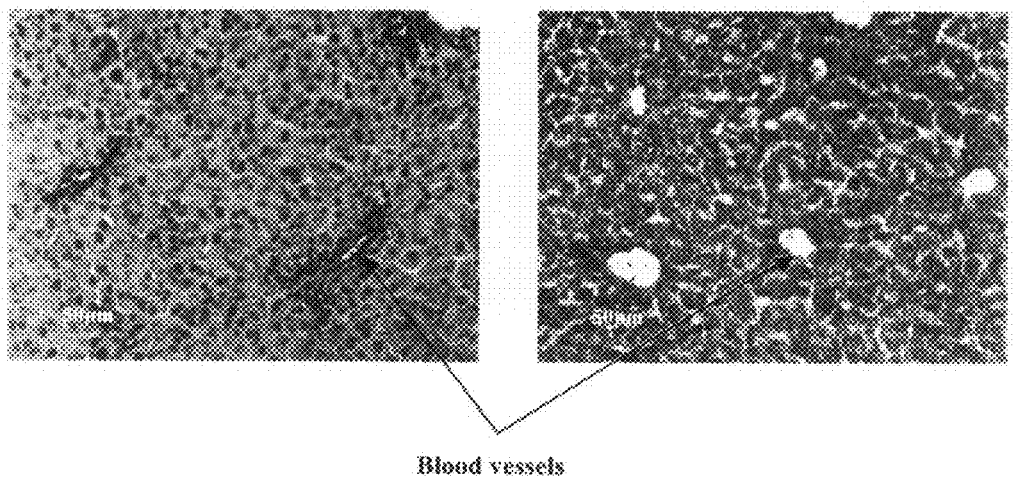
Figure 75D:
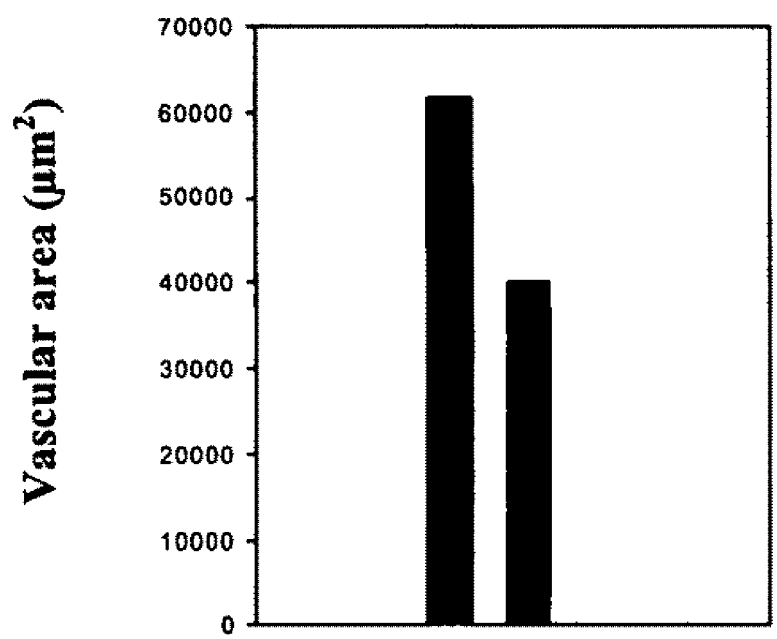
Figure 76:
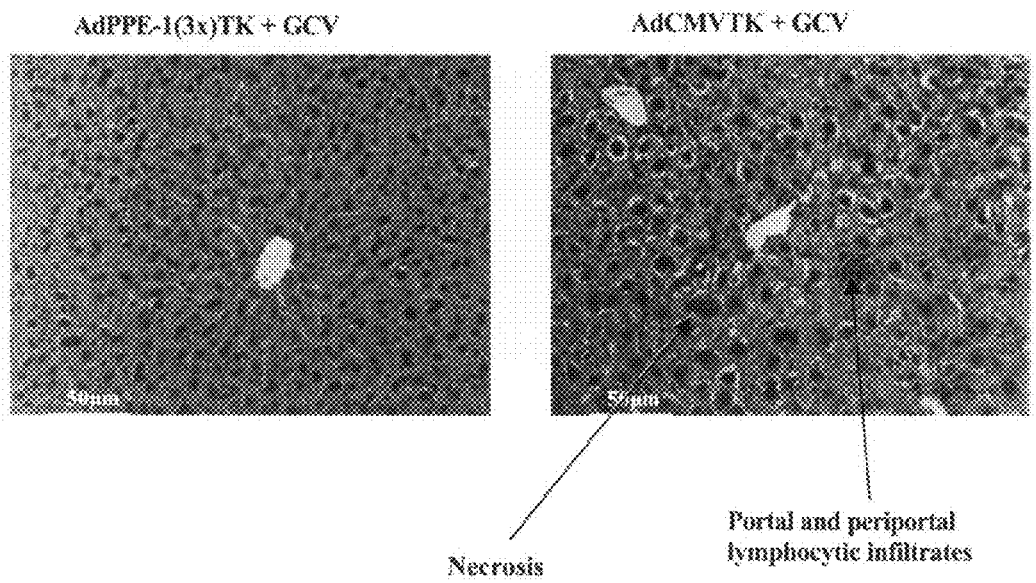
Figure 77:
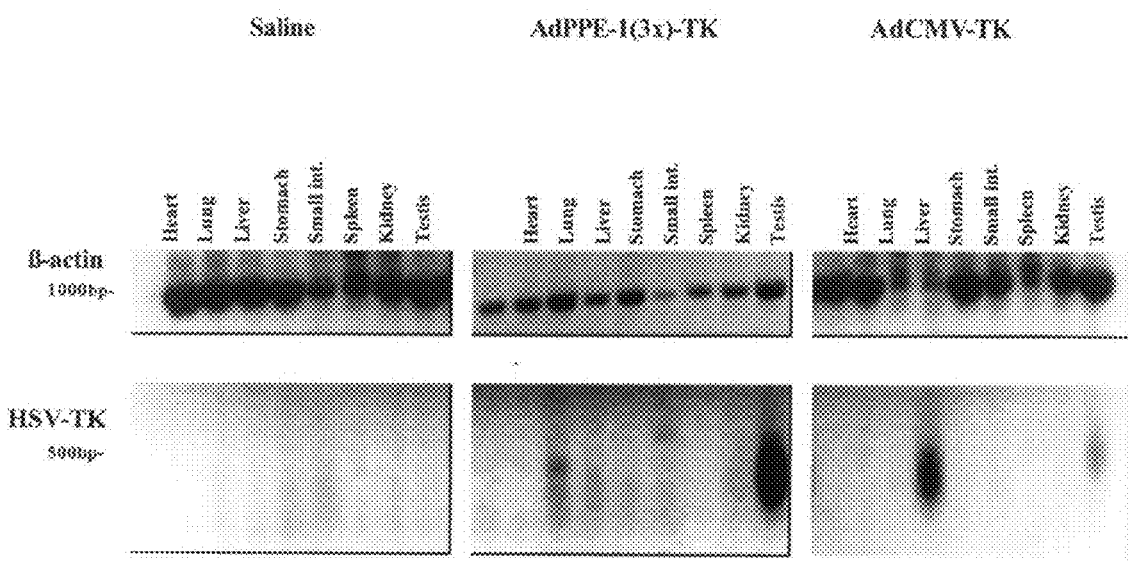
Figure 78A:
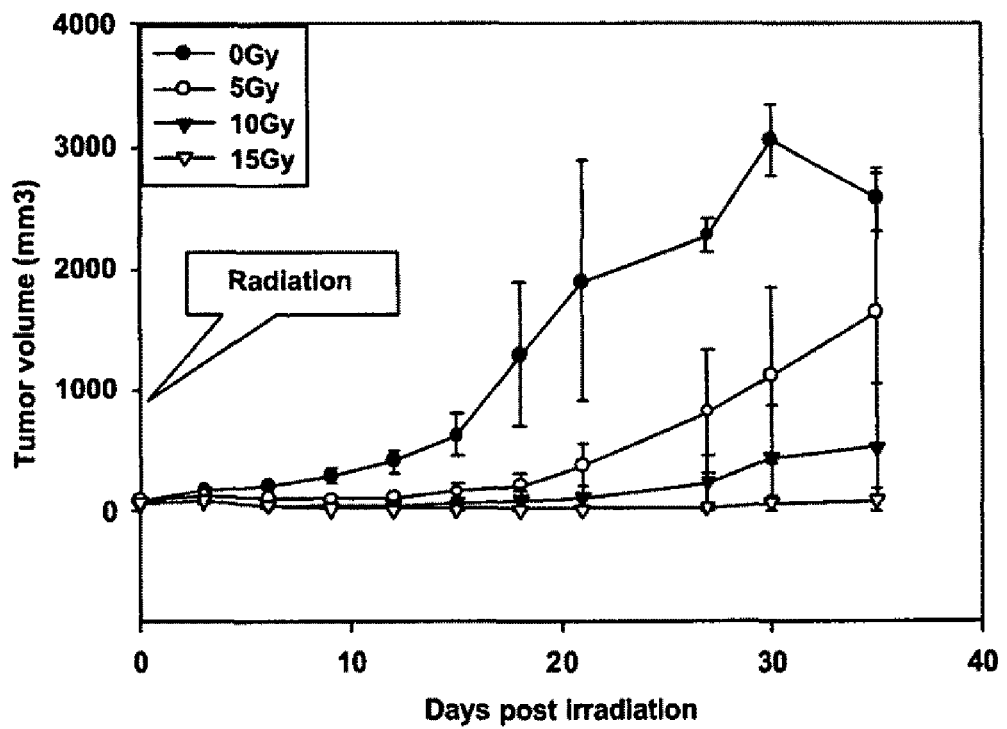
Figure 78B:
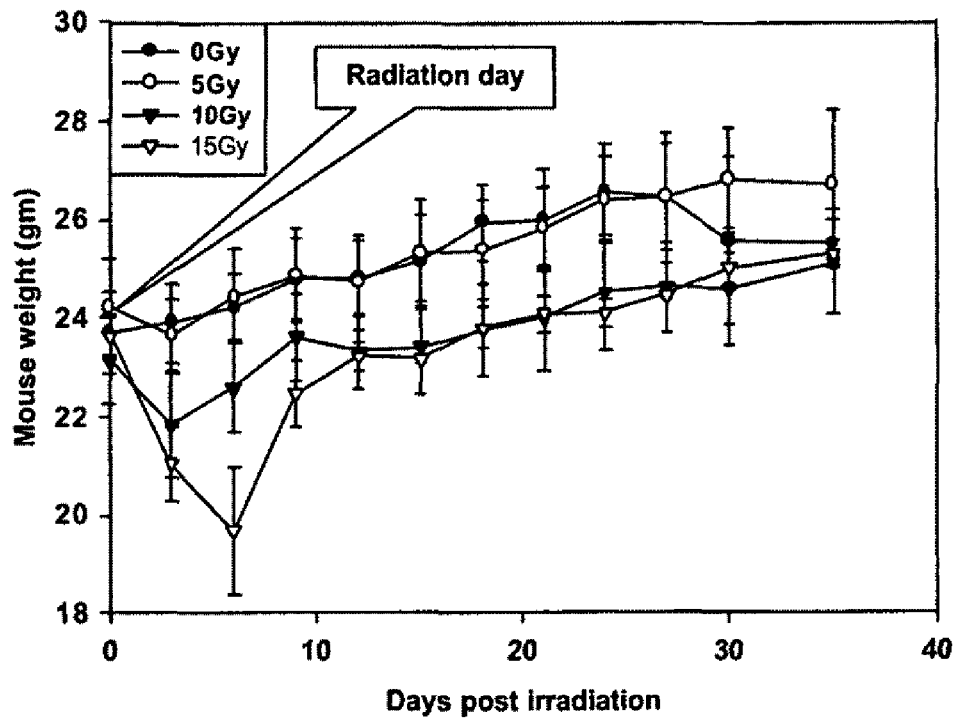
Figure 79A:
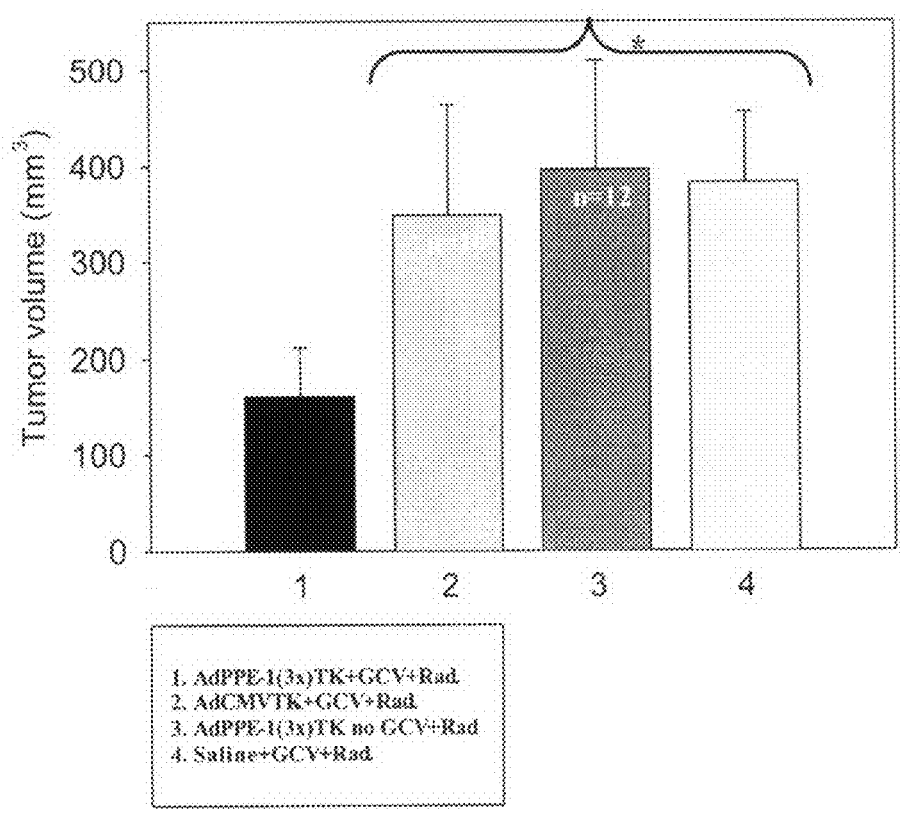
Figure 79B:
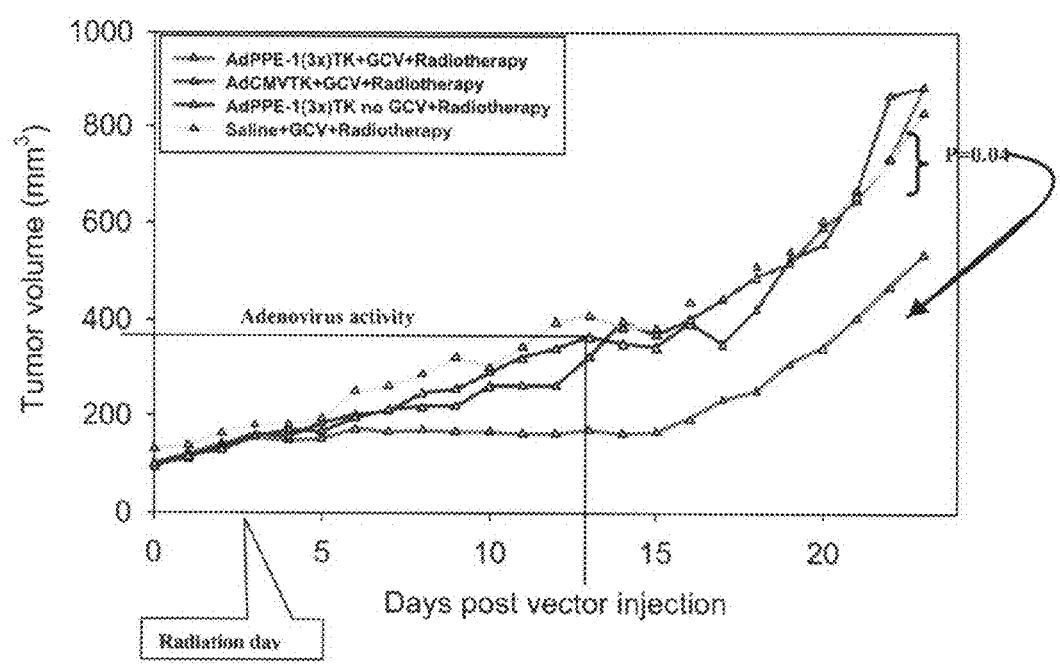
Figure 79C:
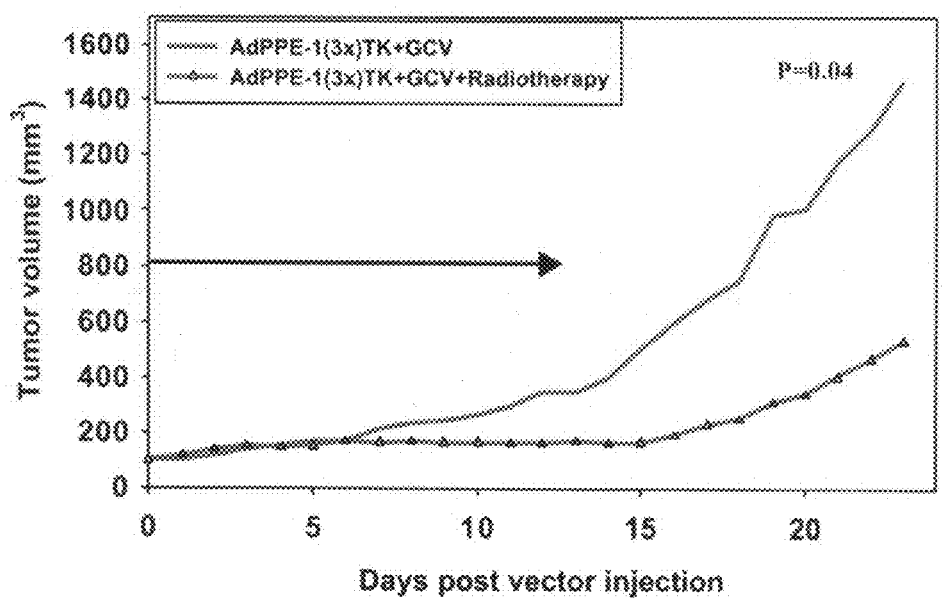
Figure 79D:
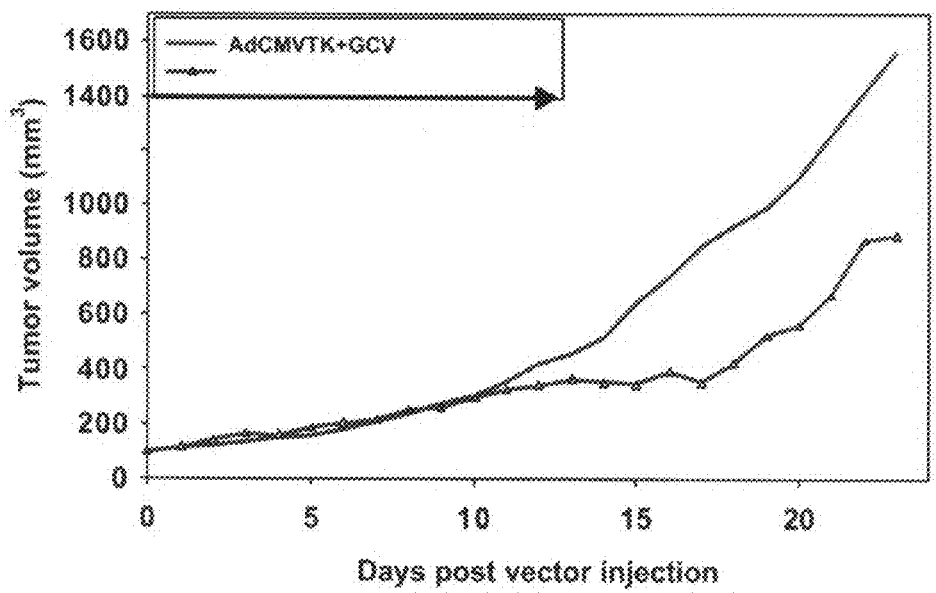
Figure 79E:
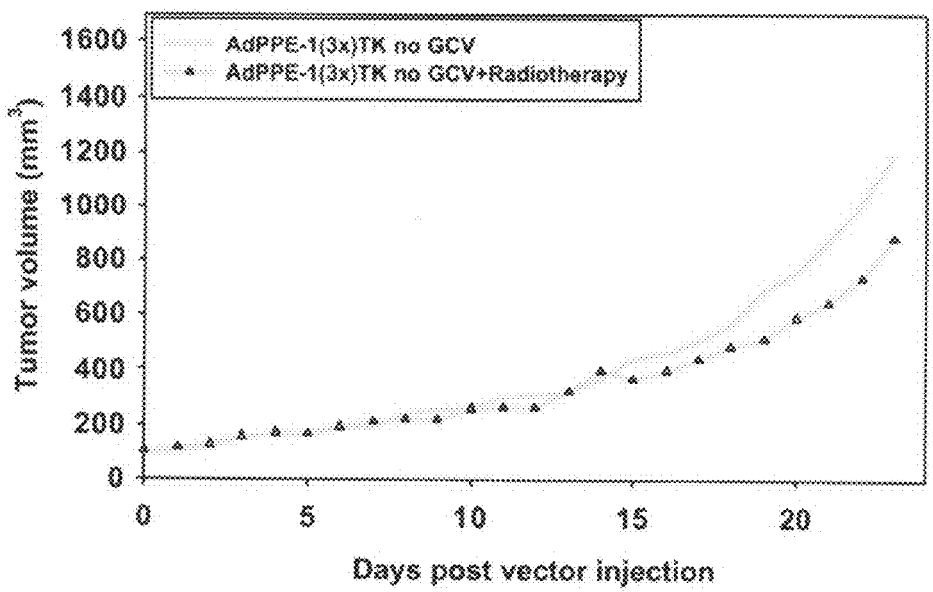
Figure 79F:
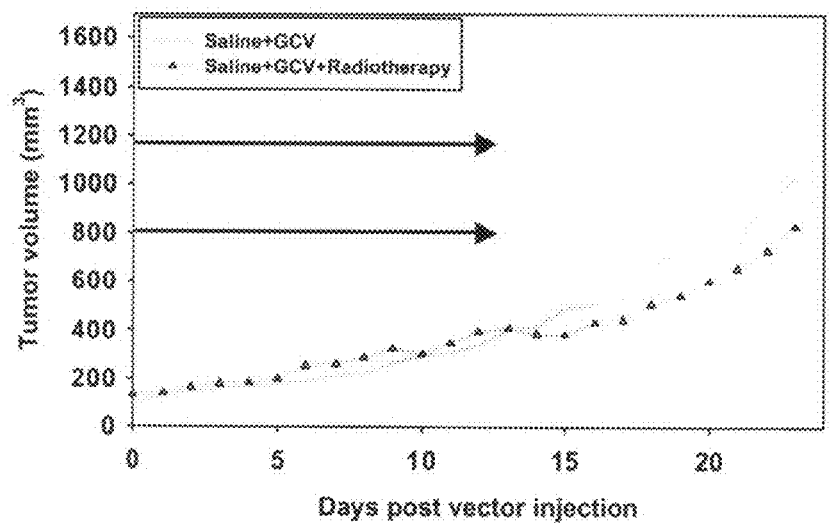
Figure 79G:
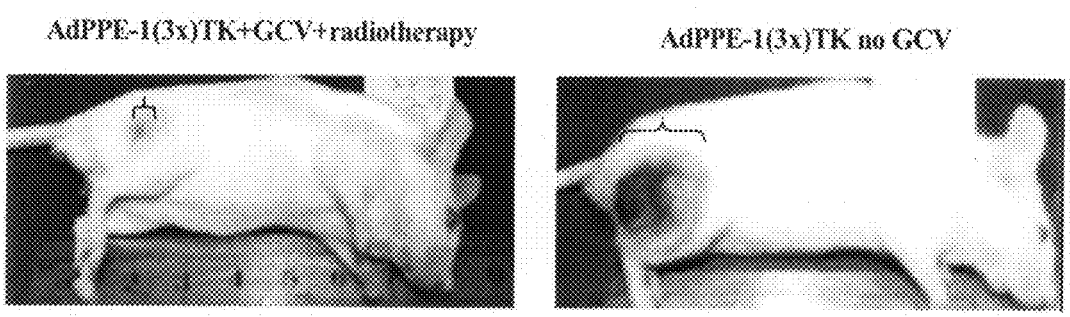
Figure 80A:
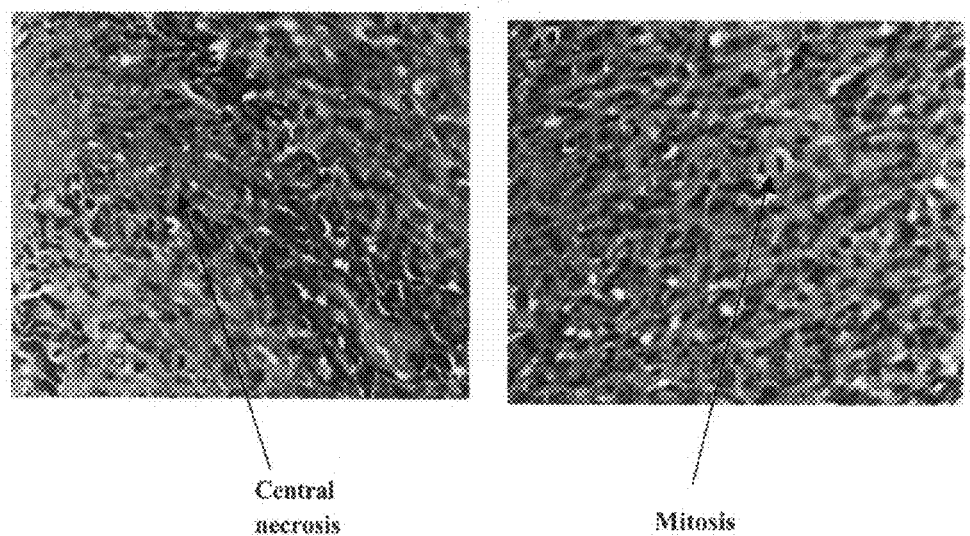
Figure 80B:
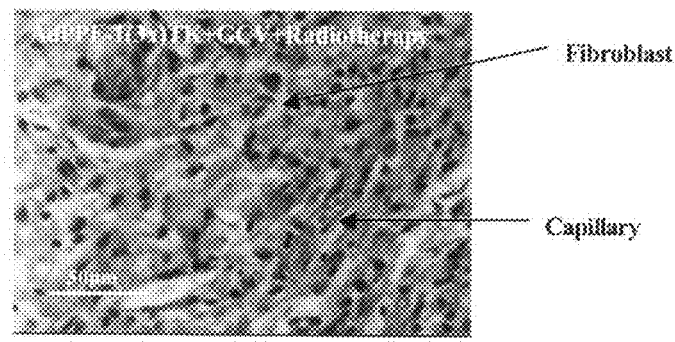
Figure 84:
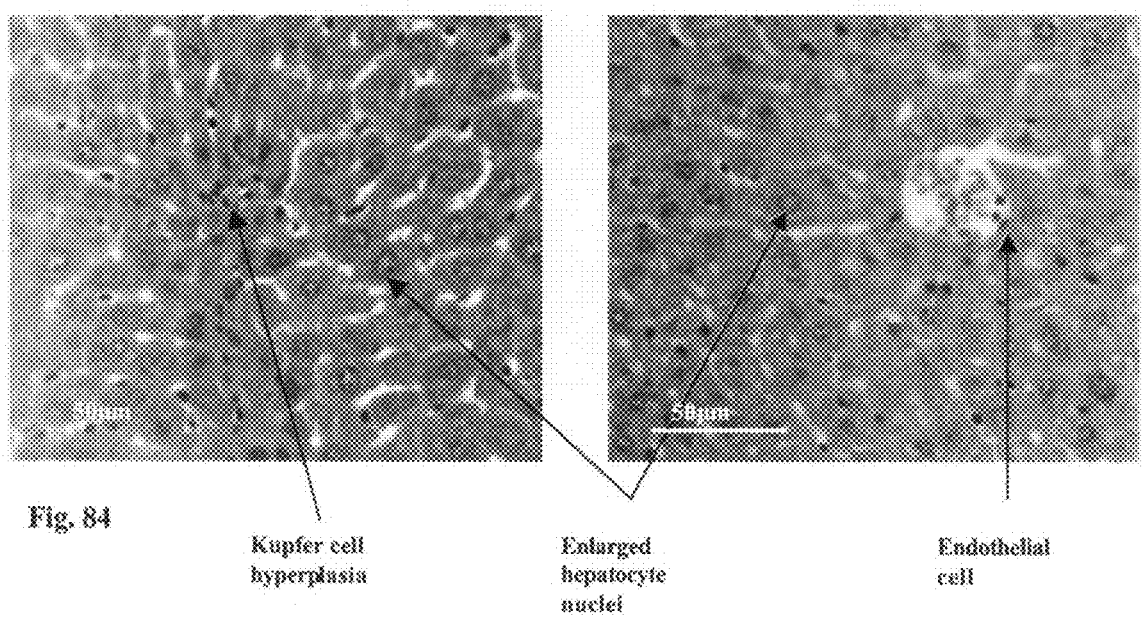
Figure 85A:
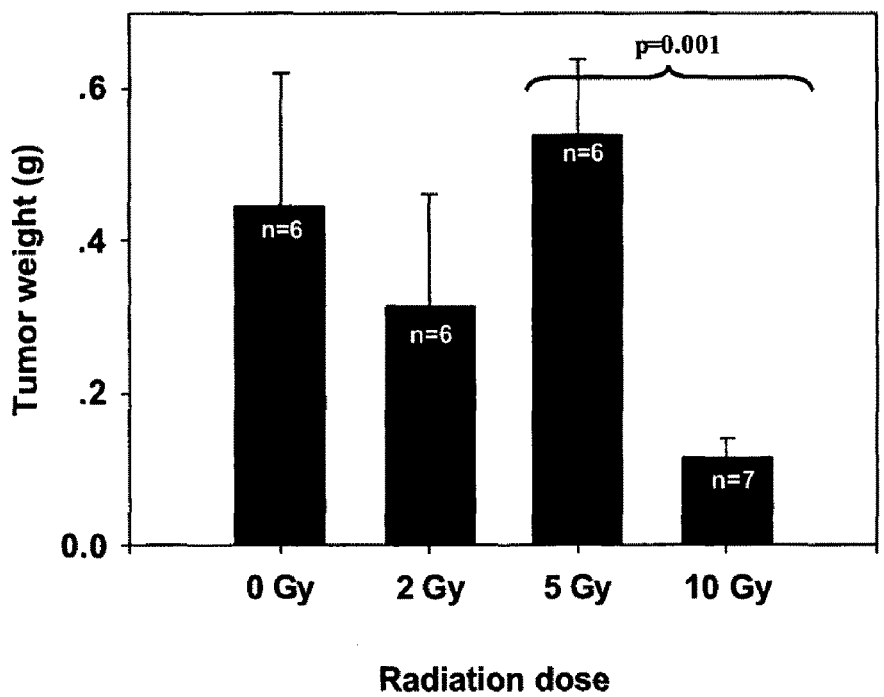
Figure 85B:
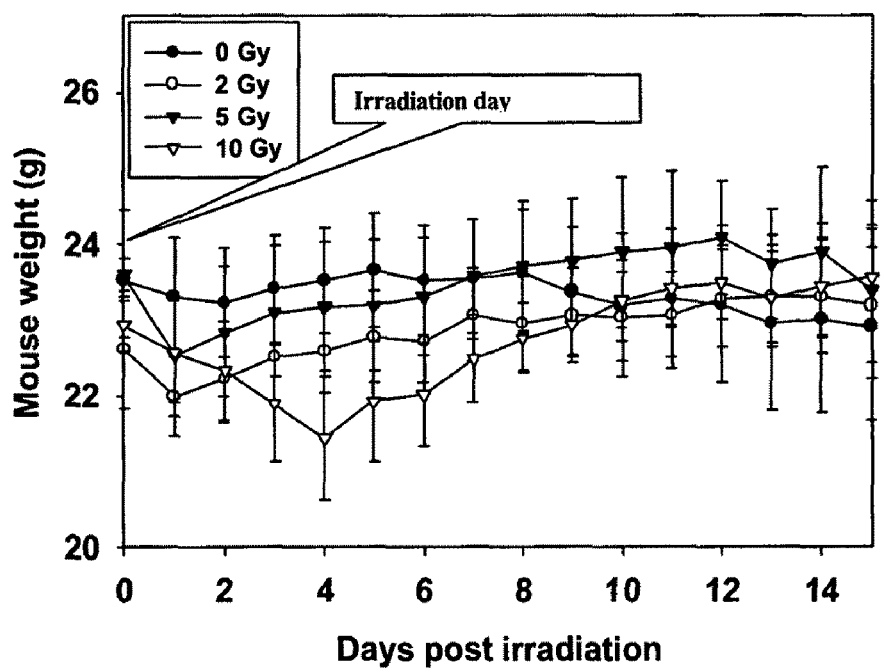
Figure 86A:
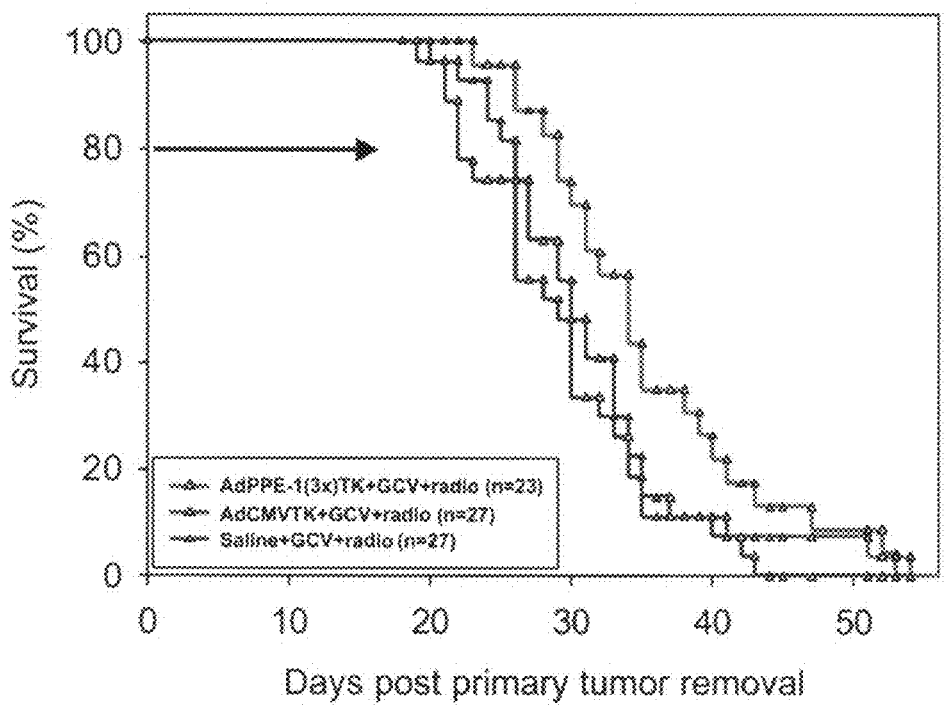
Figure 86B:
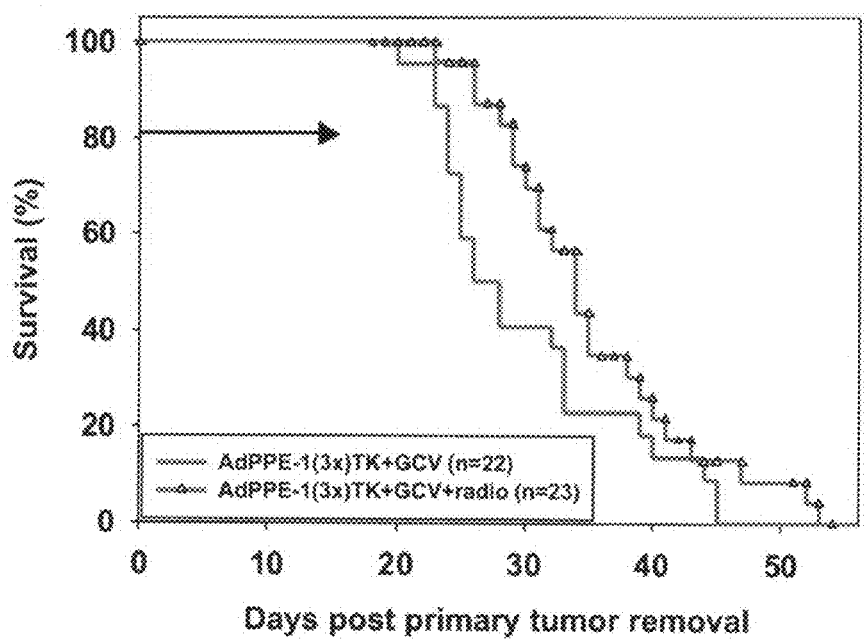
Figure 86C:
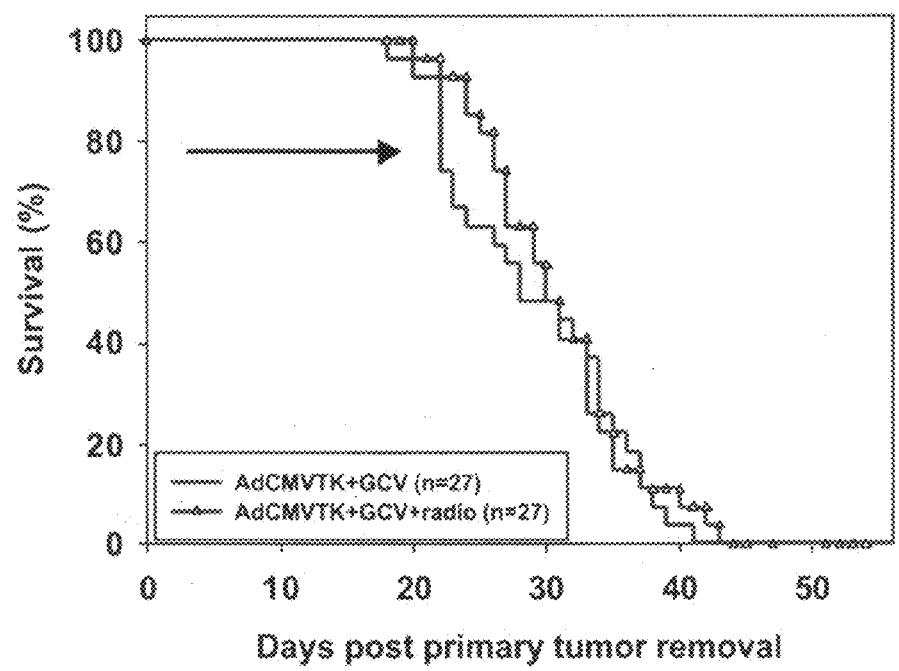
Figure 86D:
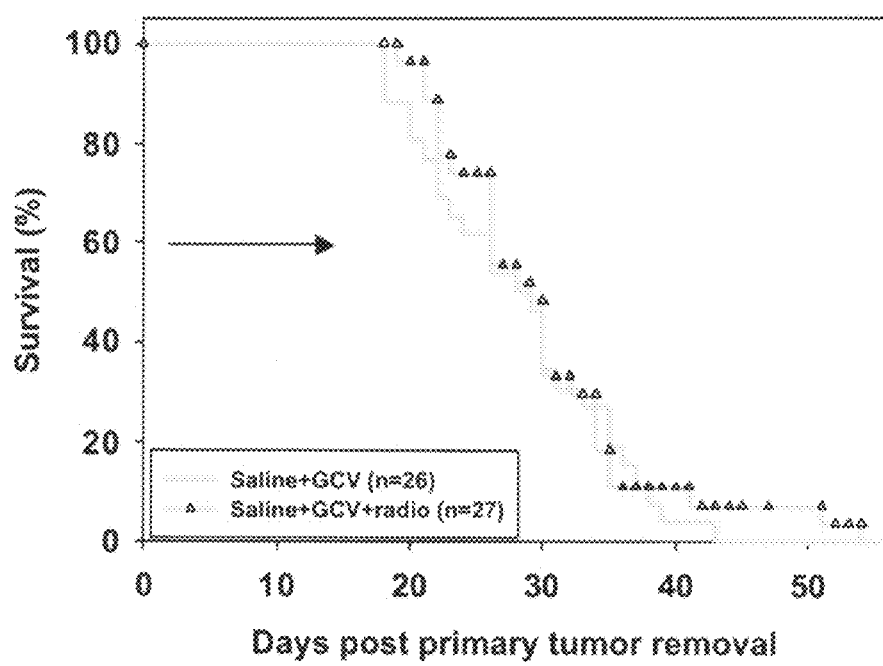
Figure 87A:
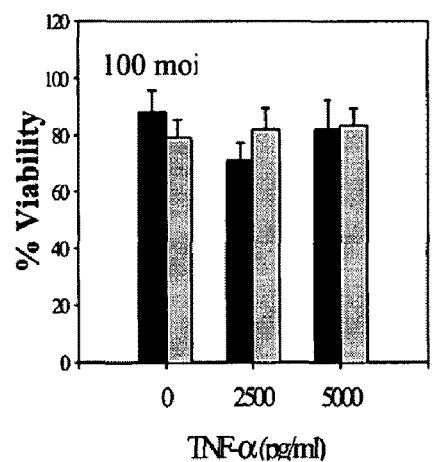
Figure 87B:
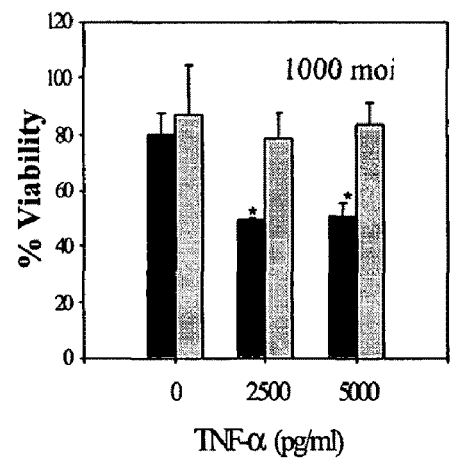
Figure 87C:
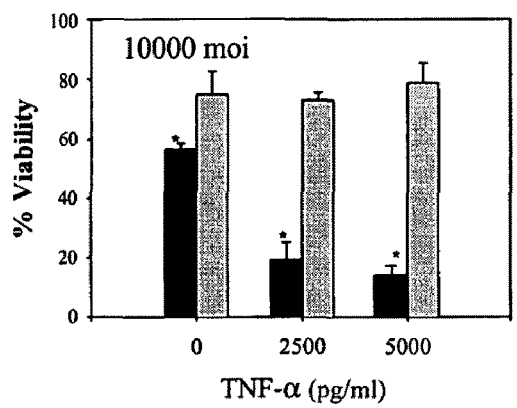
Figure 88:
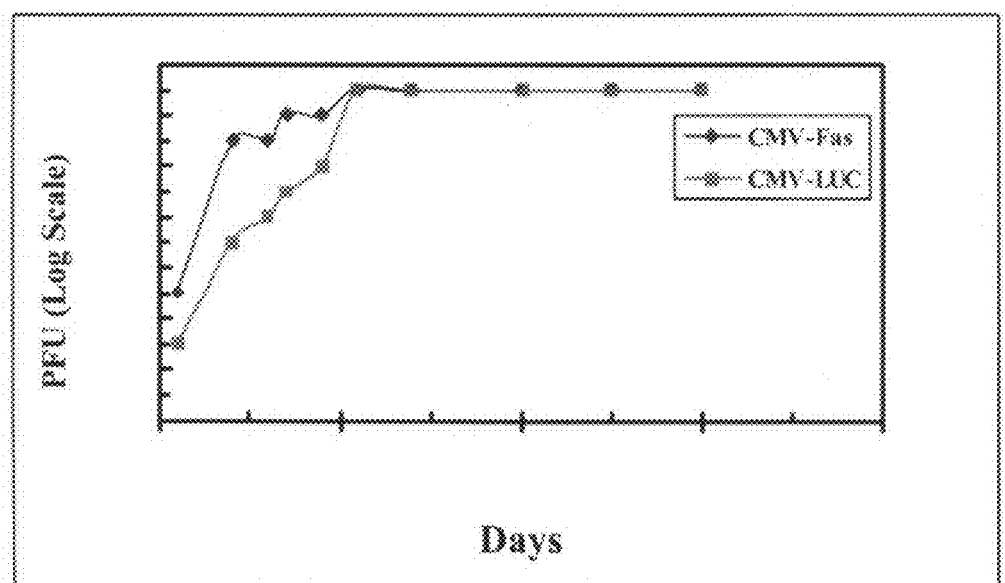
Figure 91A:
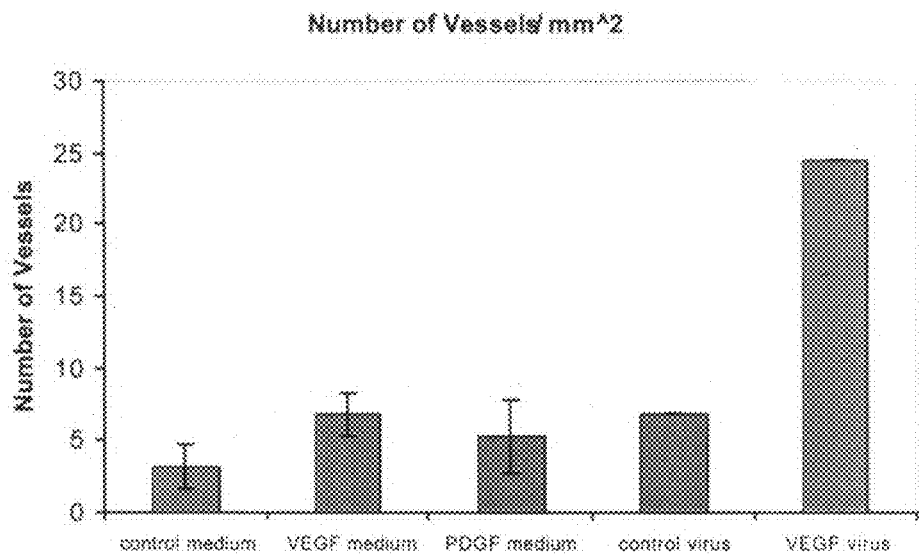
Figure 91B:
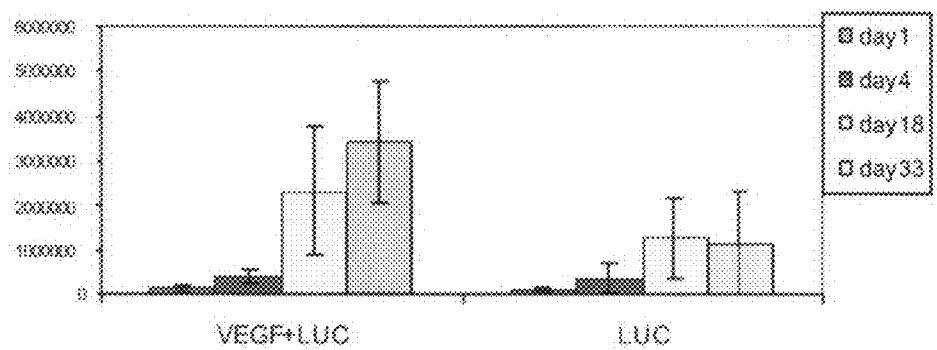
Figure 94:
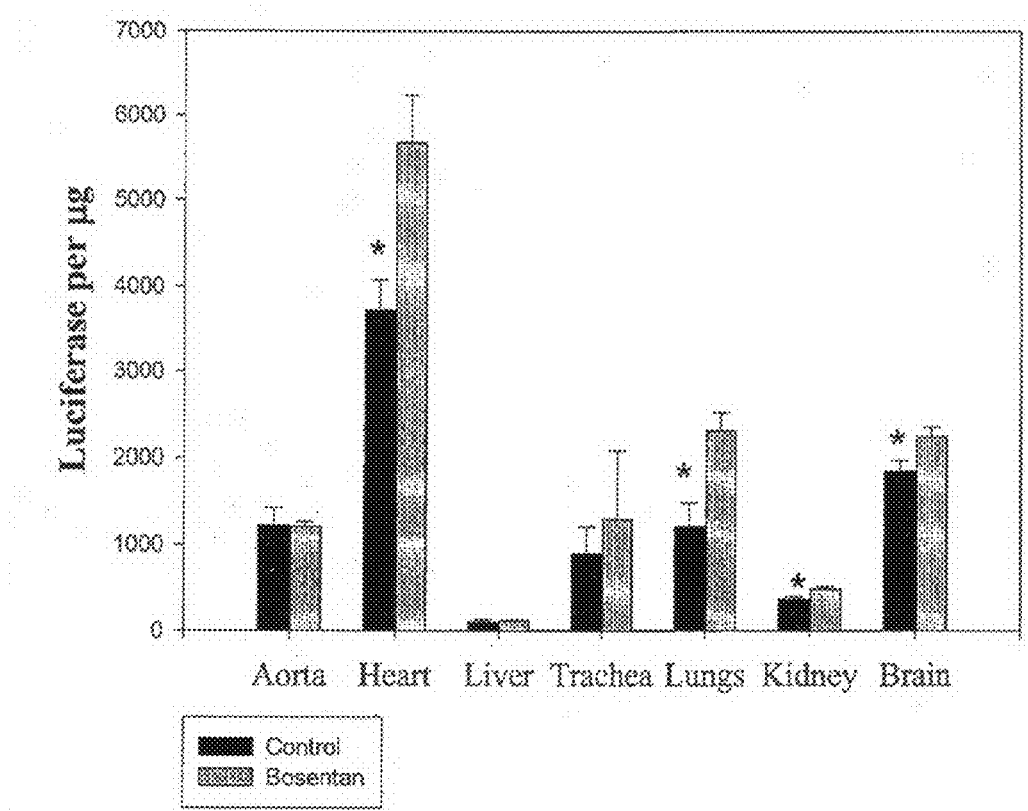
Figure 95A:
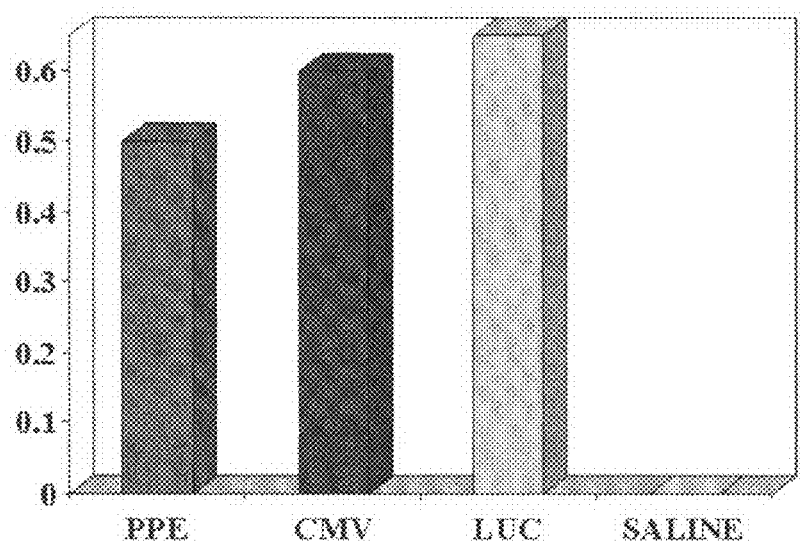
Figure 95B:
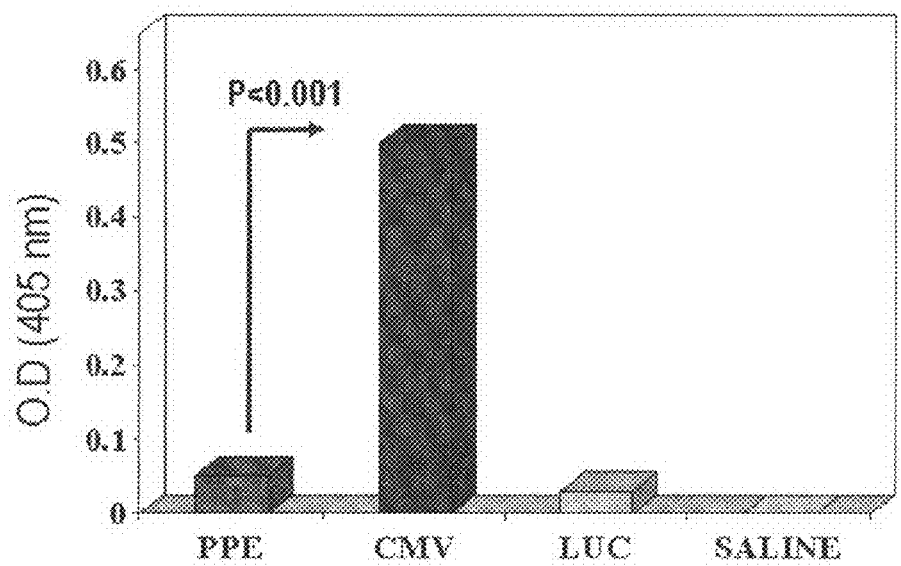
Figure 96:
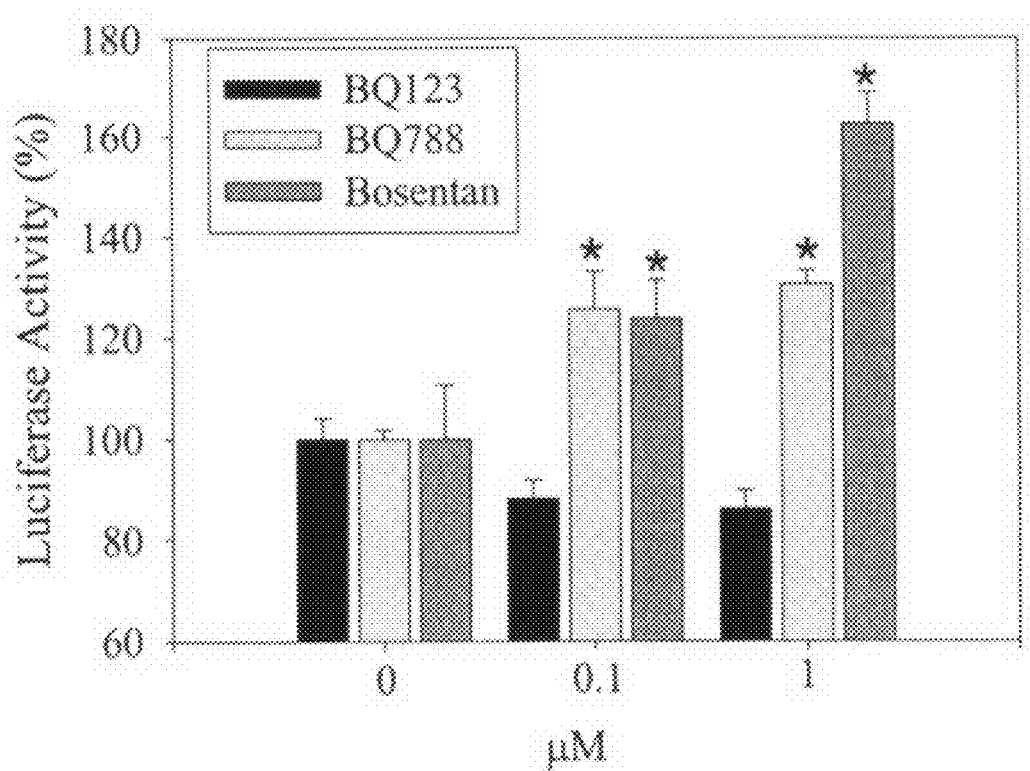
Figure 97A:
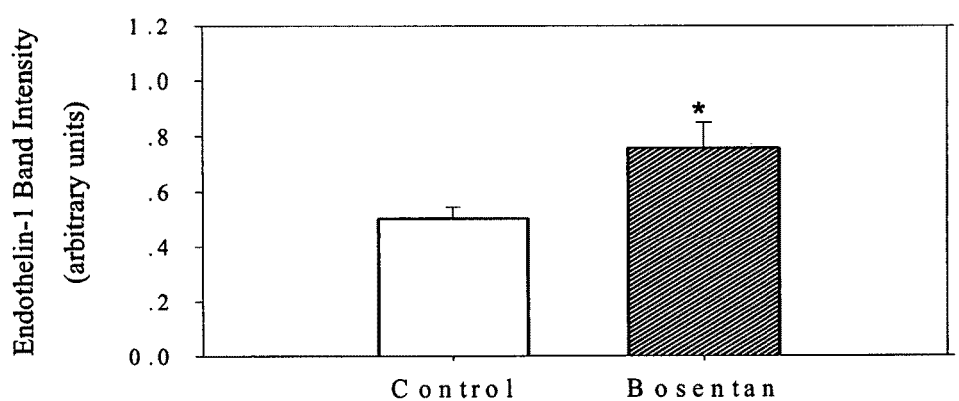
Figure 97B:
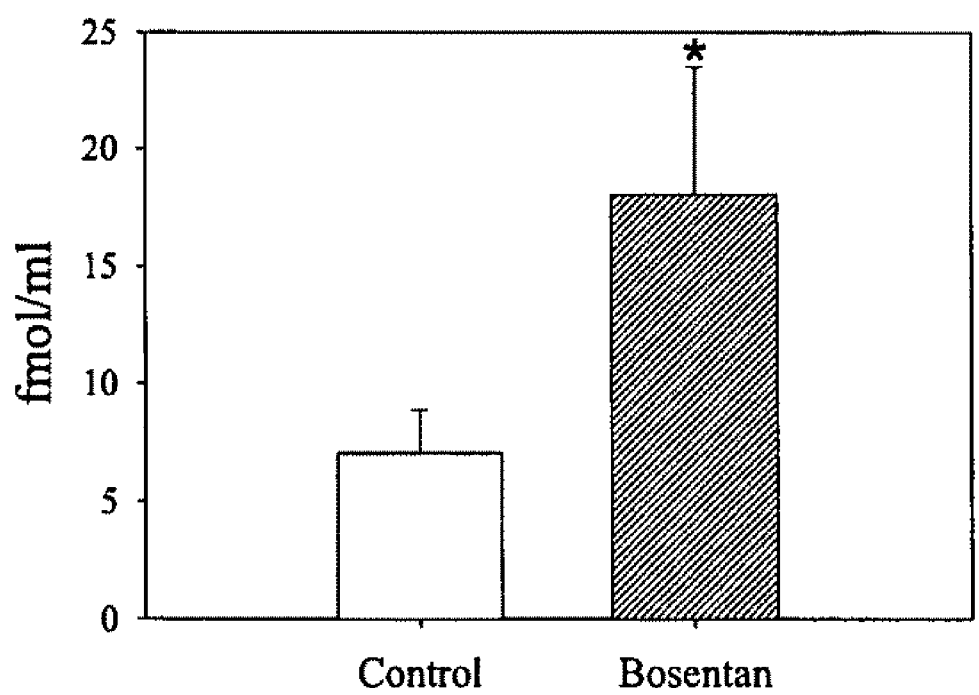
Figure 98:
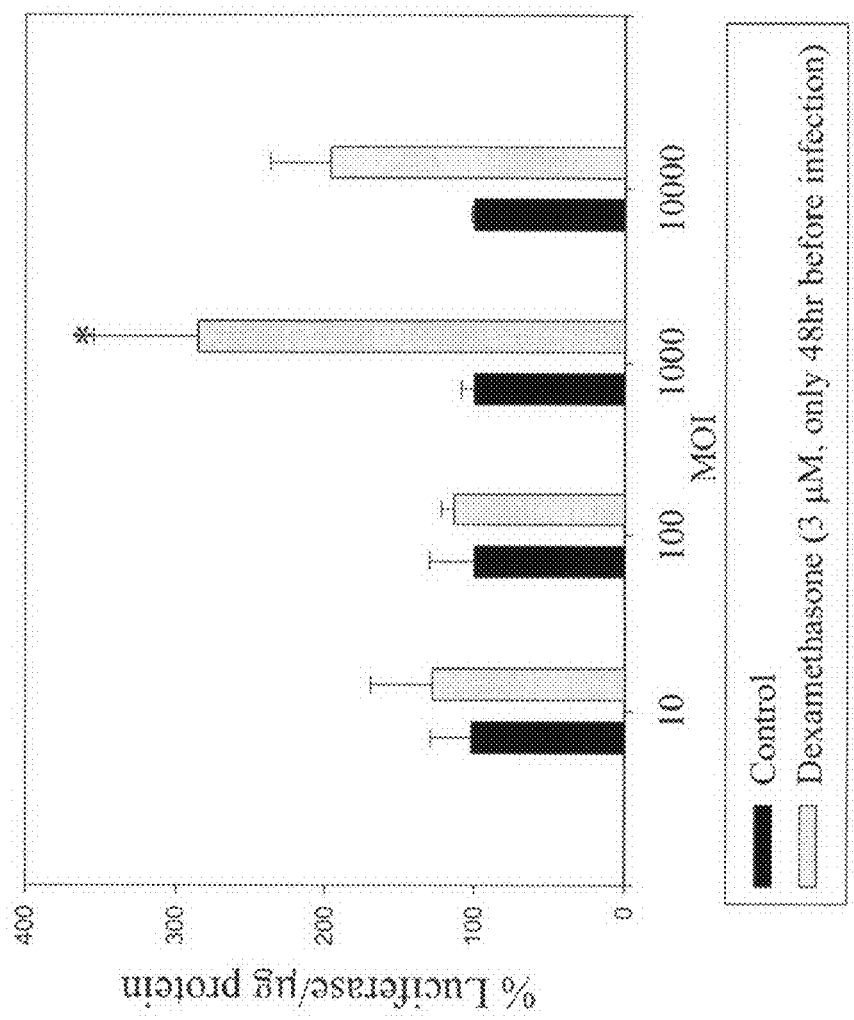

FIGS. 1a-b are schematic illustrations of Fas chimera gene constructed from the extracellular region of TNFR1 and the trans-membrane and intracellular regions of Fas and cloned into pcDNA3 plasmid (a) or into adenoviral vectors (b);

FIGS. 2a-b illustrate apoptotic activity of the pro-apoptotic genes, Fas chimera and TNFR1. FIG. 2a-illustrates Bovine Aortic Endothelial Cells (BAEC) transfected with either pcDNA-3-TNFR1 (lower panel) or control empty vector (upper panel) and an expression plasmid encoding GFP. FIG. 2b-illustrates 293 Cells transfected with either pcDNA-3-Fas-c (lower panel) or control empty vector (upper panel) and an expression plasmid encoding GFP. Transfected cells were visualized using fluorescence microscopy and apoptotic activity was morphologically determined;

FIGS. 3a-f are electron microscopy images of BAEC cells transfected with pro-apoptotic genes. 24 hours post transfection, BAEC cells were fixed in 2.5% glutaraldehyde and processed. Presented are cells in successive stages of the apoptotic process;

FIG. 4 are histograms quantifying apoptotic activity of the indicated pro-apoptotic genes in transfected BAEC and 293 cells;

FIG. 5a represents a PCR analysis of AdPPE-Fas-c. Lanes 1-2—PCR products obtained using primers encompassing the PPE-1 promoter and Fas-c gene. Lanes 3-4—PCR products obtained using Fas-c primers. Lanes 5-6—PCR products obtained in the absence of template DNA;

FIG. 5b is a western blot analysis of AdPPE-Fas-c transfected BAEC cells. Protein samples were resolved by SDS-PAGE, transferred to nitrocellulose membrane and probed with a polyclonal antibody directed against the extracellular portion of TNFR1. Lane 1-2—pcDNA3-Fas-c BAEC transfected cells (positive control). Lane 3-4—BAEC cells transfected with the indicated MOI of AdPPE-Fas-c viruses. Lane 5-non-transfected cells. Lane 6-7—BAEC cells transfected with the indicated MOI of AdPPE-Luc;

FIGS. 6a-d are photomicrographs illustrating the effect of Fas-chimera over-expression on apoptosis of endothelial cells. BAEC cells were infected with: Ad-PPE-1-3x-Fas-chimera (FIG. 6a); Ad-PPE-1-3x-luciferase (FIG. 6b); Ad-PPE-1-3x-Fas-chimera and Ad-PPE1-3x-GFP (FIG. 6c); Ad-PPE-1-3x-luciferase and Ad-PPE-1-3x-GFP; each at MOI 1000 (FIG. 6d). Photomicrographs were taken 72 h post infection at ×10 magnification;

FIG. 7 is a histogram illustrating apoptotic specific effect of Ad-PPE-1-3x-Fas-chimera on endothelial cells. Viability of endothelial (BAEC, HUVEC) and non-endothelial (Normal skin fibroblasts-NSF) cells was quantified by crystal violet staining 72 h post infection with either Ad-PPE-1-3x-Fas-chimera or control (luciferase) virus;

FIG. 8 shows a dose response effect of TNFα administration on Fas-chimera mediated apoptosis. BAEC were infected with Ad-PPE-1-3x-Fas-c. 48 h post infection TNF was added to the growth medium (at the indicated dose). Viability was determined by the crystal violet assay 24 h thereafter;

FIGS. 9a-e are photomicrographs illustrating an endothelial cell-specific apoptosis mediated by the cooperative action of TNFα ligand and Fas-c receptor. The indicated cells were incubated in the presence or absence of TNFα (10 ng/ml) 48 h following infection with Ad-PPE-1-3x-Fas-c; crystal violet staining was effected 72 h post infection;

FIG. 10a is a dose response curve illustrating the TNFα-dependent apoptotic effect of Ad-CMV-Fas-c on endothelial cells. Viability of BAEC cells infected with the indicated MOI of Ad-CMV-Fas-chimera was determined following incubation with TNFα;

FIGS. 10b-d illustrate the apoptotic effect of TNFα ligand and Ad-CMV-Fas-chimera on the non-endothelial cells NSF. FIG. 10b-NSF infected with a control virus. FIG. 10c—NSF infected with Ad-CMV-Fas-chimera. FIG. 10d—NSF infected with Ad-CMV-Fas-chimera and incubated with TNF (10 ng/ml);

FIGS. 11 a-c illustrate the In-vivo anti-tumoral effect of Ad-PPE-1-3x-Fas-c. Mice inoculated with B16 melanoma cells were injected intravenously with Ad-PPE-1-3x-Fas-c, Ad-CMV-Fas-chimera, control virus or saline when tumor was palpable;

FIG. 11a—tumor areas, measured during treatment period. FIG. 11b—tumor weights at end of treatment period. FIG. 11c—an image representing the state of the tumor in the Ad-PPE-1-3x-Fas-c treated mouse and the control mouse;

FIG. 12 is a histogram illustrating the effect of the enhancer element of the present invention on Luciferase expression in both bovine and human endothelial cell lines using the B2B cell line (bronchial cell line that expresses endothelin) as a control;

FIG. 13 is a histogram illustrating endothelial specificity of a promoter of the present invention in an adenoviral vector on Luciferase expression in various cell lines;

FIGS. 14A-B are photomicrographs illustrating GFP expression under the control of Ad5PPE-1-3X of the present invention (14A) and an Ad5CMV (14B) control construct in the BAEC cell line;

FIG. 15 is histogram of % apoptosis induced by pACPPE-1-3Xp55, pACPPE-1-3XLuciferase and pCCMVp55 in endothelial and non-endothelial cells;

FIG. 16 is a histogram illustrating the effect of introducing an enhancer element according to the present invention into a promoter construct on hypoxia response;

FIG. 17 is a histogram illustrating the effect of introducing an enhancer element according to the present invention into a promoter of an adenovector construct on hypoxia response;

FIG. 18 is a histogram illustrating the effect of introducing an enhancer element according to the present invention into a promoter on levels of expression in bovine and human endothelial, endothelin expressing cell lines;

FIG. 19 is a histogram illustrating levels of expression of a reporter gene observed in various organs following injection of an adenoviral construct containing either an endothelial promoter (PPE-1) or a control (CMV) promoter;

FIGS. 20A-B are two photomicrographs illustrating cellular expression of an Ad5CMVGFP construct (FIG. 20A) and an Ad5PPE-1-GFP construct (FIG. 20B) in liver tissue of mice injected with the constructs;

FIG. 21 is a histogram illustrating the effect of introducing an enhancer element according to the present invention into a promoter on levels of expression in endothelial and non-endothelial cell lines;

FIG. 22 is a histogram illustrating the effect of introducing an enhancer element according to the present invention into a promoter on levels of expression in endothelial and non-endothelial cell lines;

FIGS. 23A-C are photomicrographs illustrating GFP expression in Ad5PPE-1-3XGFP transduced cells, Ad5PPE-1GFP transduced cells and Ad5CMVGFP transduced cells respectively;

FIGS. 24A-B illustrate GFP expression in SMC transduced by moi-1 of Ad5PPE-1-3XGFP and Ad5CMVGFP respectively;

FIGS. 25A-B show results of an experiment similar to that of FIGS. 24A-B conducted in HeLa cells;

FIGS. 26A-B show results of an experiment similar to that of FIGS. 24A-B conducted in HepG2 cells;

FIGS. 27A-B show results of an experiment similar to that of FIGS. 24 A-B conducted in NSF cells;

FIGS. 28A-B are photomicrographs illustrating GFP expression in endothelial cells lining a blood vessel of mice injected with the Ad5PPE-1GFP and the Ad5PPE-1-3XGFP constructs respectively;

FIGS. 29A-C are photomicrographs illustrating results from kidney tissue of injected mice. Ad5CMVGFP injected mice (FIG. 29A), Ad5PPE-1GFP (FIG. 29B; slightly higher GFP expression is visible in the blood vessel wall; indicated by arrow) and Ad5PPE-1-3XGFP (FIG. 29C);

FIGS. 30A-C illustrate experiments similar to those depicted in FIGS. 29A-C, conducted on sections of spleen tissue;

FIGS. 31A-D illustrate GFP expression in metastatic lungs of control mice injected with Saline (FIG. 31A), mice injected with Ad5CMVGFP (FIG. 31 B), mice injected with Ad5PPE-1GFP (FIG. 31 C) and mice injected with Ad5PPE-1-3XGFP (FIG. 31D). Anti Cd31 immunostaining (FIGS. 31C' to 31D') confirm the co-localization of the GFP expression and CD31 expression in each metastatic tissue;

FIG. 32 is a histogram illustrating that Luciferase activity (light units/µg protein) in BAEC transfected by a plasmid containing the murine PPE-1 promoter is significantly higher when transfected cells were incubated under hypoxic conditions;

FIG. 33 is a histogram as in FIG. 32, except that Ad5PPE-1Luc and Ad5CMVLuc were employed;

FIG. 34 is a histogram as in FIG. 33 showing the effects of hypoxia in different cell lines;

FIG. 35 is a histogram illustrating the effect of the 3X sequence of the present invention on the PPE-1 hypoxia response in BAEC cells. Cells were transduced by Ad5PPE-1Luc and Ad5PPE-1-3XLuc;

FIG. 36 is a histogram showing levels of Luciferase expression in various tissues of PPE-1-Luc transgenic mice following femoral artery ligation;

FIGS. 37A-B are plasmid maps of constructs employed in conjunction with the present invention;

FIGS. 38A-F illustrate the effects of Ad5PPE-1-3XVEGF and Ad5CMVVEGF on blood perfusion and angiogenesis in mouse ischemic limbs. FIGS. 38A-D are representative ultrasonic (US) angiographic images of perfusion in the ischemic limb of mice from the various treatment groups captured 21 days following ligation. Yellow signal represents intense perfusion. The right side of the image represents the distal end of the limb. FIG. 38A-Ad5PPE-1-3XVEGF treated mouse; FIG. 38B-Ad5CMVVEGF treated mouse; FIG. 38C-control, saline treated mouse; FIG. 38D-control, normal limb. FIGS. 38E-F are histograms illustrating: mean intensity of signal in the US images of the various treatment groups (FIG. 38E); mean capillary density, measured as the number of CD31+ cells/mm$^2$ in the various treatment groups (FIG. 38F);

FIG. 39 is a histogram illustrating Luciferase activity in proliferating and quiescent Bovine Aortic Endothelial Cells (BAEC) transduced with Ad5PPE-1Luc (open bars) and Ad5CMVLuc (black bars);

FIG. 40 is a histogram illustrating Luciferase activity in BAEC transduced with Ad5PPE-1Luc. during normal proliferation, a quiescent state and rapid proliferation following addition of VEGF;

FIGS. 41A-B are histograms illustrating Luciferase activity (light units/µg protein) in the (FIG. 41A) aortas and livers (FIG. 41B) of Ad5PPE-1Luc and AdSCMVLuc normal injected C57BL/6 mice. Activities were determined 1 (n=13), 5 (n=34), 14 (n=32), 30 (n=20) and 90 (n=11) days post injection;

FIGS. 42A-B are histograms illustrating relative Luciferase activity (light units/µg protein) detected five (FIG. 42A) and fourteen (FIG. 42B) (n=10 for each time point) days post injection of Ad5PPE-1Luc (open bars) or Ad5CMVLuc (black bars) in normal injected BALB/C mice. Activity is expressed as percentage of total body Luciferase expression of each animal;

FIG. 43 is a prior art image depicting an aorta dissected from ApoE deficient mice colored by Sudan—IV. The thoracic aorta contains less red stained atherosclerotic lesion while the abdominal region includes many red stained atherosclerotic lesions. (Adapted from Imaging of Aortic atherosclerotic lesions by $^{125}$I-HDL and $^{125}$I-BSA. A. Shaish et al, Pathobiology 2001; 69:225-29);

FIG. 44 is a histogram illustrating absolute Luciferase activity (light units/µg protein) detected 5 days post systemic injections of Ad5PPE-1Luc (open bars; n=12) or Ad5CMVLuc (black bars; n=12) to ApoE deficient mice. Luciferase activity observed from the abdominal aorta contain high lesion levels and from the thoracic area (low lesion levels);

FIG. 45 is a histogram illustrating absolute Luciferase activity (light units/µg protein) 5 days post systemic injections of Ad5PPE-1Luc (black bars) or Ad5CMVLuc (open bars) to healing wound C57BL/6 induced mice;

FIG. 46 is a histogram illustrating Luciferase activity in normal lung, metastatic lung and primary tumor of Lewis lung carcinoma-induced mice. Lewis lung carcinoma was induced by D122-96 cells injection to the backs for primary tumor model and to the footpad for the metastatic model. Luciferase activity was measured five days post-systemic injection of Ad5PPE-1Luc (n=9; open bars) or Ad5CMVLuc (n=12; black bars). Activity is expressed as light units/µg protein;

FIGS. 47A-D are photomicrographs illustrating GFP expression and tissue morphology in lungs and tumors of LLC bearing mice following intra-tumoral injection of Ad5PPE-1GFP. Tissue was frozen in OCT and sectioned to 10 µm by cryostat. All pictures were taken in magnification of 25×. FIG. 47A-GFP in angiogenic blood vessels of lung metastases; FIG. 47B-CD31 antibody immunostaining of the section pictured in FIG. 47A; FIG. 47C-GFP expression in blood vessels of primary tumor; FIG. 47D-*phase* contrast of the section of C illustrating blood vessels;

FIG. 48 is a histogram illustrating Luciferase expression in normal lung and metastatic lung of Lewis lung carcinoma-induced mice, injected with Ad5CMVLuc, Ad5PPE-1Luc and Ad5PPE-1-3X-Luc Lewis lung carcinoma was induced by D122-96 cells injected to the foot pad for the metastatic model. Luciferase activity was measured five days post-systemic injection of Ad5CMVLuc (n=7; black bars), Ad5PPE-1Luc (n=6; gray bars), or Ad5PPE-1-3XLuc (n=13; brown bars). Activity is expressed as light units/µg protein;

FIG. 49 is a histogram illustrating Luciferase activity as percentage of liver activity (where the liver is 100%), in normal lung and lung metastasis of Lewis lung carcinoma-induced mice injected with Ad5CMV, Ad5PPE-1Luc and Ad5PPE-1(3X);

FIGS. 50A-B are photomicrographs illustrating co-localization of GFP expression (FIG. 50A) and CD31 immunostaining (FIG. 50B) in mice with LLC lung metastases injected with Ad5PPE-1-3X-GFP;

FIG. 51 is a histogram illustrating Luciferase activity (light units/µg protein) in muscles (ischemic and normal) of PPE-1Luciferase transgenic mice at two, five, ten and 18 days post femoral ligation and in control (non-ligated animals—day 0; n=8 for each group);

FIG. 52 is a histogram illustrating Luciferase activity (light units/µg protein) in the liver, lung and aorta in muscles (ischemic and normal) of PPE-1Luciferase transgenic mice at five (n=6), ten (n=6) and 18 (n=8) days post femoral ligation and in control (non ligated animals—day 0);

FIG. 53 is a histogram illustrating Luciferase activity, (light units/µg protein detected in the livers, lungs and primary tumors of LLC mice injected in primary tumors with Ad5CMVLuc (black bars) or Ad5PPE-1Luc (open bars);

FIGS. 54A-H are in-situ hybridization images illustrating tissue distribution of tissue-specific or constitutive expression of various transgenes. FIGS. 54A-C illustrate in-situ hybridization with a VEGF specific antisense probe on representative ischemic muscles from: A, Ad5PPE-1-3XVEGF treated mouse; B, Ad5CMVVEGF treated mouse; C, saline treated mouse; D, liver section from Ad5CMVVEGF treated mouse. An arrow indicates positively stained cells. FIGS. 54E-G, illustrate in-situ hybridization with a PDGF-B specific antisense probe of representative ischemic muscles from: E, Ad5PPE-1-3XPDGF-B treated mouse; F, Ad5CMVPDGF-B treated mouse; G, saline treated mouse; H, liver section from Ad5CMVPDGF-B treated mouse;

FIGS. 55A-B are histograms illustrating a long-term effect of Ad5PPE-1-3XVEGF or Ad5CMVVEGF on blood perfusion and angiogenesis in mouse ischemic limb. A, mean intensity of signal in the US images of the various treatment groups, 50 days following femoral artery ligation. B, mean capillary density, measured as number of CD31+ cells/mm$^2$ in the various treatment groups, 70 days following femoral artery ligation;

FIGS. 56A-C are histograms showing early and long term effects of Ad5PPE-1-3XPDGF-B on neovascularization in mouse ischemic limb. FIGS. 56A-B—mean perfusion intensity measured by US imaging (56A, 30 days following femoral artery ligation; 56B, 80 days following femoral artery ligation). FIGS. 56C—mean capillary density, measured as number of CD31+ cells/mm$^2$ in the various treatment groups (56C, 35 days following femoral artery ligation);

FIGS. 57A-G illustrate long term effects of angiogenic therapy using PDGF-B and VEGF alone or in combination under regulation of an endothelial specific or a constitutive promoter on neovascularization and blood flow in mouse ischemic limb. A, mean intensity of signal in the US images of the various treatment groups, 80 days following femoral artery ligation. B, mean capillary density, measured as number of CD31+ cells/mm$^2$ in the various treatment groups, 90 days following femoral artery ligation. FIGS. 57C-G—smooth muscle cells recruitment to mature vessels in ischemic limb muscles, 90 days following femoral artery ligation. Smooth muscle cells are immunostained with anti-α-SMactin antibodies (in red, X20). C, Ad5PPE-1-3XPDGF-B treated mouse; D, combination therapy treated mouse; E, Ad5PPE-1-3XVEGF treated mouse; F, control, Ad5PPE-1-3XGFP treated mouse; G, normal contralateral limb (note that only large vessels are stained);

FIG. 58 illustrates the effect of PDGF-B alone or in combination with the proangiogenic factor VEGF on blood perfusion in mouse ischemic limb 50 days following artery ligation;

FIG. 59 is a schematic representation of the basic principles of gene-directed enzyme prodrug therapy (GDEPT);

FIGS. 60A-B are a schematic map representing the construction of the plasmid pEL8(3x)-TK. FIG. 60A is a schematic map representing the construction of the plasmid pEL8 (3x)-TK. FIG. 60B is a map of plasmid pACPPE-1(3x)-TK;

FIG. 61 is an agarose gel separation of PCR products of the AdPPE-1(3x)-TK vector, visualized by UV fluorescence. Two primers were used: the forward primer 5'-ctcttgattct-tgaactctg-3' (455-474 bp in the pre-proendothelin promoter sequence) (SEQ ID NO:9) and the reverse primer 5'-taaggcat-gcccattgttat-3' (1065-1084 bp in the HSV-TK gene sequence) (SEQ ID NO:10). Primers specific for other vectors gave no PCR products. Note the 1 kb band, verifying the presence of the PPE-1(3x) promoter and the HSV-TK gene in the AdPPE-1(3x)-TK virus. Lane 1: 100 bp size marker ladder. Lane 2: pACPPE-1(3x)-TK plasmid. Lane 3: AdPPE-1(3x)-TK virus. Lane 4. No DNA;

FIGS. 62A-C show linear, schematic maps of the vectors AdPPE-1(3x)-TK FIG. 62a). AdPPE-1(3x)-Luc (FIG. 62b) and AdCMV-TK (FIG. 62c);

FIG. 63 is a series of photomicrographs illustrating the superior endothelial cell cytotoxicity of TK under control of the PPE-1 (3x) promoter. Bovine aorta endothelial cells (BAECs) were transduced with AdPPE-1(3x)-TK, AdCMV-TK and AdPPE-1(3x)-Luc multiplicity of infections (m.o.i.) of 0.1, 1, 10, 100, and 1000. GCV (1 µg/ml) was added four hours post-transduction. Controls were cells transduced with the vectors without GCV, or GCV without vectors. The experiment was performed twice in 96-well plates, 12 wells for every group. Both controls did not induce cell death (data not shown). Note the morphological changes characteristic to cytotoxicity (cell enlargement, elongation and bloatedness) and cytotoxicity (loss of confluence) evident in AdPPE-1 (3x)+GCV-treated cells, at a significantly lower m.o.i. than AdCMV-TK. Cells transduced with AdPPE-1 (3x)-Luc remained healthy (small size, rounded and confluent);

FIG. 64 is a graphic representation of endothelial cell cytotoxicity of TK under control of the PPE-1 (3x) promoter. BAECs were prepared in 96-well plates and transduced as in FIG. 13, followed by the addition of 1 µg/ml GCV four hours post-transduction. 10 days post vector addition, cell viability was determined using crystal violet staining. Note the superior cytotoxicity of AdPPE-1 (3x)+GCV at high m.o.i.s.;

FIG. 65 is a series of photomicrographs illustrating the superior synergy of endothelial cell cytotoxicity of TK under control of the PPE-1 (3x) promoter and ganciclovir administration. Bovine aorta endothelial cells (BAECs) were transduced with AdPPE-1(3x)-TK, AdCMV-TK and AdPPE-1 (3x)-Luc, as described hereinabove, at multiplicity of infection (m.o.i.) of 10, and exposed to increasing concentrations of GCV (0.001-10 µg/ml, as indicated), added four hours post-transduction. Controls were cells transduced with the vectors without GCV, or GCV without vectors. The experiment was performed twice in 96-well plates, 12 wells for every group. Both controls did not induce cell death (data not shown). Note the morphological changes characteristic to cytotoxicity (cell enlargement, elongation and bloatedness) and cytotoxicity (loss of confluence) evident in AdPPE-1 (3x)+GCV-treated cells, at a significantly lower concentration of GCV than cells exposed to AdCMV-TK;

FIG. 66 is a graph representing synergy of endothelial cell cytotoxicity of TK under control of the PPE-1 (3x) promoter and ganciclovir administration. BAECs were prepared in 96-well plates and transduced as in FIG. 65, followed by the addition of increasing concentrations (0.0001-10 µg/ml) GCV four hours post-transduction. 10 days post vector addition, cell viability was determined using crystal violet staining. Note the superior cytotoxicity of AdPPE-1 (3x)+GCV at GCV concentrations greater than 0.01 µg/ml, compared with the strong constitutive TK expression of AdCMV-TK;

FIG. 67 is a series of photomicrographs illustrating the specific, synergic endothelial cytotoxicity of TK under control of the PPE-1 (3x) promoter and ganciclovir administration. Endothelial [Bovine aortic endothelial cells (BAEC), Human umbilical vein endothelial cells (HUVEC)] and non-endothelial [Human hepatoma cells (HepG-2), Human normal skin fibroblasts (NSF)] cells were transduced with AdPPE-1(3x)-TK, AdPPE-1(3x)-Luc or AdCMV-TK at m.o.i. of 10, followed by the administration of 1 µg/ml GCV four hours post-transduction. The experiment was performed twice, in 96-well plates, 12 wells for every group. Cytotoxicity and cell morphological changes were detected microscopically four days post-transduction. Note the superior cytotoxic effect of AdPPE-1(3x)-TK, +GCV in the BAEC and HUVEC cultures [morphological changes characteristic to cytotoxicity (cell enlargement, elongation and bloatedness) and cytotoxicity (loss of confluence)], and the absence thereof in HepG-2 and NSF cultures (cells remained small, rounded and confluent). AdPPE-1(3x)-Luc+GCV were nontoxic to all cell types;

FIG. 68 is a histogram representing the specific, synergic endothelial cell cytotoxicity of TK under control of the PPE-1 (3x) promoter and ganciclovir administration. Endothelial (BAEC and HUVEC) and non-endothelial (HepG-2 and NSF) cells were prepared in 96-well plates and transduced as in FIG. 67, followed by the addition of increasing concentrations (1 µg/ml) GCV four hours post-transduction. 10 days post vector addition, cell viability was determined using crystal violet staining. Note the superior, endothelial specific cytotoxicity of AdPPE-1 (3x)+GCV, compared with the nonspecific cytotoxicity of AdCMV-TK+GCV;

FIG. 69 is a series of photomicrographs illustrating the endothelial selective cytotoxicity of TK under control of the PPE-1 (3x) promoter and ganciclovir administration at extreme multiplicity of infection. Non-endothelial (NSF) cells were transduced with AdPPE-1(3x)-TK, AdPPE-1(3x)-Luc or AdCMV-TK as in FIG. 66, at the higher m.o.i. of 100, followed by the administration of 1 µg/ml GCV four hours post-transduction. The experiment was performed twice, in 96-well plates, 12 wells for every group. Cytotoxicity and cell morphological changes were detected microscopically four days post-transduction. Note the lack of effect on NSF cell morphology with AdPPE-1(3x)-TK+GCV, compared to the non-specific cytotoxicity of AdCMV-TK+GCV;

FIG. 70 is a series of photographs illustrating synergic suppression of metastatic growth by in vivo expression of TK under control of the PPE-1 (3x) promoter and ganciclovir (GCV) administration. Lung metastases of Lewis Lung Carcinoma (LLC) were induced in 14 weeks old male C57BL/6 mice (n=77) by inoculation of LLC tumor cells into the left foot pad, which was amputated as soon as the primary tumor reached a size of 7 mm. 5 days later, $10^{11}$ PFUs of the adenoviral vectors [AdPPE-1(3x)-TK+GCV; AdCMV-TK+GCV; AdPPE-1(3x)-TK without GCV] were injected into the tail vein followed by 14 days of 100 mg/kg GCV injection. The mice were sacrificed on the $24^{th}$ day post vector injection, and lungs removed for inspection and analysis. Control mice received saline and GCV. Note the significantly reduced extent of metastatic spread in the lungs of AdPPE-1 (3x)+GCV treated mice, compared to those from mice treated with AdCMV-TK+GCV, AdPPE-1 without GCV and GCV without adenovirus;

FIG. 71 is a histogram illustrating synergic suppression of metastatic growth by in vivo expression of TK under control of the PPE-1 (3x) promoter and ganciclovir (GCV) administration. Lung metastases were induced in C57BL/6 mice, and the mice treated with $10^{11}$ PFUs of the adenoviral vectors [AdPPE-1 (3x)-TK+GCV; AdCMV-TK+GCV; AdPPE-1 (3x)-TK without GCV] and GCV (100 mg/kg) as described hereinabove. The mice were sacrificed on the $24^{th}$ day post vector injection, and lungs removed for assessment of the lung metastases. Control mice received saline and GCV. Note the significant suppression of metastatic mass in AdPPE-1 (3x)+GCV-treated mice, compared to metastatic mass in GCV-free (greater than 85%) and AdCMV-TK+GCV and saline+GCV controls (greater than 75%);

FIGS. 72a-72c are representative histopathology sections of lung metastases, illustrating synergic suppression of metastatic pathology by in vivo expression of TK under control of the PPE-1 (3x) promoter and ganciclovir (GCV) administration. Lung metastases were induced in C57BL/6 mice, and the mice treated with $10^{11}$ PFUs of the adenoviral vectors [AdPPE-1(3x)-TK+GCV; AdCMV-TK+GCV; AdPPE-1 (3x)-TK without GCV] and GCV (100 mg/kg), as described hereinabove. The mice were sacrificed on the $24^{th}$ day post vector injection, and lung metastatic tissue (FIGS. 72a and 72b) or lung tissue (FIG. 72c) were sectioned and stained with hematoxylin and eosin. Note the massive central necrosis and numerous clusters of mononuclear infiltrates in metastases from lungs with AdPPE-1 (3x)+GCV administration (FIGS. 72a and 72b);

FIGS. 73a-73b are representative histopathology sections of induced LLC lung metastases stained with TUNEL and anti-caspase-3 of lung metastases, illustrating synergic enhancement of tumor apoptosis by in vivo expression of TK under control of the PPE-1 (3x) promoter and ganciclovir (GCV) administration. Sections from LLC lung metastases, induced and prepared as described in FIGS. 71a-71b were fixed and embedded in paraffin, and assayed for indicators of apoptosis by the deoxynucleotide transferase-mediated dUTP-nick end-labeling (TUNEL) assay using the Klenow-FragE1 (Oncogene, Cambridge, Mass.) (FIG. 73a) and anti-caspase-3-specific immunohistopathology (73b). Note the enhanced apoptosis in the lung metastases from the mice treated with intravenous AdPPE-1 (3x)-TK+GCV;

FIGS. 74a and 74b are representative histopathology sections of induced LLC lung metastases stained with TUNEL and anti-caspase-3 of lung metastases, illustrating the endothelial-specific, synergic enhancement of tumor apoptosis by in vivo expression of TK under control of the PPE-1 (3x) promoter and ganciclovir (GCV) administration. Sections from LLC lung metastases, induced and prepared as described in FIGS. 73a-73b were fixed and embedded in paraffin, and assayed for indicators of apoptosis by the deoxynucleotide transferase-mediated dUTP-nick end-labeling (TUNEL) assay using the Klenow-FragE1 (Oncogene, Cambridge, Mass.) (FIG. 74a) and anti-caspase-3-specific immunohistopathology (74b). Black arrows indicate erythrocytes, red arrows apoptotic endothelial cells, and white arrows apoptotic tumor cells. Note the enhanced apoptosis in the vascular (endothelial) regions of the lung metastases from the mice treated with intravenous AdPPE-1 (3x)-TK+GCV;

FIGS. 75a-75d are representative immunohistopathology sections of tissue from murine lung carcinoma, illustrating the endothelial-specific, synergic inhibition of angiogenesis by in vivo expression of TK under control of the PPE-1 (3x) promoter and ganciclovir (GCV) administration. Sections from LLC lung metastases (FIG. 75a) livers (FIG. 75c) and normal lung tissue (FIG. 75b) induced and prepared as described in FIGS. 73a-73b were fixed and embedded in paraffin, and assayed for indicators of angiogenesis by anti-CD-31 immunofluorescence. Note the short, indistinct vessels and absence of continuity or branching in lung metastases from AdPPE-1(3x)-TK+GCV treated mice. FIG. 75d is a histogram showing a computer-based vascular density assessment (Image Pro-Plus, Media Cybemeticks Incorporated) of the lung metastases vascularization (angiogenesis). Left bar: AdPPE-1(3x)TK+GCV; right bar: AdPPE-1 (3x)TK no GCV;

FIG. 76 is a representative histopathology section of tissue from murine liver, illustrating the absence of hepatotoxicity in in-vivo expression of TK under control of the PPE-1 (3x) promoter and ganciclovir (GCV) administration. Sections from livers of mice bearing LLC lung metastases induced and prepared as described in FIGS. 73a-73b were fixed and embedded in paraffin, and stained with hematoxylin and eosin. Note the absence of cytotoxic indicators in livers from mice treated with AdPPE-1-TK+GCV (3x) (left panel), compared to the profound cytotoxicity in the livers from mice treated with the constitutively expressed AdCMV-TK+GCV (right panel);

FIG. 77 depicts a RT-PCR analysis illustrating the organ-specific expression of the expression of TK under control of the PPE-1 (3x) promoter and ganciclovir (GCV) administration. LLC lung metastases were induced and prepared in nine 15 week-old C57BL/6 male mice as described in FIGS. 73a-73b. Adenovirus vectors [AdPPE-1 (3x)-TK and AdCMV-TK], and saline control were delivered intravenously 14 days post primary tumor removal. The mice were sacrificed 6 days post vector injection, and organs harvested. RNA of different organs was extracted, as described hereinbelow, and PPE-1 (3x) and HSV-TK transcripts amplified by RT-PCR PCR with PPE-1(3x) promoter and HSV-TK gene primers. Note the endothelial-specific expression of TK under control of the PPE-1 (3x) promoter (center, bottom panel);

FIGS. 78a and 78b are graphs illustrating a range of sub-therapeutic and non-toxic irradiation in Balb/c murine colon carcinoma tumor model. 20 Balb/c male mice aged 8 weeks inoculated with CT-26 colon carcinoma cells into the left thigh and received local irradiation with 0, 5, 10, or 15 Gy under general anesthesia, when the tumor diameter had reached 4-6 mm. For tumor volume (76a), the tumor axis was calculated according to the formula $V=\pi/6\times\alpha^2\times\beta$ ($\alpha$ is the short axis and $\beta$ is the long axis). The 5 Gy dose induced only a partial, non-statistically significant delay in tumor progression (FIG. 78a), and no significant weight loss (FIG. 78b);

FIGS. 79a-79g illustrate synergistic suppression of tumor growth in murine colon carcinoma with combined sub-therapeutic radiotherapy and expression of TK under control of the PPE-1 (3x) promoter and ganciclovir (GCV) administration. 100 male Balb/C mice aged 8 weeks were inoculated with CT-26 colon carcinoma tumor cells. As soon as the tumor axis reached 4-6 mm, $10^{11}$ PFUs of the viral vectors [AdPPE-1 (3x)-TK or AdCMV-TK] were injected intravenously into the tail vein followed by 14 days of daily intraperitoneal GCV injection (100 mg/kg body weight), where indicated. 3 days post vector administration, the mice were irradiated with a local 5 Gy dose. Tumor volume was assessed according to the formula $V=\pi/6\times\alpha^2\times\beta$ ($\alpha$ is the short axis and $\beta$ is the long axis). FIG. 79a shows mean tumor volume±S.E. on day 14 post vector injection. FIG. 79b shows mean tumor volume progression over time, in groups treated with radiotherapy. FIG. 79c shows mean tumor volume progression over time, in AdPPE-1(3x)-TK+GCV treated mice. FIG. 79d shows mean tumor volume progression over time, in AdCMV-TK+GCV treated mice. FIG. 79e shows mean tumor volume progression over time, in control saline+GCV treated mice. FIG. 79f shows mean tumor volume progression over time, in AdPPE-1(3x)-TK treated mice without GCV. FIG. 79g is a representative example of the gross pathology of the CT-26 primary tumor in Balb/C mice on the day of sacrifice. Note that radiotherapy significantly potentiated only the angiogenic endothelial cell transcription-targeted vector, AdPPE-1(3x)-TK, compared to the non-targeted vector, AdCMV-TK (p=0.04) (FIG. 79c-79f). Treatment regimens with all virus vectors were ineffective without radiotherapy;

FIGS. 80a-80b are representative histopathology sections of primary CT-26 tumor showing synergistic induction of tumor necrosis in murine colon carcinoma with combined sub-therapeutic radiotherapy and expression of TK under control of the PPE-1 (3x) promoter and ganciclovir (GCV) administration. Sections from CT-26 colon carcinoma tumors induced and prepared as described in FIGS. 79a-79g were fixed and embedded in paraffin, and stained with hematoxylin and eosin. Note the areas of necrosis (FIG. 80a) and granulation tissue (FIG. 80b) with combined AdPPE-1 (3x)+GCV+ low dose radiotherapy;

FIGS. 81a-81b are representative histopathology sections of induced primary colon carcinoma tumors stained with TUNEL and anti-caspase-3, illustrating synergic enhancement of endothelial cell and tumor apoptosis by combined radiotherapy and in vivo expression of TK under control of the PPE-1 (3x) promoter and ganciclovir (GCV) administration. Sections from CT-26 primary colon carcinoma tumors, induced and prepared as described in FIGS. 77a-77g were fixed and embedded in paraffin, and assayed for indicators of apoptosis by the deoxynucleotide transferase-mediated dUTP-nick end-labeling (TUNEL) assay using the Klenow-FragE1 (Oncogene, Cambridge, Mass.) (FIG. 81a) and anti-caspase-3-specific immunohistopatholgy (81b). Note the massive apoptosis (FIG. 81a) and the caspase-3-positive endothelial cells (81b) in the tumors from the mice treated with combined radiotherapy and intravenous AdPPE-1 (3x)-TK+GCV;

FIG. 82 is representative histopathology sections of induced primary colon carcinoma tumors stained with anti-caspase-3, illustrating synergic enhancement of endothelial cell and tumor apoptosis by combined radiotherapy and in vivo expression of TK under control of the PPE-1 (3x) promoter and ganciclovir (GCV) administration. Sections from CT-26 primary colon carcinoma tumors, induced and prepared as described in FIGS. 79a-79g were fixed and embedded in paraffin, and assayed for indicators of apoptosis by anti-caspase-3-specific immunohistopathology. Black arrow indicates erythrocytes; red arrow indicates apoptotic endothelial cell, and white arrow indicates apoptotic tumor cell. Note the GCV-dependent apoptotic effect;

FIGS. 83a and 83b are representative histopathology sections of liver tissue and induced primary colon carcinoma tumors stained with anti-CD-31, illustrating synergic enhancement of inhibition of tumor vascularization by combined radiotherapy and in vivo expression of TK under control of the PPE-1 (3x) promoter and ganciclovir (GCV) administration. Sections from liver tissue (83b) and CT-26 primary colon carcinoma tumors (83a), induced and prepared as described in FIGS. 79a-79g were fixed and embedded in paraffin, and reacted with endothelial-specific anti-CD-31 for immunohistopathology. Black arrow indicates erythrocytes; red arrow indicates apoptotic endothelial cell, and white arrow indicates apoptotic tumor cell. Note the extensive vascular disruption in the tumors from the mice treated with combined radiotherapy and intravenous AdPPE-1 (3x)-TK+GCV (83a) compared with the normal vasculature in the liver cells (83b);

FIG. 84 is representative histopathology sections of mouse liver tissue showing tissue-specific cytotoxicity of radiotherapy and TK expression under control of the PPE-1 (3x) promoter and ganciclovir (GCV) administration. Sections from mouse livers exposed to a vectors (AdPPE-1 (3x)-TK and AdCMV-TK) and GCV, alone and in combination, were fixed and embedded in paraffin, and stained with hematoxylin and eosin. Note the typical mild hepatotoxicity with AdCMV-TK and ganciclovir (left panel), and the absence of vascular abnormalities in the AdPPE-1 (3x)-TK treated liver (right panel);

FIGS. 85a and 85b are graphs illustrating a range of sub-therapeutic and non-toxic irradiation in C57Bl/6 lung carcinoma metastatic model. 35 C57Bl/6 male mice aged 8 weeks were inoculated with Lewis Lung Carcinoma (LLC) cells into the left footpad and received irradiation into the chest wall with 0, 5, 10, or 15 Gy under general anesthesia, 8 days following removal of the primary tumor. Mice were sacrificed 28 days post tumor removal. Weight loss indicated metastatic disease. The 5 Gy dose was neither therapeutic (FIG. 85a) nor toxic (FIG. 85b);

FIGS. 86a-86d illustrate synergistic suppression of metastatic disease in murine lung carcinoma with combined sub-therapeutic radiotherapy and expression of TK under control of the PPE-1 (3x) promoter and ganciclovir (GCV) administration. 180 male Balb/C mice aged 8 weeks were inoculated with LLC cells into the left footpad. The foot was amputated under general anesthesia as soon as the primary tumor developed. 5 days post amputation, $10^{10}$ PFUs of vector [AdPPE-1(3x)-TK or AdCMV-TK] were injected into the tail vein, followed by 14 days of daily intraperitoneal injections of GCV (100 mg/kg). 3 days post vector injection, a single 5 Gy dose of radiotherapy aimed at the mouse's chest wall was administered under general anesthesia. FIG. 86a shows survival of irradiated, non-vector treated mice over 55 days. FIG. 86b shows survival of AdPPE-1(3x)-TK treated mice. FIG. 86c shows survival of AdCMV-TK treated mice. FIG. 86d shows survival of saline treated control mice. Note that radiotherapy significantly potentiated only the angiogenic endothelial cell transcription-targeted vector, AdPPE-1(3x)-TK, compared to the non-targeted vector, AdCMV-TK (FIG. 86b-86d). Treatment regimens with all virus vectors were ineffective without radiotherapy;

FIGS. 87a-87c are a series of histograms showing endothelial cell cytotoxicity of Fas-c under control of CMV promoter. Bovine aortic endothelial cells (BAEC) were stained with crystal violet 72 hours after transduction with 100 (left), 1000 (right) and 10000 (left bottom) moi's of CMV-FAS (dark) or CMV-LUC (gray, negative control), and 24 hours after the addition of human TNF-α ligand, in different concentrations. Note the reduced viability of BAE cells at high moi and TNF-α concentrations;

FIG. 88 is a graph of plaque development showing enhanced spread of viral replication in 293 cells with CMV-FAS (blue diamonds) compared to CMV-LUC (red squares). Titers of CsCl-banded stocks of CMV-FAS and CMV-LUC were determined by PFU assay, as described hereinbelow. Data is plotted as number of plaques seen on every 2-3 days of the plaque assay in log-scale;

FIGS. 89a and 89b is a series of photographs of 293 cell cultures illustrating the higher rate of cell-to-cell spread of virus infection (plaquing) with CMV-Fas-c as compared with CMV-luciferase. 4 days after infection, photographs of plaques from CMV-FAS (left) and CMV-LUC (right) with identical dilution, were taken. Plaques from CMV-FAS are clearly larger than those of CMV-LUC, indicating a higher rate of cell to cell spread, probably induced by apoptosis;

FIG. 90 is a histogram illustrating the specific, synergic endothelial cytotoxicity of Fas-c under control of the PPE-1 (3x) promoter and doxorubicin administration. BAEcells were exposed to 100 nM of Doxorubicin 48 hours after vector (PPE-1 (3x)-FAS) transduction ($10^3$ moi). Dox+PPE-fas=Doxorubicin+PPE-1 (3x)-Fas-c (orange); Dox=Doxorubicin alone (green); PPE-FAS=PPE-1 (3x)-FAS (red); no treatment=black. Cells were stained with crystal violet 96 hours after vector transduction, and cell viability was assessed microscopically. Note the significant synergy in endothelial cytotoxicity between AdPPE-1 (3x)-Fas-c and doxorubicin;

FIGS. 91a-91b are a graphic representation illustrating superior induction of angiogenesis in engineered tissue constructs by VEGF under the control of the endothelin (PPE-1 3X). Tissue engineered constructs (undisclosed procedure) were grown with or without VEGF supplementation to the medium (50 ng/ml). Parallel constructs were infected with Ad5PPEC-1-3x VEGF viruses or control Ad5PPEC-1-3x GFP adenoviruses (control virus) (for 4 hours). Following 2 weeks in culture the constructs were fixed, embedded, sectioned and stained. Vascularization was expressed as the number of vessels per mm², and the percentage of area of sections that was vascularized. FIG. 91a shows that infection of the cells with Ad5PPEC-1-3x VEGF has an inductive effect on number and size of vessels-like structures formed in the engineered constructs. Note the dramatic increase (4-5X) in both parameters of vascularization in the Ad5PPEC-1-3x VEGF-transduced tissue constructs (VEGF virus), compared to constructs exposed to VEGF to the medium (VEGF medium). FIG. 91b is a histogram of LUC luminescence intensity, illustrating the superior survival and vascularization of implanted tissue constructs grown with cells infected with Ad5PPEC-1-3x VEGF, compared with Ad5PPEC-1-3x GFP controls;

FIG. 92 is the wild-type murine PPE-1 promoter DNA sequence (SEQ ID NO:1). The promoter contains the endogenous endothelial specific positive transcriptional element (black italics), the NF-1 response element (pink italics), the GATA-2 element (red italics), the HIF-1 responsive element (blue italics), the AP-1 site (green italics), the CAAT signal (orange italics) and the TATA box (purple italics);

FIG. 93 is the sequence of the 3x fragment of the modified murine pre-proendothelin-1 promoter (SEQ ID NO:7). The fragment contains 2 complete endothelial cell specific positive transcription elements (red) and two portions that are located as inverted halves of the original sequence (blue): SEQ ID NO:15 (nucleotides from the 3' portion of the transcription elements SEQ ID NO: 6), and SEQ ID NO:16 (nucleotides from the 5' portion of the transcription elements SEQ ID NO: 6);

FIG. 94 is a histogram illustrating the tissue specific, Bosentan-induced enhancement of expression of the LUC gene under control of the PPE-1 (3x) promoter in transgenic mice;

FIGS. 95a and 95b are histograms illustrating the lack of host immune response to transgenes expressed under control of the PPE-1(3x) promoter, measured by ELISA. Note the nonspecific anti-adenovector response (FIG. 95a), compared with the minimal anti TNF-R1 response evoked in the PPE-1(3x) Fas-c treated mice (FIG. 95b);

FIG. 96 is a histogram illustrating the ET-B specific enhancement of expression of the LUC gene under control of the PPE-1 promoter in endothelial cells. Bovine Aortic Endothelial Cells were transiently transfected with a PPE-1-luciferase construct (pEL-8), as described hereinabove. One hour post treatment with different concentrations of endothelin antagonists relative luciferase activity was calculated. relative luciferase activity was calculated as the ratio of light units to β-galactosidase units, with β-galactosidase activity resulting from co-transfection of a constitutively active lacZ construct. Values are presented relative to the non-treated cells (concentration 0 μM=100%). The values represent the mean±S.E. of triplicates. * P<0.05 compared to non-treated cells (Student's t test). Note the dose-dependent, ET-$1_B$ specific enhancement of LUC expression with BQ788 (grey bars), and the lack of enhancement with the ET-$1_A$ specific inhibitor BQ123 (black bars);

FIGS. 97A and 97B are histograms illustrating the enhancement of preproendothelin synthesis and secretion by the dual ET-$1_A$ and ET-$1_B$ inhibitor Bosentan transgenic mice. Transgenic mice expressing the LUC gene under the control of preproendothelin-1(PPE-1) promoter were treated with Bosentan (100 mg/kg) for 30 days. FIG. 97A shows a histogram of total RNA extracted from lungs of the transgenic animals. FIG. 97B shows a histogram of preproendothelin-1 mRNA levels (measured by semi-quantitative RT-PCR). These values were normalized to β-actin and then represented graphically in arbitrary units. FIG. 97B shows immunoreactive endothelin-1 (ET-1) levels in control (open bars) or Bosentan-treated mice (grey hatched bars). Results are expressed as mean±S.E. of 5 mice versus control untreated mice (Student's t test);

FIG. 98 is a histogram illustrating enhancement with corticosteroids of recombinant protein expression in endothelial cells transformed with adenovirus vectors. BAEC were exposed to 3 μM dexamethasone (grey bars) or no steroids (black bars) for 48 hours prior to infection with adenovirus constructs with the LUC gene under control of the constitutive CMV promoter, at MOI of $10-10^4$. Recombinant gene expression is expressed as % Luciferase/μg total protein in the cells. Note the consistent enhancement of expression with the corticosteroid at all MOI, with up to 300% at MOI of 1000; and FIG. 99 is a fluorescent photomicrograph illustrating enhancement by corticosteroids of the expression in endothelial cells of recombinant protein under control of the PPE-1 promoter. BAEC were exposed to dexamethasone (3 μM) 48 hr before infection with AdPPE-GFP (at a MOI of 100 for 48 hr). Photomicrographs are of 2 representative wells each for controls (top) and dexamethasone-treated (bottom) BAEC. Note the significantly stronger green fluorescent signal in the dexamethasone treated cells.

DESCRIPTION OF THE PREFERRED EMBODIMENTS

The present invention is of polynucleotide sequences exhibiting endothelial cell specific promoter activity, and methods of use thereof. More particularly, the present invention relates to a modified-preproendothelin-1 (PPE-1) promoter which exhibits increased activity and specificity in endothelial cells, and nucleic acid constructs, which can be used to activate apoptosis in specific cell subsets, thus, enabling treatment of diseases characterized by aberrant neovascularization or cell growth. The invention further relates to modifications of the PPE promoter, which enhance its expression in response to physiological conditions including hypoxia and angiogenesis, and novel angiogenic endothelial-specific combined therapies.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Unbalanced angiogenesis typifies various pathological conditions and often sustains progression of the pathological state. For example, in solid tumors, vascular endothelial cells divide about 35 times more rapidly than those in normal tissues (Denekamp and Hobson, 1982 Br. J. Cancer 46:711-20). Such abnormal proliferation is necessary for tumor growth and metastasis (Folkman, 1986 Cancer Res. 46:467-73). Vascular endothelial cell proliferation is also important in chronic inflammatory diseases such as rheumatoid arthritis, psoriasis and synovitis, where these cells proliferate in response to growth factors released within the inflammatory site (Brown & Weiss, 1988, Ann. Rheum. Dis. 47:881-5). On the other hand, in ischemic conditions such as cardiac ischemia, Peripheral Vascular Diseases, wound healing, burn scarring and of the same, the induction of angiogenesis has an healing effect (Thompson, et al., PNAS 86:7928-7932, 1998) and thus will be beneficial.

Hence, regulating or modifying the angiogenic process can have an important therapeutic role in limiting the contributions of this process to pathological progression of an underlying disease state, as well as providing a valuable means of studying the etiology of such diseases. Recently significant progress in the development of endothelial regulating agents, whether designed to be inhibitory or stimulatory, has been made (for a recent review, see Mariani et al GenMedGen 2003, 5:22). However, for pro angiogenic applications and mass formation of long lasting functional blood vessel there is a need for repeated or long term delivery of the above described protein factors, thus limiting their use in clinical settings. Furthermore, in addition to the high costs associated with the production of angiogenesis-regulating factors, efficient delivery of these factors requires the use of catheters to be placed in the coronary arteries, which further increases the expense and difficulty of treatment.

To date, promising clinical trials have shown that anti angiogenic treatments like Avastin® or Bay-43906®, can blunt the metastasis progression by limiting new growth of blood vessels surrounding the tumors. However, inhibiting the formation of new blood vessels and/or partially destroying them may be insufficient in cancer pathologies where a dramatic anti angiogenic effect that destroys most or all existing angiogenic blood vessels and induce tumor necrosis is required. Further, although promising in pre-clinical models, to date systemic administration of all anti-angiogenic agents tested in clinical trials, have shown limited rate of success and considerable toxicities including thrombocytopenia, leukopenia and hemoptysis. Thus, endothelial-specific targeting of therapeutic agents is essential to pro- and anti-angiogenic therapies. Endothelial specific promoters have been described in the art, examples include flk-1, Flt-1 Tie-2 VW factor, and endothelin-1 (see U.S. Pat. No. 6,200,751 to Gu et al; U.S. Pat. No. 5,916,763 to Williams et al, and U.S. Pat. No. 5,747,340 to Harats et al, all of which are incorporated by reference herein). Endothelial cell targeting of a therapeutic gene, expressed under the control endothelial-specific promoters has also been described in the art. For example, Jagger et al used the KDR or E-selectin promoter to express TNFα specifically in endothelial cells [Jaggar R T. Et al. Hum Gene Ther (1997) 8(18):2239-47] while Ozaki et al used the von-Willebrand factor (vWF) promoter to deliver herpes simplex virus thymidine kinase (HSV-tk) to HUVEC [Hum Gene Ther (1996) 7(13):1483-90]. Although these promoters are considered endothelial cell specific, studies have shown that many of these promoters are inefficient at directing expression to endothelial cells, lacked the strict specificity required, showed only weak activity and did not allow for high levels of expression.

One approach to the construction of more efficient and specific endothelial promoters for therapeutic use has been the identification and inclusion of tissue specific enhancer elements. Enhancer elements specific to endothelial cells have previously been described, for example, by Bu et al. (J. Biol. Chem. (1997) 272(19): 32613-32622) who demonstrated that three copies of the enhancer element of PPE-1 (containing elements ETE-C, ETE-D, and ETE-E) endows promoter sequences with endothelial cell specificity in-vitro. However, no in-vivo utility of the enhancer element could be demonstrated.

As clearly illustrated in the Example section hereinbelow, the present inventors have proven the enhancer element to be suitable for use in in-vivo therapeutic applications. By creating a unique, modified, thrice-repeated (3x) enhancer element (SEQ ID NO: 7), and assessing it's activity in directing endothelial-specific gene expression in-vitro and in-vivo, the present inventors have further constructed a highly active enhancer element comprising portions of the 3x enhancer element sequence in a novel, rearranged orientation. This modified enhancer element exhibits enhanced specificity to proliferating endothelial cells participating in angiogenesis, and negligible activity in normal endothelial cells in-vivo. Thus, the present inventors have, for the first time, identified portions of the enhancer element which, when reconfigured, impart superior activity to nearby promoter sequences.

Thus, according to one aspect of the present invention, there is provided an isolated polypeptide comprising a cis regulatory element capable of directing transcription of a polynucleotide sequence transcriptionally linked hereto in eukaryotic cells. The isolated polynucleotide includes at least a portion of the sequence set forth in SEQ ID NO:15, covalently linked to at least a portion of the sequence as set forth in SEQ ID NO:16. In one preferred embodiment, the at least a portion of the sequence set forth in SEQ ID NO:15 is positioned upstream of the at least a portion of the sequence set forth in SEQ ID NO:16 in the cis regulatory element. In yet another preferred embodiment, the at least a portion of the sequence set forth in SEQ ID NO:16 is positioned upstream of the at least a portion of the sequence set forth in SEQ ID NO:15 in the cis regulatory element.

SEQ ID NO:15 is a polynucleotide sequence representing nucleotide coordinates 27 to 44 of the murine endothelial specific enhancer element (SEQ ID NO:6), with an additional guanyl nucleotide linked at the 3' terminus, and SEQ ID NO:16 is a polynucleotide sequence representing nucleotide coordinates 1 to 19 of the murine endothelial specific enhancer element (SEQ ID NO:6).

For purposes of this specification and the accompanying claims, the term "enhancer" refers to any polynucleotide sequence, which increases the transcriptional activity of a promoter, preferably, but not exclusively, in a tissue specific manner. As used herein, the phrase "tissue specific enhancer" refers to an enhancer which increases the transcriptional activity of a promoter in a tissue-or context-dependent manner. It will be appreciated that such a "tissue specific enhancer" reduces, inhibits or even silences the transcriptional activity of a promoter in non-compatible tissue or environment.

According to some embodiments of the invention, the isolated polynucleotide includes contiguous copies of at least a portion of SEQ ID Nos: 15 and 16. Such sequences are preferably positioned in a head-to tail orientation, although other orientations well known in the art can be constructed, such as inverted orientation (tail to tail, or head to head), complementary orientation (replacing "a" with "t", "t" with "a", "g" with "c", and "c" with "g"), inverted complementary orientation, and the like. The at least a portion of the sequence as set forth in SEQ ID NO:15 can be covalently linked directly to the at least a portion of the sequence as set forth in SEQ ID NO:16, or, in a preferred embodiment, the two sequences can be linked via a linker polynucleotide sequence. As used herein, the term "linker polynucleotide" refers to a polynucleotide sequence which is linked between two or more flanking polynucleotides (e.g. SEQ ID Nos: 15 and 16). One such preferred linker sequence is the trinucleotide sequence "cca", for example, which is the linker sequence as set forth in nucleotides in positions 55-57 of SEQ ID NO:7. Other suitable linker sequences can include entire additional enhancer elements, native or artificial, for example, multiple copies of SEQ ID NO.15, SEQ ID NO:16, the 1x enhancer element of PPE-1, additional entire promoters, hypoxia response element (such as SEQ ID NO: 5), and the like.

As used herein, the phrase "a portion of the sequence as set forth in SEQ ID NO:15 . . . " or "a portion of the sequence as set forth in SEQ ID NO:16 . . . " is defined as a sequence representing at least 8 contiguous nucleotides of the 5' terminus, 3' terminus or any sequence therebetween, of the indicated sequence. Thus, for example, the sequences representing nucleotide coordinates 1-8, 1-9, 1-10, 1-11 . . . , in increments of 1 nucleotide up to nucleotide coordinates 1-17 of SEQ ID NO:15 all constitute a portion of SEQ ID NO:15 according to the present invention, as do all the sequences representing nucleotide coordinates 2-9, 2-10, 2-11, . . . to 2-17 of SEQ ID NO:15, as do all the sequences representing nucleotide coordinates 3-10, 3-11, 3-12, . . . to 3-17 of SEQ ID NO:15, inclusive up to sequences representing nucleotide coordinates 10-17 of SEQ ID NO:15. Similarly, the sequences representing nucleotide coordinates 1-8, 1-9, 1-10, 1-11 . . . , in increments of 1 nucleotide up to nucleotide coordinates 1-19 of SEQ ID NO:16 all constitute a portion of SEQ ID NO:16 according to the present invention, as do the sequences representing nucleotide coordinates 2-9, 2-10, . . . , as described hereinabove.

While reducing the present invention to practice, it was uncovered that the modified enhancer PPE-1(3x) includes a sequence as set forth in SEQ ID NO:15 linked to a sequence as set forth in SEQ ID NO:16, flanked Immediately upstream and immediately downstream by a copy of the murine endothelial specific enhancer element (1x) (see SEQ ID NO:7). Thus, in one preferred embodiment, the cis regulatory element of the present invention further includes at least one copy of the sequence as set forth in SEQ ID NO:6. In a more preferred embodiment, the cis regulatory element includes at least two copies of the sequence as set forth in SEQ ID NO:6. In a most preferred embodiment, the cis regulatory element of the present invention is as set forth in SEQ ID NO:7.

Preferably the isolated polynucleotide further includes an endothelial cell-specific promoter sequence element. For purposes of this specification and the accompanying claims, the term "promoter" refers to any polynucleotide sequence capable of mediating RNA transcription of a downstream sequence of interest. The endothelial specific promoter element may include, for example, at least one copy of the PPE-1 promoter. Examples of suitable promoters/enhancers which can be utilized by the nucleic acid construct of the present invention include the endothelial-specific promoters: pre-proendothelin-1, PPE-1 promoter (Harats D, J Clin Invest. 1995 March; 95(3):1335-44)., the PPE-1-3x promoter [PCT/IL01/01059; Varda-Bloom N, Gene Ther 2001 June; 8(11): 819-27], the TIE-1 (S79347, S79346) and the TIE-2 (U53603) promoters [Sato T N, Proc Natl Acad Sci USA 1993 Oct. 15; 90(20):9355-8], the Endoglin promoter [Y11653; Rius C, Blood 1998 Dec. 15; 92(12):4677-90], the von Willebrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K,: J Biol Chem 1995 Nov. 17; 270(46): 27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J. 1989 October; 8(10):2889-96], VCAM-1 [M92431; Iademarco M F, J Biol Chem 1992 Aug. 15; 267(23):16323-9], PECAM-1 [AJ313330 X96849; CD31, Newman P J, Science 1990 Mar. 9; 247(4947):1219-22], the vascular smooth-muscle-specific elements: CArG box X53154 and aortic carboxypeptidase-like protein (ACLP) promoter [AF332596; Layne M D, Circ Res. 2002; 90: 728-736] and Aortic Preferentially Expressed Gene-1 [Yen-Hsu Chen J. Biol. Chem., Vol. 276, Issue 50, 47658-47663, Dec. 14, 2001]. Other suitable endothelial specific promoters are well known in the art, such as, for example, the EPCR promoter (U.S. Pat. No. 6,200,751 to Gu et al) and the VEGF promoter (U.S. Pat. No. 5,916,763 to Williams et al).

As used herein, the term "modulator of angiogenesis" is defined as a molecule or compound capable of inhibiting or enhancing angiogenesis in a tissue. Such modulator of angiogenesis can be anti-angiogenic factors, such as antagonists of important targets of angiogenesis, for example, the Endothelin Receptor, or angiogenic factors, causing up- or down-regulation of endothelial-specific promoter activity.

It will be appreciate that other, non-endothelial promoters can also be incorporated into the isolated polynucleotide described above, in order to direct expression of desired nucleic acid sequences in a variety of tissue. Promoters suitable for use with the construct of the present invention are well known in the art. These include, but are not limited to viral promoters (e.g., retroviral ITRs, LTRs, immediate early viral promoters (IEp) (such as herpesvirus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters)). Other suitable promoters are eukaryotic promoters which contain enhancer sequences (e.g., the rabbit .beta.-globin regulatory elements), constitutively active promoters (e.g., the .beta.-actin promoter, etc.), signal and/or tissue specific promoters (e.g., inducible and/or repressible promoters, such as a promoter responsive to RU486, the metallothionine promoter, PSA promoter, etc.), and tumor-specific promoters such as the telomerase, plastin and hexokinase promoters.

Preferably, the isolated polynucleotide further includes a hypoxia response element, for example at least one copy of the sequence set forth in SEQ ID NO: 5.

The isolated nucleic acid sequence of the present invention can be used to regulate gene expression in eukaryotic tissue, and in particular, in proliferating endothelial cells, for example endothelial cells involved in angiogenesis, or for silencing (inhibiting) gene expression in resting endothelial cells.

Thus, the isolated polynucleotide sequence of the present invention may be provided, in some cases, as part of a nucleic acid construct further including a nucleic acid sequence positioned under the regulatory control of the isolated polynucleotide of the present invention. The nucleic acid construct of the present invention can further include additional polynucleotide sequences such as for example, sequences encoding selection markers or reporter polypeptides, sequences encoding origin of replication in bacteria, sequences that allow for translation of several proteins from a single mRNA (IRES), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives. Such a nucleic acid construct is preferably configured for mammalian cell expression and can be of viral origin. Numerous examples of nucleic acid constructs suitable for mammalian expression are known in the art; the Examples section which follows provides further detail of several such constructs.

For purposes of this specification and the accompanying claims, the phrase "nucleic acid sequence positioned under regulatory control . . ." refers to any polynucleotide sequence that has the capacity to be transcribed by an RNA polymerase, which transcription thereof can be directed by a cis regulatory element, such as the cis regulatory element of the present invention. This definition includes coding sequences translatable into polypeptides, as well as sequence for antisense RNA, RNA which binds DNA, ribozymes and other molecular moieties which are not destined to undergo translation. Examples of nucleic acid sequences which may be used by the construct according to the present invention are, for example, positive and negative regulators of angiogenesis such as VEGF, FGF-1, FGF-2, PDGF, angiopoietin-1 and angiopoietin-2, TGF-β, IL-8 (for an extensive list of regulators of angiogenesis, see Table 1 hereinabove), cytotoxic drugs, reporter genes and the like. In a preferred embodiment, the nucleic acid sequence is selected from the angiogenesis regulators VEGF, p55, angiopoietin-1, bFGF and PDGF-BB. Additional transcribable nucleic acid sequences suitable for control by the cis regulatory element of the present invention are provided hereinbelow and in the Examples section which follows.

Examples presented hereinbelow illustrate that the novel cis regulatory elements of the present invention can reliably direct expression of a reporter gene (GFP and LUC) to endothelial tissue following systemic in-vivo administration, in a preferential manner in ischemic and/or angiogenic (proliferating) endothelial tissue. More significantly, the examples further show, that the isolated polynucleotide of the present invention can be used to preferentially express therapeutic genes in tumors, metastases, ischemic and/or angiogenic tissue, thus providing direct evidence as to the importance of the cis regulatory element of the present invention, and its derivatives, in therapeutic applications.

In one embodiment, the nucleic acid construct of the present invention is used in upregulating angiogenesis in a tissue, and treating or preventing a disease or condition associated with ischemia. Such disease and conditions, which would benefit from enhanced angiogenesis, are well known in the art, for example—wound healing, ischemic stroke, ischemic heart disease and gastrointestinal lesions.

As used herein, the phrase "down-regulating angiogenesis" refers to either slowing down or stopping the angiogenic process, which lead to formation of new blood vessels. The phrase "upregulating angiogenesis" refers to enhancing the expression of a dormant or minimally-functioning endothelial cell angiogenesis activator.

Thus, the present invention can be used for gene therapy. Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989, 1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in may cases, to elude host defense mechanisms. Typically, viruses infect and propagate in specific cell types. The targeting specificity of viral utilizes its natural specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with appropriate target specificity for infection.

The most common problems encountered in prior art gene therapy protocols are poor efficacy and immune response of the host to the vector. Poor efficacy may result from failure of the delivered material to enter cells, to integrate into the genome, or to be expressed at appropriate levels. In addition, response over the course of time is often poor. This means that readministration, which might be advantageous, is often problematic due to the abovementioned immune response.

Such therapeutic applications include both the enhancement, and inhibition of angiogenesis in the target tissue. Depending on the cellular response to the preferential expression of the nucleic acid sequence directed by the cis regulatory element of the present invention, proliferation of endothelial cells, leading to enhanced angiogenesis, or inhibition of endothelial cell proliferation, leading to reduced angiogenesis and ischemia, can result.

Thus, inclusion of a nucleic acid sequence the expression of which is cytotoxic in the nucleic acid construct of the invention provides a method of targeting cell death to rapidly proliferating endothelial cells in angiogenic vessels of, for example, tumors. Because such a vector may be administered systemically, it can be employed to effectively induce cell death in developing metastatic foci, in advance of any presently available ability to identify and locate such foci of metastatic spread.

Such therapeutic nucleic acid sequences that can be used with the constructs of the present invention for cancer gene therapy are often classified as either corrective gene therapy, aimed at restoring mutant gene activity and control, immunomodulatory gene therapy, aimed at sensitizing the immune system against cancer cells, and cytoreductive gene therapy, aimed at killing cancer cells by a prodrug or toxic agent (suicide gene therapy), pro-apoptotic gene, anti-angiogenic genes or enhancement of chemotherapy or radiotherapy. Nucleic acid sequences suited for corrective gene therapy with the cis regulatory element of the present invention include, but are not limited to, the p53 gene (GenBank Access. No. BC018819), an anti-neoplastic, DNA-stabilizing gene whose expression is suppressed in cancer cells; Cip/Kip (p21, GenBank Acces. No. NM000389; and p27, GenBank Accesss. No. NM004064) and Ink4 (p14, GenBank Access. No. NM058197), cyclin-dependent kinase inhibitors. Nucleic acid sequences suited for suppression of oncogene function with the cis regulatory element of the present invention include, but are not limited to, antisense oligonucleotides that interfere with the transcription and translation of oncogenes such as ras, myc, erbB2 and bcl-2, and catalytic ribozymes that interfere with their translation. Methods for the synthesis and use of anti-oncogene antisense and ribozyme polynucleotides are well known in the art, and are described in detail, for example, in U.S. Pat. No. 6,627,189 to Roth et al., U.S. Pat. No. 6,265,216 to Bennet et al. and U.S. Pat. No. 5,734,039 to Calabretta et al, all of which have been incorporated fully herein by reference. Methods for preparation and use of catalytic anti-oncogene ribozymes are described, for example, in U.S. Pat. No. 5,635,385 to Leopold et al., incorporated fully herein by reference.

In a further embodiment of the present invention, the nucleic acid sequence expressed under control of the cis regulatory element of the present invention is directed to immunomodulation gene therapy, designed to prevent avoidance of immune surveillance by tumor and metastatic cells. Nucleic acid sequences encoding immunomodulatory factors suitable for use with the cis regulatory element of the present invention are cytokine genes, intracellular molecule genes for augmenting cytotoxic T cell recognition of Tumor Antigen and exogenous foreign immunogens (in order to induce a non-specific local immune reaction). Suitable immunostimulatory factors include, but are not limited to human IL-2, interferons such as human alpha.-, beta.- or .gamma.-interferon, human T-cell granulocyte-macrophage colony stimulating factor (GM-CSF), human tumor necrosis factor (TNF), and lymphotoxin (TNF-b). The human IL-2 gene has been cloned and sequenced and can be obtained as, for example, a 0.68 kB BamHI-HinDIII fragment from pBC 12/HIV/IL-2 (available from the American Type Culture Collection ("ATCC") under Accession No. 67618). Further, the sequences of human beta.-interferon, human GM-CSF, human TNF and human lymphotoxin are known and are available. Particularly, the sequence of human .gamma.-interferon is known (Fiers et al. (1982) Philos. Trans. R. Soc. Lond., B, Biol. Sci. 299:29-38) and has been deposited with GenBank under Accession No. M25460. The sequence of human GM-CSF is known (Wong et al. (1985) Science 228: 810-815) and has been deposited with GenBank under Accession No. M10663. The sequence of human TNF has been described (Wang et al. (1985) Science 228:149-154) and is deposited with GenBank under Accession No. M10988. The sequence of human lymphotoxin (TNF-b) has also been published (Iris et al. (1993) Nature Genet. 3:137-145) and is deposited with GenBank under Accession No. Z15026.

In yet a further embodiment, the nucleic acid sequence expressed under control of the cis regulatory element of the present invention is directed to cytoreductive gene therapy, or the killing of target cells by either direct or indirect gene delivery. In one preferred embodiment, the nucleic acid sequence is a cytotoxic gene, such as, but not limited to suicide genes such as p53 and egr-1-TNF-alpha, cytotoxic pro-drug/enzymes for drug susceptibility therapy such as ganciclovir/thymidine kinase and 5-fluorocytosine/cytosine deaminase, and antimetastatic genes such as 5 E1A. Examples of specific cytotoxic constructs are described in detail in the Examples section below.

In yet another embodiment, the nucleic acid sequence expressed under control of the cis regulatory element of the present invention can be directed to genetic radioisotopic therapy: Uptake of the radio-labeled catecholamine I131-metaiodobenzyl-guanidine into cells which express the noradrenaline receptor (NAT) is an established treatment modality for pheochromocytoma, neuroblastoma, carcinoid tumor and medullary thyroid carcinoma. Alternatively, sodium iodine symporter (NIS) mediates the uptake of iodine into normal and malignant thyroid cells. The NIS gene, as a transgene, has been reported to suppress prostate cancer in in vitro and in vivo models.

An opposite approach may be used to re-vascularize tissue, for example in atherosclerotic patients or in patients that have suffered significant impairment of peripheral circulation as a result of disease or injury, such as diabetes. In this case, a construct of the type AdPPE-1-3X-GF, where GF is a growth factor (e.g., cytokine) or modificants thereof (e.g., AdPPE-1-SEQ ID NO:7-GF), can be employed. Suitable growth factors for use in this context include, but are not limited to, VEGF (GenBank accession M95200) and rat PDGF-BB (GenBank accession; 99% identity to mus-AF162784) and EGR-1 (GenBank accession M22326) FGFs (including, but not limited to, GenBank accession XM 003306) and combinations thereof.

It will be appreciated that the use of more than one angiogenic factor may be preferable according to this aspect of the present invention to avoid problems of vessel immaturity and blood vessel regression which have been shown to be associated with administration of VEGF alone (for further details see Example 27 and 31 of the Examples section). Combined therapy can mimic the first stage of endothelial channel sprouting and subsequently recruitment of smooth muscle cells to stable the nascent vessels [Richardson D M et al. (2001) Nat. Biotechnol. 19:1029-1034]. Combined therapy according to this aspect of the present invention may be practiced by cloning the polynucleotides of interest on the same nucleic acid construct each of which being under the regulation of the isolated nucleic acid of the present invention. Alternatively, or preferably, each of the polynucleotides of interest may be separately cloned into the nucleic acid constructs of the present invention, thereby enabling a closer regulation on the induced angiogenic process.

Incorporation of a hypoxia response element (e.g. SEQ ID NO: 5) within the promoter sequence of the present invention can also be used with the present invention in order to further enhance expression selectivity to ischemic tissues, thus leading to neo-vascularization of selected tissues. As the blood supply improves, ischemia is relieved, the hypoxia response element ceases to be induced, GF levels decline and the neo-vascularization process is halted.

It will be appreciated that gene therapy to endothelial tissue using the nucleic acid constructs of the present invention provides temporal coordination unattainable with other methods unable to target angiogenic endothelial cells. As illustrated in the Examples section which follows, the cis regulatory element comprising the novel enhancer element of the present invention [for example, PPE-1(3x)] directs increased expression of recombinant genes specifically in tissues undergoing vascular proliferation, while preventing recombinant gene expression in other, non-angiogenic tissues (see Examples 12, 14, 16, 19, 20, 23, 27, 29, 34 and 35). Expression of therapeutic genes, under transcriptional control of the cis regulatory elements and constructs of the present invention, coincides with the activation of the cellular processes (angiogenic growth processes) to which the gene products are directed, allowing greater effectivity and significant reduction in the effective doses required for treatment.

Thus, use of a construct including the cis regulatory element of the present invention in a gene therapy context can be expected to maximize delivery to tumors while minimizing toxic effects on surrounding normal tissue. Significantly, this is true even if the surrounding tissue contains an endothelial component, as illustrated in the Examples section that follows. This is because, as demonstrated in Example 16, the cis regulatory element of the present invention greatly increases the level of expression in rapidly proliferating endothelial tissue, even in the context of the PPE-1 promoter.

While the examples provided hereinbelow deal specifically with the use of the cis regulatory sequence of the present invention in conjunction with the PPE-1 promoter, it is anticipated that the enhancer element of the present invention will also exert its cell specific effect when used with other eukaryotic promoter sequences.

Such anticipation is based on prior art findings which show that enhancer elements are often portable, i.e., they can be transferred from one promoter sequence to another, unrelated, promoter sequence and still maintain activity. For examples, see D. Jones et al. (Dev. Biol. (1995) 171(1):60-72); N. S. Yew et al, (Mol. Ther. (2001) 4:75-820) and L. Wu. et al. (Gene Ther. (2001) 8; 1416-26). Indeed, the earlier work of Bu et al. (J. Biol. Chem. (1997) 272(19): 32613-32622) strongly suggests that enhancer elements related to those of the present invention, for example, enhancers including SEQ ID Nos. 15 and 16, or SEQ ID NO: 6 may be used with constitutive promoters, for example the SV-40 promoter. As such, constructs containing, methods employing and isolated polynucleotides including a eukaryotic promoter modified to include the enhancer sequence of the present invention are well within the scope of the claimed invention.

Thus, it is postulated that a minimal configuration of an enhancer element according to the present invention is an isolated polynucleotide including at least a portion of the sequence set forth in SEQ ID NO:15 covalently linked to at least a portion of the sequence set forth in SEQ ID NO:16. This enhancer is anticipated to function with a wide variety of promoters, including but not limited to endothelial specific promoters (e.g. PPE-1; SEQ ID NO.: 1) and constitutive promoters, for example viral promoters such as those derived from CMV and SV-40. This enhancer should be capable of imparting endothelial specificity to a wide variety of promoters. The enhancer element may be augmented, for example by addition of one or more copies of the sequence set forth in SEQ ID NO:6. These additional sequences may be added contiguously or non-contiguously to the sequence of SEQ ID NO.: 8.

The present invention further includes a method of expressing a nucleic acid sequence of interest in endothelial cells employing a construct which relies upon an enhancer element including at least at least a portion of the sequence set forth in SEQ ID NO:15 covalently linked to at least a portion of the sequence set forth in SEQ ID NO:16 and a promoter to direct high level expression of the sequence of interest specifically to endothelial cells.

As used herein "ex-vivo administration to cells removed from a body of a subject and subsequent reintroduction of the cells into the body of the subject" specifically includes use of stem cells as described in (Lyden et al. (2001) Nature Medicine 7: 1194-1201).

While adenoviruses are employed in the experiments described in examples presented hereinbelow, the constructs of the present invention could be easily adapted by those of ordinary skill in the art to other viral delivery systems.

The viral vectors, containing the endothelial cell specific promoters, can also be used in combination with other approaches to enhance targeting of the viral vectors. Such approaches include short peptide ligands and/or bispecific or bifunctional molecule or diabodies (Nettelbeck et al. Molecular Therapy 3:882; 2001).

It will be noted that the host immune response to therapeutic transgenes expressed in tissues in the context of gene therapy is a significant concern in developing and design of effective gene therapy protocols. Adverse immune response to the recombinant transgene product can both interfere with the efficacy of drug delivery, and lead to inflammation, cytotoxicity, and disease. Thus, the antigenic potential of expressed recombinant therapeutic molecules is of great importance in gene therapy.

While reducing the present invention to practice, it was unexpectedly revealed that a human polypeptide (TNF-R1) expressed as a portion of the Ad5PPE-1(3x) nucleic acid construct (Example 41, FIG. 95b) lacks antigenicity in mice, and does not induce a significant immunological response in the host, despite the clear anti-TNF-R1 response to administration of the Fas-c chimera gene under control of the CMV promoter (FIG. 95). Thus, the isolated polypeptide of the present invention can be used for reducing or eliminating a host immune response to an endogenously expressed recombinant transgene product or products, effected by expressing within a cell the recombinant transgene (or genes), under transcriptional control of the cis regulatory element of the present invention. Preferably, the cis regulatory element is the PPE-1 (3x) promoter.

While reducing the present invention to practice, it was suprisingly uncovered that the angiogenic endothelial specific promoter PPE-1 (3x) is responsive to additional potentiation by anti-angiogenic therapy. FIG. 94 shows the preferential enhancement of luciferase expression in highly vascularized organs (aorta, heart, lungs, trachea and brain) of transgenic mice bearing a nucleic acid construct including the LUC reporter transgene under PPE-1 (3x) control, in response to administration of the double endothelin receptor (ETA and ETB) antagonist Bosentan. This synergic effect of anti-angiogenic therapy combined with transgenic expression of a therapeutic recombinant gene under control of the cis regulatory element of the present invention provides a previously undisclosed possibility for drug targeting and reduced dosage requirements for anti-angiogenic therapies. Without wishing to be limited by a single hypothesis, it is believed that the endogenous tissue response to antiangiogenic therapy, in activating inducers of the endothelin promoter via an autocrine loop, in fact enhance the endothelin promoter element of the nucleic acid construct of the present invention. Thus, in one embodiment, a construct including the cis regulatory element of the present invention is administered in combination with an adjunct anti-angiogenic therapy, the anti-angiogenic therapy selected capable of inducing an endogenous enhancer of endothelial-specific promoter activity. Anti-angiogenic therapy well known in the art includes, but is not limited to endothelin receptor antagonists such as Bosentan, VEGF-receptor antagonists, angiostatin and endostatin, and antiangiogenic antibodies such as Bevacizumab and Novast.

Further, it will be appreciated that administration of a construct including the cis regulatory element of the present invention, or other cis regulatory elements having endothelial-specific promoter activity, in combination with such adjunct therapy capable of inducing endothelial-specific promoter activity, can be used to increase the expression of constructs comprising pro-angiogenic sequences, enhancing angiogenic activity, for example, in the treatment of ischemic conditions.

While further reducing the invention to practice, it was shown that incubation of Bovine Aortic Endothelial cells (BAEC) with a B-form specific endothelin receptor antagonist (BQ788) induces enhancement of the endothelial-specific promoter [PPE-1(3X)] activity, while exposure to an A-form endothelin receptor agonist (BQ123) was without effect on endothelin promoter activity (FIG. 96). Further reduction to practice with transgenic mice expressing the luciferase gene under control of the PPE-1 promoter has shown that blockade of the B-form endothelin receptor by BQ-788 resulted in increased endothelin transcription, and an increase in circulating plasma endothelin (FIGS. 97A and 97B).

Thus, in one embodiment, a construct including the cis regulatory element of the present invention is administered in combination with an adjunct therapy, wherein the adjunct therapy is a blockade of the B-form endothelin receptor. Such blockade can be via non-selective endothelin receptor antagonists such as, but not limited to Bosentan; A-186086; Ro-61-6612; SB-209,670; SB-217,243; PD142,893; and PD 145, 065, or via selective subtype B endothelin receptor antagonists such as, but not limited to A192,621; BQ788; Res 701-1 and Ro 46-8443 (Sigma-Aldrich, Inc. St Louis, Mo.).

It will be appreciated, that attenuation of the host cell's response to infection with an adenovirus vector can improve the expression of constructs encoding recombinant proteins delivered in such a vehicle. Recently, it has been shown that corticosteroid (dexamethasone) administration can prevent some of the immune- and apoptosis-related impairment of recombinant adenovirus-infected endothelium (Murata, et al Arterioscler Thromb Vasc Biol 2005; 25:1796-803), suppressing pro-inflammatory gene expression and optimizing recombinant gene expression efficiency in vitro and in vivo. This effect of corticosteroid enhancement of transgene expression in adenovirus was shown to be specific, being more pronounced in endothelial cells than in some tumor cell lines.

Further, it has been recently shown that treatment of cells with N-Acetyl Cysteine (Jornot et al, Journal of Genetic Medicine 2002; 4:54-65) enhances transgene expression and viral penetration in adenovirus-treated endothelial cells.

While reducing the present invention to practice, it was found that corticosteroid treatment enhances expression of transgenes in adenoviral-mediated transient expression. Luciferase expression, measured as percent luciferase per μg total protein, was increased more than 3 times in BAEC cells treated with 3 μM dexamethasone prior to infection with adenovirus construct expressing luciferase under control of the constitutive CMV promoter (Ad-CMV-LUC). Further, recombinant gene expression in BAEC treated with 3 μM dexamethasone prior to infection with an adenovirus construct bearing the reporter gene green fluorescent protein (GFP) under control of the endothelial-specific promoter PPE-1 was greatly enhanced, compared to untreated controls (see Example 42, hereinbelow).

Thus, in a further embodiment, a viral construct including the cis regulatory element of the present invention is administered in combination with an additional compound or compounds for enhancing copy number of virus particles and/or enhancing transgene expression in the transduced cell, wherein the additional compound or compounds is a corticosteroid (such as, for example dexamethasone) and/or N-Acetyl Cysteine (NAC).

The constructs and methods of the present invention are especially suited for use in tissue engineering. VEGF and PDGF are commonly used to induce vascularization, however methods of administration of these factors in an effective way are still not optimal. In vitro, the growth factors are added in the growth medium. In this method relatively high concentration are needed. In vivo, engineered tissue constructs need to be vascularized rapidly and to induce angiogenesis to site of implantation. The cis regulatory elements and nucleic acid constructs of the present invention can be used for neovascularization of tissue in vivo and ex-vivo, for example, for use in tissue engineering, treatment of wound healing, and the like. While reducing the present invention to practice, it was demonstrated, for the first time, that angiogeneic factors, under regulatory control of PPE-1 (3x), are preferentially expressed in vascularized in-vitro engineered tissue and provide superior neovascularization in engineered tissue in-vitro and in-vivo.

Infection of the cells with Ad5PPEC-1-3x VEGF has an inductive effect on number and size of vessels-like structures formed in the engineered constructs, resulting in a 4-5 fold increase in the number of vessels and percentages of vessel area in the samples treated with Ad5PPEC-1-3x VEGF virus comparing to addition of VEGF to the medium (FIG. 91a). In in-vivo studies. survival, differentiation, integration and vascularization of implanted scaffold-based tissue constructs were analyzed. Constructs infected with Ad5PPEC-1-3x VEGF virus show an increase in vessel structures compared to control constructs.

Thus in one prefered embodiment, the nucleic acid construct of the present invention is used to regulate angiogenesis in a tissue, the tissue being a natural or an engineered tissue.

Employing a luciferase-based imaging system, the present inventors uncovered that implanted constructs infected with Ad5PPEC-1-3x VEGF had higher signal than control constructs infected with AAV-luciferase only, indicating that in vitro infection with Ad5PPEC-1-3x VEGF can improve survival and vascularization of implanted engineered tissue constructs (FIG. 91b). Further, such engineered tissue constructs comprising cells transduced with adenovirus constructs of the present invention can constitute a source of therapeutic recombinant virus particles for surrounding tissue via cell lysis.

Thus, according to one aspect of the present invention, there is provided a cell comprising the nucleic acid construct of the present invention. According to yet another aspect of the present invention, these cells are used to seed a scaffold to be used, for example, for tissue engineering. Methods for tissue engineering using scaffolds are well known in the art (see, for example, U.S. Pat. Nos. 6,753,181; 6,652,583; 6,497,725; 6,479,064; 6,438,802; 6,376,244; 6,206,917, 6,783,776; 6,576,265; 6,521,750; 6,444,803; 6,300,127; 6,183,737; 6,110,480; 6,027,743; and 5,906,827, and US Patent Application Nos. 0040044403; 0030215945; 0030194802; 0030180268; 0030124099; 0020160510; 0020102727, incorporated herein by reference, all of which teach generation of engineered tissue on tissue scaffolds). Suitable scaffolds can be composed of synthetic polymer, a cell adhesion molecule or an extracellular matrix protein.

The cell adhesion/ECM protein used by the present invention can be any cell adhesion and/or extracellular matrix protein, including, but not limited to, fibrinogen, Collagen, integrin (Stefanidakis M, et al., 2003; J Biol Chem. 278: 34674-84), intercellular adhesion molecule (ICAM) 1 (van de Stolpe A and van der Saag P T. 1996; J. Mol. Med. 74: 13-33), tenascin, fibrinectin (Joshi P, et al., 1993; J. Cell Sci. 106: 389-400); vimentin, microtubule-associated protein ID (Theodosis D T. 2002; Front Neuroendocrinol. 23: 101-35), gicerin, Neurite outgrowth factor (NOF) (Tsukamoto Y, et al., 2001; Histol. Histopathol. 16: 563-71), polyhydroxyalkanoate (PHA), bacterial cellulose (BC), gelatin, and/or nerve injury induced protein 2 (ninjurin2) (Araki T and Milbrandt J. 2000; J. Neurosci. 20: 187-95).

The synthetic polymer used by the present invention can be polyethylene glycol (PEG), Hydroxyapatite (HA), polyglycolic acid (PGA) (Freed L E, Biotechnology (N Y). 1994 July; 12(7):689-93.), epsilon-caprolactone and 1-lactic acid reinforced with a poly-1-lactide knitted [KN-PCLA] (Ozawa T et al., 2002; J. Thorac. Cardiovasc. Surg. 124: 1157-64), woven fabric (WV-PCLA) [Ozawa, 2002 (Supra)], interconnectedporous calcium hydroxyapatite ceramics (IP-CHA), poly D,L,-lactic acid-polyethyleneglycol (PLA-PEG) (Kaito T et al., 2005; Biomaterials. 26: 73-9), unsaturated polyester poly (propylene glycol-co-fumaric acid) (PPF) (Trantolo D J et al., 2003; Int. J. Oral Maxillofac. Implants. 18: 182-8), polylactide-co-glycolide (PLAGA) (Lu H H, et al., 2003; J. Biomed. Mater. Res. 64A(3): 465-74), poly-4-hydroxybutyrate (P4HB), and/or polyphosphazene (Cohen S et al., 1993; Clin. Mater. 13(1-4): 3-10).

While reducing the present invention to practice, the present inventors have uncovered that a combination of tissue-specific expression and specific activation of a pro-apoptotic agent enables selective apoptosis of cells involved in angiogenesis without exposing non-targeted tissue or cells to these agents, thus, avoiding the toxic side effects and redundancy characterizing prior art treatment approaches.

Thus, according to one aspect of the present invention there is provided a method of down-regulating angiogenesis in a tissue of a subject. As used herein, the phrase "down-regulating angiogenesis" refers to either slowing down or stopping the angiogenic process, which lead to formation of new blood vessels.

The method according to this aspect of the present invention is effected by administering to the subject a nucleic acid construct designed and configured for cytotoxicity in a subpopulation of angiogenic cells. As used herein, the phrase "angiogenic cells" refers to any cells, which participate or contribute to the process of angiogenesis. Thus, angiogenic cells include but are not limited to, endothelial cells, smooth muscle cells.

As use herein, the term "cytotoxicity" refers to the ability of a compound or process to disrupt the normal metabolism, function and/or structure of a cell, in a potentially irreversible manner, most often leading to cell death. A "cytotoxic molecule" is herein defined as a molecule having, under defined conditions, the capability of generating cytotoxicity, or inducing a cytotoxic process or pathway within a cell. Such cytotoxic molecules include cytotoxic drugs such as, but not limited to antimetabolites such as methotrexate, nucleoside analogues, nitrogen mustard compounds, anthracyclines, inducers of apoptosis such as caspase, as well as genes encoding cytotoxic drugs and other inducers of cytotoxic processes, such as the Fas-c chimera gene. Cytotoxic drugs and molecules may be absolutely cytotoxic, independent of other factors, such as antimetabolite drugs, or conditionally cytotoxic, dependent on the interplay of other, cytotoxic or non-cytotoxic factors. A cytotoxic generating domain is defined as a portion of a cytotoxic molecule capable of inducing or initiating cytotoxicity, such as a coding sequence of a cytotoxic gene. Cytotoxic pathways include, inter alia, apoptosis and necrosis.

In one preferred embodiment of the present invention, the expression of the cytotoxic agent is directed to a subpopulation of angiogenic cells. In order to direct specific expression of a cytotoxic agent in a subpopulation of angiogenic cells, the nucleic acid construct of the present invention includes a first polynucleotide region encoding a chimeric polypeptide including a ligand binding domain which can be, for example, a cell-surface receptor domain of a receptor tyrosine kinase, a receptor serine kinase, a receptor threonine kinase, a cell adhesion molecule or a phosphatase receptor fused to an effector domain of an cytotoxic molecule such as, for example, Fas, TNFR, and TRAIL.

Such a chimeric polypeptide can include any ligand binding domain fused to any cytotoxic domain as long as activation of the ligand binding domain, i.e., via ligand binding, triggers cytotoxicity via the effector domain of the cytotoxic molecule.

Selection of the ligand binding domain and the cytotoxicity generating domain fused thereto is affected according to the type of angiogenic cell targeted for apoptosis. For example, when targeting specific subset of endothelial cells (e.g., proliferating endothelial cells, or endothelial cells exhibiting a tumorous phenotype), the chimeric polypeptide includes a ligand binding domain capable of binding a ligand naturally present in the environment of such endothelial cells and preferably not present in endothelial cells of other non-targeted tissues (e.g., TNF, VEGF). Such a ligand can be secreted by endothelial cells (autocrine), secreted by neighboring tumor cells (paracrine) or specifically targeted to these endothelial cells.

Examples of suitable chimeric polypeptides are provided hereinabove, and in Examples 7 and 33-36 of the Examples section which follows. Preferably, the chimeric polypeptide is the Fas-c chimera which is described in detail in Examples 7-9 of the Examples section which follows, or the HSV-TK gene described in Examples 33-36. Expression of the Fas-c chimera has been shown to induce apoptosis via FADD-mediated activation of the Fas death pathway. Expression of the HSV-TK transgene results in hypersusceptibility of the transduced cells to drugs such as ganciclovir and aciclovir, leading to apoptosis and necrotic cell death.

The use of such a chimeric polypeptide is particularly advantageous, since, as shown in the Examples section hereinunder, it enables efficient and robust activation of cytotoxicity in a specific subset of angiogenic cells while avoiding activation in other subset of cells, which are not targeted for cell death.

As is illustrated in Examples 33-38 that of the Examples section that follow, both in-vitro and in-vivo administration of nucleic acid constructs of the present invention, including the HSV-TK gene under transcriptional control of the PPE-1 (3x) promoter element, produced superior, ganciclovir-dependent endothelial cell cytotoxicity. Cytotoxicity was restricted to angiogenic endothelial cells, producing selective apoptotic and necrotic cell death in tumors and metastases.

Thus, the nucleic acid construct of the present invention can be used to deliver a suicide gene, capable of converting a prodrug to a toxic compound. In one preferred embodiment the nucleic acid construct includes a first polynucleotide region encoding such a suicide gene, and a second polynucleotide region encoding a cis acting regulatory element capable of directing expression of the suicide gene in angiogenic cells.

In the constructs and methods of the present invention, the therapeutic nucleic acid sequence or "suicide gene" is a nucleic acid coding for a product, wherein the product causes cell death by itself or in the presence of other compounds. It will be appreciated that the above described construct represents only one example of a suicide construct. Additional examples are thymidine kinase of varicella zoster virus and the bacterial gene cytosine deaminase which can convert 5-fluorocytosine to the highly toxic compound 5-fluorouracil.

As used herein "prodrug" means any compound useful in the methods of the present invention that can be converted to a toxic product, i.e. toxic to tumor cells. The prodrug is converted to a toxic product by the gene product of the therapeutic nucleic acid sequence (suicide gene) in the vector useful in the method of the present invention. Representative examples of such a prodrug is ganciclovir which is converted in vivo to a toxic compound by HSV-thymidine kinase. The ganciclovir derivative subsequently is toxic to tumor cells. Other representative examples of prodrugs include aciclovir. FIAU [1-(2-deoxy-2-fluoro-.beta.-D-arabinofuranosyl)-5-iodouracil], 6-methoxypurine arabinoside for VZV-TK, and 5-fluorocytosine for cytosine deambinase. Preferred suicide gene/prodrug combinations are bacteria cytosine deaminase and 5-fluorocytosine and its derivatives, varicella zoster virus TK and 6-methylpurine arabinoside and its derivatives, HSV-TK and ganciclovir, aciclovir, FIAU or their derivatives. Methods for preparation and use of suicide gene/prodrug constructs are described in detail in U.S. Pat. No. 6,066,624 to Woo et al., and in the Examples section which follows.

In one preferred embodiment, the cis acting regulatory element is an endothelial or periendothelial specific promoter. Since transduction of cells with conditionally replicating adenoviral vectors is significantly more effective in target cell lysis and spread of viral infection, the nucleic acid construct can preferably include a conditionally replicating adenovirus. Such CRAD constructs of the present invention are described in detail in the Examples section here which follows.

Preferably, the nucleic acid construct of the present invention is administered to the subject via, for example, systemic administration routes or via oral, rectal, transmucosal (especially transnasal), intestinal or parenteral administration routes. Systemic administration includes intramuscular, subcutaneous and intramedullary injections as well as intrathecal, direct intraventricular, intravenous, inrtaperitoneal, intranasal, intraocular injections or intra-tumoral.

Preferably, the subject is a mammal, more preferably, a human being, most preferably, a human being suffering from diseases characterized by excessive or abnormal neovascularization such as that characterizing tumor growth, proliferating diabetic retinopathy, arthritis and the like.

The nucleic acid constructs of the present invention can be administered to the subject per se or as part (active ingredient) of a pharmaceutical composition.

The prior art teaches of a number of delivery strategies which can be used to efficiently deliver naked or carrier provided polynucleotides into a wide variety of cell types (see, for example, Luft (1998) J Mol Med 76(2): 75-6; Kronenwett et al. (1998) Blood 91(3): 852-62; Rajur et al. (1997) Bioconjug Chem 8(6): 935-40; Lavigne et al. (1997) Biochem Biophys Res Commun 237(3): 566-71 and Aoki et al. (1997) Biochem Biophys Res Commun 231(3): 540-5).

As used herein a "pharmaceutical composition" refers to a preparation of one or more of the active ingredients or agents described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered nucleic acid construct. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient. In the context of the present invention, administration directly into tumor tissue is a relevant example of local administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredient of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., progressive loss of bone mass) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model, such as the murine Src deficient model of osteopetrosis (Boyce et al. (1992) J. Clin. Invest. 90, 1622-1627; Lowe et al. (1993) Proc. Natl. Acad. Sci. USA 90, 4485-4489; Soriano et al. (1991) Cell 64, 693-702), to achieve a desired concentration or titer. Such information can be used to more accurately determine useful doses in humans.

Toxicity, cytotoxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient are sufficient to retard tumor progression (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The pharmaceutical compositions of the present invention may further include any additional ingredients which may improve the uptake of the nucleic acid construct by the cells, expression of the chimeric polypeptide or suicide gene encoded by the nucleic acid construct in the cells, or the activity of the expressed chimeric polypeptide or suicide gene product.

For example, the uptake of adenoviral vectors into EC cells can be enhanced by treating the vectors with engineered antibodies or small peptides. Such "adenobody" treatment, was shown effective in directing adenovirus constructs to EGF receptors on cells (Watkins et al 1997, Gene Therapy 4:1004-1012). In addition, Nicklin et al have shown that a small peptide, isolated via phage display, increased specificity and efficiency of vectors in endothelial cells and decreased the expression in liver cells in culture (Nicklin et al 2000, Circulation 102:231-237). In a recent study, an FGF retargeted adenoviral vector reduced the toxicity of tk in mice (Printz et al 2000, Human Gene Therapy 11:191-204).

Low dose radiation has been shown to cause breaks in DNA strands primarily in the G2/M phase, cell membrane damage enhancing the bystander effect, and thus may potentiate other cytotoxic and anti-neoplastic therapies, when administered in combination. Vascular endothelial cells may be particularly suitable to such combination, or adjunct, therapies, since it has been demonstrated that low dose radiation specifically targets the apoptotic system of the microvascular endothelial cells (Kolesnick et al., Oncogene 2003; 22:5897-906). Angiostatin has been shown to potentiate the therapeutic effects of low dose radiation (Gorski et al. Can Res 1998; 58:5686-89). However, the effects of radiation are still poorly understood, since irradiation has also been shown to increase pro-angiogenic "tissue repair factors" (Itasaka et al., Am Assoc Canc Res, 2003; abstract 115). Similarly, certain chemotherapeutic agents have been shown to activate specific cytotoxic and apoptotic pathways [doxorubicin, cisplatin and mitomycin C induce accumulation of Fas receptor, FADD, and other proapoptotic signals in the FADD/MORT-1 pathway (Micheau et al., BBRC 1999 256:603-07)]. While reducing the present invention to practice, it was surprisingly uncovered that low dose radiation treatment has a clear synergistic effect on the anti-tumor and anti metastatic effectiveness of nucleic acid constructs including TK under control of PPE-1(3x) and ganciclovir administration (Examples 35 and 36 FIGS. 79-86). This is of specific relevance in the context of the present invention, since it has been demonstrated that such low dose radiation can activate TK expression and therapeutic effect, can specifically potentiate doxorubicin chemotherapeutic effect, and is known to activate the FADD/MORT-1 apoptotic pathway (Kim et al, JBC 2002; 277:38855-62).

Further evidence of the efficacy of such combination therapy is described in Example 37, which illustrates the synergic effect of combined doxorubicin and AdPPE-1 (3x)-Fas-c chimera construct administration in endothelial cells (BAEC) (FIG. 91). Thus, nucleic acid constructs and the pharmaceutical compositions comprising same of the present invention can be used to treat diseases or conditions associated with aberrant angiogenesis alone or in combination with one or more other established or experimental therapeutic regimen for such disorders. Therapeutic regimen for treatment of cancer suitable for combination with the nucleic acid constructs of the present invention or polynucleotide encoding same include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

It will be appreciated that although targeting of cells exposed to the ligand, or to the cytotoxic prodrug is preferred, the present invention also envisages expression of the nucleic acid construct of the present invention in cells which are not exposed to, or naturally affected by the ligand or cytotoxic prodrug. In such cases, the method of the present invention includes the step of administering such a ligand, or prodrug, to the cells transformed. Such administration can be effected by using any of the above described administration methods. Preferably, the ligand or prodrug is administrated in a cell targeted manner, using for example antibody conjugated targeting, such that activation of cytotoxicity is highly specific. This approach of cytotoxic or apoptotic activation is described in more detail in the Examples section which follows.

Thus, the present invention provides nucleic acid constructs, pharmaceutical compositions including such constructs and methods of utilizing such constructs for down-regulating angiogenesis in tissue regions characterized by excessive or abnormal angiogenesis.

Since the present invention enables targeted expression in specific cell subsets, it can also be modified and used in for treating various tumors.

Thus, according to another aspect of the present invention there is provided a method of treating tumors.

The method according to this aspect of the present invention is effected by expressing in tumor cells the chimeric polypeptide or suicide gene described above.

Thus according to this aspect of the present invention, expression of the polypeptide chimera or suicide gene is directed by a tumor specific element, such as, but not limited to, the gastrin-releasing peptide (GRP) promoter [AF293321S3; Morimoto E Anticancer Res 2001 January-February; 21(1A):329-31], the hTERT promoter [AH007699; Gu J, Gene Ther 2002 January; 9(1):30-7], the Hexokinase type II promoter [AF148512; Katabi M M, Hum Gene Ther. 1999 Jan. 20; 10(2):155-64.], or the L-plastin promoter [L05490, AH002870, MMU82611; Peng X Y, Cancer Res. 2001 Jun. 1; 61(11):4405-13].

Expression of the polypeptide chimera (e.g., Fas-c) or suicide gene in tumor cells activates cytotoxicity and/or apoptosis in these cells and thus leads to cell death, which in turn causes tumor growth slowdown or arrest, and possibly tumor shrinkage.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes 1-111 Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Specifically, experiments conducted in conjunction with the examples recited hereinbelow employed the following methods and materials:

MATERIALS AND METHODS

Cell Culture

Lewis Lung Carcinoma—(D122-96), Human Embryonic Kidney (293) and HeLa cells were grown in 4.5 gr/l DMEM, supplemented with 10% fetal calf serum (FCS), 50 U/ml penicillin, 50 µg/ml streptomycin and 2 mM glutamine (Biological industries, Beit-Haemek, Israel). Bovine Aortic Endothelial Cells—BAEC, Normal Skin Fibroblasts—NSF, HepG2 and Human Umbilical Endothelial Cells —HUVEC-304 (ATCC, USA) were grown in 1.0 gr/l DMEM (Biological industries, Beit-Haemek, Israel), supplemented with 5% FCS, 50 U/ml penicillin, 50 µg/ml streptomycine and 2 mM glutamine. The BAEC cells were supplemented with complete fibroblast growth factor (Sigma, St. Louis. Mo.). RINr1046-38 (RIN-38) were grown in 199 Earle's salts (5.5 mM glucose) medium supplemented with 5% FCS (Biological Industries, Beit-Haemek, Israel), 50 U penicillin/ml, 50 µg streptomycine/ml and 2 mM glutamine.

"HepG2" as used herein refers to ATCC-HB-8065.

"HeLa" as used herein refers to ATCC-CCL-2.

"Human Bronchial Epithelial cells" and "B2B" as used herein refers to ATCC-CRL-9609.

"HUVEC" and "Human Umbilical Vein Endothelial Cells" as used herein refers to ATCC-CRL-1730.

"CHO" and "Chinese Hamster Ovary" as used herein refers to ATCC-61.

Hypoxia Induction

Twenty six hours post transfection or transduction cells were incubated in an isolated chamber which was washed for 30 minutes by a gas flow containing 0.5% $O_2$, 5% $CO_2$, balance by $N_2$. The isolated chamber was placed in humidified 5% $CO_2$, 37° C. incubator.

Luciferase Activity in Cells and Tissues

To assay the PPE-1 promoter activity quantitatively in-vitro and in-vivo, a Luciferase gene expression system kit was employed (Promega Corp., Madison, Wis.). Forty eight hours post transfection or transduction the cells were washed and 200µl lysis buffer was added for 15 minutes. Cells lysates were collected and centrifuged for 15 minutes (14,000 rpm) at 4° C. Subsequently, 10µl of the supernatant was added to 50µl Luciferase assay buffer. The activity was measured in Luminometer over a 20 second period.

To assay Luciferase activity in solid tissue a 20 mg sample was excised and homogenized in 1 ml of the homogenization solution and centrifuged for 15 minutes (14,000 rpm) at 4° C., and 10 ml of the supernatant were assayed for Luciferase activity, as described above. Results were expressed as Luciferase light units per 1µg protein. Protein was measured using the Bradford assay with bovine serum albumin (BSA) as a standard.

GFP Activity in-vitro and in-vivo

To test GFP expression in-vitro, cells were washed twice with PBS and were fixed for 30 minutes with freshly made 4% paraformaldehyde in PBS. Following fixation, examination by fluorescent microscopy was conducted.

In order to test the cellular distribution of the delivered gene in-vivo, tissues were fixed in freshly made 4% paraformaldehyde in 0.1 M phosphate buffer for 6 hours at 4° C., soaked overnight in 30% sucrose at 4° C. and frozen in OCT compound (Sakura, USA). The tissue blocks were sliced by a cryostat at 10 µm thickness and observed directly under fluorescence microscopy (FITC filter).

Proliferating and Quiescent Cells

In order to compare the PPE-1 promoter activity in proliferating and quiescent BAEC, the cells were divided into two groups: 1. proliferating cells—growing and infecting in 10% FCS media. 2. quiescent cells—growing and infected in serum free media started in 72 hours prior to the transduction.

All cells were grown in humidified incubator, 5% $CO_2$, 37° C.

Preparation of Recombinant Replication Deficient Adenoviruses

Several recombinant replication deficient adenoviruses (type 5) were constructed. An expression cassette including the murine preproendothelin-1 (PPE-1) promoter (SEQ ID NO:1) located upstream to the Luciferase gene (originated from pGL2-basic GenBank Accession number X65323) and the SV40 polyA site (originated from pGL2-basic GenBank Accession number X65323) was ligated into the BamHI restriction site of pPAC.plpA (promoter-less construct). The GFP gene (originated from pEGFP, GenBank accession number AAB02572) was ligated to the PPE-1 promoter at the NotI restriction site. The replication deficient recombinant adenoviruses termed Ad5PPE-1Luc or Ad5PPE-1GFP were prepared by co-transfection of pPACPPE-1Luc or Ad5PPE-1GFP with adenovirus plasmid pJM17 as described by Becker, T. C. et al. (Methods Cell biol. 43, Roth M. (ed). New York. Academic Press, 1994, pp. 161-189) followed by harvest of recombinant virions.

Viruses were prepared for large-scale production. The viral stocks were stored at 4° C. at concentration of $10^9$-$10^{12}$ plaque-forming units/ml (pfu/ml). The viruses Ad5CMV-Luc and Ad5CMV-GFP (Quantum biotechnologies, Carlsbad, Canada) containing the cytomegalovirus (CMV) immediate early promoter (GenBank Accession number U47119) were prepared for large scale preparation as described for the PPE-1 viral vectors and were used as a non-tissue specific control.

Modifications of the PPE Promoter

The modified murine PPE-1 promoter was developed by inserting three copies of the positive transcription element discovered by Bu et al (J. Biol. Chem. (1997) 272(19): 32613-32622) into the NheI restriction enzyme site located downstream (−286 bp) to the 43 base pairs endogenous positive element (−364 to −320 bp).

The enhancer fragment termed herein "3X" is a triplicate copy of an endogenous sequence element (nucleotide coordinates 407-452 of SEQ ID NO:1) present in the murine PPE-1 promoter. It has been previously shown that induction of PPE-1 promoter activity in vascular endothelial cells depends on the presence of this element Bu et al (J. Biol. Chem. (1997) 272(19): 32613-32622). The 3X fragment was synthesized by using two complementary single stranded DNA strands 96 base pares in length (BioTechnology industries; Nes Tziona, Israel), (SEQ ID NO: 2 and 3). The two single stranded DNA fragment were annealed and filled using Klenow fragment (NEB); the resulting double stranded DNA was 145 base pairs long and included Nhe-1 restriction sites (SEQ ID NO: 4).

The 3X fragment was ligated into the murine PPE-1 promoter down stream of endogenous Nhe-1 site using T4 Ligase. The resulting construct was propagated in DH5 competent cells and a large-scale plasmid preparation was produced using the maxi-prep Qiagene kit.

Additional Plasmids

Wild Type PPE-1 Promoter

The PPE-1-Luciferase cassette (5249 bp) containing 1.4 kb of the murine preproendothelin-1 (PPE-1) promoter, the Luciferase gene with an SV40 polyA signal (GenBank Accession number X 65323) site and the first intron of the murine ET-1 gene is originated from the pEL8 plasmid (8848 bp) used by Harats et al (J. Clin. Inv. (1995) 95: 1335-1344). The PPE-1-Luciferase cassette was extracted from the pEL8 plasmid by using the BamHI restriction enzyme, following by extraction of the DNA fragment from a 1% agarose gel using an extraction kit (Qiagen, Hilden, Germany).

The Promoter-less pPAC.plpA Plasmid

The promoter-less pPAC.plpA plasmid (7594 bp) containing sequences of the adenovirus type 5 was originated from the pPACCMV.pLpA (8800 bp). The CMV promoter, the multiple cloning site and the SV40 polyadenylation site (1206 bp) were eliminated by NotI restriction enzyme, The fragmented DNA was extracted from 1% agarose gel. The linear plasmid (7594 bp) was filled-in by Klenow fragment and BamHI linker was ligated by rapid DNA ligation kit to both cohesive ends. The linear plasmid was re-ligated by T4 DNA ligase and transformed into DH5α competent cells, in order to amplify the pPAC.plpA with the BamHI restriction sites. The plasmid was prepared for large-scale preparation and purified by maxi prep DNA purification kit.

pPACPPE-1Luciferase Plasmid

The pPACPPE-1 Luciferase plasmid was constructed by inserting the PPE-1-Luciferase cassette into the BamHI restriction site of the pPAC.plpA plasmid, by using T4 DNA ligase. The plasmid was subsequently used to transform DH5αcompetent cells. The plasmid (12843 bp) was prepared for large-scale preparation and purified by maxi prep DNA purification kit.

pPACPPE-1GFP Plasmid

The pPACPPE-1GFP plasmid was constructed by subcloning the GFP gene (originated from pEGFP, GenBank accession number AAB02572) downstream to the PPE-1 promoter into the NotI restriction site, by T4 DNA ligase.

The plasmid was subsequently used to transform DH5α competent cells. The plasmid (11,801 bp) was prepared for large-scale preparation and purified by maxi prep DNA purification kit.

pACPPE-13X Luciferase and pACPPE-13XGFP Plasmids

The pPACPPE-1-3XLuciferase and pPACPPE-1-3XGFP were constructed by inserting the PPE-1-3XLuc or PPE-1-3XGFP cassette digested by BamHI restriction enzyme from pEL8-3X (FIG. 26B) containing Luc or GFP into the BamHI restriction site of the pPAC.plpA plasmid. pEL8-3X contains the modified murine PPE-1 promoter (1.55 kb) (red)—located between BamHI and NotI that contains the triplicate endothelial specific enhancer 3X (as set forth in SEQ ID NO.: 7) located between two NheI site. The promoter, the Luciferase or GFP gene, the SV40 poly A sites and the first intron of the endothelin-1 gene, all termed the PPE-1 modified promoter cassette was digested and extracted by BamHI restriction enzyme as described in materials and methods. The plasmids (12843 bp) were prepared for large-scale preparation and purified by maxi prep DNA purification kit.

SV40-luciferase reporter plasmid (Promega Gmbh, Manheim, Germany) were used as a non-selective promoter control in the BAEC experiments.

In-vitro experiment, DNA transduction—Cells were plated in 24 or 96 well dishes 24 hours prior to transduction. Subconfluent cells were counted in a sample well. Thereafter, growth media was aspirated from each well, and the indicated viral vectors, at the indicated multiplicity of infection (MOI), were diluted in infection media (DMEM or RPMI 1640, 2% FBS) and added to the monolayers. Cells were incubated for 4 h at room temperature. Subsequently, complete medium was added, and the cells were incubated at 37° C., 5% $CO_2$ for 72 h.

Animals

All animal procedures were approved by the "Animal Care and Use Committee" of Sheba Medical Center, Tel-Hashomer.

Different mouse strains were used:

(i) Male, 3 months old, wild type C57BL/6 mice (Harlan farms, Jerusalem, Israel).

(ii) Male 3 month old BALB/C mice (Harlan farms, Jerusalem, Israel).

(iii) Male and female 6 month old ApoE gene deficient mice hybrids of C57BL/6xSJ129 mice (Plump A S. et al. Cell (1991) 71:343-353).

(iv) Male and female 3 month old over-expressing the Luciferase gene under the control of murine PPE-1 promoter (5.9 Kb), generated by Harats et al. (J. Clin. Inv. (1995) 95: 1335-1344).

All mice were grown in the Lipids and Atherosclerosis Research Institute.

Tissue Gene Expression in Normal Mice

To assay the efficiency and tissue specificity, $10^{10}$ pfu/ml of Ad5PPE1Luc or Ad5CMVLuc (as non-tissue-specific control), were suspended in 100 µl of physiological saline and injected into the tail vein of mice as described hereinabove. Luciferase activity was assayed 1, 5, 14, 30 and 90 days post-injection. To localize cellular distribution of the expressed reporter genes, Ad5PPE-1GFP or Ad5CMVGFP ($10^{10}$ pfu/ml in 100 µl physiological saline) were injected into the tail vein of normal 3 month old, male C57BL/6 mice. GFP expression was detected five days post-injection. All mice appeared healthy and no toxicity or inflammation was noted in the liver or other tissue.

GFP Activity in Tissues

To test the cellular distribution of the delivered gene in-vivo, tissue samples from injected mice were fixed in freshly made 4% paraformaldehyde in 0.1 M phosphate buffer for 6 hours at 4° C., soaked overnight in 30% sucrose at 4° C. and frozen in OCT compound (Sakura, Calif., USA). The tissue blocks were sliced at 10 µm thickness and observed directly under fluorescence microscopy (FITC filter).

Tumor Implantation

Lewis Lung Carcinoma cells (LLC) were harvested with trypsin/EDTA, washed 3 times with PBS and counted with 0.1% trypan blue (Biological industries, Beit-Haemek, Israel) to assess their viability. In order to test the level of activity of the PPE-1 promoter activity in tumor angiogenesis in mice, two different tumor models were used.

In the primary tumor model, the cells ($1\times10^6$ cells/ml in 100 µl physiological saline) were subcutaneously injected to the mice backs (n=17). Twenty-one days post injection Ad5PPE-1, Ad5PPE-1GFP, Ad5CMV, or Ad5CMVGFP ($10^{10}$ pfu/ml) were injected into the tumor tissue (IT) or intravenously and their activity was detected as described above.

In the metastatic tumor model, the cells ($5\times10^5$ cells/ml in 50 µl physiological saline) were injected to the mice foot-pad (n=12). When the tumor tissue reached a size of 0.7 mm in diameter, the foot pad (with the primary tumor) was resected under anaesthetic and sterile conditions. Fourteen days post surgery the viruses (Ad5PPE-1, Ad5PPE-1GFP, Ad5CMVLuc or Ad5CMVGFP) were injected to the mouse tail vein.

In both tumor experimental models mice were sacrificed 5 days post viral injection, their tissues were excised and tested for Luciferase or GFP activities.

Wound Healing Model

Male 3 month old C57BL/6 mice were anaesthetized by subcutaneous injection of sodium pentobarbital (6 mg/kg). Their backs were shaved and 5 cm of straight incisions was made. The incisions were immediately sutured by 4/0 sterile silk thread. The angiogenic process in the healing wound was examined every two days by H&E and anti von-Willebrand antibody immunohistochemistry staining.

Ten days post incisions $10^{10}$ pfu/ml of Ad5PPE-1Luc or Ad5CMVLuc were systemically injected to the tail vein. Five days post injections the mice were sacrificed and Luciferase activity was assayed as described above in the skin of the incision site and in the normal contra lateral site as a control.

Histological examination—In order to evaluate the extent of angiogenesis in tumor and metastasized tissue, the tissues were sliced into 5 µm sections and stained with Haematoxylin and Eosin (H&E). Anti CD31 (rat anti mouse CD31 monoclonal Ab. Pharminogen, N.J., USA) antibodies were used for analyses of neo-vascularization in the tumor models.

Plasmids and adenoviral vectors for VEGF and PDGF-B transgenic expression—Recombinant replication-deficient adenoviruses serotype 5 were constructed as described in Varda-Bloom, N. et al. [Tissue-specific gene therapy directed to tumor angiogenesis. (2001) Gene Ther 8, 819-27]. Briefly, pACCMV.pLpA plasmid was modified to include either the cDNA for murine $VEGF_{165}$ (GenBank Accession number M95200) or rat PDGF-B (GenBank Accession number AF162784), under the regulation of the cytomegalovirus (CMV) immediate early promoter. The pACPPE-1-3X plasmids, in which the CMV promoter was replaced by the modified murine preproendothelin-1 (PPE-1-3X) promoter, were constructed with the same cDNA sequences. Each of the plasmids was co-transfected with pJM17 plasmid into HEK293 cells, to generate the various recombinant adenoviruses. The viruses were propagated in HEK293 cells and reduced to a concentration of $10^{10}$ PFUs/ml. Control vectors were generated similarly.

Mouse model of hind limb ischemia and gene therapy—Male and female C57B16 mice (Harlan Laboratories Ltd., Israel), at least 12 weeks of age, were maintained in accordance with guidelines of the Animal Care and Use Committee of Sheba Medical Center. Hind limb ischemia was induced based on previously described protocol [Couffinhal, T. et al. Mouse model of angiogenesis. Am J Pathol 152, 1667-79. (1998)]. In brief, animals were anesthetized with pentobarbital sodium (40 mg/kg, IP). Following shaving of the limb fur the right femoral artery was ligated, proximal to the bifurcation of the saphenous and popliteal arteries. Five days following ligation, $10^9$ PFUs of the various adenoviral vectors were I.V. administrated.

Ultrasonic imaging—Ultrasonic imaging was performed at 7 days intervals following ligation using Synergy ultrasound system (General Electric, USA) at 7.5 MHz in angiographic mode. Animals were awake and restrained while imaging. Animals were accommodated under conventional conditions for up to 90 days.

Immunohistochemistry—Skeletal muscles from both hind limbs and liver tissue of sacrificed ischemic mice were frozen in OCT compound and cryo-sectioned. Endothelial cells were immunostained using rat monoclonal anti-CD31 antibodies (PharMingen, San Diego, Calif.). Smooth muscle cells were immunostained using mouse polyclonal anti-α-SMactin antibodies (SIGMA, St. Louis, Mo.). Background was stained with hematoxylin.

In-situ hybridization—5 µm skeletal muscle sections were prepared from both hind limbs of ischemic animals. In-situ hybridization with either sense or antisense DIG-labeled probes to $VEGF_{165}$ or PDGF-B was performed, and digoxigenin (DIG) was detected by anti-DIG-AP conjugate (Roche Molecular Biochemicals, Mannheim, Germany). Background was stained with methyl green.

Image processing—Ultrasonic images were processed using the Image-Pro Plus software tools (Media Cybernetics, Silver Spring, Md.). Number of colored pixels indicating the most intensive perfusion was calculated for each image.

Modulators of angiogenesis—Transgenic mice were fed normal chow diet or diet supplemented with Bosentan (Actelion Ltd., Allschwil, Switzerland), a dual ET-$1_{A/B}$ receptor antagonist. Assuming that one animal consumed 4 g chow per day, each mouse was administered 100 mg Bosentan/kg body weight, for 30 days. Animals were sacrificed and tested for luciferase activity, lung ET-1 mRNA levels and irET-1 serum levels.

Statistical Analysis

Analysis between groups for statistically significant differences was performed with the use of t-test ANOVA, or the Mann-Whitney Rank test. Data are shown as mean+SE.

EXPERIMENTAL RESULTS

Example 1

In-vitro Assay for Pro-apoptotic Gene Activity in Endothelial Cells (BAEC) and 293 Cells In cancer treatment, anti-angiogenic therapy targets the evolving vasculature which nourishes the growing tumor [Folkman J. N Engl J Med (1995) 333(26):1757-63]. As the research of apoptosis, or programmed cell death, has progressed, numerous genes that encode selective and efficient cell death regulators have been identified [Strasser et al. Annu Rev Biochem (2000) 69:217-45.].

The present study screened several pro-apoptotic genes in order to identify an agent most suitable for anti-angiogenic therapy. Several pro-apoptotic genes including MORT1 (FADD—Fas associated death domain protein, GenBank Accession number NM_003824), RIP (receptor-interacting-protein, GenBank Accession number U25995), CASH (c-FLIP, GenBank Accession number AF010127), MACH (caspase 8 GenBank Accession number X98172), CPP32 (caspase 3, GenBank Accession number U13737), caspase 9 (U60521) and Fas-chimera (Fas-c), a previously described fusion of two "death receptors", constructed from the extracellular region of TNFR1 and the trans-membrane and intracellular regions of Fas [Boldin M P et al. J Biol Chem (1995) 270(14):7795-8, see FIG. 1a) were PCR amplified and cloned into the pcDNA3 (Invitrogen, Inc.) mammalian expression vector using well known prior art cloning techniques.

These pro-apoptotic gene constructs were co-expressed along with pGFP in BAEC (Bovine Aortic Endothelial Cells) and 293 cells, which were used as non-endothelial control cells. 24 hours post transfection, cells were analyzed using fluorescent microscopy. Apoptotic cells were identified based on typical morphology, (i.e., small and round shape) using fluorescence microscopy (FIGS. 2a-b). Further assessment of the apoptotic phenotype was effected using electron microscopy (FIGS. 3a-f). Quantification of the apoptotic effect showed that MORT1, TNFR1 and Fas-chimera induced the highest apoptotic activity in BAEC and 293 cells (FIG. 4a-b). Caspase 3 and 9 were less potent in this respect, probably because they were in an inactive zymogen form. Based on these results, the Fas-chimera (Fas-c) gene was selected for the generation of an adenoviral-vector to be used in anti-angiogenic therapy.

Example 2

Production of Recombinant Adenoviruses Encoding Fas-chimera Under the Control of the Modified PPE-1 Promoter (PPE-1(3x))

A cDNA encoding a full length Fas-chimera was subcloned into the plasmid pPACPPE1-3x containing the modified pre-proendothelinl promoter (see FIG. 1b). Recombinant adenoviruses were produced by co-transfection of this plasmid with pJM17 plasmid into human embryonic kidney 293 cells. Successful viral cloning was verified via PCR amplification (FIG. 5a).

In order to determine the expression of Fas-c in the target cells, endothelial BAEC cells were transduced with the indicated titer of Ad-PPE-1 (3x)-Fas-c. 72 h post transduction cells were lysed and cellular proteins resolved using a non-reducing SDS-PAGE gel. Western blot analysis was performed using anti-TNFR1 antibody (Sc-7895, Santa-Cruz Biotech). As demonstrated in FIG. 5b, a prominent band migrating at 45 kD was clearly evident and its expression was dose-dependent, suggesting correct folding and expression of the chimeric protein. In contrast, no corresponding bands were evident in non-transduced endothelial cells or in cells transduced with control empty viral vector. Thus, these results confirmed that the adenoviral-mediated gene transfer of Fas-c results in transgene expression in the target cells.

Example 3

Ad-PPE-1(3x)-Fas-c Expression Induces Apoptosis in Endothelial Cells

The ability of Ad-PPE-1(3x)-Fas chimera to induce apoptosis of endothelial cells was determined. As shown in FIGS. 6a-b, pre-proendothelin directed, adenovirus-mediated transduction of endothelial cells resulted in an evident and massive cell death; HUVEC and BAEC infected with Ad-PPE-1(3x)-Fas-c ($10^3$ MOI) had morphological features of adherent cells undergoing apoptosis including membrane blebbing, rounding and shrinking and detachment from the culture dish. In contrast, cells infected with control viruses at the same MOI, maintained normal appearance and growth rate. Cells transduced with 100 MOI presented only a minimal degree of cell death (data not shown).

Further assessment of the cytotoxic properties of Ad-PPE-1(3x)-Fas-c was effected by expressing this virus in cells expressing the reporter gene GFP under the control of the PPE-1 promoter. As is evident from FIGS. 6c-d, most of the transduced cells acquired a typical apoptotic appearance 72 hours following transduction, whereas cells co-transduced with control virus and Ad-PPE-GFP appeared normal.

The cytotoxic effect of Fas-c was quantified using crystal violet staining. As shown in FIG. 7, infection of BAEC and HUVEC with Ad-PPE-Fas-c resulted in mortality rates of 57% and 65%, respectively, while the control virus did not affect cell viability.

The endothelial cell specificity of the pro-apoptotic vector Ad-PPE-Fas- was demonstrated by infecting NSF (normal skin fibroblasts) with this vector. These cells, which express low levels of PPE-1 [Varda-Bloom, N. et al. Gene Ther 8, 819-27. (2001)] were not affected by infection with Ad-PPE-Fas-c. In contrast, the recombinant vector Ad-CMV-Fas-c induced apoptotic in these cells.

Example 4

Co-administration of Ad-PPE-1(3x)-Fas-c Receptor and TNFα Ligand Augments the Pro-apoptotic Effect in a Selective Manner The ability of TNFα to augment the apoptotic effect in Fas-c expressing cells was investigated. Human TNFα was added to an endothelial cell culture 48 h-post virus infection with Ad-PPE-Fas-c (MOI of 100). Cell viability was assayed 24 h later. As shown in FIG. 8, TNFα (10 ng/ml) induced a 73% decrease in viabilty of Ad-PPE-1(3x)-Fas-c infected cells, whereas no significant mortality was effected by TNFα alone or in cells infected with control virus (Ad-Luc).

To substantiate the effect of TNFα, cell specificity was addressed. NSF (normal skin fibroblasts), DA3 (mouse mammary adenocarcinoma), D122 (Lewis lung carcinoma) and B16 melanoma cells were infected with Ad-PPE-Fas-c or a control virus. 48 hours later, culture was supplemented with TNFα and cell morphology was assessed following staining with crystal violet. As shown in FIGS. 9*a-e*, non-endothelial cells infected with Ad-PPE-Fas-c displayed normal appearance and were not affected by TNF. On the other hand, adenoviral mediated infection of BAEC with Fas-c resulted in marked decrease in cell viability when TNF was added. The non-selective apoptotic activity of Fas-c driven by CMV promoter is demonstrated in FIG. 10*a* which illustrates the TNF-dependent apoptotic effect of Ad-CMV-Fas-c on endothelial cells. Viability of BAEC cells infected with the indicated MOI of Ad-CMV-Fas-chimera was determined following incubation with TNF.

Notably, the non-endothelial-specific vector Ad-CMV-Fas-c caused TNFα-dependent apoptosis of both endothelial and non-endothelial cells (FIGS. 10*b-d*).

Example 5

Ad-PPE1(3x)-Fas-c Induces in-vivo Growth Retardation of B16 Melanoma in Mice

The B16 melanoma mouse model was used in order to test the anti-tumoral effect of Fas-c expressed from the PPE1-3x promoter. B16 melanoma cells ($8 \times 10^5$) were injected subcutaneously to the flank region of 40 C57bl/6 mice. When the tumor was palpable (~5×5 mm), the mice were randomized into 4 groups as follows: (i) control-saline injection; (ii) control virus (Adeno virus containing luciferase controlled by PPE promoter); (iii) Ad-PPE1-3x-Fas-c-virus containing the Fas-TNF receptor chimeric gene controlled by the preproendothelin (PPE) promoter; and (iv) Ad-CMV-Fas-c-virus containing the Fas-TNF receptor chimeric gene controlled by the non-endothelial specific, CMV promoter.

Tumor size (length and width) was measured using a hand caliper. As shown in FIG. 11*a*, tumor size was lower for mice treated with Ad-PPE1-3x-Fas-c or Ad-CMV-Fas-c as compared to control mice. Tumor weights at the end of the treatment period was also lower in the Ad-PPE1-3x-Fas-c treated mice (FIG. 11*b*). Mice injected with Ad-PPE1-3x-Fas-c showed marked necrosis of their tumor (FIG. 11*c*).

Inhibition of metastatic disease: Lewis Lung Carcinoma model: Specificity of expression and efficacy of inhibition of tumor growth with PPE-1(3x)-Fas-c chimera was further tested in the metastatic Lewis Lung Carcinoma model. Lung LLC metastases were induced in male C57BL/6J as described in detail hereinbelow, and mice were injected with the viral vectors AdPPE-[(3x) LUC, AdPPE-1(3x)-Fas-c, and AdCMV-Fas-c twice, at 9 day intervals (Greenberger et al, J Clin Invest 2004; 113:1017-1024).

Organs were harvested from the mice 6 days after viral administration, and assayed for Fas-c expression by PCR. Transcriptional control of Fas-c by PPE-1(3x) promoter led to expression restricted to the tumor bearing lung (results not shown), in stark contrast to the broad distribution of Fas-c expression in the CMV-Fas-c-treated mice (data not shown, see Greenberger et al, J Clin Invest 2004; 113:1017-1024).

Further, gross pathological inspection of lungs from the treated and control groups revealed that AdPPE-1(3x)-Fas-c administration to the metastases-bearing mice inhibited tumor growth and reduced the size of growing tumors on the lung surface, while the control animals' lungs were almost completely replaced by tumoral tissue (data not shown, see Greenberger et al, J Clin Invest 2004; 113:1017-1024).

Yet further, histopathology and TUNEL and endothelial-specific CD31 staining of lung sections from treated and control mice revealed that AdPPE-1(3x)-Fas-c administration to the metastases-bearing mice caused massive apoptosis and necrosis in the tumor tissue, associated with extensive damage to the tumor vascular endothelium. In contrast, the blood vessels of the control treated mice were unaffected (data not shown, see Greenberger et al, J Clin Invest 2004; 113:1017-1024).

Example 6

Analysis of 3X-PPE-1 Plasmid Activity in-vitro

In order to analyze the activity of the PPE-1-3X, a comparison of reporter gene expression in the PPE-1-3X promoter plasmid and the unmodified PPE-1 promoter plasmid was undertaken. Reporter gene plasmids containing either the PPE-1-3X fragment or the unmodified PPE-1 fragment and the reporter gene Luciferase were transfected into endothelial and non-endothelial cell lines as well as to a bronchial epithelium cell line (B2B) which express the PPE-1 promoter (see materials and methods above). The B2B cell line was chosen to provide an indication of the 3X element's capacity to reduce expression in non-endothelial cell lines relative to the PPE-1 promoter. Transfection was accomplished using lipofectamine (Promega Corp., Madison, Wis.). A β-gal-neo plasmid was employed as an indicator of the transfection efficiency in each case according to accepted molecular biology practice.

Forty-eight hours post transfection, the cells were harvested using lysis buffer (Promega Corp., Madison, Wis.) and Luciferase activity was analyzed by a luminometer (TD-20e—Turner Designs, Sunnyvale, Calif.). In parallel, β gal activity was analyzed in order to standardize for different transformation efficiencies. The results are summarized in FIG. 12 and Table 2. Luciferase activity under the control of PPE-3X is 15-20 times higher than Luciferase activity under the control of the unmodified PPE-1. In non-endothelial cell lines minimal expression was detected using both the PPE-1 and PPE-1-3X. This demonstrates that PPE-3X is a promising candidate for delivery of a gene specifically into endothelial cells in-vivo.

TABLE 2

Luciferase activity in cells transfected with PPE-1 and PPE-1-3X Luciferase constructs

| Plasmid | Luciferase activity in: endothelial cell lines | | non endothelial cell lines |
|---|---|---|---|
| | HUVAC | BAEC | RIN |
| PPE-1 | 135.12 | 1121.3 | 0.73 |
| PPE-1-3X | 768 | 18331.7 | 0.32 |

Example 7

Activity and specificity of AdSPPE-1/Luciferase In-Vitro

The PPE-1/Luciferase, PPE-1-3X/Luciferase, PPE-1/GFP and PPE-1-3X/GFP were also ligated into the Ad5 plasmid to produce Ad5PPE-1/Luc and Ad5PPE-1-3X/luc, Ad5PPE-1/GFP and Ad5PPE-1-3X/GFP (Varda-Bloom et al., (2001)

Gene therapy 8:819-827). These constructs were assayed separately as detailed hereinbelow.

In order to test the activity of the Ad5PPE-1/luc, transfections of B2B (Human bronchial epithelial), BAEC (Bovine Aortic Endothelial Cells) and HUVEC (Human Umbilical Vein Endothelial Cells) were undertaken. These three cell lines express the endothelin gene and were chosen to indicate levels of expression of the tested construct in an endothelial cell. The RIN (Rat Insulinoma) cell line, which does not express endothelin, was employed as a negative control and transfected with the same construct. Ad5CMVLuc (Luciferase under the control of CMV promoter) was used as non-endothelial-specific control in all cell lines.

FIG. 13 clearly illustrates that higher Luciferase expression was achieved in endothelial BAEC and HUVEC cell lines with the PPE-1 promoter than with the CMV promoter. In the RIN cells, which are not of endothelial origin, the CMV promoter produced more Luciferase activity than the PPE-1 promoter. These results demonstrate the endothelial specificity of the un-modified PPE-1 promoter.

Example 8

Activity and Specificity of Ad5PPE-3XLuc and Ad5PPE-3XGFP

The Ad5PPE-3X/Luciferase and Ad5PPE-3X/GFP constructs were used to transfect the cell lines described hereinabove in Example 7 in order to ascertain the impact of the 3X element on specificity and expression levels. As in example 7, Ad5CMVLuc was used as a non-endothelial-specific control. Higher Luciferase expression in BAEC and HUVEC cell lines was detected under the control of the PPE-3X promoter as compared to the CMV promoter.

FIG. 14A is a photomicrograph illustrating GFP expression under the control of Ad5PPE-1-3X in the BAEC cell line. FIG. 14B is a photomicrograph illustrating GFP expression of Ad5CMV in the BAEC line. As is clearly shown by these Figures, the PPE-1-3X promoter is more active in endothelial cells. These results clearly indicate that the 3X element does not detract from the endothelial specificity of the PPE-1 promoter. Relative activities of the PPE-1 and PPE-1-3X promoters in cell culture are presented in Example 11 hereinbelow.

Example 9

In-vitro Assay of Pro-apoptotic Activity of the p55 Gene

Following sub cloning of P55 (TNFR1, GenBank accession number M75866) into PACPPE3X (containing the PPE-1-3X promoter), and into PACCMV, co-transfection of these plasmids and GFP (pEGFP-C1 vector; CLONTECH, Palo Alto, Calif.). was performed as described hereinabove. Briefly, the gene was subcloned downstream to the PPE-1 promoter (instead of the luciferase gene) into the NotI restriction site, by T4 DNA ligase, following by transforming it into DH5α competent cells. Twenty four hours post-transfection, small and rounded apoptotic cells were visually discernible from normal cells. Electron microscopy of cells transfected with the pro-apoptotic plasmids showed typical appearance of apoptosis, confirming the visual evaluation.

Under the control of the PPE-1-3X promoter, apoptosis was induced by p55 only in endothelial cells (FIG. 15), whereas the CMV promoter did not show any cell specific activity. Luciferase under the control of PPE-1-3X did not induce apoptosis in any tested cell lines. These results indicate that by employing the PPE-1-3X promoter, it is feasible to induce apoptosis specifically in endothelial cells.

Example 10

Hypoxia Responsive Element (HRE) can Enhance Target Gene Expression in Hypoxic Sensitive Endothelial Cells Hypoxia is an important regulator of blood vessels' tone and structure. It has also been shown to be a potent stimulus of angiogenesis (in both ischemic heart diseases and cancer (Semenza, G. L. et al. (2000) Adv Exp Med Biol.; 475:123-30; Williams, K. J. (2001) Breast Cancer Res. 2001: 3; 328-31 and Shimo, T. (2001) Cancer Lett. 174; 57-64). Further, hypoxia has been reported to regulate the expression of many genes including erythropoietin, VEGF, glycolytic enzymes and ET-1. These genes are controlled by a common oxygen-sensing pathway, an inducible transcription complex termed hypoxia inducible factor-1 (HIF-1). The HIF-1 complex mediates transcriptional responses to hypoxia by binding the cis acting hypoxia responsive element (HRE) of target genes. The HRE is a conserved sequence located in the promoters of few genes that respond to hypoxia including: VEGF, Nitric Oxide Syntase-2, erythropoietin and others including endothelin-1, ET-1. The ET-1 promoter contains an inverted hypoxia response element at position −118 bp upstream of the transcription start site, the element contain 7 base pairs and is located between the GATA-2 and API sites 5' GCACGTT 3'-50 base-pairs. (SEQ ID NO: 5.)

The preproendothelin-1 (PPE-1) promoter contains an hypoxia responsive element (HRE) that has the potential to increase its expression in the hypoxic microenvironment of tumor or ischemic tissues, thus making it "tumoral tissue specific" and/or "ischemic tissue specific". In order evaluate the actual function of this HRE, assays of the PPE-1 promoter and PPE-1-3X promoter in conjunction with a Luciferase or GFP reporter gene and delivered by an adenoviral vector were undertaken.

Luciferase activity under the control of the PPE-1 promoter or the PPE-1-3X promoter was compared in BAEC cells under normoxic and hypoxic conditions (0.5% $O_2$ for 16 h). The Luciferase activity under the control of PPE-1 promoter was 5 times higher when exposed to hypoxia (FIGS. 16 and 17). Further, the Luciferase activity under the control of PPE-1-3X promoter was 2.5 times higher under hypoxic conditions. In summary, introduction of the 3X element into the PPE 1 promoter is till capable of increasing expression levels of a downstream gene in response to hypoxia, even though the normoxic levels of expression with the PPE-1-3X gene are higher than those observed with the unmodified PPE-1 promoter.

Example 11

Further Evaluation of PPE-1-3x and PPE-1 Promoter Activity in Endothelial Cell Lines FIG. 18 summarizes the results from B2B, HUVEC and BAEC transfection experiments using pPPE-1/Luciferase and pPPE-1-3X/Luciferase. Higher Luciferase expression (30, 8.5 and 1.5 times more) was observed under the control of the PPE-1-3X promoter than under the PPE-1 promoter in B2B, HUVEC and BAEC, respectively. These results confirm those presented hereinabove and serve to establish that PPE-1-3X is well suited to directing high level expression specifically to endothelial cells. In the context of future in-vivo delivery, the higher levels of expression achieved with the PPE-1-3X construct translate into administration of smaller amounts of DNA. This, in turn, will serve to increase specificity even further.

Example 12

Efficiency, Specificity and Stability of Ad5PPE-1 Luc in-vivo

In order to confirm that the endothelial specificity of expression observed in examples 7 through 10 was not an artifact of cell culture, the Ad5PPE-1/Luciferase construct was injected into C57BL/6 mice as described hereinabove in "Tissue gene expression in normal mice". As in the in-vitro studies, Ad5CMV/Luciferase was employed as a negative control.

Following injection of adenoviral vectors, the specific activity and stability of Luciferase in vascularized and non-vascularized tissues was assayed. Results are summarized in FIG. 19 (Luciferase expression relative to expression in liver) and Table 3 (Luciferase expression as a percentage of total expression in the body). As expected, in Ad5CMV/Luciferase treated mice most of the Luciferase activity (>80% of the total body expression) was found in the liver. Luciferase activity controlled by the PPE-1 promoter was lower in the liver (37-54% of the total body expression). The PPE-1 derived expression was much higher in the aorta (23-33% of the total body expression 5 and 14 days post injection, respectively), compared to Ad5CMV/Luciferase. treated mice (up to 1.8% of total body expression; Table 2). These results confirm the endothelial specificity observed in cell culture. It should be remembered that the liver is a highly vascularized organ. Therefore examination of cellular expression within organs was undertaken, as detailed hereinbelow.

TABLE 3

Luciferase expression in organs 5 and 14 days post injection of PPE-1 and CMV based constructs

| | Day post injection | | | |
|---|---|---|---|---|
| | 5 Light units/μg protein | | 14 Light units/μg protein | |
| Organ | PPE-1 | CMV | PPE-1 | CMV |
| Aorta | 13.0 ± 2.9 (32.7%) | 1.4 ± 0.5 (0.56%) | 10.6 ± 2.4 (12.6%) | 1.3 ± 0.3 (1.1%) |
| Heart | 0.2 ± 0.1 (0.5%) | 1 ± 0.6 (0.4%) | 1.5 ± 0.3 (1.7%) | 1.8 ± 0.6 (1.6%) |
| liver | 22.7 ± 4.5 (57%) | 219 ± 111.5 (88.6%) | 34.9 ± 7.8 (41.6%) | 52.8 ± 10.6 (46.8%) |
| lung | 0.2 ± 0.1 (0.5%) | 2.3 ± 1.0 (0.9%) | 3.6 ± 0.8 (4.3%) | 2.0 ± 0.9 (1.8%) |
| muscle | 0.3 ± 0.1 (0.7%) | 0.8 ± 0.2 (0.3%) | 1.2 ± 0.3 (1.4%) | 1.5 ± 0.5 (1.3%) |
| spleen | 1.3 ± 0.8 (3.2%) | 1.6 ± 0.9 (0.6%) | 2.0 ± 0.4 (2.4%) | 2.3 ± 0.9 (2.0%) |
| pancreas | 2 ± 0.6 (5.0%) | 20.1 ± 6.8 (8.1%) | 26.4 ± 5.9 (31.5%) | 45.2 ± 24.5 (40.1%) |
| kidney | 0.1 ± 0 (0.25%) | 0.9 ± 0.6 (0.4%) | 0.6 ± 0.1 (0.71%) | 0.8 ± 0.3 (0.7%) |

FIGS. 41A and 41B demonstrate the absolute Luciferase activity (light units/μg protein) in the aortas (A) and livers (B) of the 110 injected mice. Luciferase activity was measured 1 (n=13), 5 (n=34), 14 (n=32), 30 (n=20) and 90 (n=11) days post injection. The results in the aorta represent the promoters (PPE-1 or CMV) activity mostly in endothelial cells, while the results in the livers represent their activity mostly in hepatocytes.

Example 13

Assays of Efficiency, Specificity and Stability of Ad5PPE-1 in-vivo- in BALB/C Mice The experiments of example 12 were repeated in 12 week old BALB/C mice (n=10 for each group) in order to demonstrate that the observed results were not an artifact of a particular strain of animals.

Because Absolute results with the adenoviral vectors were lower in BALB/C mice than in C57BL/6 mice, the Luciferase expression is expressed as percentage of the total Luciferase activity in all tissues.

The highest relative Luciferase expression 5 days post injection was observed in the spleens of Ad5PPE-1 (90.9%), and in the livers of Ad5CMV (86.2%) injected mice. A significant increase in the relative Luciferase activity in the aortas of Ad5PPE-1 injected mice 14 days post injection (32.9%), compared to its activity five days post injection (1.75%) was also observed (FIGS. 42A and 42B; Ad5PPE-1Luc-open bars; Ad5CMVLuc-black bars).

These results confirm that regardless of mouse strain, the tissue specificity of the PPE-1 promoter is sufficiently strong to effectively eliminate hepatocyte expression, despite preferential uptake of injected DNA by hepatocytes.

Example 14

Cellular Localization of Gene Delivered by Ad5PPE-1 in-vivo

In order to ascertain cellular expression sites of the gene expressed by PPE-1 in-vivo, Green Fluorescent Protein (GFP) delivered by the adenoviral vector Ad5PPE-1-GFP was used. Ad5CMVGFP (Quantum, Canada) was used as non-endothelial-cell-specific negative control. Five days post-intravenous injection the mice were sacrificed and their tissues were analyzed by fluorescent microscopy.

In the mice injected with Ad5CMVGFP vector, most of the expression was detected in the hepatocytes, and no expression was detected in endothelial cell in the liver (FIG. 20A). In sharp contrast, Ad5PPE-1-GFP injected mice (FIG. 20B), showed no expression in hepatocytes, but significant expression in endothelial cells in the blood vessels of the liver. Similar results were obtained in other tissues where practically all the PPE-1 derived expression was detected in the endothelium, while none of the CMV derived expression was endothelial. These results indicate endothelial specificity is preserved even within an organ containing endothelial and non-endothelial cells. This finding has important implications for prevention of angiogenesis in growing tumors.

Example 15

Assays of Efficiency and Endothelial Specificity of Ad5PPE-1-3X Luc and Ad5PPE-1-3X GFP in-vitro In order to determine the relative efficacy of Ad5PPE-1 and Ad5PPE-1-3X in driving expression of the reporter genes Luciferase and green fluorescent protein (GFP) in cells, specific activity in endothelial cells was tested in-vitro using cell lines described hereinabove. Ad5CMVLuc and Ad5CMVGFP were employed as non-tissue specific controls. Ad5PPE-1Luc and Ad5PPE-1GFP were employed to ascertain the relative change in expression level caused by addition of the 3X sequence.

Results, summarized in FIGS. 21 and 22, indicate that Luciferase activities under the control of the PPE-1-3X promoter were 5-10 times higher in EC lines (Bovine Aortic Endothelial Cells—BAEC) compared to activity in non-endothelial cells—Rat Insulinoma—RIN, HeLA, HePG2 and normal skin fibroblasts (NSF) (FIGS. 21 and 22).

FIG. 21 shows Luciferase activity as light units/μg protein in B2B, BAEC and RIN cells transduced by Ad5PPE-1Luc, Ad5PPE-1-3XLuc, and Ad5CMVLuc Highest Luciferase expression was observed in RIN cells transduced by Ad5CMVLuc, however this construct was poorly expressed in BAEC and B2B cells. The next highest level of Luciferase expression was observed in BAEC cells transduced by Ad5PPE-1-3XLuc. Ad5PPE-1Luc was expressed at lower levels in BAEC cells. In the B2B cell line Ad5PPE-1Luc and Ad5PPE-1-3XLuc were expressed at nearly identical levels.

Overall, luciferase activity in the endothelial cell lines under the control of PPE-1-3X promoter was 23 times higher than under the control of PPE-1 promoter and 23-47 times higher than under the control of the CMV promoter at the same infection conditions (moi=10). This is despite the fact that Luciferase expression in non-endothelial RIN cells was 3000 times higher under the control of the CMV promoter (FIG. 21).

In order to establish that PPE-1 and PPE-1-3X are inactive in other non-endothelial cell lineages HeLA, HepG2, NSF cell lines were transduced. BAEC was employed as an endothelial control. FIG. 22 shows Luciferase activity as light units/μg protein in HeLA, HepG2, NSF and BAEC cells transduced by Ad5PPE-1 Luc, Ad5PPE-1-3XLuc and Ad5CMVLuc. Transduction with Ad5CMVLuc caused high levels of Luciferase expression in HeLA, HepG2 and NSF cells. These cell lines failed to express Luciferase under the control of PPE-1 and expressed Luciferase at low levels with the PPE-1-3X promoter. As expected, BAEC cells transduced with Ad5PPE-1Luc or Ad5PPE-1-3XLuc exhibited high Luciferase expression.

Taken together these results indicate that introduction of the 3X sequence into the PPE-1 promoter caused higher levels of expression in endothelial cell lines while preventing unwanted expression in non-endothelial cells.

Addition of the 3X sequence to the PPE-1 promoter also increased levels of Green fluorescent protein expression in EC lines (Bovine Aortic Endothelial Cells—BAEC) as indicated in FIGS. 23 A-C which depicts GFP expression in BAEC transduced by moi=1. No expression of GFP was observed using a CMV promoter in this experiment.

In FIG. 23, panel A indicates Ad5PPE-1-3XGFP transduced cells, panel B indicates Ad5PPE-1 GFP transduced cells and panel C indicates Ad5CMVGFP. Again, introduction of the 3X sequence into the PPE-1 promoter significantly increased expression of the reporter gene. This result indicates that the ability of the 3X sequence to function as an endothelial specific enhancer is not a function of the downstream gene being transcribed.

Moreover, Ad5PPE-1-3X-GFP and Ad5PPE-1GFP transduction resulted in no GFP expression in non-endothelial cells SMC, HeLa, HePG2 and normal skin fibroblasts (NSF) compared to the high expression under the CMV promoter as summarized in FIGS. 24-27.

FIG. 24 shows GFP expression in SMC transduced by moi=1 of either Ad5PPE-1-3XGFP (panel A) or Ad5CMVGFP (panel B). While high level GFP expression resulted from Ad5CMVGFP transduction, no GFP expression resulted from transduction with Ad5PPE-1-3XGFP transduction.

FIG. 25 shows results of a similar experiment conducted in HeLa cells. As in the previous Figure, panel A indicates cells transduced with Ad5PPE-1-3XGFP and panel B indicates cells transduced with Ad5CMVGFP. Again, while high level GFP expression resulted from Ad5CMVGFP transduction, no GFP expression resulted from transduction with Ad5PPE-1-3XGFP transduction.

FIG. 26 shows results of a similar experiment conducted in HepG2 cells. As in the previous Figure, panel A indicates cells transduced with Ad5PPE-1(3X)GFP and panel B indicates cells transduced with Ad5CMVGFP. Again, while high level GFP expression resulted from Ad5CMVGFP transduction, no GFP expression resulted from transduction with Ad5PPE-1-3XGFP.

FIG. 27 shows results of a similar experiment conducted in NSF cells. As in the previous figure, panel A indicates cells transduced with Ad5PPE-1-3XGFP and panel B indicates cells transduced with Ad5CMVGFP. Again, while high level GFP expression resulted from Ad5CMVGFP transduction, very low GFP expression resulted from transduction with Ad5PPE-1-3XGFP.

These results, taken together, indicate a high level of endothelial specificity and a high level of endothelial expression is obtained by using a modified PPE-1 promoter containing the 3X sequence of SEQ ID NO.: 7.

Example 16

Cellular Localization of a Reporter Gene Delivered by Ad5PPE-1-3X in-vivo

In order to determine the cellular localization pattern of a reporter gene expressed under the control of the PPE-1-3X promoter in-vivo, Ad5PPE-1-3XGFP and Ad5PPE-1GFP were injected into mice as described hereinabove. Five days post-intravenous injection, the mice were sacrificed and their tissues were analyzed by a fluorescent microscopy.

Significantly higher GFP activity was observed in the endothelial cells of the liver, kidney and spleen blood vessels of Ad5PPE-1-3XGFP injected mice compared to the Ad5PPE-1GFP injected mice. FIGS. 28 A-B show representative results.

FIG. 28A shows low level GFP expression in endothelial cells lining a blood vessel of a mouse injected with the Ad5PPE-1GFP. FIG. 28B shows the much higher level of GFP expression resulting from addition of the 3X sequence to the construct.

Despite the high expression in the lining of the blood vessels, no expression was detected in the hepatocytes, glomeruli, epithelial cells and splenocytes (FIGS. 18 and 19).

FIG. 29 shows representative results from kidney tissue of injected mice. Ad5CMVGFP injected mice (FIG. 29A), Ad5PPE-1GFP (FIG. 29b) and Ad5PPE-1-3XGFP (FIG. 29C) injected mice all exhibited low GFP activity in kidney cells. In FIG. 29B, slightly higher GFP expression is visible in the blood vessel wall (indicated by arrow).

FIG. 30 shows representative results from spleen tissue of injected mice. Ad5CMVGFP injected mice (FIG. 30A), Ad5PPE-1GFP injected mice (FIG. 30B) and Ad5PPE-1-3XGFP injected mice (FIG. 30 C) all exhibited low level GFP activity in cells of the spleen. Higher GFP activity is visible in the blood vessels of Ad5PPE-1-3XGFP injected mice (indicated by arrow).

These results confirmed that both the PPE-1 and the PPE-1-3X promoter are endothelial cell specific in-vivo. They further suggest that activity of both promoters was limited in non-proliferating endothelial tissue (i.e. blood vessels of healthy organs. Therefore, assays in a tumor angiogenic model were undertaken.

Example 17

Assays of the Ad5PPE-1 Construct in Tumor Neovascularization in-vivo

In order to ascertain the ability of AD5PPE to specifically direct expression of a reporter gene to angiogenic blood vessels in a tumor, the murine LLC model (described hereinabove in materials and methods) was employed. In a one experiment, Luciferase expression in tumor neovascularization was tested five days post systemic injections of Ad5PPE-1Luc or Ad5CMVLuc ($10^{10}$ pfu/ml each).

In this experiment, systemic injection of Ad5CMVLuc to both primary and metastatic tumor models resulted in minimal expression in the primary tumor in the metastatic lung. This level of expression was similar to the minimal expression of Luciferase directed by CMV in naive normal lungs (FIG. 35; black bars; n=12). In sharp contrast, under the control of PPE-1 promoter (FIG. 35; open bars; n=9), the highly angiogenic lung metastases were associated Luciferase activity which was about 200 times higher than the Luciferase activity in the poorly-vascularized primary tumor and the naive lungs.

The Luciferase expression in non-metastatic tissues such as the liver, kidney, heart and pancreas was minimal. The expression level in the aorta was about 30% of the levels in the metastatic lungs.

In an additional experiment in the LLC model Ad5PPE-1GFP and Ad5CMVGFP constructs were employed to localize reporter gene expression in the primary tumor and metastatic lungs.

Ad5PPE-1GFP injected mice, showed high levels of GFP specific expression in the blood vessels of the primary tumor (FIG. 47C), although no expression was detected in the tumor cells themselves. This observation is consistent with the results of the LLC cell culture model presented in example 20. In lung metastases, high levels of GFP expression were detected in both big arteries and small angiogenic vessels of the metastatic foci (FIG. 47A). No expression was detected in the normal lung tissue. The endothelial cell localization was demonstrated by co-localization of the GFP expression (FIG. 47A) and the CD31 antibody immunostaining (FIG. 47B). In striking contrast, in Ad5CMVGFP injected mice, no GFP activity was detectable in both the primary tumor and lung metastasis.

FIG. 47C illustrates GFP expression in blood vessels of a primary tumor following intra tumoral injection of Ad5PPE-1GFP. FIG. 47D is a phase contrast image of the same filed as panel C illustrating the tumor and its blood vessels.

These results indicate that while PPE-1 does not drive high level expression in tumor cells per se, the promoter does drive high level expression in vascular endothelia within the tumor, especially in rapidly proliferating angiogenic vessels.

Intra-tumor injection of Ad5CMV into primary subcutaneous tumor model resulted in high Luciferase expression in the tumor tissue and moderately levels of expression liver (10% of the amount expressed in the tumor; FIG. 53). No expression was detected in the metastic lungs. On the other hand, when injected intra-tumoral, Luciferase expression under the control PPE-1 promoter resulted in similar Luciferase levels of expression in the primary tumor and the metastatic lungs and no expression was detected in the liver.

Example 18

Assays of the Ad5PPE-1 Construct in a Carcinoma Cell Culture System

In order to assay the efficiency of Ad5PPE-1 and Ad5CMV to drive Luciferase expression in cancerous cells, the D122-96 Lewis Lung Carcinoma cell line was employed.

In-vitro transduction at varying multiplicities of infection (moi) was performed. The results indicate that both adenoviral vectors are able to transduce the Luciferase gene to these cells (Table 4). Nevertheless, Luciferase activity directed by the PPE-1 promoter was much lower in the LLC cells than the activity detected in endothelial cells, 50 vs. 1000-2500 light units/µg protein, respectively.

TABLE 4

In-vitro transduction of Lewis lung carcinoma cell line (D122-96) with Ad5PPE-1Luc and Ad5CMVLuc.

|  | MOI = 1 | MOI = 5 | MOI = 10 |
| --- | --- | --- | --- |
| AdPPE-1 | 8.1 ± 0.06 | 33.95 ± 7.0 | 50.7 ± 5.0 |
| Ad5CMV | 9.3 ± 1.1 | 47.3 ± 4.0 | 88.13 ± 10.1 |

Example 19

Assay of the Effect of the 3X Sequence in Tumor Angiogenic Blood Vessels in-vivo In order to ascertain the effect of the 3X sequence on the PPE-1 promoter in angiogenic blood vessels, the Lewis Lung Carcinoma (LLC) metastases model (described hereinabove in material and methods) was employed. Five days post IV injection of $10^{10}$ infectious units of Ad5PPE-1GFP, Ad5PPE-1-3XGFP or Ad5CMVGFP, the mice were sacrificed and their tissues were analyzed as described in material and methods.

FIGS. 31 A-D summarize the GFP expression in metastatic lungs of control mice injected with Saline (FIG. 31A), mice injected with Ad5CMVGFP (FIG. 31 B), mice injected with Ad5PPE-1GFP (FIG. 31 C) and mice injected with Ad5PPE-1-3XGFP (FIG. 31D). Anti-CD31 immunostaining (FIGS. 31C' to 20D') confirm the location of the GFP expression in each metastatic tissue. The results show that while no GFP expression was detected in control—saline injected mice (FIG. 31A), there was a slight expression around the epithelial bronchi of the CMV injected mice, but not in the angiogenic blood vessels of the metastatic lung of these mice (FIG. 31B). Low GFP expression was observed in metastatic lungs of Ad5PPE-1GFP injected mice (FIGS. 31C and 31C'), while high and specific expression was observed in the new blood vessels of Ad5PPE-1-3XGFP injected mice (FIGS. 31D and 31D').

These results explain the apparent disparity between the in-vivo results of Example 15 and the in-vitro results of Examples 7, 8 and 11. Both the PPE-1 and the PPE-1-3X promoter are endothelial specific. However, the 3X sequence greatly increases the level of expression in rapidly proliferating endothelial tissue, such as newly forming blood vessels in a growing tumor.

Example 20

Effect of the 3X Element on the PPE-1 Promoter in Tumor Angiogenic Blood Vessels In order to study the effect of the 3X element of the present invention on efficacy and specific activity of the PPE-1 promoter in tumor angiogenic blood vessels, the LLC metastases model was employed. Five days post i.v. injection of $10^{10}$ pfu/ml of Ad5PPE-1Luc, Ad5PPE-1-3XLuc, Ad5CMVLuc, Ad5PPE-1GFP, Ad5PPE-1-3x-GFP or Ad5CMVGFP, the mice were sacrificed and their tissues were analyzed for Luciferase or GFP expression as described hereinabove.

FIG. 48 is a histogram comparing Luciferase expression in normal lungs versus that in metastatic lungs following systemic injection of Ad5PPE-1-3Xluc, Ad5PPE-1Luc or Ad5CMVLuc. Experimental groups were Ad5CMVLuc (n=7; black bars), Ad5PPE-1Luc (n=6; gray bars) and Ad5PPE-1-3XLuc (n=13; brown bars). Activity is expressed as light units/µg protein.

Luciferase expression under the control of the PPE-1-3X promoter was 35 fold greater in the metastatic lungs relative to its activity in normal lungs and 3.5 fold higher than expression driven by the PPE-1 promoter without the 3X element (p<0.001). Very low Luciferase activity was detected in other tissues of mice injected with Ad5PPE-1-3XLuc. Calculating the Luciferase expression in the lungs as percentage from the liver of each injected animal revealed that the activity increased 10 fold in the metastatic lung compared to the activity in normal lung (FIG. 49).

In order to localize reporter gene expression to specific cell types, GFP constructs were employed. FIG. 50 A-B show the GFP expression (FIG. 50A) in metastatic lungs of Ad5PPE-1-3XGFP injected mice. Immunostaining by CD31 antibody (FIG. 50B) confirm the location of the GFP expression in the new blood vessels. No GFP expression was detected in control—saline injected mice. Low level expression around the epithelial bronchi of the CMV injected mice, but not in the angiogenic blood vessels of the metastatic lung. In summary, these results indicate that large increases in expression level resulted from introduction of a 3X element into Ad5PPE-1 constructs and that this increased expression was specific to the angiogenic blood vessels of tumors. Potentially, the observed effect may be coupled with the hypoxia response described hereinabove to further boost expression levels of a sequence of interest.

Example 21

Further Characterization of the PPE-1 Hypoxia Response

In order to further characterize the effect of hypoxia on the murine PPE-1 promoter activity, bovine aortic endothelial cells (BAEC) were transfected by a DNA plasmid (pEL8; FIG. 37A). The pEL8 plasmid contains the murine PPE-1 promoter (1.4 kb) (red), the luciferase gene (1842 bp), the SV40 poly A sites and the first intron of the endothelin-1 gene, all termed the PPE-1 promoter cassette was digested and extracted by BamHI restriction enzyme as described in material and methods. Following transfection, cells were subjected to hypoxic conditions.

Luciferase expression in transfected BAEC subjected to 18 hours of hypoxia (0.5% O2) was eight times higher than Luciferase expression in cells grown in a normoxic environment (FIG. 32). FIG. 32 shows that Luciferase activity (light units/µg protein) in BAEC transfected by a plasmid containing the murine PPE-1 promoter was significantly higher when transfected cells were incubated in a hypoxic environment. Equivalent transfection efficiencies were confirmed by co-transfection with a β-galactosidase reporter vector and assays of LacZ activity.

In order to determine whether murine PPE-1 promoter delivered by adenoviral vector is also up-regulated by hypoxia, BAEC were transduced by Ad5PPE-1Luc. Ad5CMVLuc was used a non specific control in this experiment. Results are summarized in FIG. 33. Hypoxia Luciferase activity in BAEC transduced by Ad5PPE-1Luc. In stark contrast, no significant difference between normoxia and hypoxia was detected in the Ad5CMV transduced cells (FIG. 33).

To understand whether the enhancement of the PPE-1 promoter activity is specific to endothelial cells, different cell lines (BAEC, B2B, CHO, RIN and Cardiac Myocytes) were transduced by Ad5PPE-1 (moi=10) and were subjected to hypoxia (0.5% O2) or normoxia environment. Results are summarized in FIG. 34. Luciferase expression was slightly increased in B2B cells and significantly increased in BAEC cells cultured in a hypoxic environment. Luciferase expression in other cell lines was reduced by the hypoxic environment, compared to normoxia. These results confirm that hypoxic induction of the PPE-1 promoter occurs primarily in endothelial cell lineages.

Example 22

Effect of the 3X Sequence on the PPE-1 Hypoxia Response

In order to ascertain the effect of the 3X sequence on the PPE-1 hypoxia response, BAEC were transduced by Ad5PPE-1Luc and Ad5PPE-1(3X)Luc. Following transduction, the BAEC cells were incubated either in a hypoxic or a normoxic environment as detailed hereinabove. Results are summarized in FIG. 35. Luciferase expression using the Ad5PPE-1Luc construct significantly increased (seven folds) in response to hypoxia (2578 in hypoxia and 322.1 in normoxia). In contrast, the Ad5PPE-1(3X)Luc construct exhibited only 1.5 fold increase in response to hypoxia (from 2874.5 in normoxia to 4315 in hypoxia conditions). These results indicate that the high normoxic level of expression observed when the 3X sequence is added to the PPE-1 promoter serves to mask the hypoxic response to some extent.

Example 23

Assays of the PPE-1 Response to Hypoxia in a Transgenic Mouse Model

In order to examine the murine PPE-1 promoter activity in tissues subjected to regional hypoxia/ischemia, mPPE-1-Luc transgenic mice, described hereinabove in materials and methods, were employed. The mice were induced to regional hind limb ischemia as previously described (Couffinhal T. et al. (1998) Am. J. Pathol. 152; 1667-1679). In brief, animals were anesthetized with pentobarbital sodium (40 mg/kg, IP). Unilateral ischemia of the hind limb was induced by ligation of the right femoral artery, approx. 2 mm proximal to the bifurcation of the saphenous and popliteal arteries. To verify the induction of functional change in perfusion, ultrasonic imaging was performed on days 4 and 14 by Synergy ultrasound system (GE) equipped with a 7.5 MHz transducer and angiographic software. Animals were housed under conventional conditions for up to 18 days.

Luciferase expression was assayed 2, 5, 10 and 18 days post ligation in the ischemic muscle, in the normal non-ligated muscle, in the liver, lung, and aorta.

Results, summarized in FIG. 36, show that while no significant difference was detected in the liver, lung and aorta during the days post ligation, Luciferase gene expression increased following the femoral ligation in both in the normal non-ligated and in the ischemic muscle. While peak Luciferase expression in the ischemic muscle was detected five days post ligation, peak Luciferase expression in the non-ligated muscle was detected ten days post femoral artery ligation. This indicates that the hypoxic response of the PPE-1 promoter is functional in an in-vivo system. Luciferase expression in the non-ischemic muscle did not change during the days tested, compared to its expression in the control non-operated tissue (day=0). In contrast, Luciferase expression in the ischemic muscle was significantly higher on day 5 than at other time points.

On day 5, PPE-1 driven expression of Luciferase was 2.5 times higher than in control non-operated mice and compared to the ischemic muscle in days 10 and 18 (FIG. 51).

Expression of Luciferase in other non-ischemic tissues including liver, lungs and aorta of the transgenic mice subjected to regional ischemia revealed no significant changes within 18 days post ischemic induction in the Luciferase expression in these tissues (FIG. 52).

Further, these results confirm that Luciferase expression was higher in tissues containing a high percentage of endothelial tissue (lung and aorta) than in those tissues containing a low percentage of endothelial tissue (liver and non-ischemic muscle).

Example 24

Effect of Level of Cellular Proliferation on Ad5PPE-1Luc Activity in Endothelial Cells In order to ascertain the effect of level of cellular proliferation on efficiency and specific activity of Ad5PPE-1Luc, an angiogenic model of endothelial cells (BAEC), was tested in-vitro. Transduced BAEC were either induced to quiescence by serum deprivation or grown in 10% FCS for normal proliferation. Briefly, cells were transduced for 48 hours either as quiescent cells—72 hours post serum deprivation or as proliferating cells—in normal media (10% FCS). Luciferase activity is expressed as light unit/μg protein, to normalize for the difference in cell amount. The results presented are an average of triplicate test from four representative independent experiments.

Luciferase expression under the control of PPE-1 promoter (open bars; FIG. 28) was 4 times higher in normal proliferating BAEC than in quiescent cells, and 25 times higher in normal proliferating BAEC than Luciferase expression under control of the CMV promoter (Black bars; FIG. 28). Further, in proliferating cells, the activity under the control of PPE-1 promoter was 10 times higher than that under the CMV promoter control.

In order to simulate angiogenic conditions in-vitro, Ad5PPE-1Luc activity was tested in BAEC induced to rapid proliferation by addition of 40 ng/ml vascular endothelial growth factor (VEGF). Activity under these conditions was compared activity in normal proliferating cells and quiescent cells as described hereinabove. Luciferase expression in BAEC induced to cell proliferation with VEGF was 44 times higher than in normal proliferating cells, and 83 times higher than in quiescent cells (FIG. 40).

Together, these experiments indicate that the level of activity of a sequence of interest under transcriptional control of the PPE-1 Promoter is a function of the level of cellular proliferation, with rapid proliferation causing higher levels of expression.

Example 25

Assays of the PPE-1 Promoter in Atherosclerosis Induced Mice

In order to test the efficiency and specificity of the Ad5PPE-1 vector in atherosclerotic blood vessels, $10^{10}$ pfu/ml of the viral vectors were systemically injected to 6 month old ApoE deficient mice (Plump, A. S. et al. Cell; 1991; 71:343-353).

As ApoE deficient mice age, they develop high cholesterol values and extensive atherogenic plaques with no induction of lipid reach diet. FIG. 43 is a picture of an aorta dissected from an ApoE deficient mouse colored by Sudan—IV. Note that the thoracic aorta contains less red stained atherosclerotic lesions while the abdominal region is highly atherosclerotic. (FIG. 43 adapted from Imaging of Aortic atherosclerotic lesions by 125I-HDL and 125I-BSA. A. Shaish et al, Pathobiology—Pathobiol 2001; 69:225-9).

FIG. 44 summarizes Luciferase expression observed 5 days post systemic injections of Ad5PPE-1Luc (open bars; n=12) and Ad5CMVLuc (black bars; n=12) to ApoE deficient mice. Results are presented as absolute Luciferase expression in the thoracic area that contains less atherosclerotic lesion, and the abdominal aorta that is rich atherosclerotic lesion.

Luciferase expression controlled by the PPE-1 promoter was 6 fold higher in the highly atherosclerotic abdominal, and 1.6 fold higher in the slightly atherosclerotic thoracic aorta as compared to expression under the control CMV promoter.

No significant difference was observed between the two aorta regions in the Ad5PPE-1Luc injected mice, while higher Luciferase expression was observed in thoracic aorta of the Ad5CMVLuc injected group compared to low expression in the abdominal aorta that contain lesion.

These results indicate that while a constitutive promoter (CMV) has a tendency to shut down in areas where atherosclerosis is most severe, the PPE-1 promoter is relatively unaffected by disease progression.

Example 26

Assays of the PPE-1 Promoter in a Wound Healing Model

In order to test the Ad5PPE-1 constructs efficiency and specific activity in directing Luciferase expression to healing wound blood vessels, a murine wound healing as described hereinabove in Material and Methods was employed.

As in other experiments, Ad5CMVLuc was used as a non-tissue specific control. Luciferase activity under the PPE-1 promoter (FIG. 45; open bars) control was higher both in the normal (6.8±3.2) and in healing wound region (5±1.6) compared to the activity observed under the CMV control (FIG. 45; black bars).

Because both the CMV and PPE-1 promoter exhibited reduced expression levels in the healing wound, these results are difficult to interpret. Despite this unexpected observation, it is clear that the PPE-1 promoter drives higher levels of expression than the CMV promoter in both normal and healing tissue. The presence of necrotic scar tissue may account for the reduced expression levels observed with both promoters in the healing wound.

Example 27

Targeted Expression of VEGF and PDGF-B to Ischemic Muscle Vessels

In-vivo induction of angiogenesis oftentimes results in a primitive vessel network consisting of endothelial cells. These nascent vessels rupture easily, prone to regression and leakiness and poorly perfused. To overcome these limitations localized, timed and dose-controlled delivery of various angiogenic factors, capable of recruiting endothelial cells as well as periendothelial cells (i.e., pericytes in small vessels or smooth muscle cells in larger vessels) is desired.

The modified preproendothelin-1 promoter, PPE-1-3X was used to express in the endothelium of ischemic limb muscles either VEGF or PDGF-B, an endothelial secreted factor which recruits smooth muscle cells towards the origin of secretion thereby preventing hyper permeability of newly formed vessels.

To determine expression of VEGF and PDGF-B in ischemic tissues, in-situ hybridization was performed. As shown in FIGS. 54A-C, while a significant expression of VEGF mRNA could be detected in ischemic muscle sections from Ad5PPE-1-3XVEGF treated mice, essentially no signal could be seen in muscle sections of Ad5CMVVEGF or saline-treated mice. Similarly, the presence of mRNA of PDGF-B was detected in ischemic limb muscles of mice treated with Ad5PPE-1-3XPDGF-B, but not in Ad5CMVPDGF-B or saline-treated mice (FIGS. 54E-G). Interestingly, the pattern of the signal in FIGS. 12A and 12E resembled vascular structure. Notably, representative liver sections from the various treatment groups demonstrated massive expression of VEGF or PDGF-B in Ad5CMV treated animals (FIGS. 54D and 54H), while no expression was detected in the livers of Ad5PPE-1-3X vectors treated mice (data not shown).

Altogether, the assay indicates that the Ad5PPE-1-3X vectors mediate measurable expression of angiogenic factors in a target organ, while the constitutive Ad5CMV vectors expressed their transgene almost exclusively in hepatic tissues.

Example 28

Enhanced Angiogenesis by PPE-mediated VEGF Expression

The therapeutic effect of Ad5PPE-1-3XVEGF was compared to that of previously reported Ad5CMVVEGF. $10^9$ PFUs of either therapeutic vectors, as well as reporter vector Ad5CMVluciferase and equivalent volume of saline as control were systemically administered to mice, 5 days following femoral artery ligation. Ultrasonic (US) images of the medial aspect of both limbs were taken in angiographic mode. As shown in FIGS. 38A-D, 21 days following ligation, the signal of perfusion was diminished and truncated in the control animals; however, continuous, enhanced signal was seen in the US images of both Ad5PPE-1-3XVEGF and Ad5CMVVEGF treated mice. The mean intensity of perfusion on the $21^{st}$ day in the two VEGF treatment groups was over 3 times higher than that of the control group (p<0.01), and similar to that recorded from the normal, contralateral limbs of the animals (FIG. 38E). Immunohistochemistry analysis done 21 days following femoral artery ligation and using anti CD-31, an endothelial specific marker, showed a mean of 546 CD31+ cells/mm$^2$ in the ischemic muscle sections of Ad5PPE-1-3XVEGF treated mice, comparing to 585 and 485 CD31+ cells/mm$^2$ in the Ad5CMVVEGF and control groups, respectively (FIG. 38F). This data shows that in the short term treatment with Ad5PPE-1-3XVEGF is as effective as the treatment with the potent CMV promoter of Ad5CMVVEGF. Furthermore, liver sections of the mice stained in H&E showed no indications for hepatitis or other pathological chronic changes (data not shown), thereby ruling out adenovirus tropic effect on hepatocytes.

Example 29

Prolonged Effect of VEGF Gene Therapy by PPE-regulated Expression

Tissue specific expression versus constitutive expression of pro-angiogenic factors was addressed with respect to the induction of angiogenesis. The effects of PPE-regulated and CMV-regulated VEGF expression on perfusion and angiogenesis were tested in 70 days long experiments. Mice with ischemic limb were treated as above (see Example 28). US imaging revealed significant improvement in perfusion in both treatment groups beginning 1-2 weeks following virus administration, while minor changes were detected in the control group (data not shown). The long-term effect of the Ad5PPE-1-3XVEGF treatment was detected 50 and 60 days following femoral artery ligation. Perfusion was significantly increased in the Ad5PPE-1-3XVEGF treated mice, as compared to Ad5CMVVEGF or saline-treated mice. The difference in perfusion between Ad5CMVVEGF and control treated animals decreased over that time interval. On the $50^{th}$ day, mean intensity of perfusion in the Ad5PPE-1-3XVEGF treated group was about 50% higher than in the Ad5CMVVEGF or saline treated mice, and similar to that of the contralateral normal limb (p<0.01, FIG. 55A). Upon sacrifice of the animals on the $70^{th}$ day, the capillary density in the muscle sections of Ad5PPE-1-3XVEGF treated mice was 747 CD31+ cells/mm$^2$, which is 57% and 117% higher than in the Ad5CMVVEGF (474 CD31+ cells/mm$^2$) and control (342 CD31+cells/mm$^2$) groups, respectively (p<0.01, FIG. 55B).

Example 30

Enhanced Angiogenesis by PPE-promoter Endothelial-specific PDGF-B Expression

PDGF-B is a paracrine endothelial secreted factor, which has been shown to be involved in vessel maturation by recruitment of smooth muscle cells, and probably also in angiogenesis [Edelberg, J. M. et al. *Circulation* 105, 608-13. (2002); Hsu et al. *J Cell Physiol* 165, 239-45. (1995); Koyama, N. et al. *J Cell Physiol* 158, 1-6. (1994)]. It has also been shown that PDGF-B is involved in intimal thickening [Sano, H. et al. *Circulation* 103, 2955-60. (2001); Kaiser, M., et al. *Arthritis Rheum* 41, 623-33. (1998)] and in fibroblast proliferation [Nesbit, M. et al. *Lab Invest* 81, 1263-74. (2001); Kim, W. J. et al. *Invest Ophthalmol Vis Sci* 40, 1364-72. (1999).]. The ability of PDGF-B to induce angiogenesis under endothelial specific regulation was tested in vitro and in-vivo.

Ad5PPE-1-3XPDGF-B vector induced angiogenic changes in endothelial cells in-vitro, like Ad5PPE-1-3XVEGF (data not shown). Transduction of endothelial cells cultured on fibrin coated cultureware with 10 MOI of Ad5PPE-1-3X PDGF-B resulted in the formation of 2-dimensional circular structures and fibrin degradation.

For in-vivo effect, mice were systemically treated with 109 PFUs of Ad5PPE-1-3XPDGF-B, 5 days following femoral artery ligation. 30 days following ligation the mean intensity of perfusion in the Ad5PPE-1-3XPDGF-B treated mice was about 90% higher than that in the control group (FIG. 56A). 80 days following ligation the intensity of perfusion in the Ad5PPE-1-3XPDGF-B treated group was 60% higher than in the control group (FIG. 56B)

Capillary density was measured 35 and 90 days following ligation. In the short time interval, the mean capillary density in ischemic muscle sections of the Ad5PPE-1-3XPDGF-B treated mice was 516 CD31+ cells/mm$^2$, while in the saline-treated group it was 439 (FIG. 56C). 90 days following ligation the mean capillary density in Ad5PPE-1-3XPDGF-B treated mice increased slightly to 566 CD31+ cells/mm², while a moderate decrease was detected in the control group (378 CD31+ cells/mm²).

The results indicate that Ad5PPE-1-3XPDGF-B vector by itself is a potent angiogenic treatment, which not only induces angiogenesis in the short term following administration, but is capable of retaining a therapeutic effect for a long period of time. No chronic changes were detected in the livers of the mice treated with Ad5PPE-1-3XPDGF-B.

Example 31

Vessel Maturation by PDGF-B Expression in Endothelial Cells

Figure 57A:
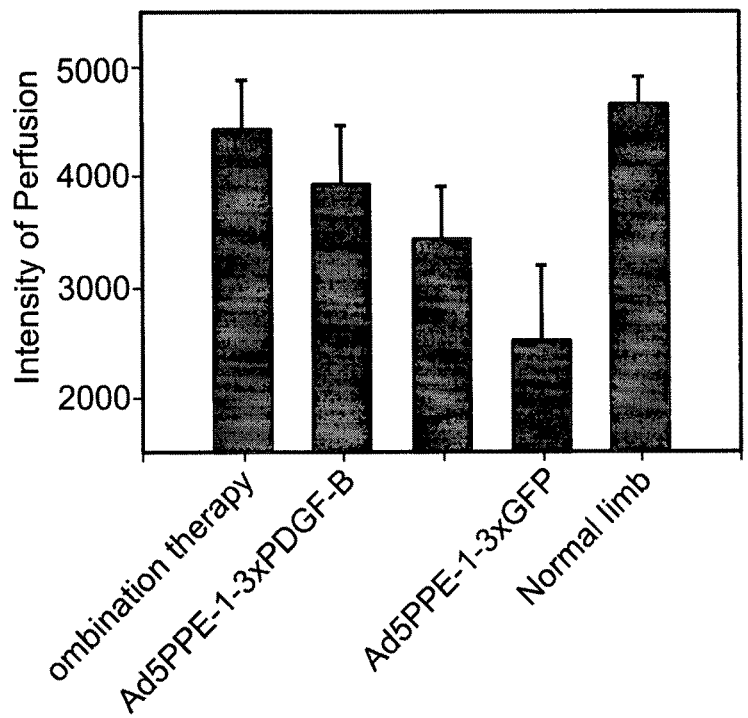
Figure 57B:
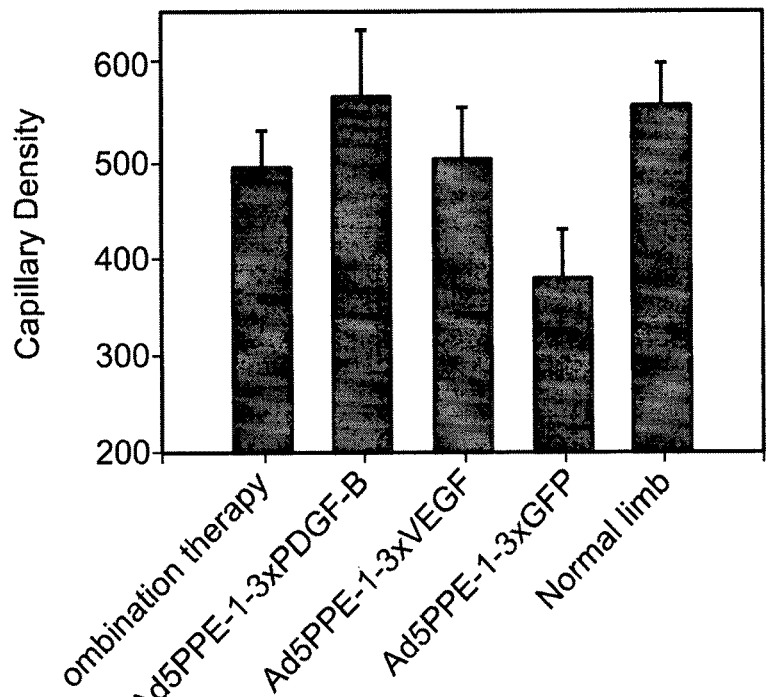
Figure 57C:
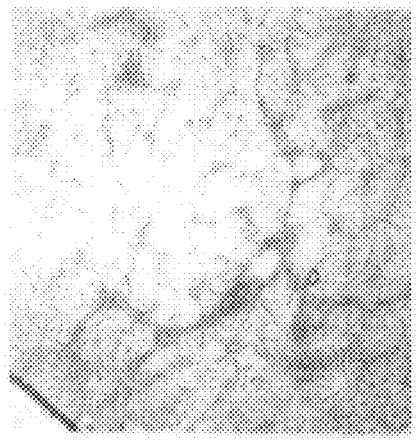
Figure 57D:
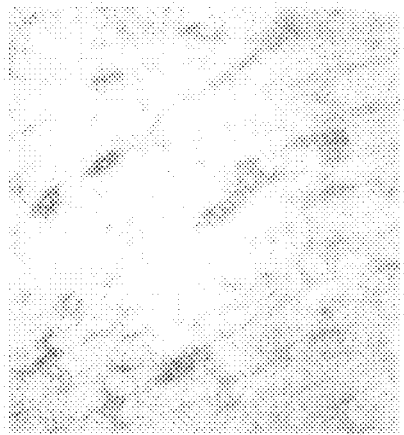
Figure 57E:
Figure 57F:
Figure 57G:

The assumption that further enhancement of angiogenesis and maturation of vasculature can be achieved by utilizing both VEGF and PDGF-B in a combination therapy was tested using two modalities of treatment: (i) single administration of $10^9$ PFUs of Ad5PPE-1-3XVEGF and of Ad5PPE-1-3XPDGF-B; (ii) administration of similar dose of Ad5PPE-1-3XPDGF-B 5 days following administration of Ad5PPE-1-3XVEGF. Both modalities yielded the same results, and therefore are referred to as one. 90 days following ligation, both the combination therapy and the Ad5PPE-1-3XVEGF treated mice exhibited significantly higher capillary density as compared to the control, Ad5PPE-1-3XGFP treated mice, but there was no significant difference among the various therapeutic groups (FIG. 57B). However, the mean intensity of perfusion in US imaging in the combination therapy group was up to 42% higher than the Ad5PPE-1-3XVEGF treated group (FIG. 57A). This can be explained by maturation of small vessels in the ischemic muscles of the combination therapy groups and Ad5PPE-1-3XPDGF-B treated mice. Significant staining for vascular smooth muscle cells was seen in muscle sections from mice treated with the combination therapy or Ad5PPE-1-3XPDGF-B, immunostained for α-SMactin (FIGS. 57C-D). Sparse staining could be seen in control and Ad5PPE-1-3XVEGF treated mice (FIGS. 57E-F). In the normal limb muscles there was prominent staining around larger arterioles and venules (FIG. 57G). Similar results were obtained as early as 35 days following ligation in mice treated with Ad5PPE-1-3XPDGF-B (data not shown). No chronic changes were apparent in liver sections of treated mice 35 days following ligation.

These results were further substantiated in a separate experiment, which addressed the effect of PDGF-B alone and in combination therapy on blood perfusion 50 days following ligation. As shown in FIG. 58, 50 days following ligation, blood perfusion intensity in the combination therapy group resembled completely that of normal limb. This effect was PPE-3X dependent, as constitutive expression (CMV promoter) of both growth factors resulted in only half perfusion capacity. Interestingly, PPE-3X dependent expression of PDGF-B alone could mediate nearly the same perfusion (i.e., 77%) as induced by the combination therapy. However, such results were not apparent using a constitutive promoter.

These results corroborate that the PPE-1-3X promoter is capable of strong enough activation of the therapeutic genes, in spite of the systemic administration, without compromising the preferential expression in angiogenic endothelial cells. Furthermore, these results substantiate PDGF-B as a pro-angiogenic factor which can mediate its angiogenic action without further addition of well established angiogenic growth factors, such as VEGF.

Example 32

Construction and Characterization of the AdPPE-1(3x)-TK Vector

The HSV-TK/GCV is the most widely studied and implemented cytoreductive gene-drug combination. Cells transfected with an HSV-TK-containing plasmid or transduced with an HSV-TK containing vector, are made sensitive to the drug super-family including aciclovir, ganciclovir (GCV), valciclovir and famciclovir. The guanosine analog GCV is the most active drug in combination with TK. HSV-TK positive cells produce a viral TK, which is three orders of magnitude more efficient in phosphorylating GCV into GCV monophosphate (GCV-MP) than the human TK. GCV-MP is subsequently phosphorylated by the native thymidine kinase into GCV diphosphate and finally to GCV triphosphate (GCV-TP).

Initially, two plasmids were prepared. One plasmid contains the HSV-TK gene controlled by the modified murine pre-proendothelin-1 (PPE-13x) promoter and was prepared in order to test the efficacy of the gene controlled by the PPE-1(3x) promoter in vitro. A larger plasmid containing the HSV-TK gene controlled by the PPE-1(3x) promoter as well as adenoviral sequences was prepared for virus vector preparation by homologous recombination. The HSV-TK gene (1190 bp) was digested from the 4348 bp plasmid pORF-HSV1TK by two restriction enzymes. The SalI restriction site was positioned against the 5' end of the HSV-TK gene and the EcoRI site was positioned against the 3' end. The HSV-TK gene was ligated to the multiple cloning site of the 3400 bp plasmid pBluescript-SK that contains a NotI restriction site upstream to the inserted gene (against the 3' end of the HSV-TK gene). The SalI site underwent the Klenow procedure and the NotI linker was ligated to the 5' end of the HSV-TK gene. The HSV-TK gene (now outflanked by two NotI restriction sites) was ligated into the NotI restriction site of two plasmids, pEL8(3x)-Luc and pACPPE-1(3x)-GFP, described hereinabove:

1. The 8600 bp plasmid designated pEL8(3x)-Luc, instead of the 1842 bp luciferase gene, flanked by two NotI restriction sites. The pEL8(3x)-TK plasmid contains the PPE-1(3x) promoter, the HSV-TK gene, an SV-40 poly-adenylation site and the first intron of the murine endothelin-1 gene (FIG. 60a).

2. The 11946 bp plasmid pACPPE-1(3x)-GFP instead of the 1242 bp green fluorescent protein (GFP) gene, outflanked by two NotI restriction sites (FIG. 60b).

Constructing an adenovirus-5 vector armed with the HSV-TK gene controlled by the modified murine pre-proendothelin-1 promoter. The replication-deficient vector, designated AdPPE-1(3x)-TK, was constructed on the basis of a first generation (E1 gene deleted, E3 incomplete) adenovirus-5 vector. The recombinant vector was prepared by co-transfection of the plasmids pACPPE-1(3x)-TK and pJM-17 (40.3 kb) in human embryonal kidney-293 (HEK-293) using well-known conventional cloning techniques. The pJM-17 plasmid contains the entire adenovirus-5 genome except for the E1 gene. The HEK-293 cell line substitutes the E1 deletions, since they contain an E1 gene in trans. One out of 40 homologous recombinations induced the vector AdPPE-1 (3x)-TK.

AdPPE-1(3x)-TK vector characterization. PCR analysis was performed on the viral DNA in order to verify the existence of the TK transgene and the promoter in the recombinant adenovirus. Two primers were used: the forward primer 5'-ctcttgattcttgaactctg-3' (455-474 bp in the pre-proendothelin promoter sequence)(SEQ ID No: 9) and the reverse primer 5'-taaggcatgcccattgttat-3' (1065-1084 bp in the HSV-TK gene sequence)(SEQ ID No:10). Other primers of vectors, produced in our laboratories, were used in order to verify the purity of the vector. A band of approximately 1 kb verified the presence of the PPE-1(3x) promoter and the HSV-TK gene in the AdPPE-1 (3x)-TK virus (FIG. 61). However, none of the other primers of the adenovirus vectors constructed afforded any product. Thus, the vector was a pure colony.

The virus was further purified in HEK-293 cells in order to isolate a single viral clone.

Viral DNA of AdPPE-1(3x)-TK was sequenced by cycle sequencing reactions in the presence of a dideoxy nucleotides, chemically modified to fluoresce under UV light. Four primers were used to verify the existence of the whole transgene:

1. Forward primer 5'-ctcttgattcttgaactctg-3' (455-474 bp in the pre-proendothelin promoter)(SEQ ID NO: 9) preceding the "3x" element.
2. Reverse primer 5'-gcagggctaagaaaaagaaa-3' (551-570 bp in the pre-proendothelin promoter)(SEQ ID NO:1).
3. Forward primer 5'-tttctttttcttagccctgc-3' (551-570 bp in the pre-proendothelin promoter)(SEQ ID NO:12).
4. Reverse primer 5'-taaggcatgcccattgttat-3' (1065-1084 bp in the HSV-TK gene)(SEQ ID NO:10) within the HSV-TK gene.

The primers designated 2 (SEQ ID NO:11) and 3 (SEQ ID NO:12) were used, since no product was obtained by the primers 1 (SEQ ID NO:9) and 3 (SEQ ID NO:10) alone. The result exhibited 99% identity to the *Mus musculus* Balb/c pre-proendothelin-1 gene, promoter region gi|560542|gb|U07982.1|MMU07982[560542] (SEQ ID NO:1), as well as 99.4% identity to the thymidine kinase gene of the herpes simplex virus gi|59974|emb|V00470.1|HERPES[59974]. The sequence of AdPPE-1(3X) is detailed in FIG. 92.

The 3x sequence (FIG. 93) contains an additional triplicate repeat of the endothelial specific positive transcription elements. In this 145 bp sequence there are two complete endothelial specific positive transcription elements and one sequence cut into two fragments in opposite order, as described hereinabove.

Control vectors. Two adenovirus vectors, one lacking the PPE-1(3x) promoter, and a second lacking the Luc gene, were constructed to serve as controls for the AdPPE-1(3X) vector. The vector AdCMV-TK (used as a non tissue-specific promoter control) contains the HSV-TK gene controlled by the early cytomegalovirus (CMV) promoter (FIG. 62*c*). The vector AdPPE-1(3x)-Luc contains the luciferase (Luc) gene controlled by the modified murine pre-proendothelin-1 promoter (FIG. 62*b*). The viruses were grown in scaled up batches and stored at −20° C. at a concentration of $10^9$-$10^{12}$ particles/ml.

Example 33

Cytotoxicity of Ganciclovir and TK Under Control of the PPE-1 (3x) Promoter: Superior Endothelial Cell Cytotoxicity of TK Under Control of the PPE-1 (3x) Promoter in-vitro Specific endothelial cell-targeted cytotoxicity of AdPPE-1 (3x)-TK was assessed in-vitro in endothelial cell lines by comparison to control vectors AdCMV-TK and AdPPE-1 (3x)-Luc.

AdPPE-1(3x)-TK+GCV is cytotoxic at low multiplicity of infection (moi): Bovine aorta endothelial cells (BAECs) were transduced with AdPPE-1(3x)-TK, AdCMV-TK and AdPPE-1(3x)-Luc multiplicity of infections (m.o.i.) of 0.1, 1, 10, 100, and 1000. GCV (1 µg/ml) was added four hours post-transduction. Controls were cells transduced with the vectors without GCV, or GCV without vectors. Both controls did not induce cell death (data not shown). Note the morphological changes characteristic to cytotoxicity (cell enlargement, elongation and bloatedness) and loss of confluence evident in AdPPE-1 (3x)+GCV-treated cells, at a significantly lower m.o.i. than AdCMV-TK. Cells transduced with AdPPE-1 (3x)-Luc remained healthy (small size, rounded and confluent, FIG. 63). Assessment of cell viability, determined by staining with crystal violet (FIG. 64), confirmed that the AdPPE-1(3x)-TK vector, combined with GCV administration, exhibited greater cytotoxicity, at lower m.o.i. in BAE-cells than the TK gene controlled by the strong constitutive CMV promoter.

AdPPE-1(3x)-TK+GCV is cytotoxic at low concentrations of GCV: Bovine aorta endothelial cells (BAECs) were transduced with AdPPE-1(3x)-TK, AdCMV-TK and AdPPE-1 (3x)-Luc, as described hereinabove, at multiplicity of infection (m.o.i.) of 10, and exposed to increasing concentrations of GCV (0.001-10 µg/ml, as indicated), added four hours post-transduction. Control cells transduced with the vectors without GCV, or receiving GCV without vectors show no indication of cell death (data not shown) at any concentrations. Note the morphological changes characteristic to cytotoxicity (cell enlargement, elongation and bloatedness) and loss of confluence evident in AdPPE-1 (3x)-TX+GCV treated cells (FIG. 65), at a significantly lower concentration of GCV than cells exposed to AdCMV-TK (middle series). Assessment of cell viability, determined by staining with crystal violet (FIG. 66), confirmed that the AdPPE-1(3x)-TK vector, combined with GCV administration, exhibited greater cytotoxicity in BAEcells, and at lower GCV concentrations than the TK gene controlled by the strong constitutive CMV promoter.

AdPPE-1(3x)-TK+GCV cytotoxicity is specific for endothelial cells: In order to evaluate the specificity and the efficacy of the vector AdPPE-1(3x)-TK for endothelial cells, endothelial [Bovine aortic endothelial cells (BAEC), Human umbilical vein endothelial cells (HUVEC)] and non-endothelial [Human hepatoma cells (HepG-2), Human normal skin fibroblasts (NSF)] cells were transduced with AdPPE-1(3x)-TK, AdPPE-1(3x)-Luc or AdCMV-TK at m.o.i. of 10, followed by the administration of 1 µg/ml GCV four hours post-transduction. Cytotoxicity and cell morphological changes were detected four days post-transduction. AdPPE-1(3x)-TK+GCV induced cytotoxicity, specifically in BAEC and HUVEC, while AdCMV-TK+GCV induced cytotoxicity only in HepG-2. NSF were resistant to all vectors at m.o.i.=10. AdPPE-1 (3x)-Luc+GCV were nontoxic to all cell types (FIG. 67). Assessment of cell viability, determined by staining with crystal violet (FIG. 68), confirmed that the AdPPE-1(3x)-TK vector, combined with GCV administration, exhibited synergic endothelial cell-specific cytotoxicity, compared to the non-specific cytotoxicity of the TK gene controlled by the strong constitutive CMV promoter (AdCMV-TK+GCV).

When non-endothelial NSF cells were transduced with AdPPE-1(3x)-TK, AdPPE-1(3x)-Luc or AdCMV-TK, at the higher m.o.i. of 100, followed by the administration of 1 µg/ml GCV four hours post-transduction, no effect of AdPPE-1(3x)-TK+GCV on cell morphology was observed (FIG. 69). In contrast, cells treated with TK under control of the strong constitutive CMV promoter (AdCMV-TK+GCV) showed strong non-specific cytotoxicity, confirming the endothelial selective cytotoxicity of TK under control of the PPE-1 (3x) promoter and ganciclovir administration, even at extreme multiplicity of infection.

Taken together, these results show, for the first time, that the vector AdPPE-1(3x)-TK is able to specifically induce the killing of endothelial cells, including human endothelial cells. Moreover, the vector AdPPE-1(3x)-TK is fully controlled by the prodrug GCV and is quite active at relatively low GCV concentrations. Finally, although the endothelial cell transduction efficacy of the adenovirus vector is relatively low, endothelial cell killing is highly effective.

Example 34

Therapeutic Effect of Administration of Ganciclovir and TK Under Control of the PPE-1 (3x) Promoter: Superior Endothelial Cell Cytotoxicity of TK Under Control of the PPE-1 (3x) Promoter in-vivo The therapeutic efficacy of the specific endothelial cell-targeted cytotoxicity of AdPPE-1(3x)-TK was assessed in-vivo by comparison to systemic administration of GCV and control vectors AdCMV-TK and AdPPE-1(3x)-Luc, in animal models of cancer tumorigenesis and metastatic growth.

Synergic suppression of metastatic growth in Lewis Lung Carcinoma (LLC) by in vivo expression of TK under control of the PPE-1 (3x) promoter and ganciclovir (GCV) administration: Lewis Lung Carcinoma is a well-characterized animal model of severely aggressive, malignant cancer with high metastatic potential. Combination therapy with HSV-TK has been attempted using cytokine IL-2 (Kwong et al, Chest 119; 112:1332-37), with the endothelial promoter Tie/Tek and GCV (depalma et al, Nat Med 2003; 9:789-795) and with the VEGF promoter and GCV in-vitro (Koshikowa et al Canc Res 2000; 60:2936-41). In order to test the effect of systemic administration of AdPPE-1(3x) and GCV on metastatic disease, LLC lung metastases were induced by the inoculation of the left foot with tumor cells and foot amputation as soon as the primary tumor developed. Adenovirus vectors [AdPPE-1 (3x)-TK+GCV; AdCMV-TK+GCV; AdPPE-1(3x)-TK without GCV] were administered intravenously five days post primary tumor removal, followed by daily intraperitoneal GCV administration for 14 days.

Mice exclusion was as follows: 22 mice were excluded since no primary tumor developed, one mouse was excluded due to vector injection failure, 8 mice died without any traces of lung metastasis. Of the excluded mice, 18 mice were excluded before enrollment, 6 were excluded from group 1(AdPPE-1(3x)-TK+GCV), 2 from group 2(AdCMV-TK+ GCV), 3 from group 3(AdPPE-1(3x)-TK without GCV) and 2 from group 4 (Saline+GCV). The mice were sacrificed on the 24$^{th}$ day post vector injection. On that day 25% of the mice in the control groups (saline+GCV and AdPPE-1(3x)-TK without GCV) had died from the spread of lung metastases. FIG. 70 shows representative lung tissue from treated and control groups, showing the significantly reduced extent of metastatic spread in the lungs of AdPPE-1 (3x)-TK+GCV treated mice, compared to those from mice treated with AdCMV-TK+GCV, AdPPE-1 (3x)-TK without GCV and GCV without adenovirus.

Upon sacrifice, the mean weight (an indication of extent of metastatic disease) of the metastases of mice treated with AdPPE-1(3x)-TK+GCV was 3.3 times lower than that of mice treated with AdPPE-1(3x)-TK without GCV (mean±SE: 0.3 g+0.04 vs. 0.8 g±0.2, respectively; $p<0.05$). The mean weight of the metastases of mice treated with AdCMV-TK+GCV or with saline+GCV was not statistically different from that of the other groups (FIG. 71).

Cytotoxic effect of in vivo expression of TK under control of the PPE-1 (3x) promoter and ganciclovir (GCV) on metastatic lung tissue: In order to determine the mechanism of the effect of AdPPE-1(3x) and GCV administration on LLC metastatic growth, hematoxylin and eosin staining was performed on lung tissue from metastatic lungs (FIGS. 72a-72c).

Mild peripheral necrosis was detected in lung metastases taken from mice treated with AdPPE-1(3x)-TK without GCV or saline+GCV (FIG. 72a). Lung tissue taken from mice treated with AdPPE-1(3x)-TK+GCV demonstrated alveolar and peribronchial mononuclear infiltrates, while no infiltrates were detected in lungs taken from mice treated with AdPPE-1(3x)-TK without GCV or saline+GCV. Lung metastases taken from mice treated with AdPPE-1(3x)-TK+GCV demonstrated clusters of mononuclear infiltrates compared to metastases taken from mice treated with AdPPE-1(3x)-TK without GCV or saline+GCV (FIG. 72b,c). Minimal necrosis and mononuclear infiltrates were also detected in specimens taken from mice treated with AdCMV-TK+GCV. The result suggest that AdPPE-1(3x)-TK+GCV induce increased central necrosis and mononuclear infiltrates in lung metastases.

To determine the character of cell death responsible for the inhibitory effect of AdPPE-1(3x)-TK+GCV on LLC lung metastases, TUNEL and anti-caspase-3 staining were performed on lung tissue for assessment of apoptosis. Lung metastases from AdPPE-1(3x)-TK+GCV treated mice demonstrated numerous apoptotic tumor cells compared to mice treated with AdPPE-1(3x)-TK without GCV or saline+GCV (FIGS. 73a and 73b). Histopathology sections of specimens taken from lungs of mice treated with AdPPE-1(3x)-TK+ GCV demonstrated a significantly higher extent of both DNA damage (TUNEL, FIG. 73a) and caspase-3 (FIG. 73b), indicating tumor cell apoptosis, than specimens from mice treated with AdCMV-TK+GCV. More significantly, TUNEL and caspase-3 staining of histopathology sections from the metastatic lungs exhibited enhanced apoptosis in the vascular (endothelial) regions of the lung metastases from the mice treated with intravenous AdPPE-1 (3x)-TK+GCV (FIG. 74), indicating synergic enhancement of metastatic cell apoptosis by in vivo expression of TK under control of the PPE-1 (3x) promoter and ganciclovir (GCV) administration. The results suggest that systemic administration of AdPPE-1(3x)-TK+ GCV induces massive tumor cell apoptosis. Moreover, angiogenic endothelial cell apoptosis may be the mechanism for massive central metastatic necrosis and apoptosis.

Expression of TK under control of the PPE-1 (3x) promoter and ganciclovir (GCV) administration have anti-angiogenic effects in metastatic disease in-vivo: CD-31 is a characteristic endothelial cell marker of angiogenesis. Anti CD-31 staining was performed on metastatic lung tissue in order to determine the involvement of endothelial cells in the anti-metastatic effects of systemic AdPPE-1(3x)+GCV. FIGS. 75a-75d reveal that angiogenic vessels in lung metastases from AdPPE-1(3x)-TK+GCV treated mice were short, without continuity or branching and with indistinct borders (FIGS. 75a-75c). Angiogenic blood vessels in lung metastases from mice treated with AdPPE-1(3x)-TK without GCV or saline+ GCV demonstrated long blood vessels with abundant branching and distinct borders (FIG. 75a). Minimally abnormal vasculature was also detected in lung metastases of AdCMV-TK+GCV treated mice, although much smaller than those of mice treated with AdPPE-1(3x)-TK (not shown). The specificity of this anti-angiogeneic effect for proliferating endothelial tissue is shown by the absence of effect on hepatic blood vessels (FIG. 75c). Computer based vascular density measurement (Image Pro-Plus, Media Cybernetics Incorporated), demonstrated 1.5 times smaller vascular density in lung metastases of the AdPPE-1(3x)-TK+GCV group than in the group treated with AdPPE-1(3x)-TK without GCV (40107.7 µm$^2$ versus 61622.6 µm$^2$, respectively) (FIG. 75d).

Taken together, these results indicate that systemic administration of AdPPE-1(3x)-TK+GCV induces central metastatic necrosis and apoptosis via highly selective induction of angiogenic endothelial cell apoptosis.

Systemic AdCMV-TK+GCV administration induces hepatotoxicity in mice bearing LLC lung metastases. Since one of the major side effects of systemic administration of adenovirus vectors is liver toxicity, liver morphology was assayed in C57Bl/6 mice with induced LLC tumors. Analysis of hematoxylin and eosin stained sections of treated and control liver tissues revealed that livers from treated mice treated with TK under control of the constitutive promoter AdCMV-TK+GCV exhibited portal and periportal mononuclear infiltrates and small confluent necrotic areas, whereas livers from mice treated with AdPPE-1(3x)-TK+GCV, and control groups, exhibited only minimal mononuclear infiltrates and hepatocyte nuclear enlargement (FIG. 76). The results demonstrate that while constitutive expression of TK under control of the CMV promoter is clearly hepatotoxic, no adverse side effects on liver morphology were observed with the angiogenesis-specific AdPPE-1(3x)-TK+GCV treatment.

Strict organ specificity of expression of TK under control of the PPE-1 (3x) promoter in-vivo: In order to assess the extent of organ-and tissue specificity of the anti-metastatic effects HSV-TK expression under control of the PPE-1(3x) promoter, PCR analysis using HSV-TK and β-actin primers was performed on a variety of tissues from different organs of mice bearing LLC lung metastases treated with adenovirus vectors.

Nine C57BL/6 male mice aged 15 weeks were enrolled. LLC lung metastases were induced by inoculation of the left foot with tumor cells and foot amputation as soon as the primary tumor developed. Adenovirus vectors (AdPPE-1 (3x)-TK and AdCMV-TK) or saline were delivered intravenously 14 days post primary tumor removal. The mice were sacrificed 6 days post vector injection and RNA was extracted from the harvested organs, as described. Reverse transcriptase-PCR was performed on RNA followed by PCR using HSV-TK and β-actin primers. Positive HSV-TK expression was detected in the lungs of mice treated with AdPPE-1(3x)-TK, while no HSV-TK expression was detected in the liver. In contradistinction, highly positive HSV-TK expression was detected in the livers of mice treated with AdCMV-TK and no expression was detected in the lungs (FIG. 77). Computer based densitometery (Optiquant, Packard-Instruments), corrected for β-actin, demonstrated lung/liver expression ratio of 11.3 in the AdPPE-1(3x)-TK treated mice, compared with the liver/lung expression ratio of 5.8 in the AdCMV-TK treated mice. These results demonstrate that the AdPPE-1(3x)-TK treated mice express the HSV-TK gene predominantly in angiogenic-rich organs, i.e. the metastatic lung, whereas expression of TK under control of the CMV promoter (AdCMV-TK treated mice) was prominent in Coxsackie adenovirus receptor-rich organs, such as the liver (FIG. 77). Strong positive HSV-TK expression was also detected in testis of AdPPE-1(3x)-TK treated mice. While not wishing to be limited by a single hypothesis, it will be appreciated that the positive expression in the AdPPE-1(3x)-TK treated mouse is likely explained by a high expression of endothelin promoter in the gonads. The positive expression in the AdCMV-TK treated mouse is explained by the relatively high RNA elution, as mirrored by the highly positive β-actin band.

Taken together, these results indicate that systemic administration of AdPPE-1(3x)-TK+GCV can efficiently inhibit even highly aggressive metastatic spread of cancer in a safe and tissue specific manner, via induction of central metastatic necrosis and selective induction of angiogenic endothelial cell apoptosis.

Example 35

Administration of Ganciclovir and TK Under Control of the PPE-1 (3x) Promoter in Combination with Radiotherapy: Synergic Endothelial Cell Cytotoxicity in-vivo Multiple modality anticancer therapies provide significant advantages over individual therapies, both in terms of reduction in required dosages and duration of treatment, leading to a reduction in undesirable side effects, and in terms of greater efficacy of treatment arising from synergic convergence of different therapeutic mechanisms (for a recent review, see Fang et al, Curr Opin Mol Ther 2003; 5:475-82). In order to test the efficacy of AdPPE-1(3x)-TK+GCV administration in multimodality therapy, the effect of systemic AdPPE-1(3x)-TK+GCV administration on a slow growing primary CT-26 colon carcinoma in Balb/C mice, and metastatic Lewis Lung Carcinoma in C57Bl/6 mice, combined with single-dose radiotherapy was assessed.

Local single-dose 5 Gy radiotherapy is non-toxic and sub-therapeutic to Balb/C mice bearing a primary CT-26 colon cancer tumor: Twenty BALB/C male mice aged 8 weeks were inoculated with CT-26 colon carcinoma into the left thigh in order to find a radiation dose which is both sub-therapeutic and non-toxic. As soon as the tumor diameter reached 4-6 mm, the mice were treated with a local single-dose of radiation. Four radiation doses were examined: 0 (black circles), 5 (open circles), 10 (black triangles), or 15 (open triangles) Gy. Tumor volume [calculated according to the formula $V=\pi/6 \times \alpha^2 \times \beta$ ($\alpha$ is the short axis and $\beta$ is the long axis)] was assessed daily by measuring the large and small axes. Mouse well-being was monitored daily by observation and weighing. 10 and 15 Gy doses suppressed tumor progression development compared to untreated mice (p=0.039, p=0.029, respectively). However, the 5 Gy dose induced only a partial, non-statistically significant delay in tumor progression (FIG. 78a), and no significant weight loss (FIG. 78b) nor abnormal behavior was detected in mice treated with 5 Gy. Based on these results, a single 5 Gy dose of radiotherapy was used in the combined treatment experiment.

Suppression of primary colon carcinoma tumor progression by in-vivo expression of TK under control of the PPE-1 (3x) promoter and ganciclovir (GCV) administration combined with local 5 Gy radiotherapy: 100 male Balb/C mice aged 8 weeks were inoculated with CT-26 colon carcinoma tumor cells. As soon as the tumor axis reached 4-6 mm, $10^{11}$ PFUs of the viral vectors [AdPPE-1 (3x)-TK or AdCMV-TK] were injected intravenously into the tail vein followed by 14 days of daily intraperitoneal GCV injection (100 mg/kg body weight), where indicated. 3 days post vector administration, the mice were irradiated with a local 5 Gy dose. Tumor volume was assessed according to the formula $V=\pi/6 \times \alpha^2 \times \beta$ ($\alpha$ is the short axis and $\beta$ is the long axis). Upon sacrifice, the mice were photographed and tumor and liver specimens were harvested for histological analysis.

AdPPE-1(3x)-TK+GCV+radiotherapy suppressed tumor progression compared to the other treatment regimens. The duration of mean tumor suppression was approximately 2 weeks, which is compatible with the duration of adenovirus activity. Mean tumor volume progression of the AdPPE-1 (3x)-TK+GCV+radiotherapy treated group was smaller than that of the AdPPE-1(3x)-TK+GCV treated group (p=0.04) and the AdCMV-TK+GCV treated group (p=0.008). Furthermore, mean tumor volume progression in this group (AdPPE-1(3x)-TK+GCV+radiotherapy) was smaller than the cumulative mean tumor volume progression in all the other groups (p=0.0025), the cumulative mean tumor volume progression in all non-irradiated groups (AdPPE-1(3x)-TK+GCV, Ad5CMV-TK+GCV, AdPPE-1(3x)-TK no GCV and saline+GCV; p=0.0005) and the cumulative mean tumor volume progression in the other irradiated groups (Ad5CMV-TK+GCV+radiotherapy, AdPPE-1(3x)-TK no GCV+radiotherapy and saline+GCV+radiotherapy; p=0.041) (FIG. 79*a, b*). Radiotherapy significantly potentiated only the angiogenic endothelial cell transcription-targeted vector, AdPPE-1(3x)-TK, compared to the non-targeted vector, AdCMV-TK (p=0.04) (FIG. 79*c-f*). Treatment regimens with all virus vectors were ineffective without radiotherapy.

Taken together, these results indicate the remarkable synergic tumor suppressive effect of combined AdPPE-1(3x)-TK+GCV and radiotherapy on CT-26 colon cancer tumor development in vivo.

AdPPE-1(3x)-TK+GCV combined with radiotherapy induces massive tumor necrosis: In order to determine the mechanisms of the anti-tumorigenic effects of combined AdPPE-1(3x)-TK+GCV and radiotherapy, hematoxylin and eosin staining was performed on tumor tissue. Tumor tissue was hypercellular, condensed and with a high mitotic index. Two elements were detected in all groups: necrosis and granulation tissue within the necrotic area. Tumors taken from mice treated with regimens that included radiation exhibited larger necrotic areas and granulated tissue than tumors taken from non-irradiated mice. In these groups, necrosis (FIG. 80*a*) and granulation tissue (FIG. 80*b*) were mostly central. Mice treated with AdPPE-1(3x)-TK+GCV combined with radiotherapy exhibited the most extensive necrosis and granulation tissue (FIGS. 80*a* and 80*b*), estimated at approximately 55%-80% of the specimen area (FIG. 80). Tumors taken from mice treated with AdPPE-1(3x)-TK+GCV without radiotherapy exhibited a relatively larger necrotic area than the other non-irradiated groups (data not shown). The results suggest that AdPPE-1(3x)-TK+GCV+radiotherapy induce massive central tumor necrosis, which is partially replaced by granulation tissue.

AdPPE-1(3x)-TK+GCV combined with radiotherapy induce endothelial cell and massive tumor apoptosis: To determine the character of cell death responsible for the inhibitory effect of AdPPE-1(3x)-TK+GCV and radiotherapy on colon cancer tumors, TUNEL and anti-caspase-3 staining were performed on tumor tissues in order to demonstrate apoptotic cells. TUNEL staining demonstrated apoptotic tumor cells surrounding a central necrotic area in irradiated groups. More apoptotic tumor cells were detected in tumors taken from mice treated with AdPPE-1(3x)-TK+GCV combined with radiotherapy than in any other group (FIG. 30*a*). The same apoptotic cell pattern was detected by anti-caspase-3 staining of the tumor sections. Furthermore, necrotic areas surrounded by apoptotic tumor cells (white arrows) had a serpentine shape and were unique in containing an increased vascular density (FIG. 81*b*). Endothelial cells of blood vessels within apoptotic areas exhibited positive anti-caspase-3 staining (FIG. 82).

Taken together these results suggest that AdPPE-1(3x)-TK+GCV combined with radiotherapy induces massive tumor cell apoptosis surrounding a necrotic area in colon cancer tumors. Moreover, the increased angiogenic vessel density within tumor apoptotic areas, the shape of the necrosis and apoptotic areas and the existence of endothelial cell apoptosis indicate perivascular necrosis secondary to angiogenic tissue damage.

Combined AdPPE-1(3x)-TK+GCV combined with radiotherapy has anti-angiogenic effects in suppression of tumor development in-vivo: CD-31 is a characteristic endothelial cell marker of angiogenesis. Anti CD-31 immuno-staining was performed on tumor tissues in order to demonstrate direct effects of the combined therapy on endothelial cells. Angiogenic vessels in sections of tumors taken from mice treated with a regimen that includes irradiation alone were short, without continuity or branching and with indistinct borders. Administration of vector alone, without GCV, caused no abnormalities (FIG. 83*a*), while AdPPE-1(3x)-TK+GCV combined with radiotherapy demonstrated the most extensive vascular abnormalities (FIG. 32*a*). Hepatic blood vessels were not affected (FIG. 83*b*). The results indicate that administration of AdPP1(3x)-TK+GCV, combined with radiotherapy induces extensive vascular disruption in angiogenic vessels.

Systemic AdCMV-TK+GCV, but not AdPPE-1(3x) administration induces hepatotoxicity in mice bearing CT-26 colon cancer tumors: Since one of the major side effects of systemic administration of adenovirus vectors is liver toxicity hematoxylin and eosin staining was performed on liver tissues from vector-treated, combination therapy and control mice. Liver specimens in every treatment group exhibited enlarged hepatocyte nuclei and Kupfer cell hyperplasia. The most distinctive changes were demonstrated in mice treated with AdCMV-TK+GCV with or without radiotherapy (FIG. 84). No differences in plasma markers of liver function (liver enzymes SGOT, SGPT) or kidney function (urea, creatinine) were found between groups. It should be noted that hepatic endothelial cells were not affected by the vector AdPPE-1(3x)-TK+GCV combined with radiotherapy (FIG. 84, right panel). The results demonstrate that the adenovirus vector expressing HSV-TK controlled by the CMV promoter is relatively hepatotoxic.

Taken together, these results suggest that AdPPE-1 (3x)-TK+GCV is safe for intravenous administration. Moreover, the vector efficiently suppresses slow growing primary tumor progression only in combination with non-toxic, locally-delivered radiotherapy is added. Without wishing to be limited to a single hypothesis, it seems likely that specific suppression of tumor angiogenesis, via apoptosis, appears to be the mechanism for tumor suppression. Moreover, the cytotoxic activity of the AdPPE-1 (3x)-TK vector is dependent upon administration of GCV and radiotherapy.

Example 36

Administration of Ganciclovir and TK Under Control of the PPE-1 (3x) Promoter in Combination with Radiotherapy: Synergic Enhancement of Survival in Metastasizing Cancer in-vivo In order to evaluate the combined effect of the antiangiogenic activity of AdPPE-1(3x)-TK+GCV and single dose radiotherapy on long term survival in cancer, systemic administration of the vector and GCV and radiotherapy in the rapidly metastasizing Lewis Lung Carcinoma model was chosen.

Local single-dose 5 Gy radiotherapy is non-toxic and sub-therapeutic to C57Bl/6 mice bearing Lewis Lung Carcinoma metastases: 35 C57BL/6 male mice aged 8 weeks were inoculated with LLC cells into the left footpad. The foot was amputated under general anesthesia as soon as the primary tumor developed. 8 days post foot amputation a single dose of radiotherapy aimed at the mouse's chest wall was administered under general anesthesia. Five radiation doses were examined: 0, 2, 50, 10 and 15 Gy. 3-4 weeks post primary tumor removal the non-irradiated mice began to loose weight, which is a sign of metastatic disease. Mouse sacrifice was therefore scheduled for the $28^{th}$ day post primary tumor removal. Mouse well-being was monitored daily by observation and weighing. 5 out of 6 mice treated with 15 Gy died within 5 days post-irradiation, without any signs of lung metastasis. Mouse exclusion was as follows: one mouse was excluded because of a two-week delay in primary tumor development compared to the other groups. 3 mice died during follow-up and no autopsy was performed. Of the excluded mice, one mouse was excluded before enrollment, one from the non-treated group, one from the 2 Gy group and one from the 5 Gy group. The mean metastatic weight of mice treated with 10 Gy was lower than that of the other groups, but was only statistically different from the group treated with 5 Gy (p=0.001) (FIG. 85a). As previously mentioned, mice treated with 15 Gy radiation died within 5 days, without any trace of metastases. Mice treated with 10 Gy exhibited a non-significant transient weight reduction 10 days post-radiation (FIG. 85b). Since a single 5 Gy dose of radiotherapy was neither therapeutic (FIG. 85a) nor toxic (FIG. 85b), it was used in the combined treatment experiment.

Synergistic suppression of metastatic disease in murine lung carcinoma with combined sub-therapeutic radiotherapy and expression of TK under control of the PPE-1 (3x) promoter and ganciclovir (GCV) administration: 180 male Balb/C mice aged 8 weeks were inoculated with LLC cells into the left footpad. The foot was amputated under general anesthesia as soon as the primary tumor developed. 5 days post amputation, $10^{10}$ PFUs of vector [AdPPE-1(3x)-TK or AdCMV-TK] were injected into the tail vein, followed by 14 days of daily intraperitoneal injections of GCV (100 mg/kg). 3 days post vector injection, a single 5 Gy dose of radiotherapy aimed at the mouse's chest wall was administered under general anesthesia.

The mice were divided into 6 groups: 1. Ad5PPE-1(3x)-TK+GCV, 2. Ad5CMV-TK+GCV, 3. saline+GCV, 4. Ad5PPE-1(3x)-TK+GCV+radiotherapy, 5. Ad5CMV-TK+GCV+radiotherapy, and 6. saline+GCV+radiotherapy. Mouse exclusion: Four mice died soon after leg amputation, four mice were excluded since the primary tumor was too large for enrollment, 7 mice were excluded because of late primary tumor development, 12 mice died without any trace of lung metastasis, 1 mouse was excluded because of bilateral eye discharge. Of the excluded mice, 14 were excluded before enrollment, 2 were excluded from group 1, 2 from group 2, 2 from group 3, 4 from group 4, 3 from group 5 and 1 from group 6.

Mice treated with AdPPE-1(3x)-TK+GCV+radiotherapy survived significantly longer than the mice in any other treatment group (p=0.05) (FIG. 86a). Moreover, radiotherapy significantly potentiated only the angiogenic endothelial cell transcription-targeted vector, AdPPE-1(3x)-TK, compared to the non-targeted vector, AdCMV-TK (p=0.04) (FIG. 86b-d). The results show that combined treatment of systemically administered AdPPE-1(3x)-TK vector+GCV+single dose radiotherapy synergically prolongs survival in metastatic disease.

Example 37

Dual Therapy with Fas and TNFR Chimeric Gene Under Control of the PPE-1 (3x) Promoter: Synergic Enhancement of Endothelial Cell Specificity in-vitro with Doxorubicin In order to test the efficacy of combined chemotherapy and angiogenic endothelial-specific expression of "suicide genes" other than HSV/TK, AdPPE-1 (3x)-Fas-c, having a PPE-1(3x) promoter in combination with Fas-chimera (Fas-c, see detailed description hereinabove) was administered to BAEcells alone, and in combination with the anthracycline glycoside doxorubicin (DOX).

Apoptosis, as measured by cell survival (% viability, assessed by crystal violet staining) of BAE cells, was significantly greater in mice treated with AdPPE-1 (3x)-Fas-c+DOX than with either AdPPE-1 (3x)-Fas-c or DOX alone (FIG. 91).

These results indicate that the PPE-1 (3x) promoter can be used to direct efficient, endothelium-specific expression of additional therapeutic gene constructs, and that the combination of PPE-1 (3x) dependent, apoptosis-inducing Fas-c expression and chemotherapy results in highly efficient synergic endothelial apoptosis.

Example 38

Conditionally Replicating Adenovirus Vectors
Materials and Experimental Methods

Cell culture: Bovine Aortic Endothelial cells (BAEC) and Human Normal skin fibroblasts—NSF cell-lines are cultured in low glucose DMEM containing 10% heat inactivated FCS, 100 µg/ml penicillin and 100 µg/ml streptomycin. HeLa (Human cervix epithelial adenocarcinoma), Lewis Lung Carcinoma cells (D122-96) and 293 (human embryonic kidney) cell-lines are cultured in high glucose DMEM containing 10% heat inactivated FCS, 100 µg/ml penicillin, 100 µg/ml streptomycin. Human Umbilical Endothelial Cells —HUVEC (Cambrex Bio Science Walkersville, Inc.) are cultured in EGM-2 Bullet kit (Clonetics, Bio-Whittaker, Inc., MD, USA). Human lung carcinoma cell line (A549) are cultured in MEM containing 10% heat inactivated FCS, 100 µg/ml penicillin and 100 µg/ml streptomycin. All cells are grown in 37° C., 5% $CO_2$, humidified atmosphere.

Plasmids and Viral Vectors Construction:

Plasmid cloning: The cDNA of firefly luciferase was sub-cloned into the multiple cloning site of pcDNAIII expression plasmid (containing CMV promoter region, Invitrogen), and into pPACPPE-1.plpA, which contains PPE1-3x promoter and parts of the adenovirus-5 DNA sequence. A third plasmid was cloned by deleting the first intron of PPE-1 promoter from pPACPPE-1.plpA plasmid. The three plasmids were previously cloned in our lab and were used in cell culture transfections.

Replication deficient vectors cloning: The cDNA of FAS-chimera was sub-cloned into pPACPPE-1.plpA and pPACC-MV.plpA plasmids. These plasmids were co-transfected with pJM17 that contains most of the adenovirus-5 genome and were co-transfected with calcium phosphate method into 293 human embryonic kidney cell-line (ATCC). This cell-line was designed to include the E1 gene that is necessary for viral replication but is not included in the pPAC.plpA or pJM17 plasmids. The plasmids undergo homologous recombination within the cells, and after approximately two weeks recombinant viruses are formed and start to replicate and finally cause cell lysis. Viral colonies are separated and propagated and their accurate insert orientation is verified by PCR. The replication deficient vectors were previously prepared by conventional prior art cloning techniques.

Conditionally replicating adenovirus (CRAD) construction: The CRADs were constructed using the AdEasy method (Stratagene, LaJolla Calif.). PShuttle-MK, a plasmid containing parts of the adenovirus-5 DNA sequence, has been modified as follows: the multiple cloning site and right arm in pShuttle (Stratagene, La Jolla, Calif.) were replaced by Midkine (mk) promoter and the consecutive adenoviral E1 region. Later, the MK promoter was replaced by PPE1-3x without intron. A second plasmid was constructed by subcloning IRES sequence (from p IRES-EYFP plasmid, BD Biosciences) and FAS-chimera cDNA between the promoter and E1. IRES permits translation of two proteins from the same transcript. The resultant two shuttles were linearized with PmeI digestion and subsequently transformed into *Escherichia coli* BJ5183ADEASY-1 (Stratagene). This type of bacteria has already been transformed with pADEASY-1 plasmid, which contains most of the adenovirus-5 sequence, except E1 and E3 gene regions. The plasmids undergo homologous recombination within the bacteria (between pShuttle and pADEASY-1), thus creating the complete vector genome. The recombinants were later PacI digested and transfected with calcium phosphate method into 293 human embryonic kidney cell-line (ATCC). The rest of the procedure is as described for the replication deficient vectors.

The positive control virus CMV-E1 was constructed by subcloning the general promoter CMV (cytomegalovirus) before the E1 gene. CMV-E1 virus is ubiquitous and has no specificity to endothelial cells.

The following replication deficient vectors and CRADs were constructed according to the abovementioned methods:

Replication Deficient Vectors:
PPE-1(3x)-FAS, CMV-FAS, CMV-LUC (LUC—abbreviation for firefly luciferase reporter gene), PPE-1(3x)-LUC.

CRADs:
PPE-1(3x)-CRAD, PPE-1(3x)-Fas-CRAD, CMV-E1

Transfection experiments: BAEC and HeLa cells were cultured in 24-wells plates to 60-70% confluence. Cotransfection was done using 0.4 μg/well of expression construct and 0.04 μg/well of pEGFP-C1 vector (CLONTECH, Palo Alto, Calif.) as a control for transfection efficiency. Lipofectamine and Lipofectamine plus (Invitrogen, Carlsbad, Calif.) were used for transfection. After 3 hours of incubation at 37° C., transfection mixture was replaced with growth medium.

Transduction experiments: Vectors (PPE-FAS, CMV-FAS, CMV-LUC, PPE-LUC) were diluted with the infection growth media (Contains 2% FCS instead of 10% in normal growth media) in order to reach to multiplicity of infection (moi) of 10, 100, 1000, 10000. The multiplicity of infection was calculated as the number of viruses per target cell. Target cells (BAEC and 293) had been seeded 24 hours before transduction. At the transduction day, cell's growth media was replaced with solution containing the viruses in the desired moi's mixed in 0.1 or 2 ml infection media for 96 wells plate or 60 mm plate, respectively. The cells were incubated for 4 hours, followed by the addition of fresh medium to the transduced cells.

Evaluations of vector replication and apoptotic induction is by PFU titering (see below) and ApoPercentage kit (Accurate Chemical, Westbury, N.Y.), respectively. Crystal Violet staining was also used to evaluate the amount of cells attached to the plate's surface, as an indicator for cell viability.

Testing the viral titer—Plaque Forming Unit assay (PFU): The viral stocks were titered and stored at −80° C. Sub-confluent (80%) culture of 293 cells was infected for 2 hours by the viral vector diluted with the infection media for serial dilutions ($10^{-2}$-$10^{-13}$). After two hours the medium was washed by PBS and was replaced by agar overlay. The highest dilution in which plaques are apparent after approximately 2 weeks, is considered the concentration in units of PFU/ml (PFU—plaque forming units).

Results

Cytotoxic gene expression enhances Adenovirus replication: In order to test the influence of apoptotic induction on viral replication, CMV-FAS replication was tested in the 293 (human embryonic kidney) cell-line. In this cell-line the virus can induce apoptosis by FAS-c or cell lysis as a result of its replication. Early (a few hours after viral infection) apoptosis might interfere with viral replication, while late apoptosis (a few days after viral infection) might enhance viral spread.

In order to test the ability of CMV-FAS to induce apoptosis, BAEC were transduced, and cell apoptosis was evaluated by ELISA-crystal violet assay of viability (FIG. 89). CMV-FAS at higher concentration (10000 moi) induced apoptosis without the activating ligand (TNF-α), while in lower concentrations there was a need for addition of the ligand in order to induce apoptosis.

CMV-FAS spread from cell to cell was assayed by plaque development in 293 cells. Plaque development occurred at a higher rate with the CMV-FAS vector, compared to a non-apoptosis inducing vector—CMV-LUC, as observed (FIGS. 88 and 89) according to the rate of plaque development and size of plaques.

The ability of PPE 1-3x promoter, with and without the intron, to induce RNA transcription, was assessed by the luciferase reporter gene (not shown). No significant differences were observed.

These results indicate that replication of adenovirus vectors, such as the angiogenic, endothelial-specific viral construct AdPPE-1(3x) described hereinabove, bearing apoptosis-inducing "killer" genes such as FAS, can be enhanced by the additional apoptotic lysis of the host cells.

Example 39

PPE-1 (3x) Control of VEGF Expression Enhances Neovascularization and Survival of Engineered Tissues In order to study the effect of expression of VEGF under the control of endothelin promoter on the vascularization of engineered tissue construct in vitro and in vivo, cells were infected with Ad5PPEC-1-3x VEGF and constructs were analyzed to see the effect on vascularization.

FIG. 91*a* shows that infection of the cells with Ad5PPEC-1-3x VEGF has an inductive effect on number and size of vessels-like structures formed in the engineered constructs. Constructs were grown with or without VEGF supplementation to the medium (50 ng/ml). Parallel constructs were infected with Ad5PPEC-1-3x VEGF viruses or control GFP adenoviruses (for 4 hours). Following 2 weeks in culture the constructs were fixed, embedded, sectioned and stained.

Comparing between addition of VEGF to the medium and infection the cells with Ad5PPEC-1-3x VEGF, a 4 to 5-fold increase in the number of vessels and percentages of vessel area in the samples treated with Ad5PPEC-1-3x VEGF virus was found (FIG. 91*a*).

In in-vivo studies, three different models were used to analyze survival, differentiation, integration and vascularization of the implant in vivo. These models included (i) Subcutaneous Implantation in the back of SCID mice, (ii) Implantation into the quadriceps muscle of nude rats, and (iii) Replacement of anterior abdominal muscle segment of nude mice with the construct.

The constructs were permeated with host blood vessels. Constructs infected with Ad5PPEC-1-3x VEGF virus showed an increase in vessel structures compared to control constructs.

To evaluate tissue-engineered construct survival and integration in vivo, we employed a luciferase-based imaging system. The in vivo imaging system (IVIS) works by detecting light generated by the interaction of systemically administered luciferin with locally produced luciferase. Constructs were infected with Adeno Associated Virus (AAV) vector encoding luciferase for 48 hours prior to transplantation. The constructs were then placed in situ in the anterior abdominal muscle walls of nude mice. AAV-Luciferase was injected into the left lower extremity of each mouse at the time of surgery to serve as a positive control. Three-four weeks following surgery, the mice received luciferin to assess perfusion to the tissue-engineered construct.

Constructs infected with Ad5PPEC-1-3x VEGF (and infected later with AAV-luciferase) had higher signal than control constructs infected with AAV-luciferase only (results not shown). Taken together, these results suggest that in vitro infection with Ad5PPEC-1-3x VEGF can improve survival and vascularization of implanted engineered tissue constructs.

Example 40

In-vivo Activation of PPE-1(3x) Promoter by Antiangiogenic Treatment

A common response of many tissues to repression of angiogenesis is the upregulation of endogenous angiogenic pathways, in response to complex signaling generated by the auto-regulated autocrine feedback loops governing vascular homeostasis (see Hahn et al, Am J Med 1993, 94:13S-19S, and Schramek et al, Senim Nephrol 1995; 15:195-204). In order to determine how such a mechanism would effect the expression of nucleic acid sequences under control of the PPE-1 (3x) promoter, the in-vivo level of luminescence was measured in tissues in transgenic mice transformed with a nucleic acid construct of the present invention including the luciferase (LUC) gene under PPE-1(3x) control [PPE-1 (3x)-LUC], with and without administration of the potent antiangiogenic drug Bosentan. Bosentan (Tracleer™) is a dual endothelin receptor (ETA and ETB) antagonist presently clinically approved for a variety of indications, most importantly pulmonary arterial hypertension and pulmonary fibrosis.

Transgenic mice bearing the PPE-1(3x)-LUC construct of the present invention or the PPE-1-LUC construct as described in detail by Harats et al. (J Clin Invest 1995; 95:1335-44) were produced by cloning methods well known in the art, as described in detail hereinabove. 10 week old PPE-1(3x)-Luc or PPE-1-LUC transgenic mice, (n=5 in each group) were either fed orally with chow diet or chow diet with 100 mg/kg/day Bosentan for 30 days. Mice were sacrificed on the last day of treatment and organs, the organs of the mice removed for measurement of luminescence intensity, as described in the Methods section hereinabove.

FIG. 94 shows that the PPE-1 (3x) promoter confers tissue specific over-expression of the recombinant gene in the transgenic mice. Organs having normally greater endothelin activity, such as heart and aorta, and to a lesser extent, brain, trachea and lungs, showed an increased luminescence intensity, as compared with liver or kidney. In most organs, however, luminescence intensity was remarkably enhanced (up to 40% in heart tissue) by Bosentan administration (FIG. 94), thus indicating that endothelin receptor antagonists, in particular, and inhibitors of angiogenesis in general, can activate the endothelial specific promoters of the present invention, and induce further enhancement of expression of transgenes under PPE-1 (3x) transcriptional control, in a tissue specific manner. Measurement of levels of intracellular preproendothelin-1 mRNA, and circulating endothelin-1 show that administration of endothelin receptor antagonists (such as Bosentan) to the transgenic mice expressing Luciferase under control of the PPE-1 promoter, in fact results in increased tissue endothelin-1 transcription (FIG. 97A), and increased immunoreactive endothelin-1 detected in the plasma (FIG. 97B).

In order to further determine the specificity of the enhancement of expression of gene products under control of the PPE-1 promoter, the effect of inhibition of endothelin receptor activity with the dual endothelin antagonist Bosentan was compared to the effect of inhibition by individual specific antagonists of ET-$1_A$ (BQ123, Sigma-Aldrich, St. Louis, Mo., USA) and ET-$1_B$ (BQ788, Sigma-Aldrich, St. Louis, Mo., USA). FIG. 96 shows the luciferase activity measured in Bovine Aortic Endothelial Cell (BAEC) cultures transfected with luciferase expression plasmids under the control of PPE-1 promoter (plasmid pEL8-LUC, described hereinabove) or control SV40 promoter, followed by 1 hour treatment with ET-1 receptor antagonists Bosentan, BQ123 or BQ788, expressed as a percent of the untreated controls.

A significant increase in luciferase activity under the control of PPE-1 promoter was measured with Bosentan and BQ788 treatment but not with BQ123 (ET-$1_A$ antagonist). Bosentan and BQ788 treatment (at 1 µM) resulted in a 1.6 and 1.3 fold increase in luciferase activity compared to untreated control, respectively (FIG. 96). No significant increase was observed in the SV40-luciferase transfected cells (data not shown).

Taken together, these results show that the increased preproendothelin-1 mRNA levels in response to ETB blockade are mediated by increased PPE-1 promoter activity, implying enhanced transcription of genes under PPE-1 control in response to ET-1 receptor blockade. Further, the increased PPE-1 promoter activity can be detected both in-vitro and in-vivo, for short and long term period treatments, respectively.

As shown herein, PPE-1 mRNA levels correlate with luciferase activity in transgenic mice expressing the luciferase reporter gene under the control of PPE-1 promoter. Thus, this model can be also used for evaluating ET-1 expression in different pathophysiological states, including hypertension, cancer and acute renal failure.

Example 41

Transgenes Expressed in-vivo Under Control of the PPE-1(3x) Promoter are Not Immunogenic As described hereinabove, gene therapy, as other long-term therapeutic modalities, is often complicated by endogenous host immune reaction to continued exposure to expressed transgenic protein. Immune stimulation by the transgenic protein can cause reduced efficacy of treatment, inflammation, and sometimes severe side effects. In order to test the host immune response to transgenes expressed using the cis reacting regulatory element of the present invention, antibody titers against adenoviral hexone and TNF-R1 were assayed in mice bearing LLC micrometastases, and treated with vectors bearing the Fas-TNF-R1 chimera (Ad5PPE-1(3x) Fas-c and Ad5CMV Fas-c), or the LUC reporter gene (Ad5PPE-1(3x) Luc) (6 mice per group). Control mice were treated with saline.

Vectors were injected 3 times, at an interval of 5 days between injection. Mice were sacrificed 10 days after last vector injection, for determination of levels of antibodies against the adenovirus and against human TNF-R1, the protein expressed by the transgene inserted, using an ELISA assay.

Unexpectedly, the levels of antibodies against human TNF-R1 were found to be below the level of detection in Ad5-PPE (3x)-Fas-c treated mice, whereas these levels were relatively high in the mice treated with the non-specific Ad5-CMV-fas vector (FIG. 95b). Antibody titers against the adenoviral hexone antigen were similar among the different virus-injected groups (FIG. 95a). These results indicate that transgenes expressed using the PPE-1(3x) construct of the present invention are well tolerated by the host immune system, irrespective of phylogenetic proximity.

Example 42

Corticosteroid Treatment Enhances Expression of Transgenes in Endothelial Cells

Recently, it has been shown that corticosteroid (dexamethasone) administration can prevent some of the immune- and apoptosis-related impairment of recombinant adenovirus-infected endothelium (Murata, et al Arterioscler Thromb Vasc Biol 2005; 25:1796-803), suppressing pro-inflammatory gene expression and optimizing recombinant gene expression efficiency in vitro and in vivo. In order to test whether corticosteroids can enhance viral-mediated transgene expression in endothelial cells, BAEC cells transfected with an adenovirus construct including the luciferase reporter coding sequence or the green fluorescent protein (GFP) reporter coding sequence were treated with dexamethasone prior to transfection.

FIG. 98 shows that luciferase expression, measured as percent luciferase per μg total protein, was increased more than 3 times in BAEC cells treated with 3 μM dexamethasone prior to infection with adenovirus expressing luciferase under control of the CMV promoter (Ad-CMV-LUC). The most pronounced effect was with 1000 multiplicity of infection. FIG. 99 illustrates the expression in endothelial BAEC of active recombinant green fluorescent protein (GFP) under the control of the PPE-1 promoter, indicated by the enhanced green color of the corticosteroid-treated cells.

Thus, corticosteroids can enhance viral-mediated transgene expression in endothelial cells, and can be used along with the methods of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of downregulating angiogenesis in a tissue of a subject, the method comprising administering directly or intravenously to the subject a nucleic acid construct including:
   (a) a first polynucleotide region encoding a chimeric polypeptide including:
      i) the extracellular region of the type I tumor necrosis factor receptor (TNFR1); and
      ii) the trans-membrane and intracellular regions of the Fas receptor; and
   (b) a second polynucleotide region comprising:
      i) a pre-proendothelin 1 (PPE-1) promoter;
      ii) and endothelial regulatory element comprising a nucleotide sequence as set forth in SEQ ID NO: 8 and at least one copy of a nucleotide sequence as set forth in SEQ ID NO: 6, thereby down-regulating angiogenesis in the tissue, wherein said subject is being treated with a chemotherapeutic agent.

2. The method of claim 1, wherein said chemotherapeutic agent is doxorubicin.

3. The method of claim 1, wherein said nucleic acid construct is administered intravenously.

4. The method of claim 1, further comprising administering to said subject at least one modulator of angiogenesis further potentiating activity of said promoter and endothelial regulatory element in a synergic manner.

5. The method of claim 4, wherein said modulator of angiogenesis is an endothelin receptor antagonist.

6. The method of claim 5, wherein said endothelin receptor antagonist is a dual A-form and B-form endothelin receptor antagonist.

7. The method of claim 5, wherein said endothelin receptor antagonist is a B-form specific endothelin receptor antagonist.

8. The method of claim 7, wherein said B-form specific endothelin receptor antagonist is selected from the group consisting of A192621; BQ788; Res 701-1 and Ro 46-8443.

9. The method of claim 5, wherein said endothelin receptor antagonist is any endothelin receptor antagonist excluding Bosentan.

10. The method of claim 1, further comprising administering to the subject a tumor necrosis factor receptor ligand, thereby down-regulating angiogenesis in the tissue.

11. The method of claim 1, wherein said tissue is a tumor.

12. The method of claim 1, wherein said second polynucleotide region comprises a pre-pro endothelin (PPE)-1-3X promoter directing expression of said chimeric polypeptide.

13. The method of claim 1, wherein said nucleic acid construct further comprises an adenovirus vector.

14. The method of claim 13, further comprising administering to said subject at least one compound enhancing copy number of said adenovirus or enhancing transgene expression or both.

15. The method of claim 14, wherein said compound is a corticosteroid or N-acetyl cysteine or both.

16. The method of claim 13, wherein said adenovirus vector is an adenovirus type 5 vector.

17. The method of claim 1, wherein said endothelial regulatory element is as set forth in SEQ ID NO: 7.

18. The method of claim 1, wherein said nucleic acid construct further comprises a hypoxia responsive element as set forth in SEQ ID NO: 5.

19. The method of claim 1, wherein said preproendothelin-1 promoter comprises the nucleic acid sequence as set forth in SEQ ID NO: 1.

20. The method of claim 1, wherein said endothelial regulatory element comprises at least two copies of the nucleotide sequence as set forth in SEQ ID NO: 6.

21. A method of downregulating angiogenesis in a tissue of a subject, the method comprising:
I) directly or intravenously administering to the subject a nucleic acid comprising:
(a) a first polynucleotide region encoding a chimeric polypeptide including:
i) the extracellular region of the type I tumor necrosis factor receptor (TNFR1); and
ii) the trans-membrane and intracellular regions of the Fas receptor; and
(b) a second polynucleotide region comprising:
i) a pre-proendothelin 1 (PPE-1) promoter;
ii) and endothelial regulatory element comprising a nucleotide sequence as set forth in SEQ ID NO: 8 and at least one copy of a nucleotide sequence as set forth in SEQ ID NO: 6; and
II) administering to said subject an endothelin-1 receptor antagonist, thereby downregulating angiogenesis in the tissue.

22. The method of claim 21, wherein said second polynucleotide region comprises a pre-pro endothelin (PPE)-1-3X promoter.

23. The method of claim 21, wherein said nucleic acid construct further comprises an adenovirus vector.

24. The method of claim 23, further comprising administering to said subject at least one compound enhancing copy number of said adenovirus or enhancing transgene expression or both.

25. The method of claim 24, wherein said compound is a corticosteroid or N-acetyl cysteine or both.

26. The method of claim 23, wherein said adenovirus vector is an adenovirus type 5 vector.

27. The method of claim 21, wherein said endothelin receptor antagonist is a dual A-form and B-form endothelin receptor antagonist.

28. The method of claim 21, wherein said endothelin receptor antagonist is a B-form specific endothelin receptor antagonist.

29. The method of claim 28, wherein said B-form specific endothelin receptor antagonist is selected from the group consisting of A192621; BQ788; Res 701-1 and Ro 46-8443.

30. The method of claim 21, wherein said endothelin receptor antagonist is any endothelin receptor antagonist excluding Bosentan.

31. The method of claim 21, wherein said subject is being treated with a chemotherapeutic agent.

32. The method of claim 21, wherein said nucleic acid construct is administered intravenously.

33. The method of claim 21, wherein said tissue is a tumor.

34. The method of claim 21, wherein said endothelial regulatory element is as set forth in SEQ ID NO: 7.

35. The method of claim 21, further comprising administering to the subject a tumor necrosis factor receptor ligand, thereby down-regulating angiogenesis in the tissue.

36. The method of claim 21, wherein said nucleic acid construct further comprises a hypoxia responsive element as set forth in SEQ ID NO: 5.

37. The method of claim 23, wherein said subject is being treated with doxorubicin.

38. The method of claim 21, wherein said preproendothelin-1 promoter comprises the nucleic acid sequence as set forth in SEQ ID NO: 1.

39. The method of claim 21, wherein said endothelial regulatory element comprises at least two copies of the nucleotide sequence as set forth in SEQ ID NO: 6.

* * * * *

SEQUENCE LISTING

```
<160> NUMBER OF SEQ ID NOS: 16

<210> SEQ ID NO 1
<211> LENGTH: 1334
<212> TYPE: DNA
<213> ORGANISM: Mus musculus

<400> SEQUENCE: 1
gtgtgtgtgt gtgtgtgtgt gtgtgtgtgt gtgtgtgtgt gtgtagtgta cttctgatcg      60
gcgatactag ggagataagg atgtacctga caaaaccaca ttgttgttgt tatcattatt     120
atttagtttt ccttccttgc taactcctga cggaatcttt ctcacctcaa atgcgaagta     180
ctttagttta gaaaagactt ggtggaaggg gtggtggtgg aaaagtaggg tgatcttcca     240
aactaatctg gttccccgcc cgccccagta gctgggattc aagagcgaag agtggggatc     300 gtcccttgt ttgatcagaa agacataaaa ggaaaatcaa gtgaacaatg atcagcccca     360
cctccacccc accccctgc gcgcgcacaa tacaatctat ttaattgtac ttcatacttt     420
tcattccaat ggggtgactt tgcttctgga gaaactcttg attcttgaac tctggggctg     480
gcagctagca aaaggggaag cgggctgctg ctctctgcag gttctgcagc ggtctctgtc     540
tagtgggtgt tttcttttc ttagccctgc ccctggattg tcagacggcg ggcgtctgcc     600
tctgaagtta gccgtgattt cctctagagc cgggtcttat ctctggctgc acgttgcctg     660
tgggtgacta atcacacaat aacattgttt agggctggaa taaagtcaga gctgtttacc     720
cccactctat aggggttcaa tataaaaagg cggcggagaa ctgtccgagt cagacgcgtt     780
cctgcaccgg cgctgagagc ctgacccggt ctgctccgct gtccttgcgc gctgcctccc     840
ggctgcccgc gacgctttcg ccccagtgga agggccactt gctgaggacc gcgctgagat     900
ctaaaaaaaa aacaaaaaac aaaaacaaa aaacccaga ggcgatcaga gcgaccagac     960
```

```
accgtcctct tcgttttgca ttgagttcca tttgcaaccg agttttcttt ttttccttt      1020 tccccactct tctgacccct ttgcagaatg gattatttc ccgtgatctt ctctctgctg      1080
ttcgtgactt tccaaggagc tccagaaaca ggtaggcgcc acttgcgaat cttttctactt    1140 cagcgcagca gttatcgctt ctgttttcca cttttctttc tttctttct ttcattcttt     1200 ccttttatt tatttttta attactgaag ctccagcagc aagtgcctta caattaatta       1260
acttctgtgt gaagcgaaag aaataaaacc cctgtttgaa tacagctgac tacaaccgag     1320
tatcgcatag cttc                                                       1334

<210> SEQ ID NO 2
<211> LENGTH: 96
<212> TYPE: DNA
<213> ORGANISM: Artificial sequence
<220> FEATURE:
<223> OTHER INFORMATION: Single strand DNA oligonucleotide

<400> SEQUENCE: 2
gctagcgtac ttcatacttt tcattccaat ggggtgactt tgcttctgga gggtgacttt      60
gcttctggag ccaatgggta cttcatactt ttcatt                                96

<210> SEQ ID NO 3
<211> LENGTH: 96
<212> TYPE: DNA
<213> ORGANISM: Artificial sequence
<220> FEATURE:
<223> OTHER INFORMATION: Single strand DNA oligonucleotide

<400> SEQUENCE: 3
gctagcctcc agaagcaaag tcaccccatt ggaatgaaaa gtatgaagta caatgaaaag      60
tatgaagtac ccattggctc cagaagcaaa gtcacc                                96

<210> SEQ ID NO 4
<211> LENGTH: 6
<212> TYPE: DNA
<213> ORGANISM: Artificial sequence
<220> FEATURE:
<223> OTHER INFORMATION: Nhe-1 restriction site

<400> SEQUENCE: 4 gctagc                                                                 6

<210> SEQ ID NO 5
<211> LENGTH: 6
<212> TYPE: DNA
<213> ORGANISM: Mus musculus
<220> FEATURE:
<221> NAME/KEY: misc_feature
<223> OTHER INFORMATION: Hypoxia responsive element - E-box

<400> SEQUENCE: 5 gcacgt                                                                 6

<210> SEQ ID NO 6
<211> LENGTH: 44
<212> TYPE: DNA
<213> ORGANISM: Mus musculus
<220> FEATURE:
<221> NAME/KEY: misc_feature
<223> OTHER INFORMATION: Murine endothelial specific enhancer elemet

<400> SEQUENCE: 6
gtacttcata cttttcattc caatggggtg actttgcttc tgga                       44
```

```
<210> SEQ ID NO 7
<211> LENGTH: 143
<212> TYPE: DNA
<213> ORGANISM: Artificial sequence
<220> FEATURE:
<223> OTHER INFORMATION: A triplicate copy of a murine enhancer sequence
      originated from the PPE-1 promoter

<400> SEQUENCE: 7
gtacttcata cttttcattc caatggggtg actttgcttc tggagggtga ctttgcttct      60
ggagccagta cttcatactt ttcattgtac ttcatacttt tcattccaat ggggtgactt     120
tgcttctgga ggctagctgc cag                                             143

<210> SEQ ID NO 8
<211> LENGTH: 47
<212> TYPE: DNA
<213> ORGANISM: Artificial sequence
<220> FEATURE:
<223> OTHER INFORMATION: EDC fragment

<400> SEQUENCE: 8
ctggagggtg actttgcttc tggagccagt acttcatact tttcatt                   47

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
ctcttgattc ttgaactctg                                                 20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
taaggcatgc ccattgttat                                                 20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gcagggctaa gaaaaagaaa                                                 20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12 tttcttttc ttagccctgc                                                  20

<210> SEQ ID NO 13
```

<211> LENGTH: 1334
<212> TYPE: DNA
<213> ORGANISM: Mus musculus

<400> SEQUENCE: 13

```
gtgtgtgtgt gtgtgtgtgt gtgtgtgtgt gtgtgtgtgt gtgtagtgta cttctgatcg     60
gcgatactag ggagataagg atgtacctga caaaaccaca ttgttgttgt tatcattatt    120
atttagtttt ccttccttgc taactcctga cggaatcttt ctcacctcaa atgcgaagta    180
ctttagttta gaaaagactt ggtggaaggg gtggtggtgg aaaagtaggg tgatcttcca    240
aactaatctg gttccccgcc cgccccagta gctgggattc aagagcgaag agtggggatc    300
gtccccttgt ttgatcagaa agacataaaa ggaaaatcaa gtgaacaatg atcagcccca    360
cctccacccc accccctgc gcgcgcacaa tacaatctat ttaattgtac ttcatacttt     420
tcattccaat ggggtgactt tgcttctgga gaaactcttg attcttgaac tctggggctg    480
gcagctagca aaaggggaag cgggctgctg ctctctgcag gttctgcagc ggtctctgtc    540
tagtgggtgt tttcttttc ttagccctgc cctggattg tcagacggcg ggcgtctgcc      600
tctgaagtta gccgtgattt cctctagagc cgggtcttat ctctggctgc acgttgcctg    660
tgggtgacta atcacacaat aacattgttt agggctggaa taaagtcaga gctgtttacc    720
cccactctat aggggttcaa tataaaaagg cggcggagaa ctgtccgagt cagacgcgtt    780
cctgcaccgg cgctgagagc ctgacccggt ctgctccgct gtccttgcgc gctgcctccc    840
ggctgcccgc gacgctttcg ccccagtgga agggccactt gctgaggacc cgctgagat     900
ctaaaaaaaa aacaaaaaac aaaaaacaaa aaacccaga ggcgatcaga gcgaccagac     960
accgtcctct tcgttttgca ttgagttcca tttgcaaccg agttttcttt ttttcctttt   1020
tccccactct tctgaccct ttgcagaatg gattatttc ccgtgatctt ctctctgctg    1080
ttcgtgactt tccaaggagc tccagaaaca ggtaggcgcc acttgcgaat cttctactt    1140
cagcgcagca gttatcgctt ctgttttcca cttttctttc tttctttct ttcattcttt   1200
cctttttatt tattttttta attactgaag ctccagcagc aagtgcctta caattaatta   1260
acttctgtgt gaagcgaaag aaataaaaacc cctgtttgaa tacagctgac tacaaccgag  1320
tatcgcatag cttc                                                    1334
```

<210> SEQ ID NO 14
<211> LENGTH: 1799
<212> TYPE: DNA
<213> ORGANISM: human herpesvirus 1

<400> SEQUENCE: 14

```
cagctgcttc atccccgtgg cccgttgctc gcgtttgctg gcggtgtccc cggaagaaat     60
atatttgcat gtctttagtt ctatgatgac acaaaccccg cccagcgtct tgtcattggc    120
gaattcgaac acgcagatgc agtcggggcg gcgcggtccg aggtccactt cgcatattaa    180
ggtgacgcgt gtggcctcga acaccgagcg accctgcagc gacccgctta acagcgtcaa    240
cagcgtgccg cagatcttgg tggcgtgaaa ctcccgcacc tcttcggcca gcgccttgta    300
gaagcgcgta tggcttcgta ccccggccat caacacgcgt ctgcgttcga ccaggctgcg    360
cgttctcgcg gccatagcaa ccgacgtacg gcgttgcgcc ctcgccggca gcaagaagcc    420
acggaagtcc gcccggagca gaaaatgccc acgctactgc gggtttatat agacggtccc    480
cacgggatgg ggaaaaccac caccacgcaa ctgctggtgg ccctgggttc gcgcgacgat    540
atcgtctacg tacccgagcc gatgacttac tggcgggtgc tgggggcttc cgagacaatc    600
```

```
gcgaacatct acaccacaca acaccgcctc gaccagggtg agatatcggc cggggacgcg    660
gcggtggtaa tgacaagcgc ccagataaca atgggcatgc cttatgccgt gaccgacgcc    720
gttctggctc ctcatatcgg gggggaggct gggagctcac atgccccgcc cccggccctc    780
accctcatct tcgaccgcca tcccatcgcc gccctcctgt gctacccggc cgcgcggtac    840
cttatgggca gcatgacccc ccaggccgtg ctggcgttcg tggccctcat cccgccgacc    900
ttgcccggca ccaacatcgt gcttgggcc cttccggagg acagacacat cgaccgcctg    960
gccaaacgcc agcgccccgg cgagcggctg gacctggcta tgctggctgc gattcgccgc   1020
gtttacgggc tacttgccaa tacggtgcgg tatctgcagt gcggcgggtc gtggcgggag   1080
gactggggac agctttcggg gacggccgtg ccgccccagg gtgccgagcc ccagagcaac   1140
gcgggcccac gaccccatat cggggacacg ttatttaccc tgtttcgggc ccccgagttg   1200
ctggccccca acggcgacct gtataacgtg tttgcctggg ccttggacgt cttggccaaa   1260
cgcctccgtt ccatgcacgt ctttatcctg gattacgacc aatcgcccgc cggctgccgg   1320
gacgccctgc tgcaacttac ctccgggatg gtccagaccc acgtcaccac ccccggctcc   1380
ataccgacga tatgcgacct ggcgcgcacg tttgcccggg agatgggga ggctaactga   1440 aacacggaag gagacaatac cggaaggaac ccgcgctatg acggcaataa aaagacagaa   1500
taaaacgcac gggtgttggg tcgtttgttc ataaacgcgg ggttcggtcc cagggctggc   1560
actctgtcga taccccaccg agaccccatt ggggccaata cgcccgcgtt tcttcctttt   1620
ccccacccca cccccaagt tcgggtgaag gcccagggct cgcagccaac gtcggggcgg   1680
caggccctgc catagccact ggccccgtgg gttagggacg gggtccccca tggggaatgg   1740
tttatggttc gtggggtta ttattttggg cgttgcgtgg ggtctggtgg acgacccag    1799
```

<210> SEQ ID NO 15
<211> LENGTH: 19
<212> TYPE: DNA
<213> ORGANISM: Artificial sequence
<220> FEATURE:
<223> OTHER INFORMATION: A portion of an endothelial transcription element

<400> SEQUENCE: 15

```
ggtgactttg cttctggag                                                 19
```

<210> SEQ ID NO 16
<211> LENGTH: 19
<212> TYPE: DNA
<213> ORGANISM: Artificial sequence
<220> FEATURE:
<223> OTHER INFORMATION: A portion of an endothelial transcription element

<400> SEQUENCE: 16

```
gtacttcata cttttcatt                                                 19
```